US009593142B2

(12) United States Patent
Arora et al.

(10) Patent No.: US 9,593,142 B2
(45) Date of Patent: Mar. 14, 2017

(54) ALDEHYDE CAPTURE LIGATION TECHNOLOGY FOR SYNTHESIS OF AMIDE BONDS

(71) Applicants: Paramjit S. Arora, Cold Spring Harbor, NY (US); Monika Raj, Jersey City, NJ (US); Huabin Wu, Ningde (CN)

(72) Inventors: Paramjit S. Arora, Cold Spring Harbor, NY (US); Monika Raj, Jersey City, NJ (US); Huabin Wu, Ningde (CN)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/583,586

(22) Filed: Dec. 26, 2014

(65) Prior Publication Data
US 2015/0232504 A1 Aug. 20, 2015

Related U.S. Application Data

(60) Provisional application No. 61/920,844, filed on Dec. 26, 2013.

(51) Int. Cl.
| | |
|---|---|
| *C07K 1/107* | (2006.01) |
| *C07K 7/06* | (2006.01) |
| *C07K 5/083* | (2006.01) |
| *C07D 209/20* | (2006.01) |
| *C07C 231/12* | (2006.01) |
| *C07C 391/02* | (2006.01) |
| *C07D 233/64* | (2006.01) |
| *C07C 319/12* | (2006.01) |
| *C07C 231/10* | (2006.01) |
| *C07D 207/16* | (2006.01) |
| *C07C 245/08* | (2006.01) |
| *C07K 5/062* | (2006.01) |
| *C07K 5/103* | (2006.01) |
| *C07K 5/065* | (2006.01) |
| *C07K 5/078* | (2006.01) |

(52) U.S. Cl.
CPC .......... *C07K 1/1075* (2013.01); *C07C 231/10* (2013.01); *C07C 231/12* (2013.01); *C07C 245/08* (2013.01); *C07C 319/12* (2013.01); *C07C 391/02* (2013.01); *C07D 207/16* (2013.01); *C07D 209/20* (2013.01); *C07D 233/64* (2013.01); *C07K 5/06026* (2013.01); *C07K 5/06034* (2013.01); *C07K 5/06052* (2013.01); *C07K 5/06078* (2013.01); *C07K 5/06165* (2013.01); *C07K 5/0806* (2013.01); *C07K 5/0808* (2013.01); *C07K 5/1008* (2013.01); *C07K 7/06* (2013.01)

(58) Field of Classification Search
CPC ...... C07K 1/1075; C07K 7/06; C07K 5/0806; C07D 207/16; C07D 233/64; C07D 245/08; C07D 209/20; C07C 245/08; C07C 231/10; C07C 231/12; C07C 391/02
See application file for complete search history.

(56) References Cited

U.S. PATENT DOCUMENTS 8,859,730 B2 * 10/2014 Li .................. C07K 1/1075
530/300
2012/0253011 A1 10/2012 Li

FOREIGN PATENT DOCUMENTS

EP 1651664 B9 5/2006

OTHER PUBLICATIONS

Silvana et al. J. Med. Chem., 2010, 53(20), 7452-60.*
Murata et al, Bioorg. & Med. Chem. Letters, 2010, 20(23), 6905-8.*
Ishiwata et al., "Chemoselective Peptide Bond Formation Using Formyl-Substituted Nitrophenylthio Ester," Tetrahedron Lett. 44:3187-90 (2003).
Raj et al., Abstract, "Aldehyde Capture Ligation for Synthesis of Peptides and Proteins," NYAS Chemical Biology Symposium (Jun. 5, 2013).
Bernal-Perez et al., "Selective N-Terminal Fluorescent Labeling of Proteins Using 4-Chloro-7-Nitrobenzofurazan: A Method to Distinguish Protein N-Terminal Acetylation," Anal. Biochem. 428:13-15 (2012).
Blanco-Canosa & Dawson, "An Efficient Fmoc-SPPS Approach for the Generation of Thioester Peptide Precursors for Use in Native Chemical Ligation," Angew Chem. Int. Ed. Engl. 47(36):6851-55 (2008).
Chan et al., "Modification of N-Terminal α-Amino Groups of Peptides and Proteins Using Ketenes," J. Am. Chem. Soc. 134:2589-98 (2012).
Choudhary & Raines, "Signature of n→π* Interactions in α-Helices," Protein Sci. 20:1077-81 (2011).
Chu & Mautner, "Analogs of Neuroeffectors. V. Neighboring-Group Effects in the Reactions of Esters, Thiolesters, and Selenolesters. The Hydrolysis and Aminolysis of Benzoylcholine, Benzoylthiolcholine, Benzoylselenolcholine, and of Their Dimethylamino Analogs," J. Org. Chem. 31:308-12 (1966).
Coltart, "Peptide Segment Coupling by Prior Ligation and Proximity-Induced Intramolecular Acyl Transfer," Tetrahedron 56:3449-91 (2000).

(Continued)

*Primary Examiner* — Shailendra Kumar
(74) *Attorney, Agent, or Firm* — LeClairRyan, a Professional Corporation

(57) ABSTRACT

The present invention relates to ligation agents and their use in making an amide ligation product. Methods of making the ligation agents are also disclosed.

12 Claims, 97 Drawing Sheets

(56) References Cited

OTHER PUBLICATIONS

Durek & Alewood, "Preformed Selenoesters Enable Rapid Native Chemical Ligation at Intractable Sites," Angew. Chem. Int. Ed. 50:12042-45 (2011).
Gilmore et al., "N-Terminal Protein Modification Through a Biomimetic Transamination Reaction," Angew. Chem. Int. Ed. 45:5307-11 (2006).
Grimsley et al., "A Summary of the Measured pK Values of the Ionizable Groups in Folded Proteins," Protein Sci. 18:247-51 (2009).
Hackenberger & Schwarzer, "Chemoselective Ligation and Modification Strategies for Peptides and Proteins," Angew. Chem Int. Ed. 47:10030-74 (2008).
Hackeng et al., "Protein Synthesis by Native Chemical Ligation: Expanded Scope by Using Straightforward Methodology," Proc. Natl. Acad. Sci. USA 96:10068-73 (1999).
Holmquist & Bruice, "Electrostatic Catalysis. III. Comparison of the Reactivity of α-Substituted o-Nitrophenyl Esters with Anionic and Amine Nucleophiles," J. Am. Chem. Soc. 91(11):2985-93 (1969).
Jencks & Gilchrist, "Nonlinear Structure-Reactivity Correlations. The Reactivity of Nucleophilic Reagents Toward Esters," J. Am. Chem. Soc. 90(10):2622-37 (1968).
Kemp, "The Amine Capture Strategy for Peptide Bond Formation—An Outline of Progress," Biopolymers 20:1793-804 (1981).
Kemp & Vellaccio, Jr., "Rapid Intramolecular Acyl Transfer from Phenol to Carbinolamine—Progress Toward a New Class of Peptide Coupling Reagent," J. Org. Chem. 40(20):3003-04 (1975).
Li et al., "Addressing Mechanistic Issues in the Coupling of Isonitriles and Carboxylic Acids: Potential Routes to Peptidic Constructs," J. Am. Chem. Soc. 130:13225-27 (2008).
Li et al., "Salicylaldehyde Ester-Induced Chemoselective Peptide Ligations: Enabling Generation of Natural Peptidic Linkages at the Serine/Threonine Sites," Organic Lett. 12(8):1724-27 (2010).
Liu & Tam, "Chemical Ligation Approach to Form a Peptide Bond Between Unprotected Peptide Segments. Concept and Model Study," J. Am. Chem. Soc. 116(10):4149-53 (1994).
Liu & Tam, "Peptide Segment Ligation Strategy Without Use of Protecting Groups," Proc. Natl. Acad. Sci. USA 1:6584-88 (1994).
Mautner et al., "The Aminolysis of Thioacyl and Selenoacyl Analogs," J. Am. Chem. Soc. 85:3458-62 (1963).
McGrath & Raines, "Chemoselectivity in Chemical Biology: Acyl Transfer Reactions with Sulfur and Selenium," Accounts Chem. Res. 44(9):752-61 (2011).
Pollock & Kent, "An Investigation into the Origin of the Dramatically Reduced Reactivity of Peptide-Prolyl-Thioesters in Native Chemical Ligation," Chem. Commun. 47:2342-2344 (2011).
Theile et al., "Site-Specific N-Terminal Labeling of Proteins Using Sortase-Mediated Reactions," Nat. Protoc. 8(9):1800-07 (2013).
Townsend et al., "Advances in Proline Ligation," J. Am. Chem. Soc. 134(8):3912-16 (2012).
Trmčić & Hodgson, "Kinetic Studies and Predictions on the Hydrolysis and Aminolysis of Esters of 2-S-Phosphorylacetates," Beilstein J. Org. Chem. 6:732-41 (2010).
Williamson et al., "Efficient N-Terminal Labeling of Proteins by Use of Sortase," Angew. Chem. Int. Ed. 51:9377-80 (2012).
Yang & Drueckhammer, "Computational Studies of the Aminolysis of Oxoesters and Thioesters in Aqueous Solution," Organic Lett. 2(26):4133-36 (2000).
Zhang et al., "Protein Chemical Synthesis by Serine and Threonine Ligation," Proc. Natl. Acad. Sci. 110(17):6657-62 (2013).

* cited by examiner

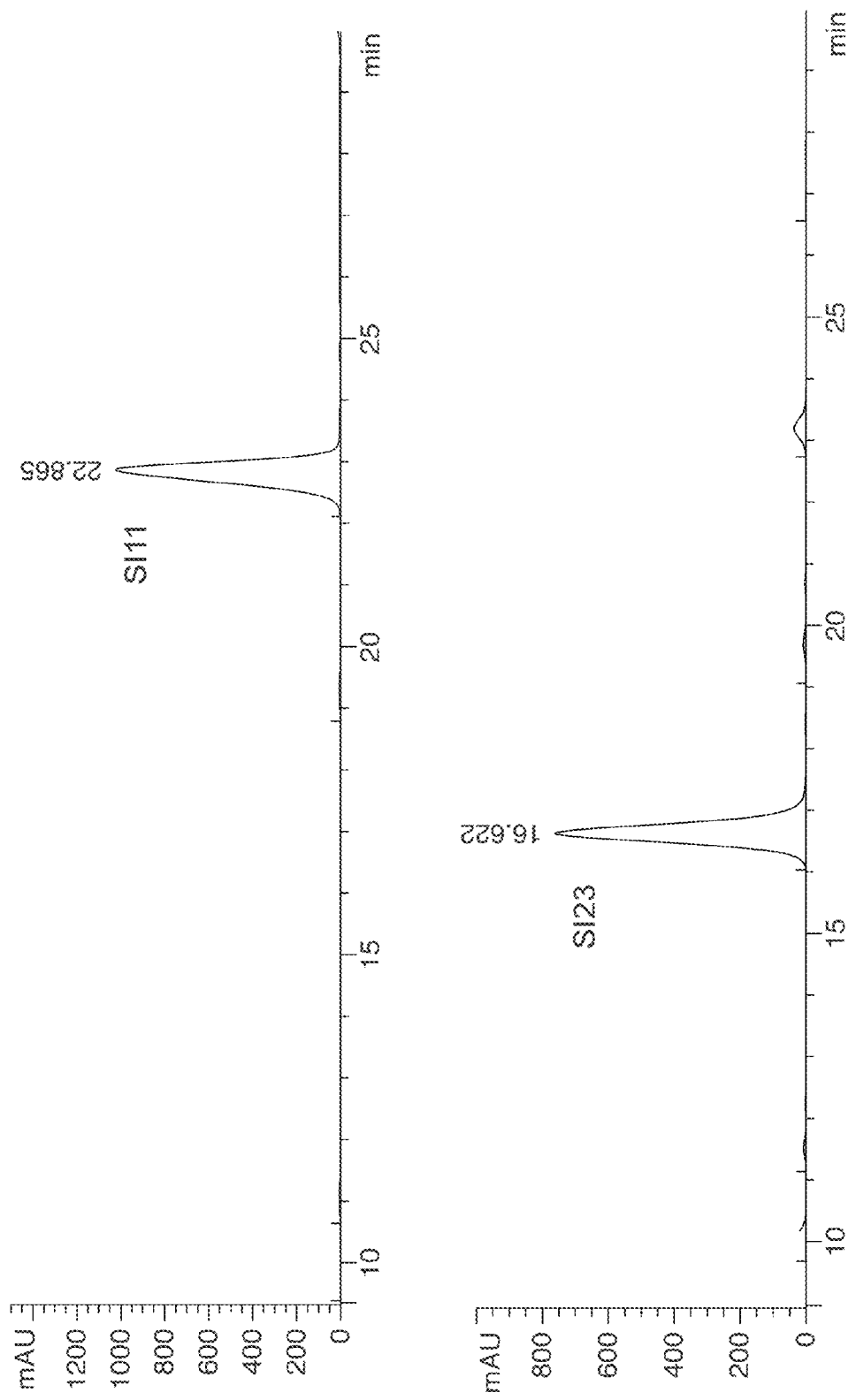

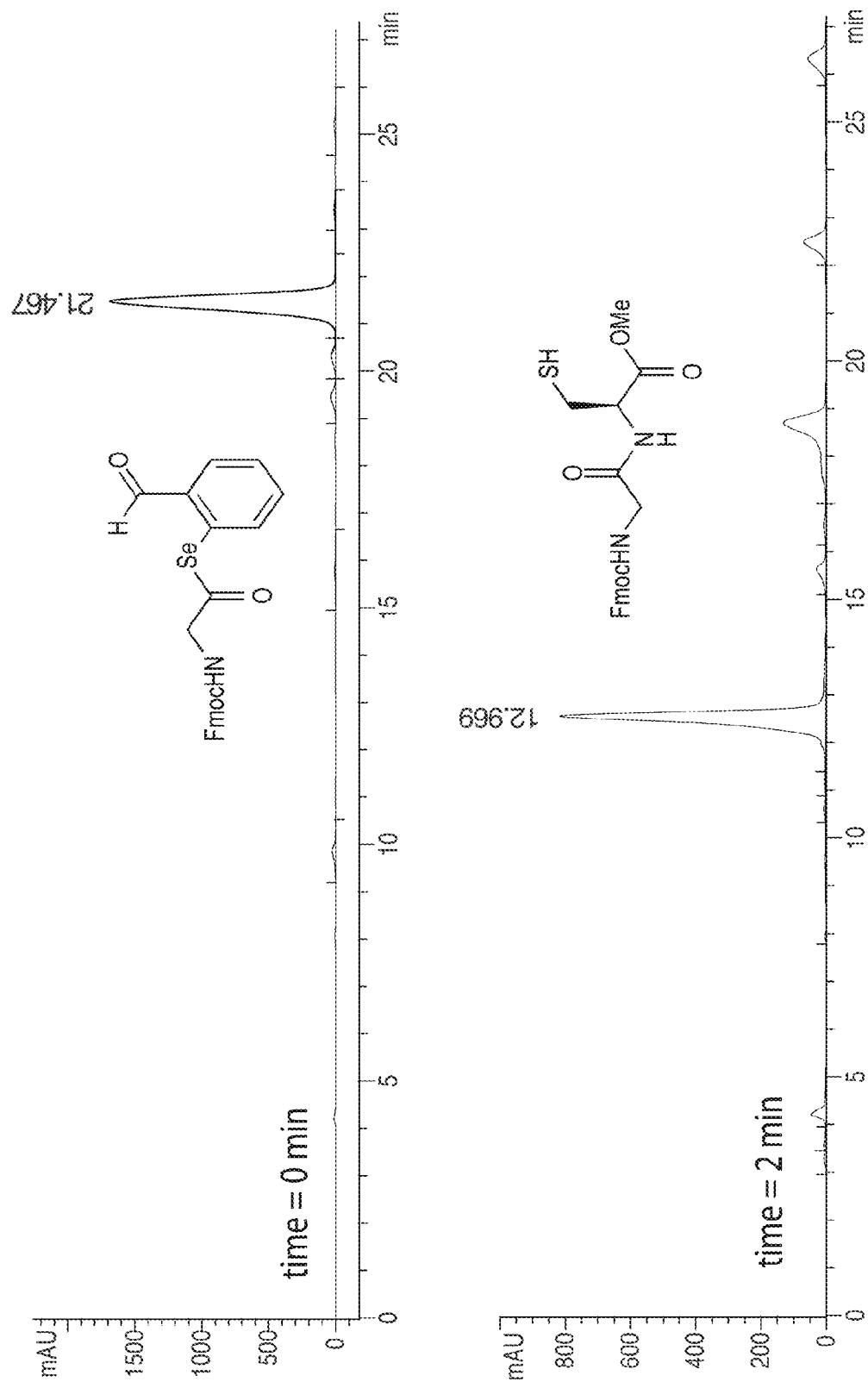

Peptide-SI30
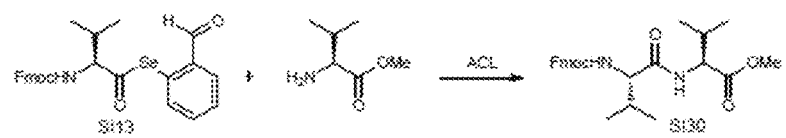
exact mass calcd. [M + Na]+ 475.1, found 475.2
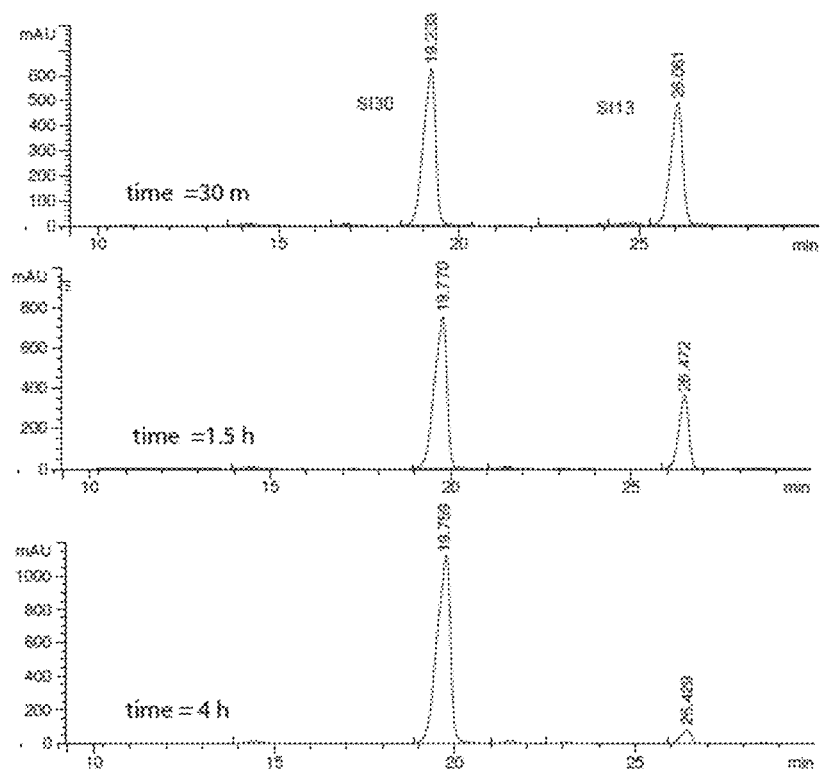
Figure 37

Peptide-SI31
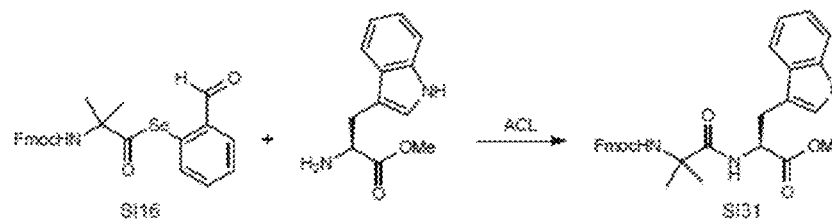
exact mass calcd. [M + H]⁺ 654.2, found 654.1
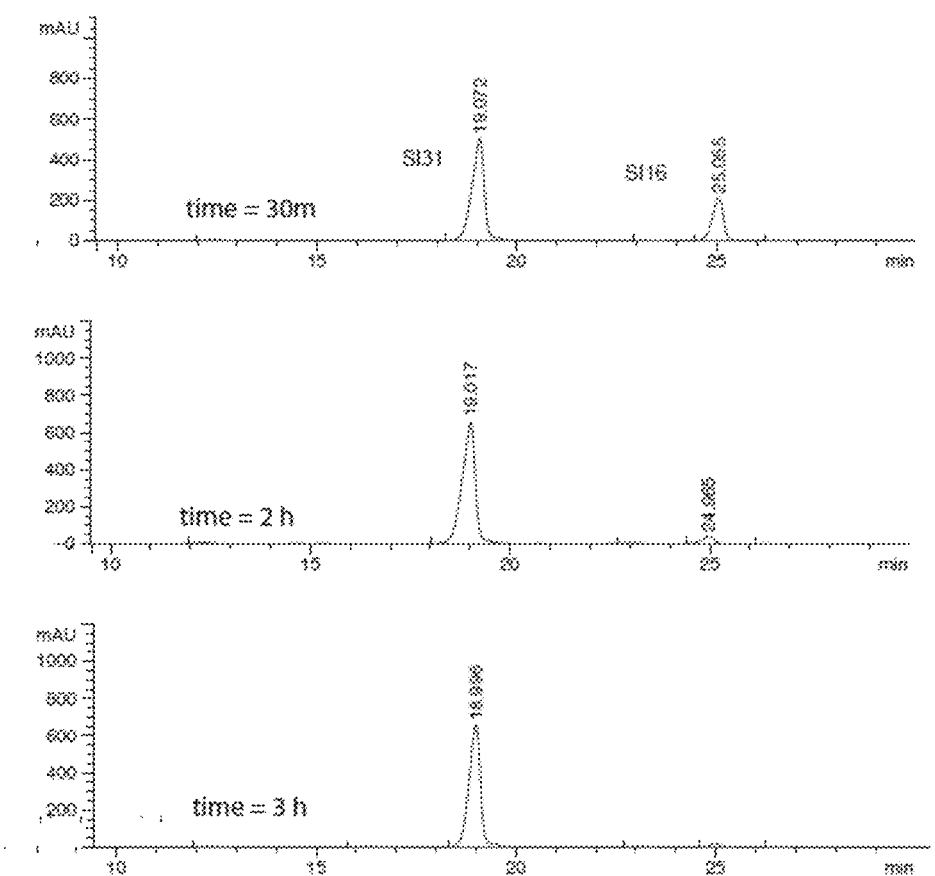
Figure 38

Peptide-S139
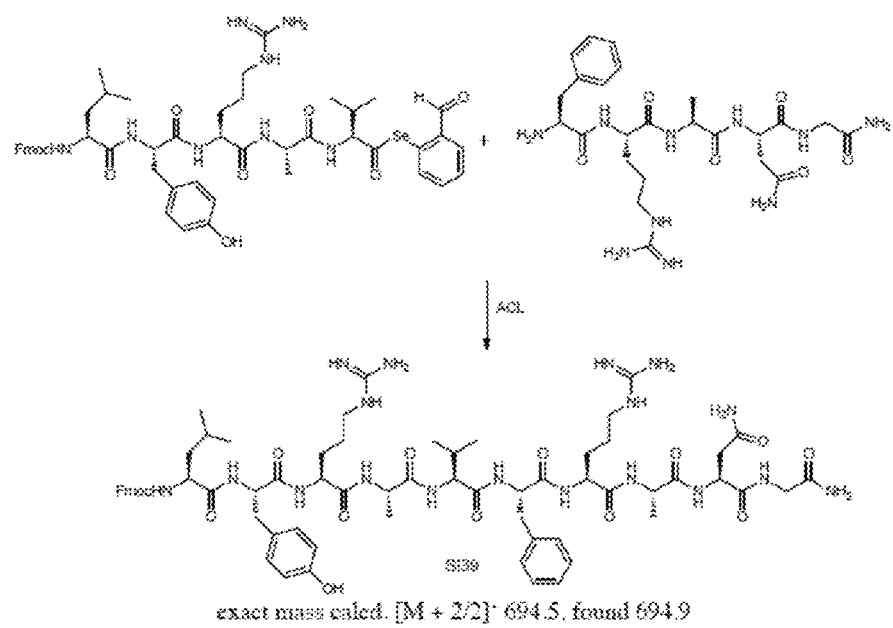
exact mass calcd. [M + 2/2]+ 694.5, found 694.9
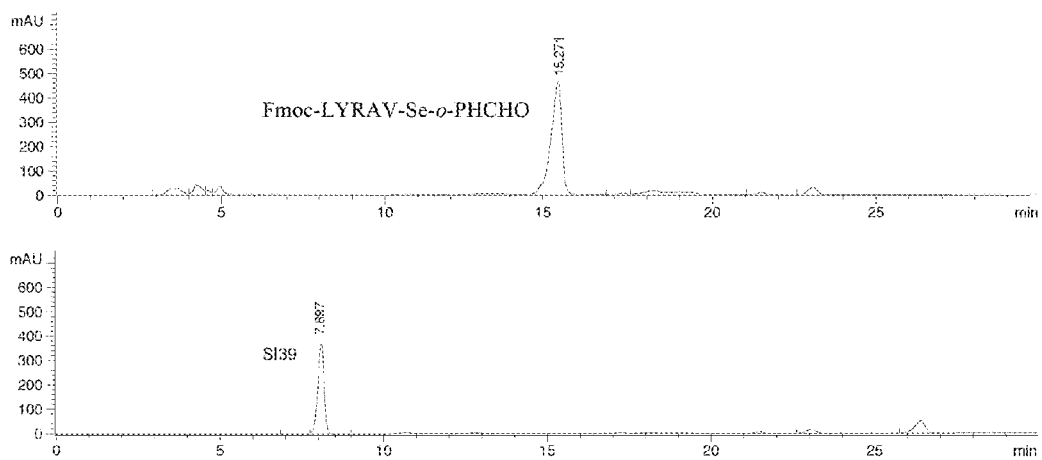
Figure 46

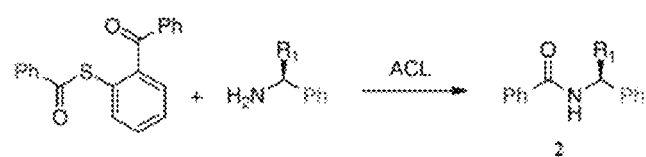
Proposed Mechanism:
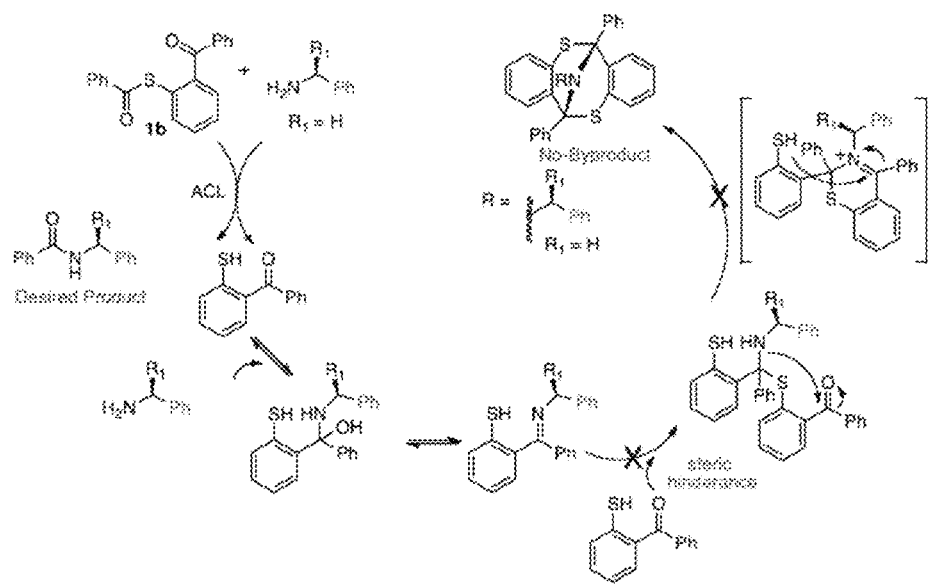
Figure 53C

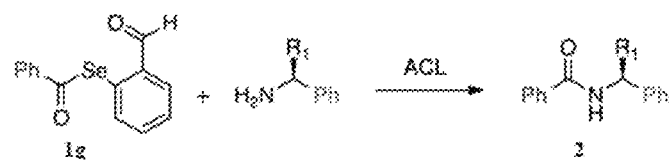
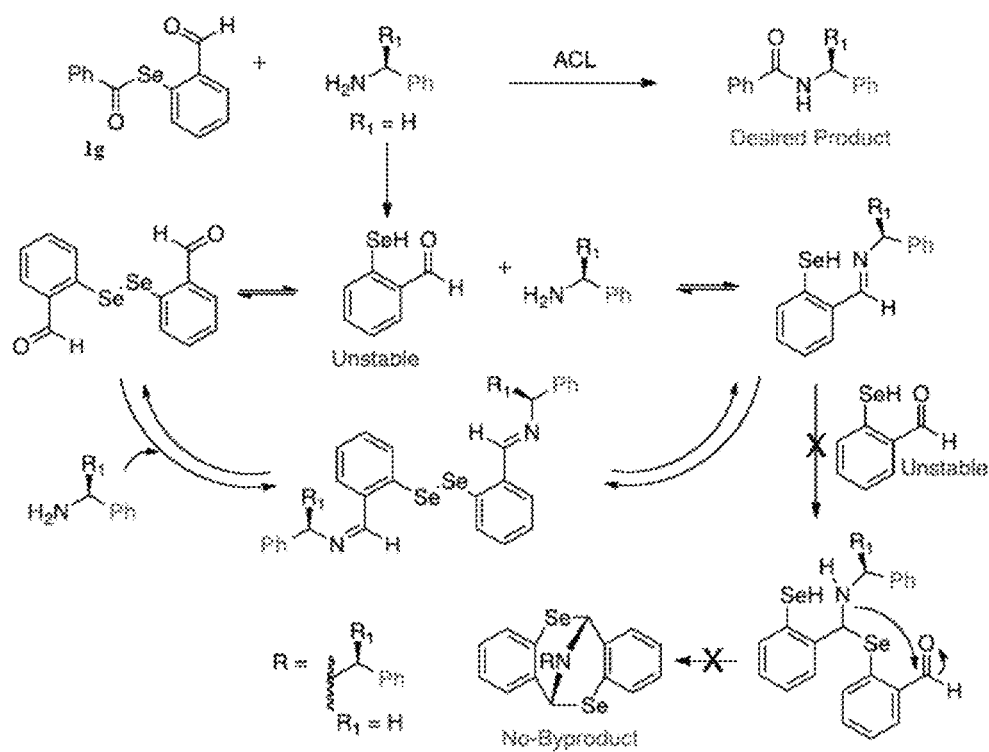
Proposed Mechanism
Figure 53D

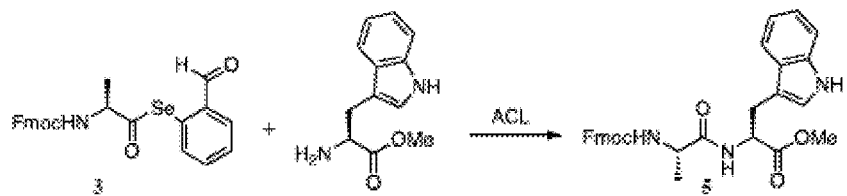
| Entry | [selenoester₀] (M) | [amine₀] (M) | Initial Rate (M/s) |
|---|---|---|---|
| 1 | 10⁻³ | 10⁻³ | 1.27 X 10⁻⁶ |
| 2 | 2 X 10⁻³ | 2 X 10⁻³ | 4.84 X 10⁻⁶ |
| 3 | 2 X 10⁻³ | 4 X 10⁻³ | 9.68 X 10⁻⁶ |
Rate order = [selenoester]¹ [amine]¹
Figures 54A
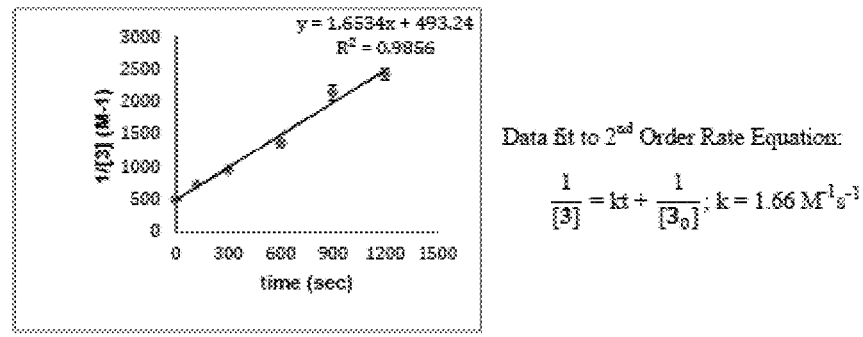
Data fit to 2$^{nd}$ Order Rate Equation:
$$\frac{1}{[3]} = kt + \frac{1}{[3_0]}; k = 1.66 \, M^{-1}s^{-1}$$
Figures 54B
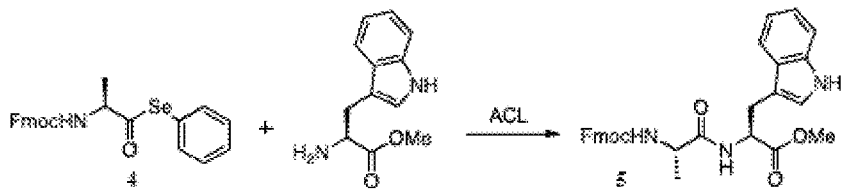
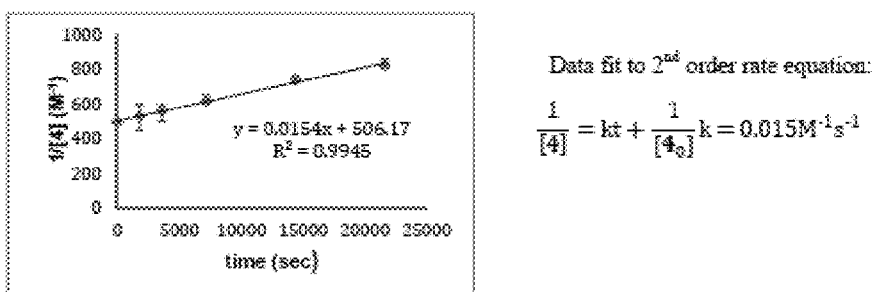
Data fit to 2$^{nd}$ order rate equation:
$$\frac{1}{[4]} = kt + \frac{1}{[4_0]} \quad k = 0.015 M^{-1}s^{-1}$$
Figures 54C

(a)

| Entry | pH | Time[a] | % hydrolysis[b] |
|---|---|---|---|
| 1 | 6.5 | 80 min | 0 |
| 2 | 7.0 | 60 min | 0 |
| 3 | 7.5 | 50 min | 2.9 |
| 4 | 8.5 | 30 min | 10 |
| 5 | 9.3 | 20 min | 20 |

[a]Time for the consumption of the starting material. [b]Hydrolysis of the starting material.

(b)

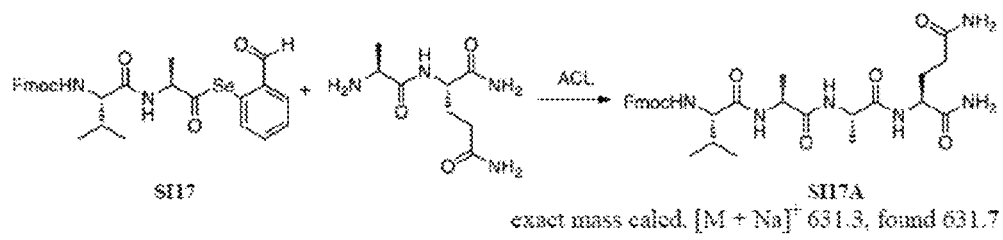
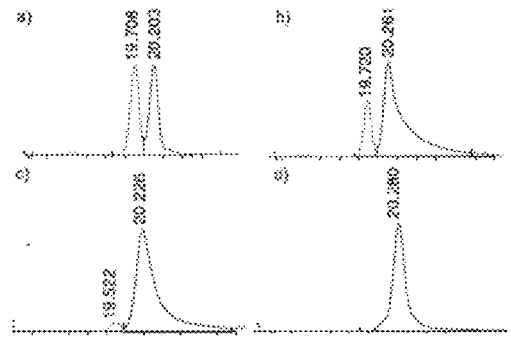
Figures 57A–D
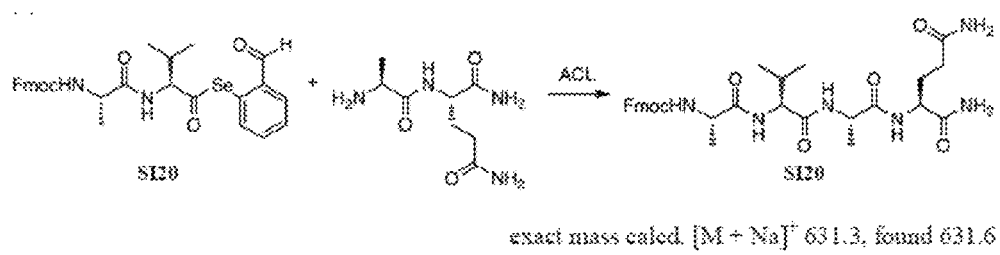
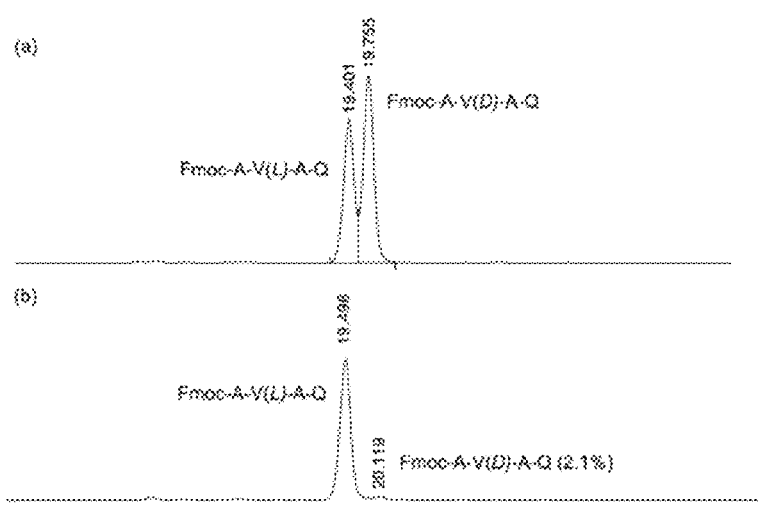
Figures 58A–B (a)

(b)

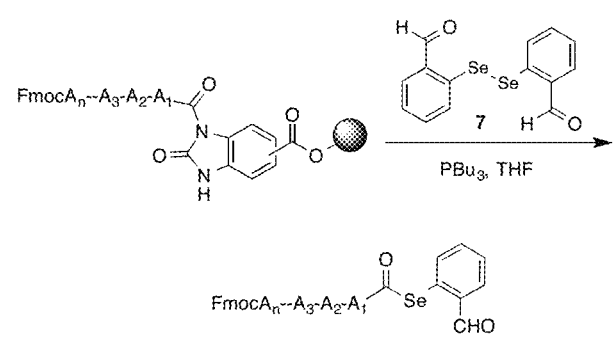
Figure 60
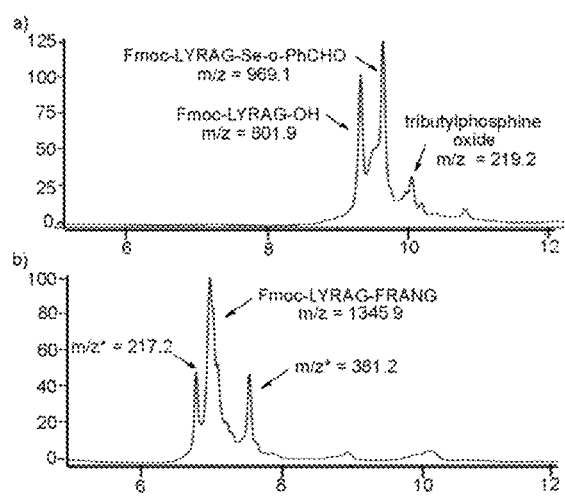
Figures 61A–B

ALDEHYDE CAPTURE LIGATION TECHNOLOGY FOR SYNTHESIS OF AMIDE BONDS

CROSS-REFERENCE TO RELATED APPLICATIONS

This application claims the benefit of U.S. Provisional Patent Application Ser. No. 61/920,844, filed Dec. 26, 2013, which is hereby incorporated by reference in its entirety.

This invention was made with government support under grant number R01 GM073943 awarded by the National Institutes for Health and grant number CHE-1151554 awarded by the National Science Foundation. The government has certain rights in this invention.

FIELD OF THE INVENTION

This invention is directed to amide ligation agents.

BACKGROUND OF THE INVENTION

Methods for chemoselective formation of amide bonds between unprotected peptide fragments have provided valuable access to recombinant proteins and have become reliable methods for the synthesis of bioconjugates (Muir, *Annu. Rev. Biochem.* 72:249-289 (2003); Davis, *Science* 303:480-482 (2004); Nilsson et al., *Annu. Rev. Biophys. Biomol. Struct.* 34:91-118 (2005); Pattabiraman et al., *Nature* 480:471-479 (2011); Stephanopoulos et al., *Nat Chem Biol* 7:876-84 (2011); Hackenberger et al., *Angew. Chem. Int. Ed.,* 47:10030-74 (2008); Ogunkoya et al., *Angew. Chem. Int. Ed.* 51:9693-97 (2012); Tam et al., *Peptide Science* 60:194-205 (2001); Mao et al., *J. Am. Chem. Soc.* 126:2670-71 (2004)). These advances have made total synthesis of therapeutic peptides and proteins, hormones, and modified antibodies a credible objective (Wang et al., *Science* 342:1357-60 (2013); Payne et al., *Chem. Commun.* 46:21-43 (2010); Scheck et al., *ACS Chem. Biol.* 2:247-51 (2007); Gamblin et al., *Chem. Rev.* 109:131-63 (2008); Chalker et al., *Acc. Chem. Res.* 44:730-41 (2011); Kiessling et al., Annu. Rev. Biochem. 79:619-53 (2010); Dawson et al., *Annu. Rev. Biochem.* 69:923-60 (2000); Raibaut et al., *Chem. Soc. Rev.* 41:7001-15 (2012)). The key concept underlying peptide ligation approaches is that the amide bond formation step can be accelerated by capturing the carboxyl and the amine functionalities and enforcing intramolecular bond formation (FIG. 1). Various ligation technologies (Bode et al., *Angew. Chem. Int. Ed.* 45:1248-1252 (2006); Wang & Danishefsky, *Am. Chem. Soc.* 134:13244-47 (2012); Shen et al., *Nature* 465:1027-32 (2010); Noda et al., *J. Am. Chem. Soc.* DOI 10.1021/ja5018442 (2014); Pattabiraman et al., *Agnew. Chem. Int. Ed.* 51:5114-18 (2012); Aimoto, *Peptide Sci.* 51:247-265 (1999); Payne et al., *Angew. Chem. Int. Ed.* 47:4411-15 (2008)), including native chemical ligation (NCL) (Dawson et al., *Science* 266:776-779 (1994)) and the Staudinger Ligation (Saxon et al., *Org. Lett.* 2:2141-2143 (2000); Nilsson et al., *Org. Lett.* 2:1939-1941 (2000)), as well as auxiliary based methods (Kemp, *Biopolymers* 20:1793-1804 (1981); Hackenberger et al., *Angew. Chem. Int. Ed.* 47:10030-10074 (2008); Coltart, *Tetrahedron* 56:3449-3491 (2000)), utilize this concept and are widely used.

Some shortcomings of these and other methods is that they are not completely general. For example, NCL and most auxiliary-based approaches require the presence of an N-terminal cysteine or modified residues that contain a thiol group (Hackenberger et al., *Angew. Chem. Int. Ed.* 47:10030-10074 (2008)). Moreover, ligation rate and yield can be inefficient with bulky amino acid residues at the ligation junction (Hackeng et al., *Proc. Natl. Acad. Sci. USA* 96:10068-10073 (1999)).

The present invention is directed to overcoming these and other deficiencies in the art.

SUMMARY OF THE INVENTION

A first aspect of the present invention relates to a ligation agent of Formula I:

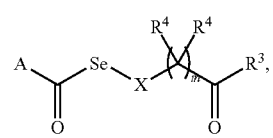

wherein
A is selected from the group consisting of

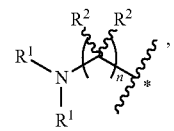

fluorescent dyes, and cytotoxic small molecule drugs;
X is selected from the group consisting of

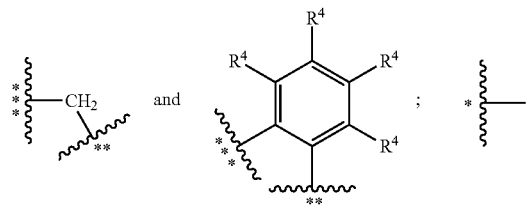

represents a point of attachment to —C(O)—Se—X—$(CR^4{}_2)_mC(O)R^3$;

represents a point of attachment to —$(CR^4{}_2)_mC(O)R^3$;

represents a point of attachment to —Se—C(O)-A;
n is 1-3;
m is 0-3;
each $R^1$ is independently selected from the group consisting of H, $C_1$-$C_6$ alkyl, $C_2$-$C_6$ alkenyl, $C_2$-$C_6$ alkynyl, aryl, amino acids, peptides, and protecting groups for the protection of an amine;

each $R^2$ is independently selected from the group consisting of H, —C(O)$R^7$, —C(O)O$R^8$, —C(O)N$R^5R^6$, NO$_2$, —N$R^5R^6$, halogen, OH, $C_1$-$C_6$ alkyl, $C_2$-$C_6$ alkenyl, $C_2$-$C_6$ alkynyl, aryl, $C_1$-$C_6$ alkoxy, and amino acid side chains;

$R^3$ is selected from the group consisting of H, $C_1$-$C_6$ alkyl, and aryl;

each $R^4$ is independently selected from the group consisting of H, —C(O)$R^7$, —C(O)O$R^8$, NO$_2$, —N$R^5R^6$, halogen, OH, $C_1$-$C_6$ alkyl, aryl, and $C_1$-$C_6$ alkoxy; and $R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl;

with the proviso that m is 0-3 when A is $(R^1)_2N(C(R_2)_2)_n$— and X is

[chemical structure: *—CH$_2$—**]

and with the proviso that m is 0-2 when A is $(R^1)_2N(C(R^2)_2)_n$— and X is

[chemical structure: benzene ring with $R^4$ substituents, connected to * and **]

A second aspect of the present invention relates to a method of forming an amide ligation product. This method involves reacting a compound containing an amino group with a ligation agent, the ligation agent including a seleno ester group, under conditions effective to produce an amide ligation product.

A third aspect of the present invention relates to a compound of Formula II:

[chemical structure II: $R^3$C(O)—X—C($R^4$)$_2$—Se—Se—C($R^4$)$_2$—X—C(O)$R^3$ with $(R^4)_2$ groups and subscript m]

wherein
X is selected from the group consisting of

[chemical structure: *—CH$_2$—**] and [chemical structure: benzene ring with $R^4$ substituents];

each

[chemical structure: *—]

represents a point of attachment to —Se—Se—X—(CR$^4_2$)$_m$C(O)$R^3$;

each

[chemical structure: **—]

represents a point of attachment to —(CR$^4_2$)$_m$C(O)$R^3$;

each m is independently 0-3;

each $R^3$ is independently selected from the group consisting of H, $C_1$-$C_6$ alkyl, and aryl;

each $R^4$ is independently selected from the group consisting of H, —C(O)$R^7$, C(O)O$R^8$, NO$_2$, —N$R^5R^6$, halogen, OH, $C_1$-$C_6$ alkyl, aryl, and $C_1$-$C_6$ alkoxy; and $R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl;

with the proviso that m is 0-3 when X is

[chemical structure: *—CH$_2$—**]

and with the proviso that m is 0-2 when X is

[chemical structure: benzene ring with $R^4$ substituents]

A fourth aspect of the present invention relates to a method of making a ligation agent of Formula I:

[chemical structure I: A—C(O)—Se—X—(C$R^4_2$)$_m$—C(O)—$R^3$]

wherein
A is selected from the group consisting of

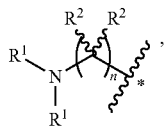

fluorescent dyes, and cytotoxic small molecule drugs;
X is selected from the group consisting of

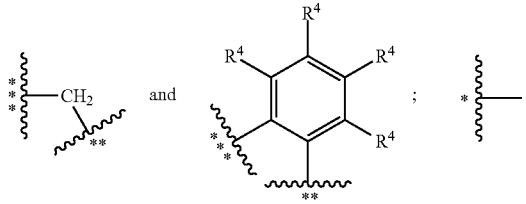

represents a point of attachment to —C(O)—Se—X—$(CR^4{}_2)_m C(O)R^3$;

represents a point of attachment to —$(CR^4{}_2)_m C(O)R^3$;

represents a point of attachment to —Se—C(O)-A;
n is 1-3;
m is 0-3;
each $R^1$ is independently selected from the group consisting of H, $C_1$-$C_6$ alkyl, $C_2$-$C_6$ alkenyl, $C_2$-$C_6$ alkynyl, aryl, amino acids, peptides, and protecting groups for the protection of an amine;
each $R^2$ is independently selected from the group consisting of H, —C(O)$R^7$, —C(O)O$R^8$, —C(O)N$R^5R^6$, $NO_2$, —$NR^5R^6$, halogen, OH, $C_1$-$C_6$ alkyl, $C_2$-$C_6$ alkenyl, $C_2$-$C_6$ alkynyl, aryl, $C_1$-$C_6$ alkoxy, and amino acid side chains;
$R^3$ is selected from the group consisting of H, $C_1$-$C_6$ alkyl, and aryl;
each $R^4$ is independently selected from the group consisting of H, —C(O)$R^7$, —C(O)O$R^8$, $NO_2$, —$NR^5R^6$, halogen, OH, $C_1$-$C_6$ alkyl, aryl, and $C_1$-$C_6$ alkoxy; and
$R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl;
with the proviso that m is 0-3 when A is $(R^1)_2 N(C(R^2)_2)_n$— and X is

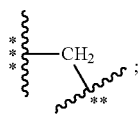

and
with the proviso that m is 0-2 when A is $(R^1)_2 N(C(R^2)_2)_n$— and X is

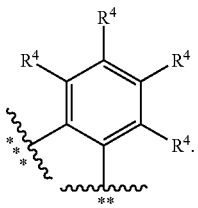

This method includes:
(i) providing a compound of Formula II:

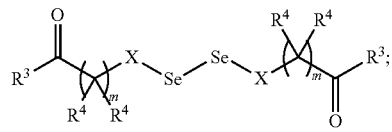

II wherein
X is selected from the group consisting of

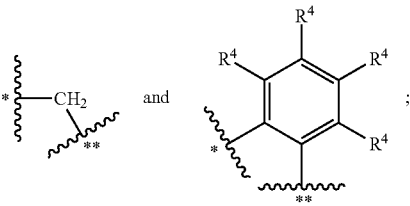

each X is selected from the group consisting of

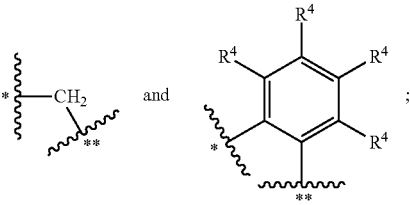

each

represents a point of attachment to —Se—Se—X—$(CR^4{}_2)_m C(O)R^3$;
each

represents a point of attachment to —(CR$^4_2$)$_m$C(O)R$^3$;
each m is independently 0-3;
each R$^3$ is independently selected from the group consisting of H, C$_1$-C$_6$ alkyl, and aryl;
each R$^4$ is independently selected from the group consisting of H, —C(O)R$^7$, —C(O)OR$^8$, NO$_2$, —NR$^5$R$^6$, halogen, OH, C$_1$-C$_6$ alkyl, aryl, and C$_1$-C$_6$ alkoxy; and
R$^5$, R$^6$, R$^7$, and R$^8$ are each independently selected from the group consisting of H, C$_1$-C$_6$ alkyl, C$_2$-C$_6$ alkenyl, C$_2$-C$_6$ alkynyl, and aryl;
with the proviso that m is 0-3 when X is

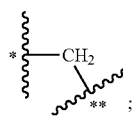

and
with the proviso that m is 0-2 when X is

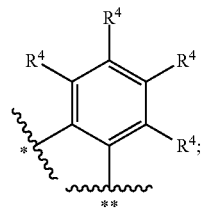

(ii) (a) providing a compound of Formula III:

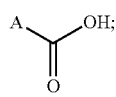

wherein
A is selected from the group consisting of

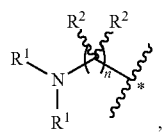

fluorescent dyes, and cytotoxic small molecule drugs;

represents a point of attachment to —C(O)—OH;
n is 1-3;
each R$^1$ is independently selected from the group consisting of H, C$_1$-C$_6$ alkyl, C$_2$-C$_6$ alkenyl, C$_2$-C$_6$ alkynyl, aryl, amino acids, peptides, and protecting groups for the protection of an amine; and each R$^2$ is independently selected from the group consisting of H, —C(O)R$^7$, —C(O)OR$^8$, —C(O)NR$^5$R$^6$, NO$_2$, —NR$^5$R$^6$, halogen, OH, C$_1$-C$_6$ alkyl, C$_2$-C$_6$ alkenyl, C$_2$-C$_6$ alkynyl, aryl, C$_1$-C$_6$ alkoxy, and amino acid side chains;
each R$^4$ is independently selected from the group consisting of H, —C(O)R$^7$, —C(O)OR$^8$, NO$_2$, —NR$^5$R$^6$, halogen, OH, C$_1$-C$_6$ alkyl, aryl, and C$_1$-C$_6$ alkoxy; and
R$^5$, R$^6$, R$^7$, and R$^8$ are each independently selected from the group consisting of H, C$_1$-C$_6$ alkyl, C$_2$-C$_6$ alkenyl, C$_2$-C$_6$ alkynyl, and aryl; or
(ii) (b) providing a compound of Formula III':

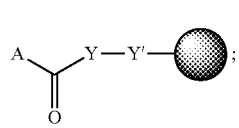

wherein
A is selected from the group consisting of

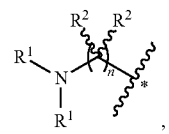

fluorescent dyes, and cytotoxic small molecule drugs;
Y is selected from the group consisting of O, S, Se, a good leaving group, and Dawson's auxiliary;
Y' is optionally present and, if present, is a C$_1$-C$_6$ alkyl, an ester, or an amide;

represents a point of attachment to ;

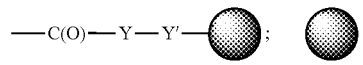

is a solid support;
n is 1-3;
each R$^1$ is independently selected from the group consisting of H, C$_1$-C$_6$ alkyl, C$_2$-C$_6$ alkenyl, C$_2$-C$_6$ alkynyl, aryl, amino acids, peptides, and protecting groups for the protection of an amine; and
each R$^2$ is independently selected from the group consisting of H, —C(O)R$^7$, —C(O)OR$^8$, —C(O)NR$^5$R$^6$, NO$_2$, —NR$^5$R$^6$, halogen, OH, C$_1$-C$_6$ alkyl, C$_2$-C$_6$ alkenyl, C$_2$-C$_6$ alkynyl, aryl, C$_1$-C$_6$ alkoxy, and amino acid side chains;
each R$^4$ is independently selected from the group consisting of H, —C(O)R$^7$, —C(O)OR$^8$, NO$_2$, —NR$^5$R$^6$, halogen, OH, C$_1$-C$_6$ alkyl, aryl, and C$_1$-C$_6$ alkoxy; and
R$^5$, R$^6$, R$^7$, and R$^8$ are each independently selected from the group consisting of H, C$_1$-C$_6$ alkyl, C$_2$-C$_6$ alkenyl, C$_2$-C$_6$ alkynyl, and aryl; and (iii) reacting the compound of Formula II with the compound of Formula III or the compound of Formula III' under conditions effective to make a ligation agent of Formula I.

Introduced herein is an approach for amide ligation, i.e., aldehyde capture ligation ("ACL"), that is, in principle, applicable to any N-terminal amino acid residue for peptide synthesis while allowing rapid ligation of challenging residues. The method is general, beyond peptide synthesis, for the formation of an amide bond between any carboxylic acid and amine. One feature of ACL is that it employs the rapid association between an aldehyde group and an amine to enforce an intramolecular reaction leading to the desired native amide bond formation. ACL also allows for the synthesis of large molecules.

BRIEF DESCRIPTION OF THE DRAWINGS

FIGS. 12A-B show $^1$H-NMR and $^{13}$C-NMR spectra of peptide SI9 in CDCl$_3$.

FIGS. 13A-B show $^1$H-NMR and $^{13}$C-NMR spectra of peptide SI10 in CDCl$_3$.

FIG. 37 shows HPLC traces related to the synthesis of peptide SI130.

FIG. 38 shows HPLC traces related to the synthesis of peptide SI131.

FIG. 46 shows HPLC spectra of the starting material and the crude reaction mixture of peptide SI139 after 8 hours of incubation; the product peak is labeled.

FIG. 52A shows that when ubiquitin ($^{15}$N labeled) was treated with selenoester 10 in 10% DMF in 1× phosphate buffered saline (PBS), pH 7.0, mono-labeling of ubiquitin was observed as the exclusive product. FIG. 52B shows that ubiquitin contains seven lysine residues and provides a stringent test for evaluation of the specificity of reaction at the N-terminus. FIG. 52C shows that the reaction progress was evaluated by MALDI and LCMS; the MALDI spectrum after 96 hours is shown. MS/MS analysis confirms that labeling is localized to the N-terminus (see FIGS. 52D-F). FIG. 52D shows LCMS spectra of the reaction mixture of ubiquitin (Ub) and mono-labeled ubiquitin (Ub′′′). FIG. 52E shows MS/MS spectra of ubiquitin (Ub). FIG. 52F shows MS/MS spectra of mono-labeled ubiquitin (Ub′′′). Important fragments in the figures are labeled.

FIGS. 53A-D relate to ACL with amino acids and illustrate the possible side reactions of thio and seleno-ortho-benzyladehyde esters (Krinsky et al., *Organometallics* 26:897-909 (2007); Still et al., *Can. J. Chem.* 77:113-121 (1999), each of which is hereby incorporated by reference in its entirety). FIG. 53A shows a comparison of the reaction rate of ACL with different auxiliaries; reaction conditions: Fmoc-Gly-oxo, -thio or -seleno ester (10 µmol), HClNH$_2$-Phe-COOMe (20 µmol) and Et$_3$N (20 µmol) in 1 mL DMF. FIG. 53B shows the reaction of thioester 1d with benzyl amine shows the formation of a bicyclic byproduct. FIG. 53C shows that formation of this side product can be suppressed by employing a phenyl ketone analog. FIG. 53D shows that reaction of selenoester 1g does not lead to the byproduct.

FIGS. 54A-C illustrate the kinetics of ACL. FIG. 54A shows that ACL follows second order rate constant. Doubling of substrate concentration leads to doubling of the initial rate of the reaction. Studies were performed with model reactants consisting of alanine and tryptophan analogs. FIG. 54B shows a plot of 1/[3], where [3] refers to the selenoester concentration, versus time, showing a linear fit to the second order rate equation. The average of three values are plotted, with the calculated rate constant, k=1.66 M$^{-1}$s$^{-1}$. FIG. 54C shows a plot of 1/[4], where [4] refers to the selenoester concentration, versus time, showing a linear fit to the second order rate equation. The average of three values are plotted. The rate constant of the alanine selenoester without the ortho-aldehyde functionality is 100-fold slower, k=0.015 M$^{-1}$s$^{-1}$.

FIG. 55A shows tabulated data with % hydrolysis observed for each selenoester at the indicated pH and time interval. FIG. 55B shows time course for each reaction. FIGS. 55C-G show HPLC spectra for each reaction after the indicated time period. Reaction conditions: Fmoc-Ala-seleno-ortho-benzaldehyde esters, 3 (2 µmol), HCL.NH$_2$-Trp-OMe (4 µmol), and Et$_3$N (4 µmol) in 1 mL DMF or (1:1) DMF:100 mM Na$_2$HPO$_4$ buffer (pHs~6.5-9.3). Plotted values are the average of two independent experiments.

FIGS. 57A-D relate to epimerization studies. FIG. 57A shows an analytical HPLC trace of a 1:1 mixture of diastereoisomers, Fmoc-V-A$^D$-AQ and Fmoc-V-A$^L$-AQ. FIG. 57B shows an analytical HPLC trace of a 1:4 mixture of diastereoisomers, Fmoc-V-A$^D$-AQ and Fmoc-V-A$^L$-AQ. FIG. 57C shows an analytical HPLC trace of a 1:49 mixture of diastereoisomers, Fmoc-V-A$^D$-AQ and Fmoc-V-A$^L$-AQ. FIG. 57D shows a crude HPLC trace of ACL reaction mixture Fmoc-Val-L-Ala-seleno-ortho-benzaldehyde ester (10 µmol), HCl.NH$_2$-Ala-Gln-NH$_2$ (20 µmol), and Et$_3$N (20 µmol) in 1 mL DMF. HPLC Conditions: 0.1% TFA (v/v) in water (solvent A): acetonitrile (solvent B); gradient 35-65% in 60 min, flow rate=0.5 mL/min.

FIGS. 58A-B relate to epimerization studies. FIG. 58A shows a representative analytical HPLC trace of a 1:1 mixture of diastereoisomers, Fmoc-A-VD-AQ and Fmoc-A-V$^L$-AQ. FIG. 58B shows the crude HPLC trace of the ACL reaction mixture Fmoc-Ala-Val$^L$-seleno-ortho-benzaldehyde ester (10 µmol), HCl.NH$_2$-Ala-Gln-NH$_2$ (20 µmol), and Et$_3$N (20 µmol) in 1 mL DMF. HPLC Conditions: 1% TFA (v/v) in water (solvent A):acetonitrile (solvent B); gradient 35-65% in 60 min, flow rate=0.5 mL/min.

FIG. 59A shows competing pathways for reactions of N-terminal serine and cysteine with seleno-o-benzaldehyde esters. FIG. 59B shows representative analytical HPLC traces of a reaction of Fmoc-Ala-selenobenzaldehyde ester and HClNH$_2$-Ser-OBn. FIG. 59C shows representative analytical HPLC traces of a reaction of Fmoc-Gly-selenobenzaldehyde ester and HClNH$_2$-Cys-OMe. Reaction conditions: Fmoc-AA-selenobenzaldehyde ester (10 µmol), HClNH$_2$-Ser-OBn or HClNH$_2$-Cys-OMe (20 µmol), and Et$_3$N (20 µmol) in 1 mL DMF or 1 mL (1:1) Py:AcOH (Syper et al., *Tetrahedron* 44:6119-30 (1988), which is hereby incorporated by reference in its entirety).

FIG. 60 illustrates the solid phase synthesis of peptide seleno-o-benzaldehyde esters.

FIGS. 61A-B relate to the HPLC analysis of peptide-selenoester condensation. FIG. 61A shows the crude analytical HPLC trace of FmocLYRAG-Se-o-PhCHO synthesized from the corresponding resin bound Nbz-peptide. FIG. 61B shows the crude HPLC trace of FmocLYRAGFRANG-CONH$_2$ obtained from the condensation of unpurified FmocLYRAG-Se-o-PHCHO from FIG. 61A and FRANG-CONH$_2$. HPLC Conditions: 0.1% TFA (v/v) in water (solvent A): 0.1% acetonitrile (solvent B); gradient 5-95% B in 30 min, flow rate=0.5 mL/min. m/z*=Masses of these peaks do not correspond to the starting selenoester or identifiable side products.

DETAILED DESCRIPTION OF THE INVENTION

Figure 1:
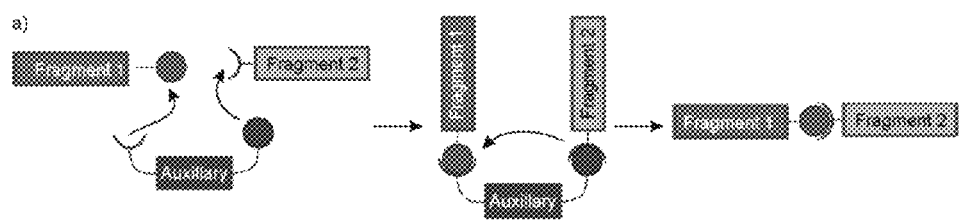
FIG. 1 is a schematic illustration showing that peptide ligation methods and auxiliaries function by capturing the carboxyl and the amine functionalities and enforcing intramolecular bond formation.

One aspect of the present invention relates to a ligation agent of Formula I:

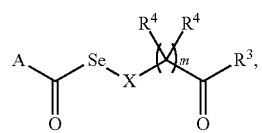

wherein

A is selected from the group consisting of

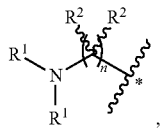

fluorescent dyes, and cytotoxic small molecule drugs;

X is selected from the group consisting of

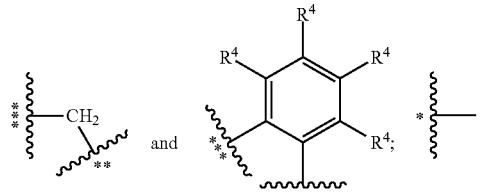

represents a point of attachment to —C(O)—Se—X—$(CR^4_2)_mC(O)R^3$;

represents a point of attachment to —$(CR^4_2)_mC(O)R^3$;

represents a point of attachment to —Se—C(O)-A;

n is 1-3;

m is 0-3;

each $R^1$ is independently selected from the group consisting of H, $C_1$-$C_6$ alkyl, $C_2$-$C_6$ alkenyl, $C_2$-$C_6$ alkynyl, aryl, amino acids, peptides, and protecting groups for the protection of an amine;

each $R^2$ is independently selected from the group consisting of H, —C(O)$R^7$, —C(O)O$R^8$, —C(O)N$R^5R^6$, $NO_2$, —N$R^5R^6$, halogen, OH, $C_1$-$C_6$ alkyl, $C_2$-$C_6$ alkenyl, $C_2$-$C_6$ alkynyl, aryl, $C_1$-$C_6$ alkoxy, and amino acid side chains;

$R^3$ is selected from the group consisting of H, $C_1$-$C_6$ alkyl, and aryl;

each $R^4$ is independently selected from the group consisting of H, —C(O)$R^7$, —C(O)O$R^8$, $NO_2$, —N$R^5R^6$, halogen, OH, $C_1$-$C_6$ alkyl, aryl, and $C_1$-$C_6$ alkoxy; and $R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl;

with the proviso that m is 0-3 when A is $(R^1)_2N(C(R^2)_2)_n$— and X is

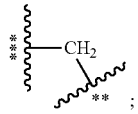

with the proviso that m is 0-2 when A is $(R^1)_2N(C(R^2)_2)_n$— and X is

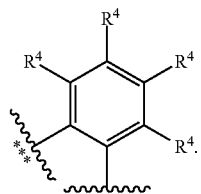

As used above, and throughout the description of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

As used herein, the term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Exemplary alkynyl groups include ethynyl, propynyl, n-butynyl, 2-butynyl, 3-methylbutynyl, and n-pentynyl.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

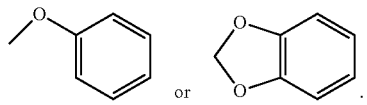

The term "halogen" means fluorine, chlorine, bromine, or iodine.

An amino acid according to this and all aspects of the present invention can be any natural or non-natural amino acid.

A "peptide" as used herein is any oligomer of two or more natural or non-natural amino acids, including alpha amino acids, beta amino acids, gamma amino acids, L-amino acids, D-amino acids, and combinations thereof. In preferred embodiments, the peptide is ~5 to ~30 (e.g., ~5 to ~10, ~5 to ~17, ~10 to ~17, ~10 to ~30, or ~18 to ~30) amino acids in length. Typically, the peptide is 5-17 amino acids in length.

Amino acid side chains according to this and all aspects of the present invention can be any amino acid side chain from natural or nonnatural amino acids, including from alpha amino acids, beta amino acids, gamma amino acids, L-amino acids, and D-amino acids.

Protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G.M. WUTS, PROTECTIVE GROUPS IN ORGANIC SYNTHESIS 494-615 (1999), which is hereby incorporated by reference in its entirety. Suitable protecting groups according to this and all aspects of the present invention include, e.g., tert-butyloxycarbonyl ("Boc"), 9-fluorenylmethyloxycarbonyl ("Fmoc"), carbobenzyloxy ("Cbz"), and trityl. Protecting groups that are suitable for the protection of an alcohol are also well known in the art. Suitable alcohol protecting groups include, without limitation, silyl ethers, esters, and alkyl/aryl ethers. Protecting groups that are suitable for the protection of a thiol group are also well known in the art. Suitable thiol protecting groups include, without limitation, aryl/alkyl thio ethers and disulfides. As will be apparent to those of ordinary skill in the art, amino acid side chains of Asn, Asp, Gln, Glu, Cys, Ser, His, Lys, Arg, Trp, or Thr will typically need to be protected while carrying out the methods described herein. Protecting groups that are suitable for protecting these amino acid side chains are also well known in the art. Methods of protecting and deprotecting functional groups vary depending on the chosen protecting group; however, these methods are well known in the art and described in THEODORA W. GREENE & PETER G.M. WUTS, PROTECTIVE GROUPS IN ORGANIC SYNTHESIS 372-450 and 494-615 (1999), which is hereby incorporated by reference in its entirety.

In some preferred embodiments X in Formula I is

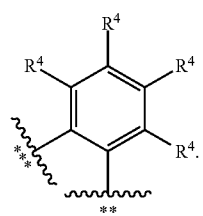

Suitable ligation agents according to this embodiment include, e.g.,

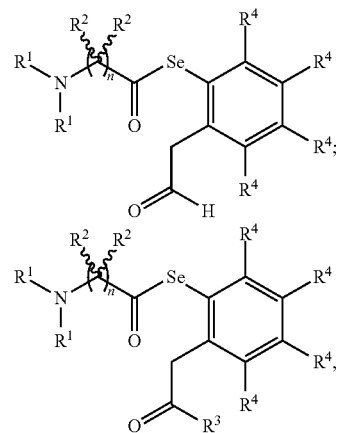

wherein $R^3$ is an aryl or an alkyl;

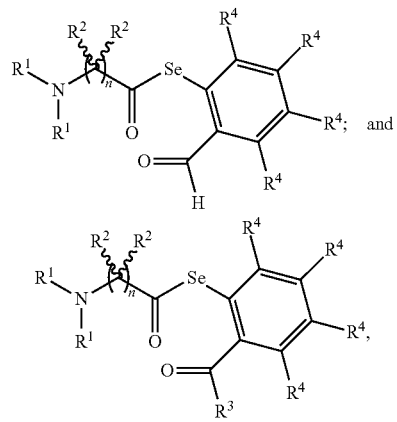

wherein $R^3$ is an aryl or an alkyl.

In some preferred embodiments X in Formula I is

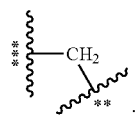

Suitable ligation agents according to this embodiment include, e.g.,

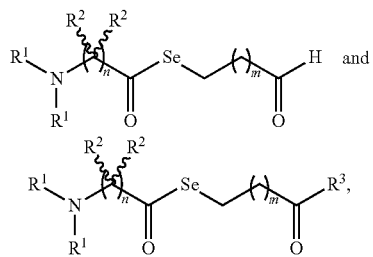

wherein $R^3$ is an aryl or an alkyl.

A second aspect of the present invention relates to a method of forming an amide ligation product. This method involves reacting a compound containing an amino group with a ligation agent that includes a seleno ester group, under conditions effective to produce an amide ligation product.

Suitable amide ligation products that can be formed using the method of this aspect of the present invention include those having the formula A-C(O)—N(R$^9$)—B, wherein A and B are each independently selected from the group consisting of H, (R$^1$)$_2$N(C(R$^2$)$_2$)$_n$—, —NR$^5$R$^6$, C$_1$-C$_6$ alkyl, C$_2$-C$_6$ alkenyl, C$_2$-C$_6$ alkynyl, —OH, C$_1$-C$_6$ alkoxy, aryl, amino acids, peptides, proteins, carbohydrates, nucleic acids, cytotoxic small molecule drugs, dyes, and polymers;

n is 1-3;

each R$^1$ is independently selected from the group consisting of H, C$_1$-C$_6$ alkyl, C$_2$-C$_6$ alkenyl, C$_2$-C$_6$ alkynyl, aryl, amino acids, peptides, and protecting groups for the protection of an amine;

each R$^2$ is independently selected from the group consisting of H, —C(O)R$^7$, —C(O)OR$^8$, —C(O)NR$^5$R$^6$, NO$_2$, —NR$^5$R$^6$, halogen, OH, C$_1$-C$_6$ alkyl, C$_2$-C$_6$ alkenyl, C$_2$-C$_6$ alkynyl, aryl, C$_1$-C$_6$ alkoxy, and amino acid side chains;

R$^5$, R$^6$, R$^7$, and R$^8$ are each independently selected from the group consisting of H, C$_1$-C$_6$ alkyl, C$_2$-C$_6$ alkenyl, C$_2$-C$_6$ alkynyl, and aryl; and R$^9$ is selected from the group consisting of H, OH, C$_1$-C$_6$ alkyl, C$_2$-C$_6$ alkenyl, C$_2$-C$_6$ alkynyl, aryl, C$_1$-C$_6$ alkoxy, amino acids, peptides, proteins, carbohydrates, and nucleic acids.

In this and all aspects of the present invention, suitable cytotoxic small molecule drugs include, without limitation, cisplatin, doxorubicin, paclitaxel, camptothecin, and doxorubicin.

In this and all aspects of the present invention, suitable dyes include, for example, fluorescein, rhodamine, diazobenzene, BODIPY, and ALEXA.

In this and all aspects of the present invention, suitable polymers include, without limitation, N-(2-hydroxypropyl) methacrylamide (HPMA), poly(ethylene glycol) (PEG), poly(lactide-co-glycolide) (PLGA), PAMAM dendrimers, poly(L-lysine), poly(L-glutamic acid), poly ((N-hydroxyalkyl)glutamine), dextrins, hydroxyethylstarch (HES), polysialic acid, the polyacetal Fleximer, poly-(acrylamide) (PAAm), poly(methacrylic acid) (PMAA), poly-(acrylic acid) (PAA), poly(2-(dimethylamino)ethyl meth-acrylate (PDMAEMA), and poly(N-isopropylacrylamide) (poly(NIPAAM). In at least one embodiment, the polymer is PEG.

Suitable compounds containing an amino group that can be used in this aspect of the present invention include, without limitation, amino acids, peptides, proteins, carbohydrates, nucleic acids, and compounds having the formula B—N(R$^9$)H, wherein B is selected from the group consisting of H, (R$^1$)$_2$N(C(R$^2$)$_2$)$_n$—, —NR$^5$R$^6$, C$_1$-C$_6$ alkyl, C$_2$-C$_6$ alkenyl, C$_2$-C$_6$ alkynyl, —OH, C$_1$-C$_6$ alkoxy, aryl, amino acids, peptides, proteins, carbohydrates, nucleic acids, cytotoxic small molecule drugs, dyes, and polymers;

R$^5$ and R$^6$ are each independently selected from the group consisting of H, C$_1$-C$_6$ alkyl, C$_2$-C$_6$ alkenyl, C$_2$-C$_6$ alkynyl, and aryl; and R$^9$ is selected from the group consisting of H, OH, C$_1$-C$_6$ alkyl, C$_2$-C$_6$ alkenyl, C$_2$-C$_6$ alkynyl, aryl, C$_1$-C$_6$ alkoxy, amino acids, peptides, proteins, carbohydrates, and nucleic acids.

Suitable ligation agents that can be used in this aspect of the present invention include those having the formula:

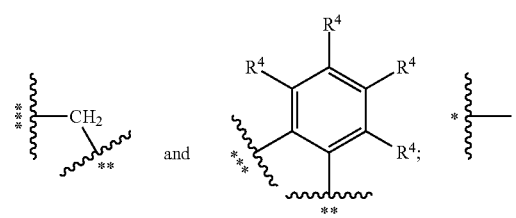

wherein

A is selected from the group consisting of H, (R$^1$)$_2$N(C(R$^2$)$_2$)$_n$—, —NR$^5$R$^6$, C$_1$-C$_6$ alkyl, C$_2$-C$_6$ alkenyl, C$_2$-C$_6$ alkynyl, —OH, C$_1$-C$_6$ alkoxy, aryl, amino acids, peptides, proteins, carbohydrates, nucleic acids, cytotoxic small molecule drugs, dyes, and polymers;

X is selected from the group consisting of

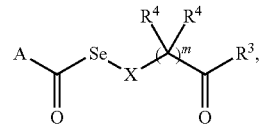

represents a point of attachment to —C(O)—Se—X—(CR$^4$$_2$)$_m$C(O)R$^3$;

represents a point of attachment to (CR$^4$$_2$)$_m$C(O)R$^3$;

represents a point of attachment to —Se—C(O)-A;

n is 1-3;

m is 0-3;

each R$^1$ is independently selected from the group consisting of H, C$_1$-C$_6$ alkyl, C$_2$-C$_6$ alkenyl, C$_2$-C$_6$ alkynyl, aryl, amino acids, peptides, and protecting groups for the protection of an amine;

each R$^2$ is independently selected from the group consisting of H, —C(O)R$^7$, C(O)OR$^8$, —C(O)NR$^5$R$^6$, NO$_2$, —NR$^5$R$^6$, halogen, OH, C$_1$-C$_6$ alkyl, C$_2$-C$_6$ alkenyl, C$_2$-C$_6$ alkynyl, aryl, C$_1$-C$_6$ alkoxy, and amino acid side chains;

R$^3$ is selected from the group consisting of H, C$_1$-C$_6$ alkyl, and aryl;

each R$^4$ is independently selected from the group consisting of H, —C(O)R$^7$, C(O)OR$^8$, NO$_2$, —NR$^5$R$^6$, halogen, OH, C$_1$-C$_6$ alkyl, aryl, and C$_1$-C$_6$ alkoxy; and $R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl;

with the proviso that m is 0-3 when A is $(R^1)_2N(C(R^2)_2)_n$— and X is

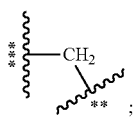

with the proviso that m is 0-2 when A is $(R^1)_2N(C(R^2)_2)_2$— and X is

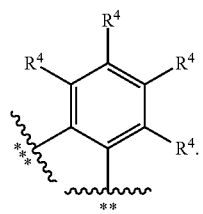

In some preferred embodiments, the ligation agent is a compound of Formula I.

A third aspect of the present invention relates to a compound of Formula II:

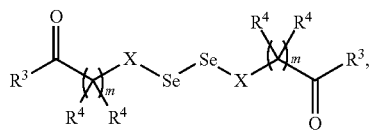

II wherein
each X is selected from the group consisting of

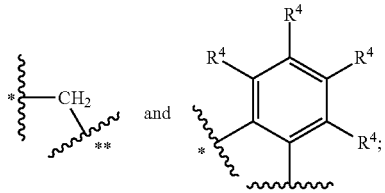

each

represents a point of attachment to —Se—Se—X—$(CR^4{}_2)_mC(O)R^3$;

each

represents a point of attachment to —$(CR^4{}_2)_mC(O)R^3$;
each m is independently 0-3;
each $R^3$ is independently selected from the group consisting of H, $C_1$-$C_6$ alkyl, and aryl;
each $R^4$ is independently selected from the group consisting of H, —$C(O)R^7$, —$C(O)OR^8$, $NO_2$, —$NR^5R^6$, halogen, OH, $C_1$-$C_6$ alkyl, aryl, and $C_1$-$C_6$ alkoxy; and
$R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl;
with the proviso that m is 0-3 when X is

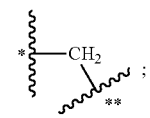

and
with the proviso that m is 0-2 when X is

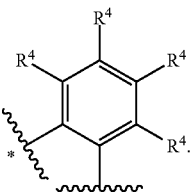

In some embodiments X in Formula II

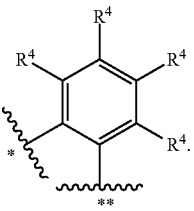

Suitable compounds according to this embodiment include, e.g.,

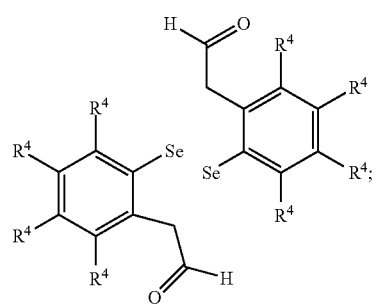

-continued

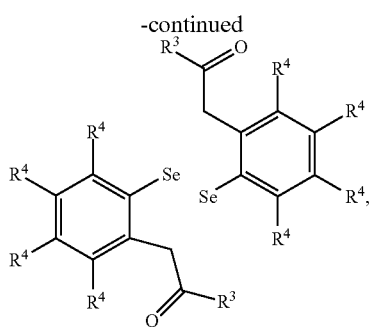

wherein $R^3$ is an aryl or an alkyl;

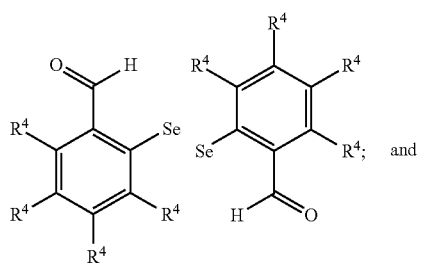

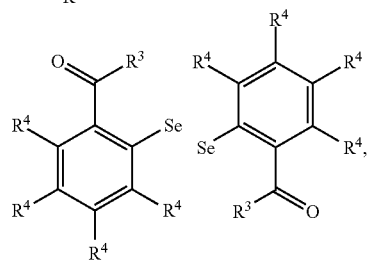

wherein $R^3$ is an aryl or an alkyl.

In some embodiments X in Formula II is

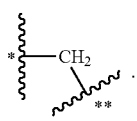 [SMILES: *C*]

Suitable compounds according to this embodiment include, e.g.,

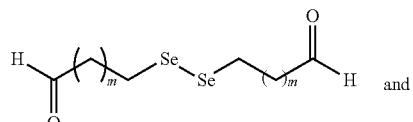

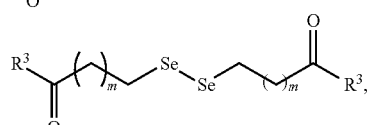

wherein $R^3$ is an aryl or an alkyl.

A fourth aspect of the present invention relates to a method of making a ligation agent of Formula I. This method involves:

(i) providing a compound of Formula II;
(ii) (a) providing a compound of Formula III:

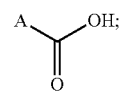

wherein
A is selected from the group consisting of

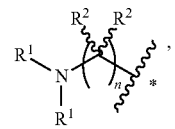

fluorescent dyes, and cytotoxic small molecule drugs;

represents a point of attachment to —C(O)—OH;
n is 1-3;
each $R^1$ is independently selected from the group consisting of H, $C_1$-$C_6$ alkyl, $C_2$-$C_6$ alkenyl, $C_2$-$C_6$ alkynyl, aryl, amino acids, peptides, and protecting groups for the protection of an amine; and
each $R^2$ is independently selected from the group consisting of H, —C(O)$R^7$, —C(O)O$R^8$, —C(O)N$R^5R^6$, $NO_2$, —N$R^5R^6$, halogen, OH, $C_1$-$C_6$ alkyl, $C_2$-$C_6$ alkenyl, $C_2$-$C_6$ alkynyl, aryl, $C_1$-$C_6$ alkoxy, and amino acid side chains;
each $R^4$ is independently selected from the group consisting of H, —C(O)$R^7$, —C(O)O$R^8$, $NO_2$, —N$R^5R^6$, halogen, OH, $C_1$-$C_6$ alkyl, aryl, and $C_1$-$C_6$ alkoxy; and
$R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl; or
(ii) (b) providing a compound of Formula III':

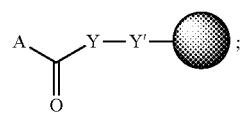

wherein
A is selected from the group consisting of

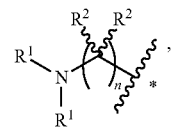

fluorescent dyes, and cytotoxic small molecule drugs;
Y is selected from the group consisting of O, S, Se, a good leaving group, and Dawson's auxiliary;

Y' is optionally present and, if present, is a $C_1$-$C_6$ alkyl, an ester (e.g., —C(O)—O—), or an amide (e.g., —N(R)—, where R is H, $C_1$-$C_6$ alkyl, or aryl);

represents a point of attachment to —C(O)—Y—Y'—

is a solid support;
n is 1-3;
each $R^1$ is independently selected from the group consisting of H, $C_1$-$C_6$ alkyl, $C_2$-$C_6$ alkenyl, $C_2$-$C_6$ alkynyl, aryl, amino acids, peptides, and protecting groups for the protection of an amine; and
each $R^2$ is independently selected from the group consisting of H, —C(O)$R^7$, —C(O)O$R^8$, —C(O)N$R^5R^6$, $NO_2$, —N$R^5R^6$, halogen, OH, $C_1$-$C_6$ alkyl, $C_2$-$C_6$ alkenyl, $C_2$-$C_6$ alkynyl, aryl, $C_1$-$C_6$ alkoxy, and amino acid side chains;
each $R^4$ is independently selected from the group consisting of H, —C(O)$R^7$, —C(O)O$R^8$, $NO_2$, —N$R^5R^6$, halogen, OH, $C_1$-$C_6$ alkyl, aryl, and $C_1$-$C_6$ alkoxy; and $R^5$, $R^6$, $R^7$, and $R^8$ are each independently selected from the group consisting of H, $C_1$-$C_6$ alkyl, $C_2$-$C_6$ alkenyl, $C_2$-$C_6$ alkynyl, and aryl; and
reacting the compound of Formula II with the compound of Formula III or the compound of Formula III'under conditions effective to make a ligation agent of Formula I.

As will be apparent to the skilled artisan, compounds of Formula II can be prepared by providing a substituted halogenated benzene aldehyde or substituted halogenated benzene ketone and reacting the substituted halogenated benzene aldehyde or substituted halogenated benzene ketone with a diselenide in the presence of a cation scavenger under conditions effective to produce a compound of Formula II.

Suitable solid supports for use in compounds of Formula III'include, for example, Tenta gel, Rink amide resin, Merrifield resin, trityl resin, PAM resin, and Kaiser resin.

In at least some embodiments, the compound of Formula III'contains a good leaving group. Leaving groups are displaced as stable species taking with it the bonding electrons, resulting in coupling of one compound to another. Good leaving groups that are suitable in the methods of the present invention are well known in the art and include, without limitation, those employed in standard solution or solid phase peptide synthesis.

Suitable substituted halogenated benzene aldehydes and substituted halogenated benzene ketones include those of Formula IV:

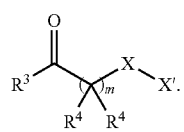

IV

Suitable diselenides include, without limitation, any alkaline metal diselenide, such as sodium diselenide, potassium diselenide, lithium diselenide, etc.

Suitable cation scavengers will be apparent to the skilled artisan. Exemplary cation scavengers include, without limitation, HMPA, DMPU, DMI, tetraalkyl ureas, and cyclic alkyl ureas.

Figure 2:
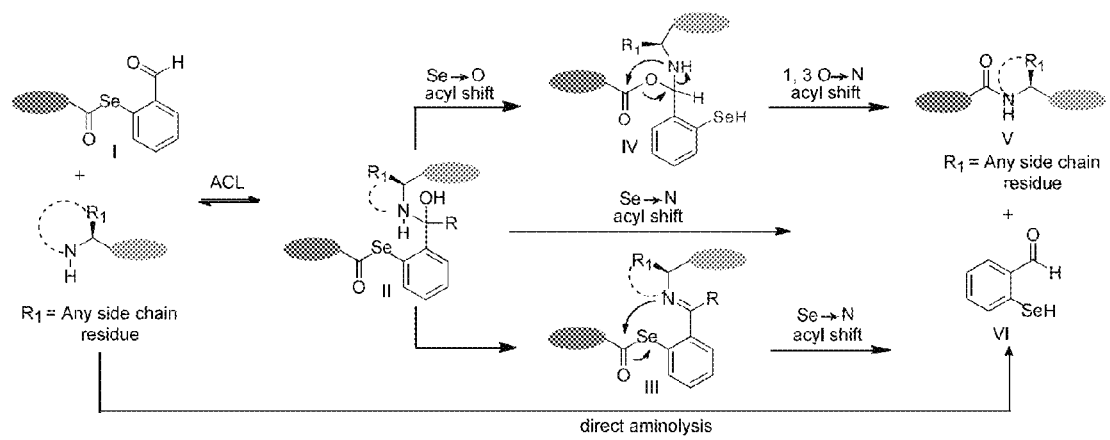
FIG. 2 is a schematic illustration showing the rationale for ACL. The efficient union of amines and aldehydes accelerates amide bond formation.

Described herein are compounds and methods useful for, e.g., aldehyde capture ligation ("ACL") (Kemp, Biopolymers 20:1793-804 (1981); Kemp et al., J. Org. Chem. 40:3003-3004 (1975), each of which is hereby incorporated by reference in its entirety), which utilizes an o-selenobenzaldehyde ester to enforce an intramolecular reaction between the carboxyl and the amine partners (Coltart, Tetrahedron 56:3449-91 (2000), which is hereby incorporated by reference in its entirety). As shown generally in FIG. 2, the first step involves conversion of the carboxylic acid into the selenobenzaldehyde ester featuring an aldehyde group at the ortho position (I) followed by capture of the amine functionality as the hemiaminal (II), imine (III), or hemiaminal ester (IV) intermediate (Kemp et al., J. Org. Chem. 40:3003-04 (1975), which is hereby incorporated by reference in its entirety). Subsequent rearrangement of the hemiaminal/imine/hemiaminal ester intermediate through a cyclic transition state yields the amide product (V) and the ortho-selenobenzaldehyde auxiliary (VI).

The 1,3-O→N acyl transfer was postulated based on suggestions of a similar rearrangement underlying the amide bond forming reaction between carboxylic acids and isonitriles (Li et al., J. Am. Chem. Soc. 130:13225-27 (2008), which is hereby incorporated by reference in its entirety). The ortho-aldehyde group in the auxiliary was designed to reversibly capture the amine and intramolecularly deliver it to an activated acid. The selenoesters may also directly condense with the amine (Durek & Alewood, Angew. Chem. Int'l Ed. 50:12042-45 (2011); McGrath & Raines, Acc. Chem. Res. 44:752-61 (2011); Mautner et al., J. Am. Chem. Soc. 85:3458-62 (1963); Chu & Mautner, J. Org. Chem. 31:308-12 (1966), each of which is hereby incorporated by reference in its entirety), although studies described herein suggest that this is not a major pathway. Prior efforts of Kemp et al. investigated auxiliaries derived from naphthyl oxo-esters and observed the formation of the competing imine byproduct which did not convert to the amide (Kemp et al., J. Org. Chem. 40:3003-04 (1975), which is hereby incorporated by reference in its entirety). The present invention uses a more reactive selenoester, and a less rigid scaffold, to favor the acyl transfer.

The present invention may be further illustrated by reference to the following examples.

EXAMPLES

Example 1

General Materials and Methods

All commercial materials (Aldrich, Fluka, Nova) were used without further purification. All solvents were reagent grade or HPLC grade (Fisher). Anhydrous THF, diethyl ether, $CH_2Cl_2$, and DMF were obtained from a dry solvent system (passed through column of alumina) and used without further drying. All reactions were performed under an atmosphere of pre-purified anhydrous argon or nitrogen. Yields refer to chromatographically pure compounds; % conversions were obtained by comparison of HPLC peak areas of products and starting esters. Thin Layer Chromatography or HPLC was used to monitor reaction progress. Flash column chromatography was performed using Silica Gel 60 Å (32-63 micron).

Example 2

Nuclear Magnetic Resonance

Proton NMR spectra were recorded on a 400 MHz spectrometer and carbon NMR spectra on a 101 MHz, spectrometer at ambient temperature. All NMR chemical shifts (δ) are referenced in ppm relative to residual solvent or internal tetramethylsilane. Solvent reference ppm in $^1$H-NMR and $^{13}$C-NMR for CDCl$_3$ are 7.26 ppm and 77.16 ppm, respectively. Carbon NMR spectra are proton decoupled. NMR spectral data are reported as chemical shift (multiplicity, coupling constants (J), integration). Multiplicity is reported as follows: singlet (s), broad singlet (bs), doublet (d), doublet of doubles (dd), doublet of triplet (td), triplet (t), and multiplet (m). Coupling constant (J) in Hertz (Hz).

Example 3

High-Performance Liquid Chromatography

Preparative HPLC chromatography (HPLC) was performed on Beckman Coulter equipped with System Gold 168 detector and 125P solvent module HPLC with a 10 mm C-18 reversed-phase column. All separations involved a mobile phase of 0.1% TFA (v/v) in water (solvent A) and 0.1% TFA (v/v) in acetonitrile (solvent B).

Analytical HPLC chromatography (HPLC) was performed on an Agilent 1200 series HPLC equipped with a 4.6 mm C-18 reversed-phase column. All separations involved mobile phase of 0.1% TFA (v/v) in water (solvent A) and 0.1% TFA (v/v) in acetonitrile (solvent B). The detection wavelength was set to 263 and 280 nm. Products were not calibrated by internal standard unless otherwise specified. % Conversion was calculated as the integrated area of the peptide product divided by the sum of the areas of the starting material and peptide product.

For determination of reaction rates, the reaction mixture was diluted 20-fold in acetonitrile and kept over dry-ice until HPLC analysis. HPLC (C-18 columns): 0.1% TFA (v/v) in water (solvent A):acetonitrile (solvent B); gradient 45-85% in 30 min, flow rate=0.5 mL/min, detection wavelength 280 nm.

Example 4

FT-IR Spectroscopy

Attenuated total reflectance-infrared (ATR-IR) spectra were obtained on the Thermo Nicolet AVATAR FTIR Spectrometer; υ (cm$^{-1}$) are partially reported.

Example 5

Thin Layer Chromatography

Analytical thin-layer chromatography (TLC) was performed using Silica Gel 60 Å F$_{254}$ pre-coated plates (0.25 mm thickness) and visualized using irradiation by a UV lamp and/or staining with I$_2$/silica.

Example 6

Mass Spectrometry

Mass spectrometry was performed using ultra high performance liquid chromatography-mass spectrometry using the Agilent 1100 Series LCMSD VL MS Spectrometer. High-resolution liquid chromatography-mass spectrometry (HRMS) was performed on an Agilent 6224 TOF LC/MS Mass Spectrometer. Protein MALDI data was collected on Bruker MALDI-TOF/TOF UltrafleXtreme MS Spectrometer. MS/MS analysis was performed on Agilent 1100 Series LCMSD VL MS Spectrometer.

Example 7

Fmoc Solid-Phase Peptide Synthesis

Automated peptide synthesis was performed on CEM Liberty microwave peptide synthesizer. Peptides were synthesized using Fmoc solid-phase chemistry (FMOC SOLID PHASE PEPTIDE SYNTHESIS: A PRACTICAL APPROACH (Weng C. Chan & Peter D. White eds., 2000), which is hereby incorporated by reference in its entirety) on Knorr amide resin or PAM resin (for Nbz peptides). The peptide was cleaved from the resin using a cocktail of 95:2.5:2.5, trifluoroacetic acid: triisopropyl silane:water for 2 hours. The resin was removed by filtration and the resulting solution was concentrated. The oily residue was triturated with diethyl ether to obtain a white suspension. The resulting solid was purified by HPLC. The identity and the purity of the peptides were confirmed by ESI-MS.

Example 8

Synthesis of Auxiliary 2,2'-Dithiodibenzaldehyde SI1/6

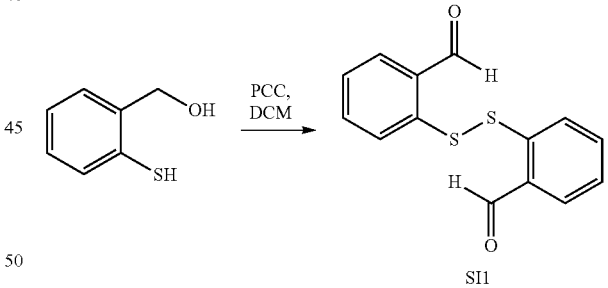

Figure 3A:
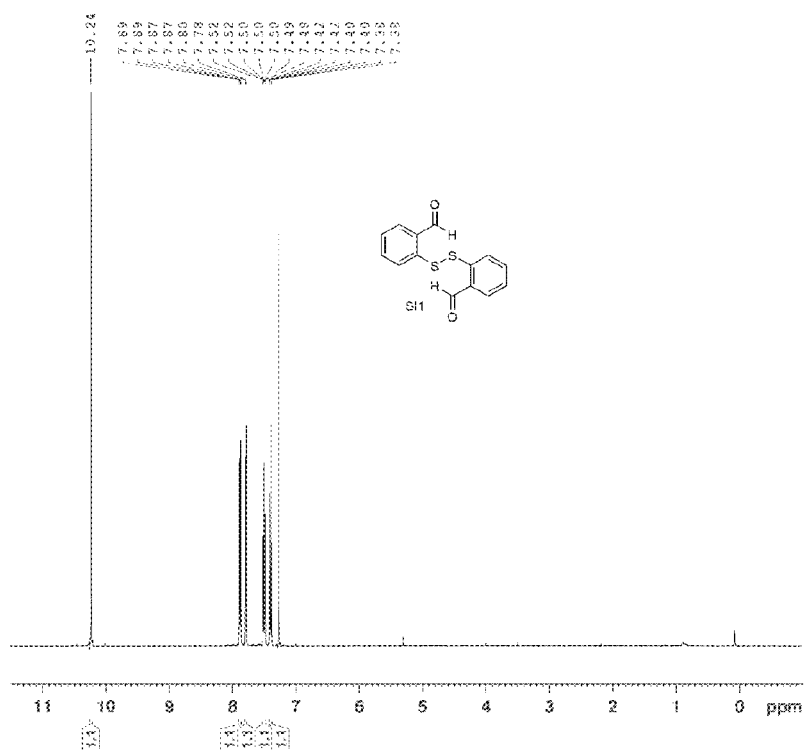
FIGS. 3A-B show $^1$H-NMR and $^{13}$C-NMR spectra of auxiliary SI1/6 in CDCl$_3$.
Figure 3B:
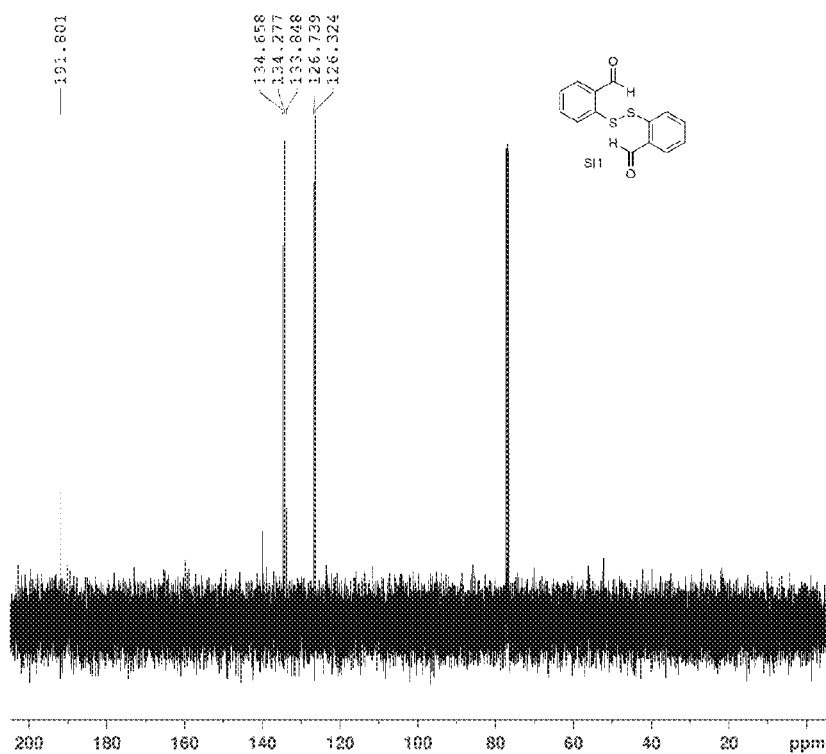

To a 100-mL oven dried two neck round-bottom flask containing PCC (2.33 g, 10.57 mmol) in 10 mL anhydrous dichloromethane (CH$_2$Cl$_2$) was added a solution of 2-mercaptobenzyl alcohol (0.61 g, 4.30 mmol) in anhydrous CH$_2$Cl$_2$ (6 mL) in a dropwise fashion. The mixture was stirred at room temperature for 5 hours and diluted with CH$_2$Cl$_2$ (2×10 mL). The diluted mixture was washed with H$_2$O (2×20 mL). The CH$_2$Cl$_2$ layer was passed through a short pad of Florisil, and concentrated under vacuum to afford SI1 (also referred to as 6 herein) as a white solid; yield: 0.30 g (40%) (Kasmai et al., *Synthesis* 1989:763-65 (1989), which is hereby incorporated by reference in its entirety). TLC (EtOAc:Hexane 1:3), R$_f$=0.3, irradiated by a UV lamp. $^1$H NMR (FIG. 3A): (400 MHz, CDCl$_3$) δ 10.24 (s, 2H), 7.88 (dd, J=7.4, 1.4 Hz, 2H), 7.79 (d, J=8 Hz, 2H), 7.50 (td, J=7.6, 1.6 Hz, 2H), 7.40 (td, J=7.2, 0.8 Hz, 2H). $^{13}$C NMR (FIG. 3B): (101 MHz, CDCl$_3$) δ 191.8, 134.6, 134.3, 133.8, 126.7, 126.3. FT-IR: 1622.69 cm$^{-1}$, 1729.99 cm$^{-1}$.

Example 9

Synthesis of Auxiliary 4,4'-Dithiodibenzaldehyde SI1A

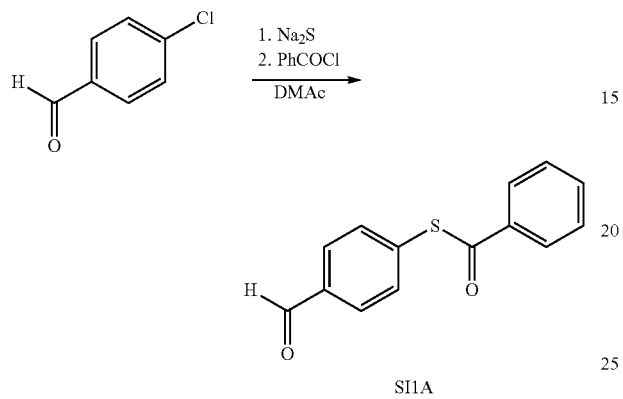

Figure 4A:
FIGS. 4A-B show $^1$H-NMR and $^{13}$C-NMR spectra of auxiliary SI1A in CDCl$_3$.
Figure 4B:
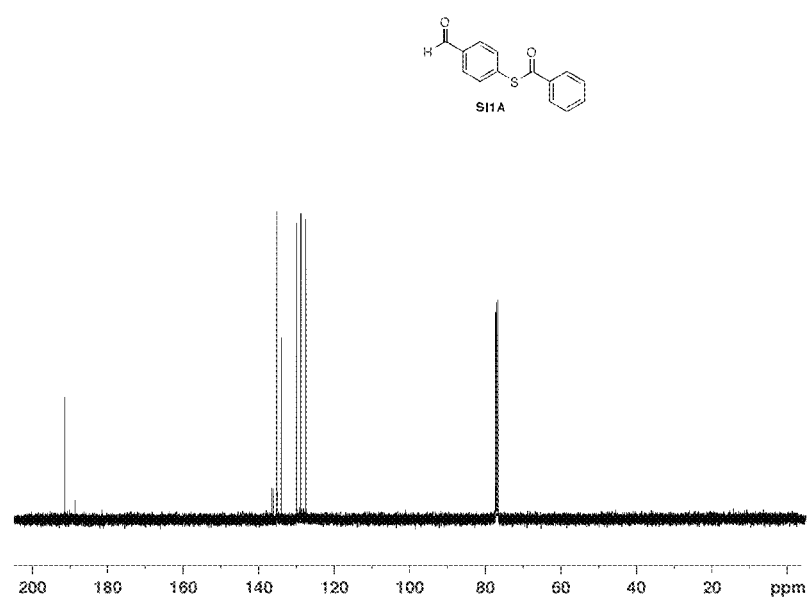

A solution of Na$_2$S.9H$_2$O (864.7 mg, 3.6 mmol) in N,N-dimethylacetamide (DMAc, 10 mL) was heated to 80° C. under N$_2$. To this solution, 4-chlorobenzaldhyde (420 mg, 3 mmol) was added and solution was stirred at 80° C. for 1 hour. The resulting mixture was cooled in ice bath, and benzoyl chloride (673 mg, 4.5 mmol) was added dropwise, and the reaction mixture was stirred at 0° C. for another 1 hour. It was then poured into water (30 mL) and extracted with diethyl ether (20 mL×3). The organic layers were combined, washed with saturated NaHCO$_3$ solution, brine and dried over MgSO$_4$. The solution was filtered, concentrated, and purified by flash chromatography (20% ethyl acetate in hexane) to afford SI1A as a white solid; yield 401 mg, 55%. TLC (EtOAc:Hexane 1:4), R$_f$=0.4, irradiated by a UV lamp. 1H NMR (FIG. 4A): (400 MHz, CDCl$_3$) δ 10.06 (s, 1H), 8.02 (d, J=8.0 Hz, 2H), 7.95 (d, J=8.0 Hz, 2H), 7.70 (d, J=8.0 Hz, 2H), 7.63 (t, J=8.0 Hz, 2H), 7.50 (t, J=8.0 Hz, 2H). $^{13}$C NMR (FIG. 4B): (101 MHz, CDCl$_3$) δ 191.4, 188.6, 136.6, 136.2, 135.2, 135.2, 134.0, 130.0 128.9, 127.6.

Example 10

Synthesis of Auxiliary 2-Mercapto Benzophenone SI2

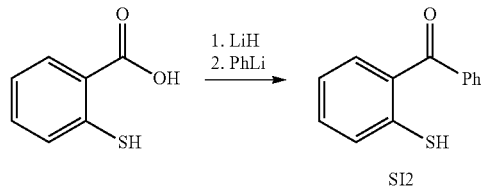

Figure 5A:
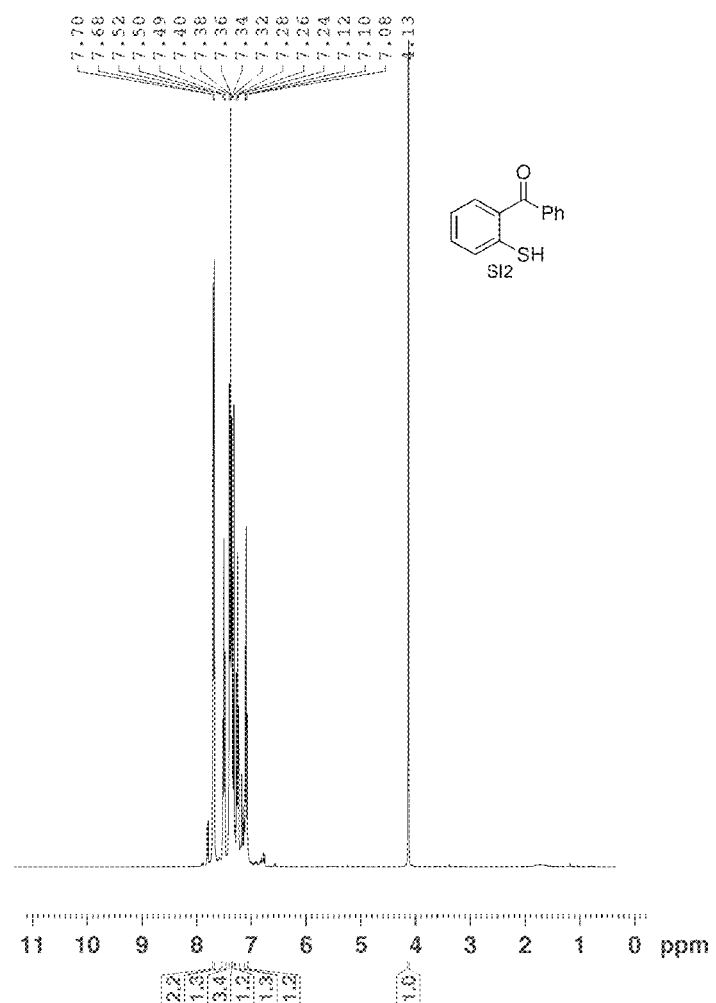
FIGS. 5A-B show $^1$H-NMR and $^{13}$C-NMR spectra of auxiliary SI2 in CDCl$_3$.
Figure 5B:
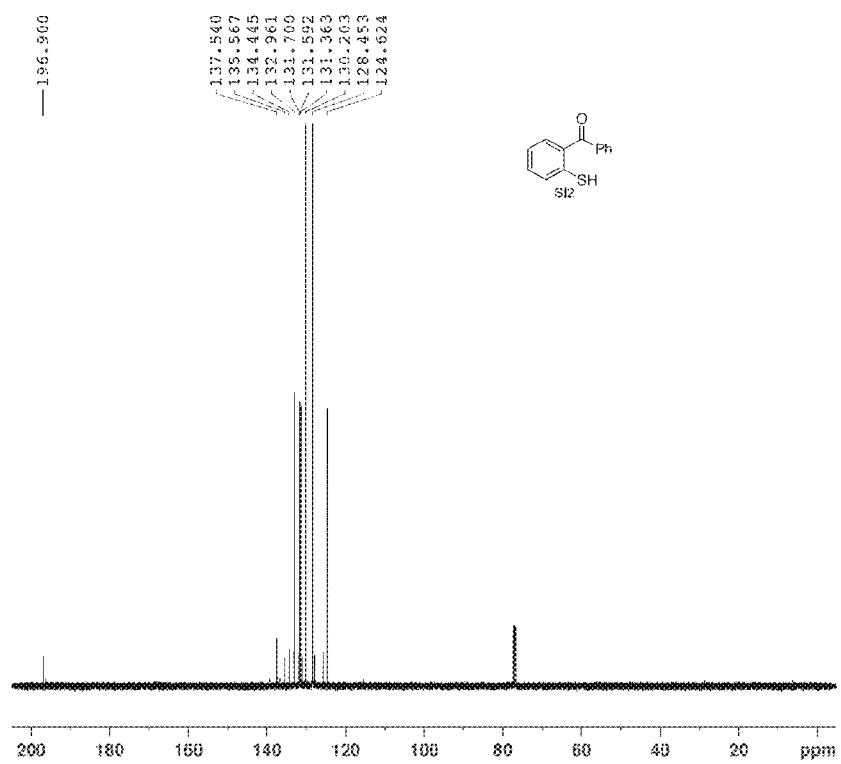

Thiosalicylic acid (6.0 g, 39 mmol), LiH (0.80 g, 100 mmol) and anhydrous THF (25 mL) were added to an oven dried round bottom flask. The resulting solution was refluxed under N$_2$ for 1 hour. The resulting mixture was cooled to room temperature, and 50 mL of 1.8 M PhLi in Et$_2$O was added slowly and the mixture stirred at 22° C. After 14 hours, 50 mL of H$_2$O was added to the reaction mixture and the organic layer was separated, concentrated, and purified by flash chromatography to obtain SI2 as a light yellow solid; yield: 2.66 g (32%) (Devarie-Baez et al., *Org. Lett.* 12:752-754 (2010), which is hereby incorporated by reference in its entirety). TLC (EtOAc:Hexane, 1:3), R$_f$=0.5, irradiated by a UV lamp. 1H NMR (FIG. 5A): (400 MHz, CDCl$_3$) δ 7.69 (d, J=7.2 Hz, 2H), 7.50 (m, 1H), 7.38 (m, 3H), 7.33 (m, 1H), 7.26 (t, J=7.2 Hz, 1H), 7.09 (t, J=7.6 Hz, 1H), 4.13 (s, 1H, SH). $^{13}$C NMR (FIG. 5B): (101 MHz, CDCl$_3$) δ 196.9, 137.5, 135.6, 134.4, 132.9, 131.7, 131.6, 131.4, 130.2, 128.5, 124.6. FT-IR: 1652.57 cm$^{-1}$.

Example 11

Synthesis of Auxiliary 2,2'-Diselenodibenzaldehyde SI3/7

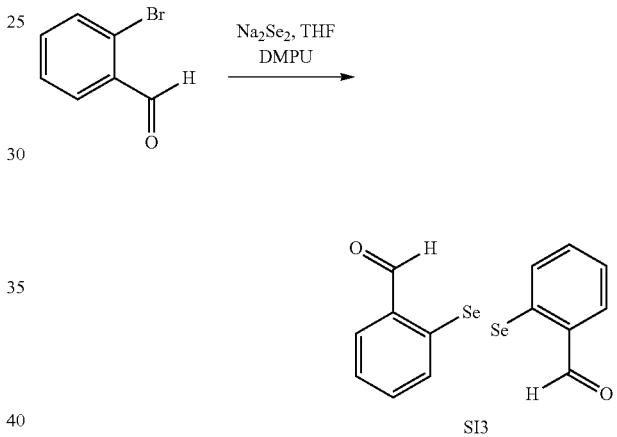

Figure 6A:
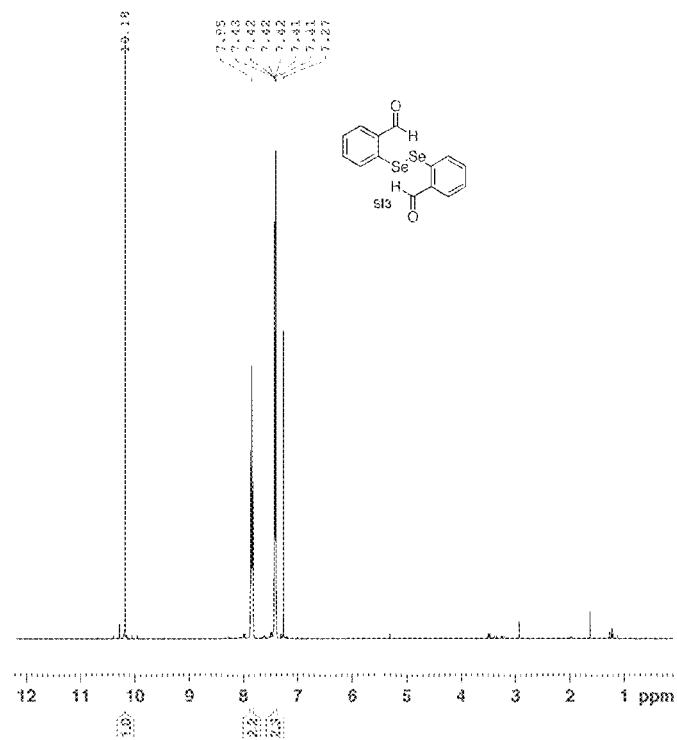
FIGS. 6A-B show $^1$H-NMR and $^{13}$C-NMR spectra of auxiliary SI3/7 in CDCl$_3$.
Figure 6B:
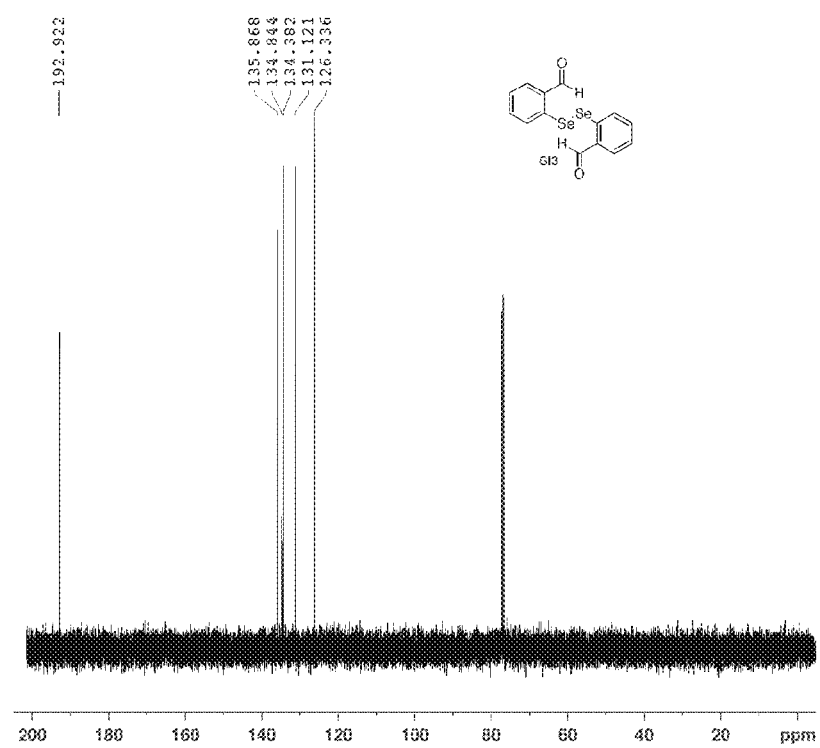

Na (0.46 g, 20 mmol) and a catalytic amount of naphthalene (~1 mmol) were added in anhydrous THF under N$_2$ in an oven dried round bottom flask. The suspension was stirred at room temperature for 1 hour, during which time it turned deep blue. Se (2.0 g, 25 mmol) was added and the solution was refluxed under N$_2$ for 12 hours. The mixture was cooled to room temperature, 2-bromobenzaldehyde (3.3 g, 18 mmol) and DMPU (6 mL) were added, and the resulting mixture was refluxed for 20 hours. After cooling, the reaction mixture was poured into water (50 mL) and extracted with CH$_2$Cl$_2$ (3×20 mL). The combined organic layers were washed with water and dried over Na$_2$SO$_4$. The solvent was concentrated under vacuo and the residue was purified by flash chromatography to obtain SI3 (also referred to as 7 herein) as a yellow solid; yield 1.03 g (28%) (Syper et al., *Tetrahedron* 44:6119-6130 (1988), which is hereby incorporated by reference in its entirety). TLC (EtOAc: Hexane 1:3), R$_f$=0.3, irradiated by a UV lamp. $^1$H NMR (FIG. 6A): (400 MHz, CDCl$_3$) δ 10.18 (s, 2H), 7.85 (m, 4H), 7.43-7.41 (m, 4H). $^{13}$C NMR (FIG. 6B): (101 MHz, CDCl$_3$) δ 192.9, 135.8, 134.8, 134.4, 131.1, 126.3. $^{77}$Se NMR: (CDCl$_3$) δ 456.340. FT-IR: 1689.23 cm$^{-1}$, 1665.21 cm$^{-1}$.

Example 12

General Procedure for Synthesis of Salicylaldehyde and Thio Benzophenone Esters

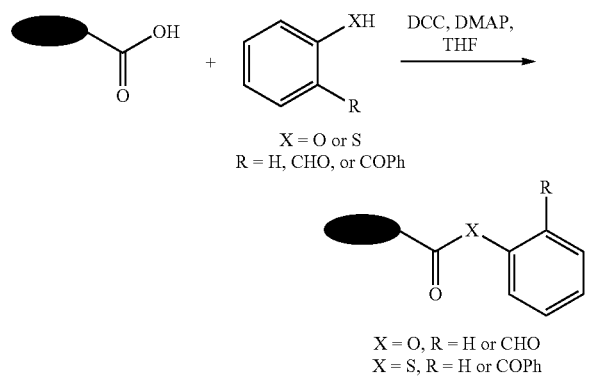

Amino acid (AA)/peptide (1 mmol) was dissolved in anhydrous THF (5 mL) in an oven-dried round bottom flask under $N_2$. The solution was stirred and cooled at 0° C. in an ice-bath for 10 minutes. Then, DCC (1 mmol) and DMAP (0.25 mmol) were added at 0° C. The reaction was further stirred at 0° C. for 30 minutes. Then, salicylaldehyde or thio benzophenone (1 mmol) was added. The resulting mixture was stirred at room temperature for 2 hours. The progress of the reaction was analyzed by TLC after regular intervals of time. After the completion of the reaction, it was cooled in an ice bath and filtered under vacuum to remove dicyclohexyl urea. The filtrate was concentrated under vacuum and the residue was purified by flash chromatography to give AA/peptide-salicylaldehyde ester or AA/peptide-thio-benzophenone ester as a white solid; yield 60-85%.

Example 13

General Procedure for Synthesis of Thiobenzaldehyde and Selenobenzaldehyde Derived Esters

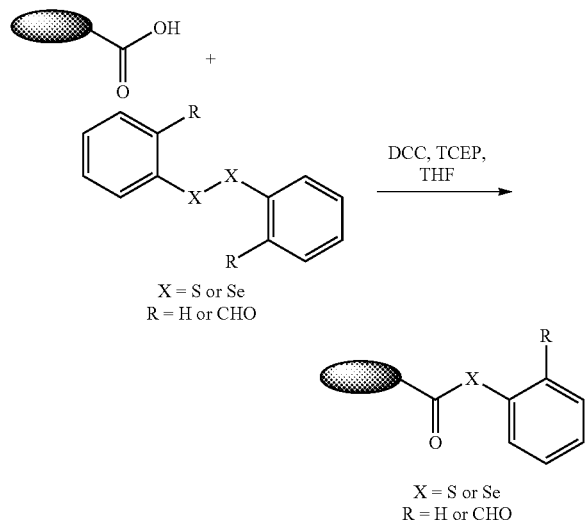

Amino acid (AA)/peptide (1 mmol) was dissolved in anhydrous THF (5 mL) in an oven-dried round bottom flask under $N_2$. The resulting solution was stirred and cooled at 0° C. in an ice-bath for 10 minutes. Then, DCC (1 mmol) was added at 0° C. The reaction was stirred at 0° C. for 30 minutes. Then, di-thio (SI1) or di-seleno benzaldehyde (SI3) (0.5 mmol), TCEP.HCl (0.6 mmol), $Et_3N$ (0.6 mmol), and 2 drops of water were added. The resulting reaction mixture was stirred at room temperature for 30 minutes. The reaction was then cooled in ice bath and filtered to remove dicyclohexyl urea. The filtrate was concentrated under vacuum and purified by flash chromatography or HPLC to give AA/peptide-thio-benzaldehyde or AA/peptide-seleno-benzaldehyde ester, respectively, as a pale yellow solid (55-70% yield).

Example 14

General Procedure for the Solid Phase Synthesis of Peptide Seleno-Esters

The peptide N-acyl-benzimidazolinone (Nbz) was prepared according to procedure described by Blanco-Canosa & Dawson, *Angew. Chem. Int. Ed.*, 47:6851-55 (2008), which is hereby incorporated by reference in its entirety). The PAM-resin bound Nbz peptide was treated with TFA:TIPS:anisole:thioanisole (95:2.5:2.5:1) for 1 hour to remove the side-chain protecting groups. The on-resin selenolysis for the synthesis of peptide seleno-ester was conducted by adding diselenide (2.0 eq) in Nbz-peptide (1.0 eq) in a dried round bottom flask, thoroughly flushed with argon. Then, dry THF (0.5 mL) and tributylphosphine (2.0 equiv.), flushed with argon, were added to the round bottom flask. The resulting suspension was stirred on heated shaker for 14 hours at 55° C. The resin was then filtered and washed with THF/DCM. For complete removal of peptide from the resin, selenolysis was repeated twice on the same resin. The combined filtrates were concentrated and the crude product was triturated with cold diethyl ether to give a white suspension, which was centrifuged and the ether subsequently decanted to obtain crude peptide-selenoester in 59% yield from the resin. The yield of the peptide was determined using Fmoc absorbance.

Example 15

Synthesis of Salicylaldehyde Ester SI4

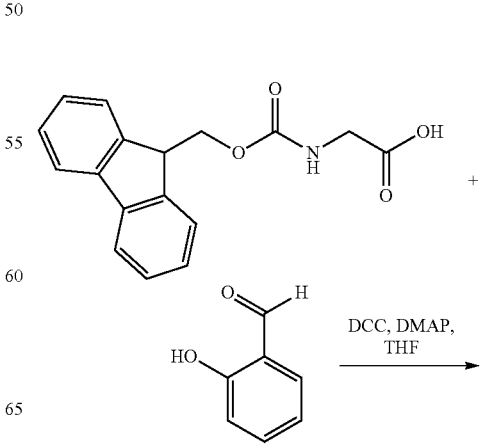

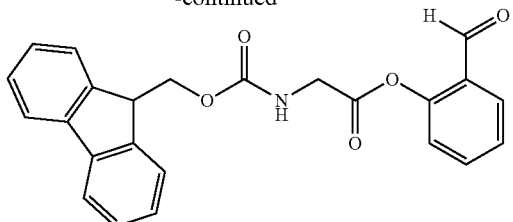

SI4

Figure 7A:
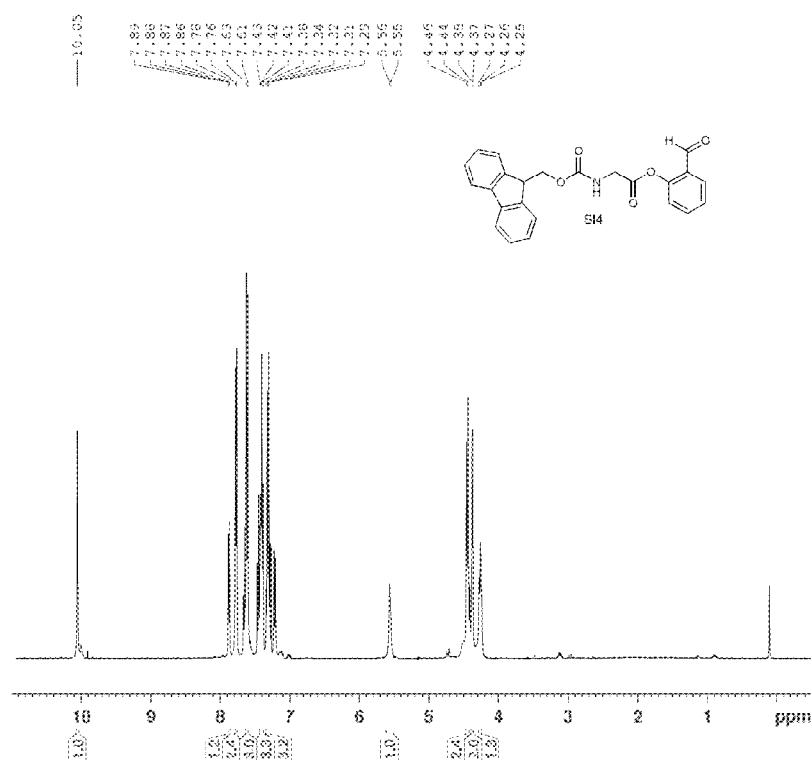
FIGS. 7A-B show $^1$H-NMR and $^{13}$C-NMR spectra of peptide SI4 in CDCl$_3$.
Figure 7B:
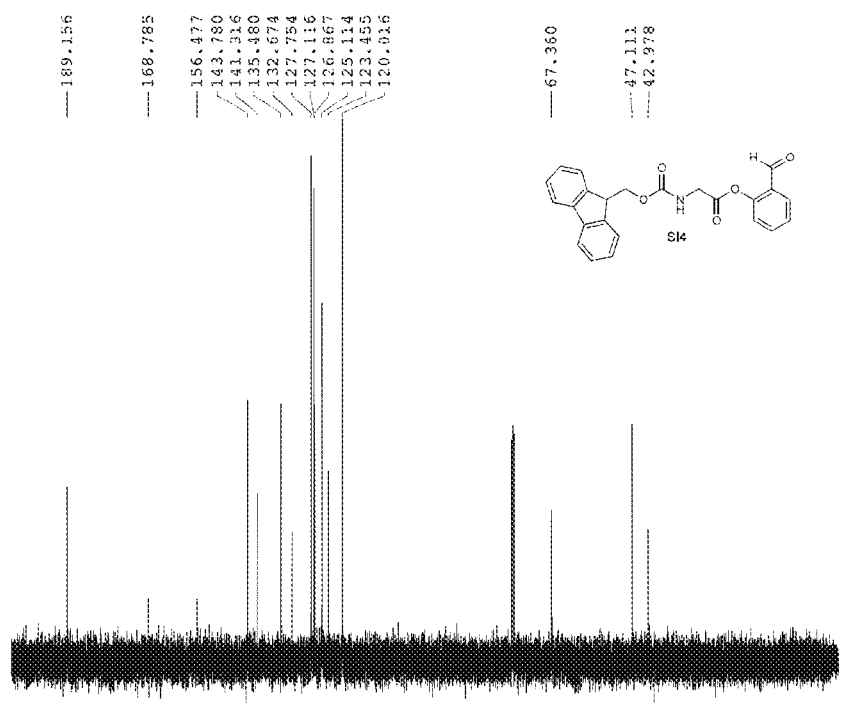

Salicylaldehyde ester SI4 was synthesised as described in Example 12. Isolated yield: 82%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=24.2 min. 1H NMR (FIG. 7A): (400 MHz, CDCl$_3$) δ 10.05 (s, 1H), 7.87 (dd, J=7.6, 1.2 Hz, 1H), 7.77 (d, J=7.6 Hz, 2H), 7.63-7.61 (m, 3H), 7.43-7.38 (m, 3H), 7.34-7.29 (m, 3H), 5.56 (bs, 1H), 4.45 (d, J=7.2 Hz, 2H), 4.37 (m, 2H), 4.26 (m, 1H). $^{13}$C NMR (FIG. 7B): (101 MHz, CDCl$_3$) δ 189.2, 168.8, 156.5, 143.8, 141.3, 135.5, 132.7, 127.8, 127.1, 126.9, 125.1, 123.5, 120.0, 67.4, 47.1, 42.9. HRMS: exact mass calcd. for C$_{24}$H$_{19}$NO$_5$ [M+Na]$^+$ 424.1155. found 424.1160. FT-IR: 1749.70 cm$^{-1}$, 1724.56 cm$^{-1}$, 1701.37 cm$^{-1}$.

Example 16

Synthesis of Oxo-Ester SI5

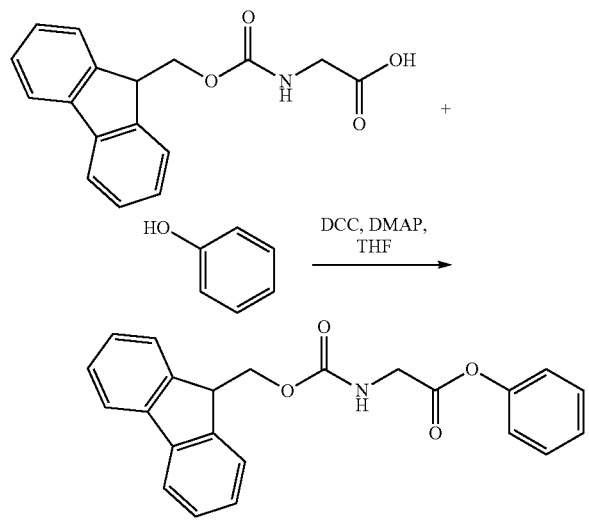

SI5

Figure 8A:
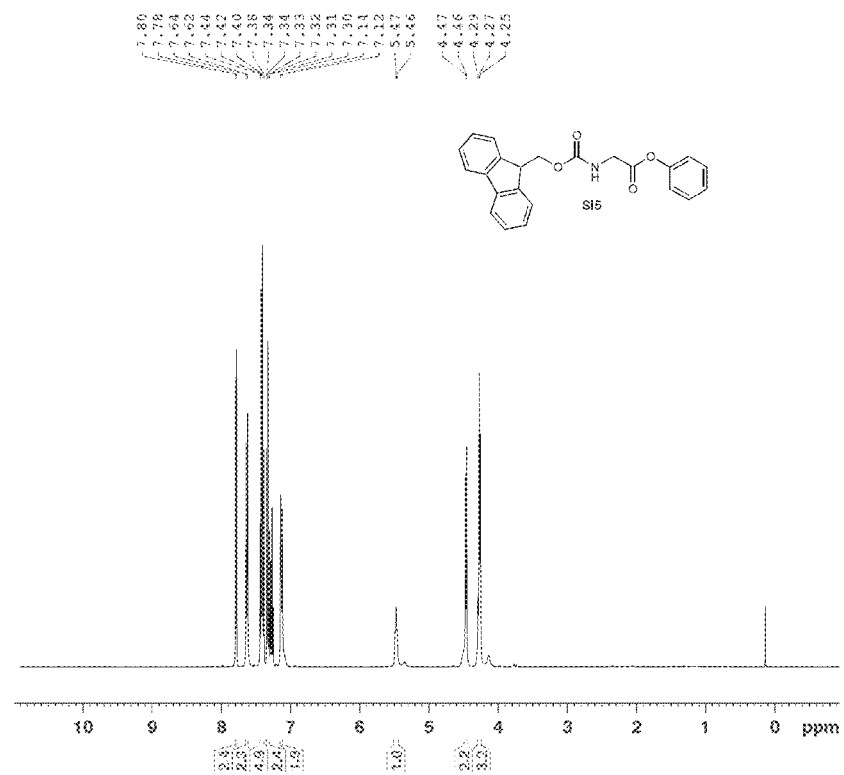
FIGS. 8A-B show $^1$H-NMR and $^{13}$C-NMR spectra of peptide SI5 in CDCl$_3$.
Figure 8B:
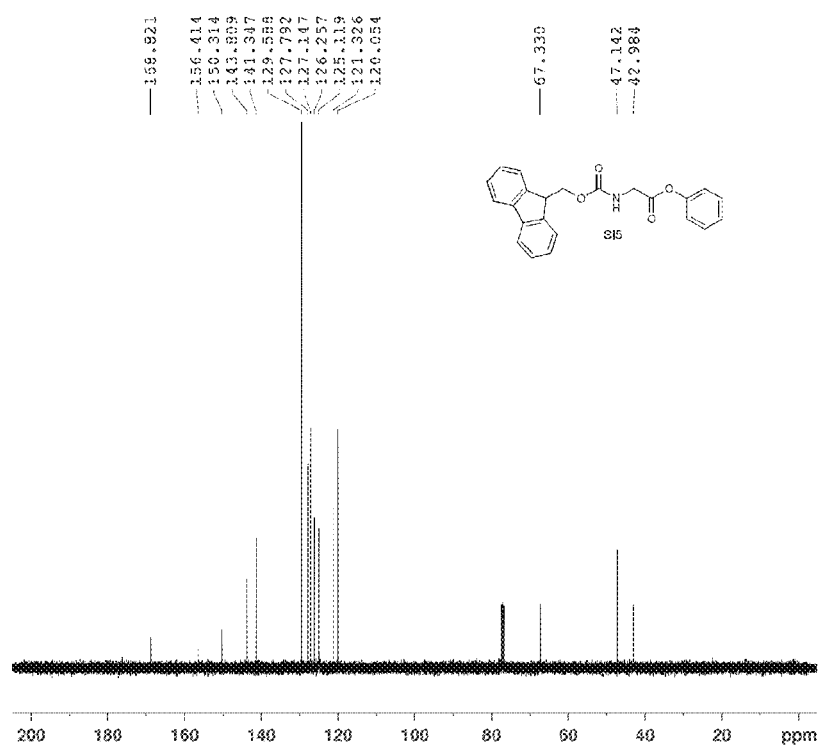

Oxo-ester SI5 was synthesized as described in Example 12. Isolated yield: 85%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=19.9 min. 1H NMR (FIG. 8A): (400 MHz, CDCl$_3$) δ 7.78 (d, J=7.6 Hz, 2H), 7.62 (d, J=7.6 Hz, 2H), 7.44-7.38 (m, 5H), 7.34-7.31 (m, 2H), 7.13 (d, J=8 Hz, 2H), 5.47 (bs, 1H), 4.46 (d, J=7.2 Hz, 2H), 4.27 (m, 3H). $^{13}$C NMR (FIG. 8B): (101 MHz, CDCl$_3$) δ 168.8, 156.4, 150.3, 143.8, 141.3, 129.6, 127.8, 127.1, 126.3, 125.1, 121.3, 120.0, 67.3, 47.1, 42.9. HRMS: exact mass calcd. for C$_{23}$H$_{19}$NO$_4$ [M+Na]$^+$ 396.1206. found 396.1222. FT-IR: 1769.40 cm$^{-1}$, 1724.87 cm$^{-1}$.

Example 17

Synthesis of Thio-Benzaldehyde Ester SI6

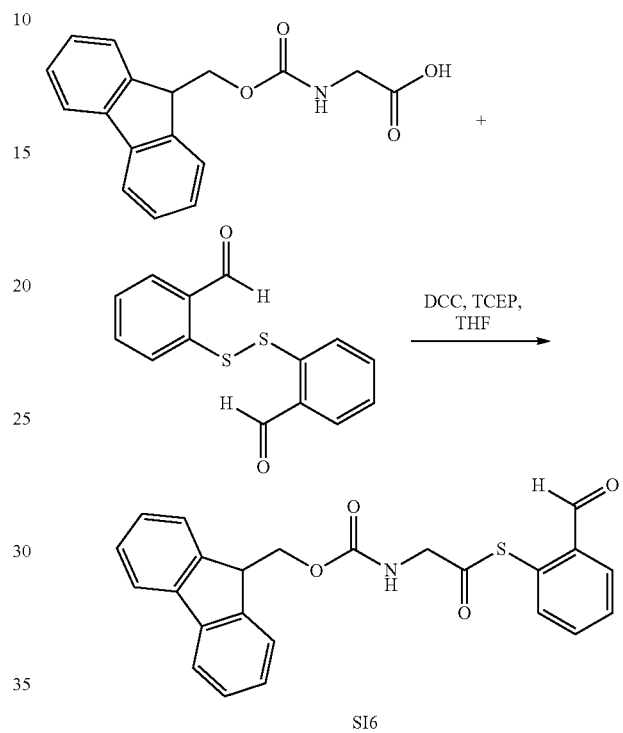

SI6

Figure 9A:
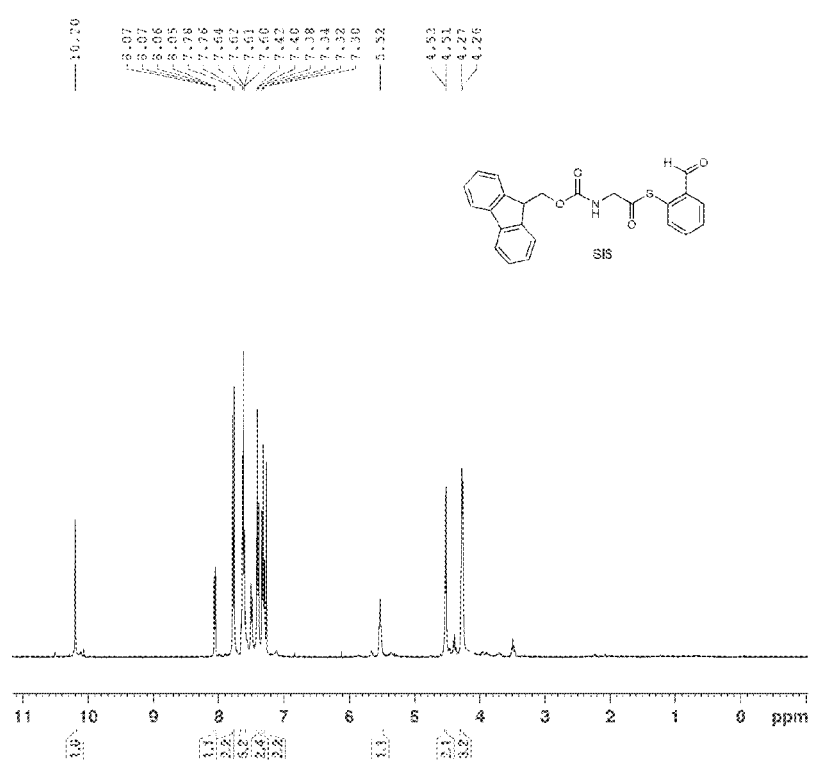
FIGS. 9A-B show $^1$H-NMR and $^{13}$C-NMR spectra of peptide SI6 in CDCl$_3$.
Figure 9B:
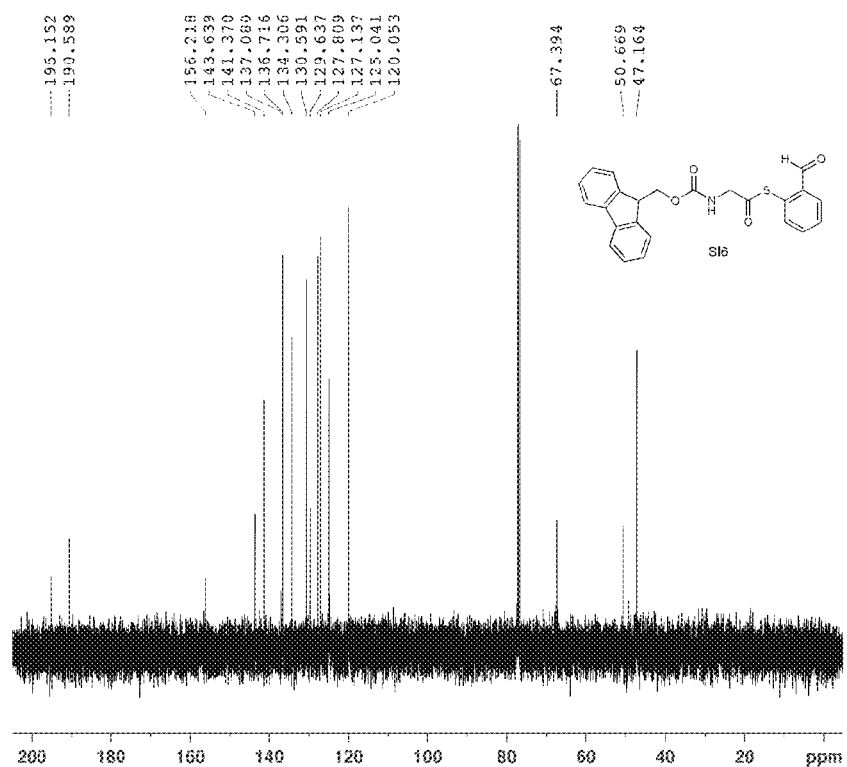

Thio-benzaldehyde ester SI6 was synthesized as described in Example 13. Isolated yield: 60%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=20.9 min. $^1$H NMR (FIG. 9A): (400 MHz, CDCl$_3$) δ 10.21 (s, 1H), 8.06 (m, 1H), 7.77 (d, J=7.6 Hz, 2H), 7.64-7.60 (m, 5H), 7.40 (m, 2H), 7.32 (t, J=7.2 Hz, 2H), 5.52 (bs, 1H), 4.51 (d, J=6.8 Hz, 2H), 4.26 (m, 3H). $^{13}$C NMR (FIG. 9B): (101 MHz, CDCl$_3$) δ 195.2, 190.6, 156.2, 143.6, 141.3, 137.1, 136.7, 134.3, 130.6, 129.6, 127.8, 127.1, 125.0, 120.0, 67.4, 50.4, 47.1. HRMS: exact mass calcd. for C$_{30}$H$_{23}$NO$_4$S [M+Na]$^+$ 440.0952. found 440.0959. FT-IR: 1724.64 cm$^{-1}$, 1669.08 cm$^{-1}$.

Example 18

Synthesis of Thio-Phenyl Ester SI7

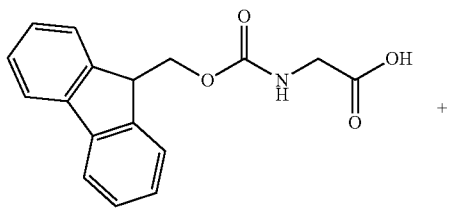

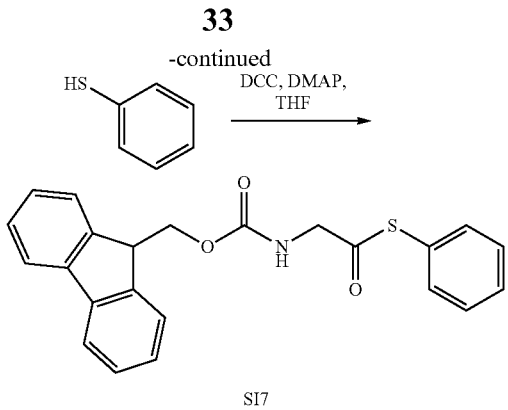

SI7

Figure 10A:
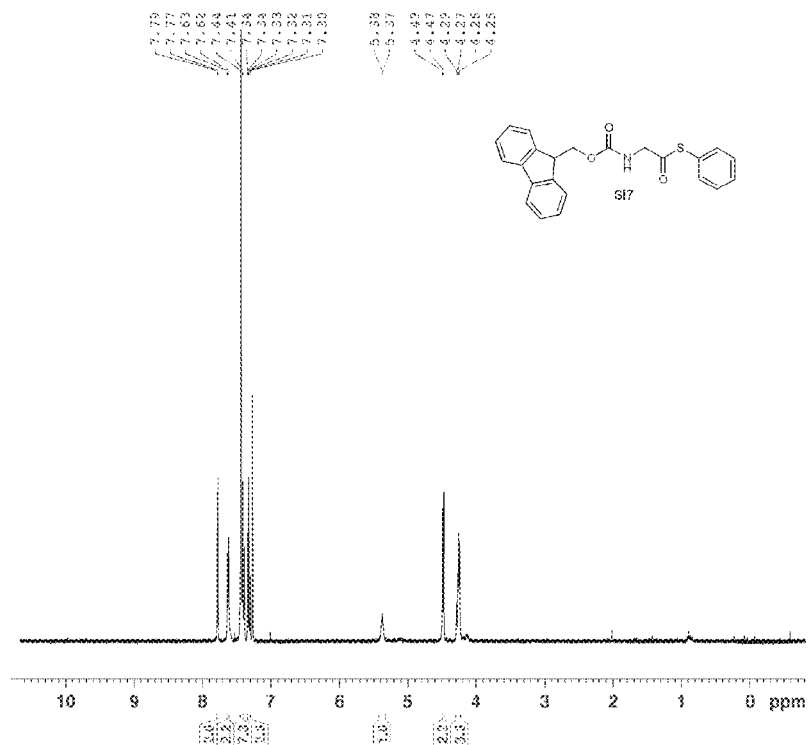
FIGS. 10A-B show $^1$H-NMR and $^{13}$C-NMR spectra of peptide SI7 in CDCl$_3$.
Figure 10B:
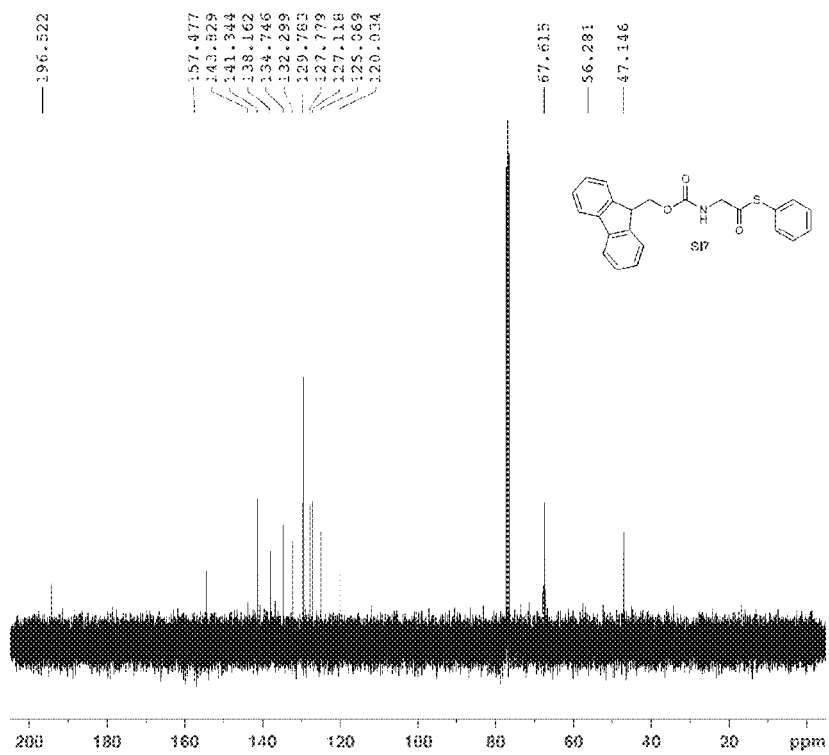

Thio-phenyl ester SI7 was synthesized as described in Example 12. Isolated yield: 83%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time $(R_t)$=22.4 min. 1H NMR (FIG. 10A): (400 MHz, CDCl$_3$) δ 7.78 (d, J=7.6 Hz, 2H), 7.62 (d, J=7.6 Hz, 2H), 7.44-7.41 (m, 7H), 7.32 (td, J=7.6, 1.2 Hz, 2H), 5.37 (bs, 1H), 4.48 (d, J=6.8 Hz, 2H), 4.27 (m, 3H). $^{13}$C NMR (FIG. 10B): (101 MHz, CDCl$_3$) δ 196.5, 157.5, 143.8, 141.3, 138.2, 134.7, 132.3, 129.8, 127.8, 127.1, 125.1, 120.0, 67.6, 56.3, 47.1. HRMS: exact mass calcd. for C$_{23}$H$_{19}$NO$_3$S [M+Na]$^+$ 412.0978. found 412.1007. FT-IR: 1732.59 cm$^{-1}$, 1717.93 cm$^{-1}$, 1700.78 cm$^{-1}$.

Example 19

Synthesis of Thio-Benzophenone Ester SI8

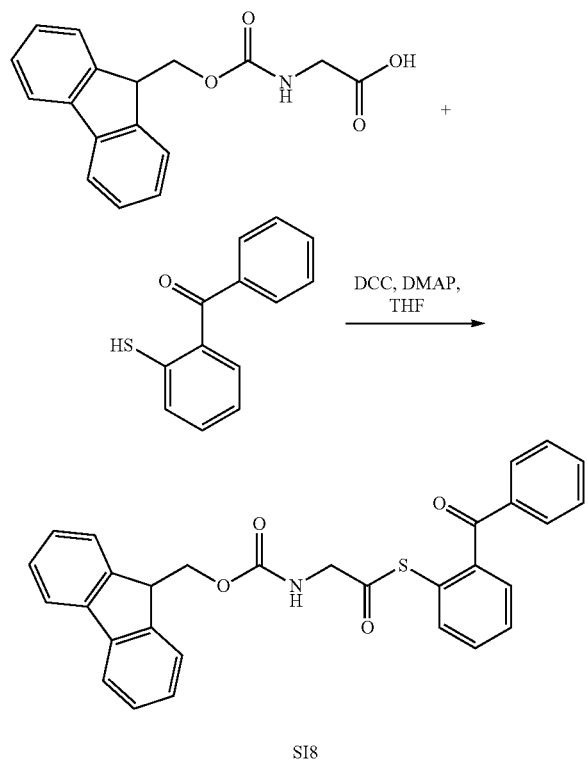

SI8

Figure 11A:
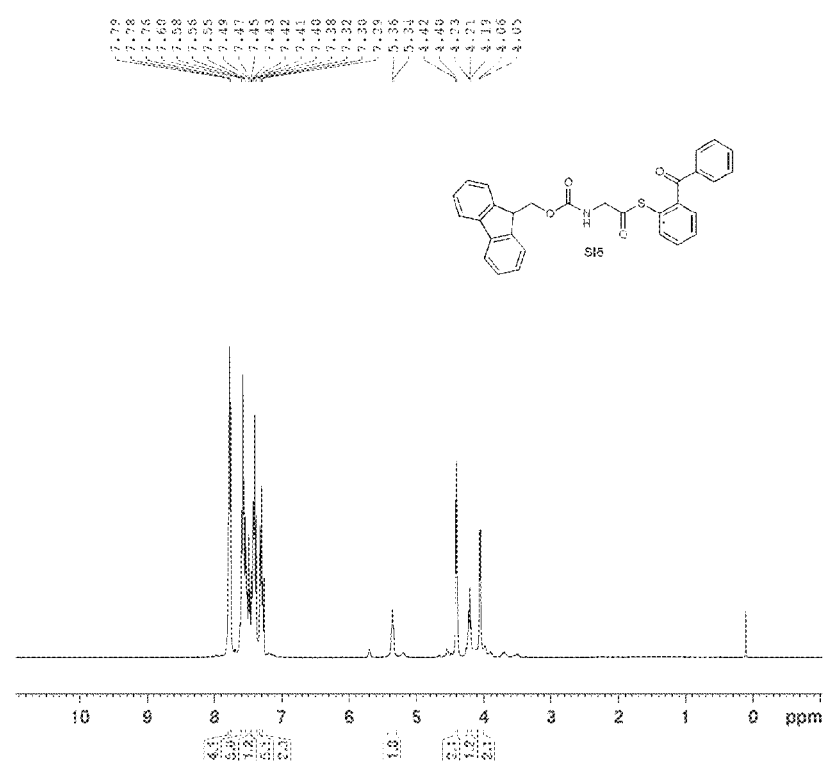
FIGS. 11A-B show $^1$H-NMR and $^{13}$C-NMR spectra of peptide SI8 in CDCl$_3$.
Figure 11B:
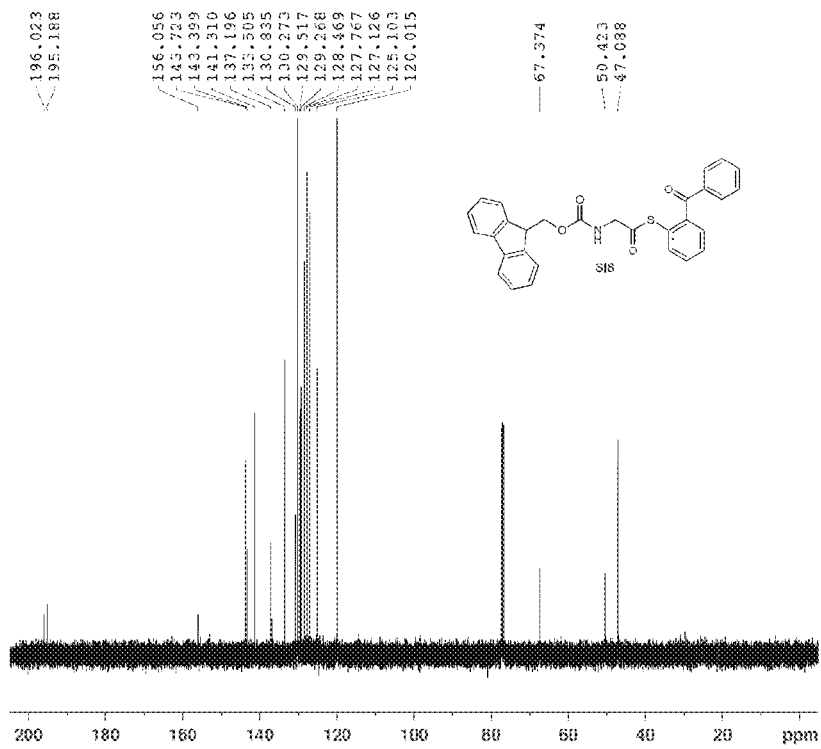

Thio-benzophenone ester SI8 was synthesized as described in Example 12. Isolated yield: 72%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time $(R_t)$=25.1 min. 1H NMR (FIG. 11A): (400 MHz, CDCl$_3$) δ 7.78 (m, 4H), 7.60-7.55 (m, 5H), 7.48 (m, 1H), 7.43-7.38 (m, 5H), 7.31 (m, 2H), 5.35 (bs, 1H), 4.40 (d, J=6.8 Hz, 2H), 4.21 (t, J=6.8 Hz, 1H), 4.05 (d, J=6 Hz, 2H). $^{13}$C NMR (FIG. 11B): (101 MHz, CDCl$_3$) δ 196.0, 195.2, 156.1, 143.7, 143.4, 141.3, 137.2, 136.8, 133.5, 130.8, 130.3, 129.5, 129.3, 128.5, 127.8, 127.1, 125.1, 120.0, 67.4, 50.4, 47.1. HRMS: exact mass calcd. for C$_{30}$H$_{23}$NO$_4$S [M+Na]$^+$ 516.1240. found 516.1260. FT-IR: 1724.64 cm$^{-1}$, 1669.08 cm$^{-1}$.

Example 20

Synthesis of Seleno-Benzaldehyde Ester SI9

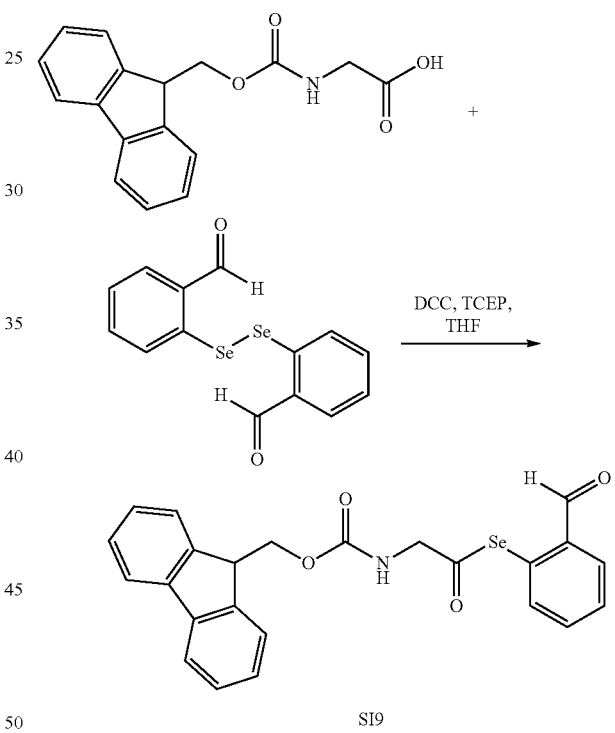

SI9

Figure 12A:
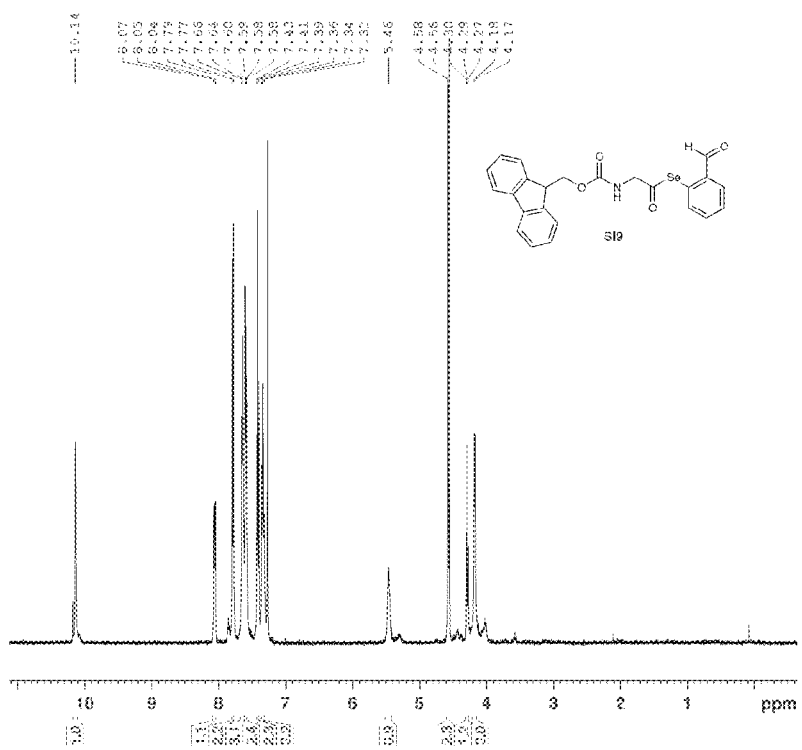
Figures 12B, 13A:
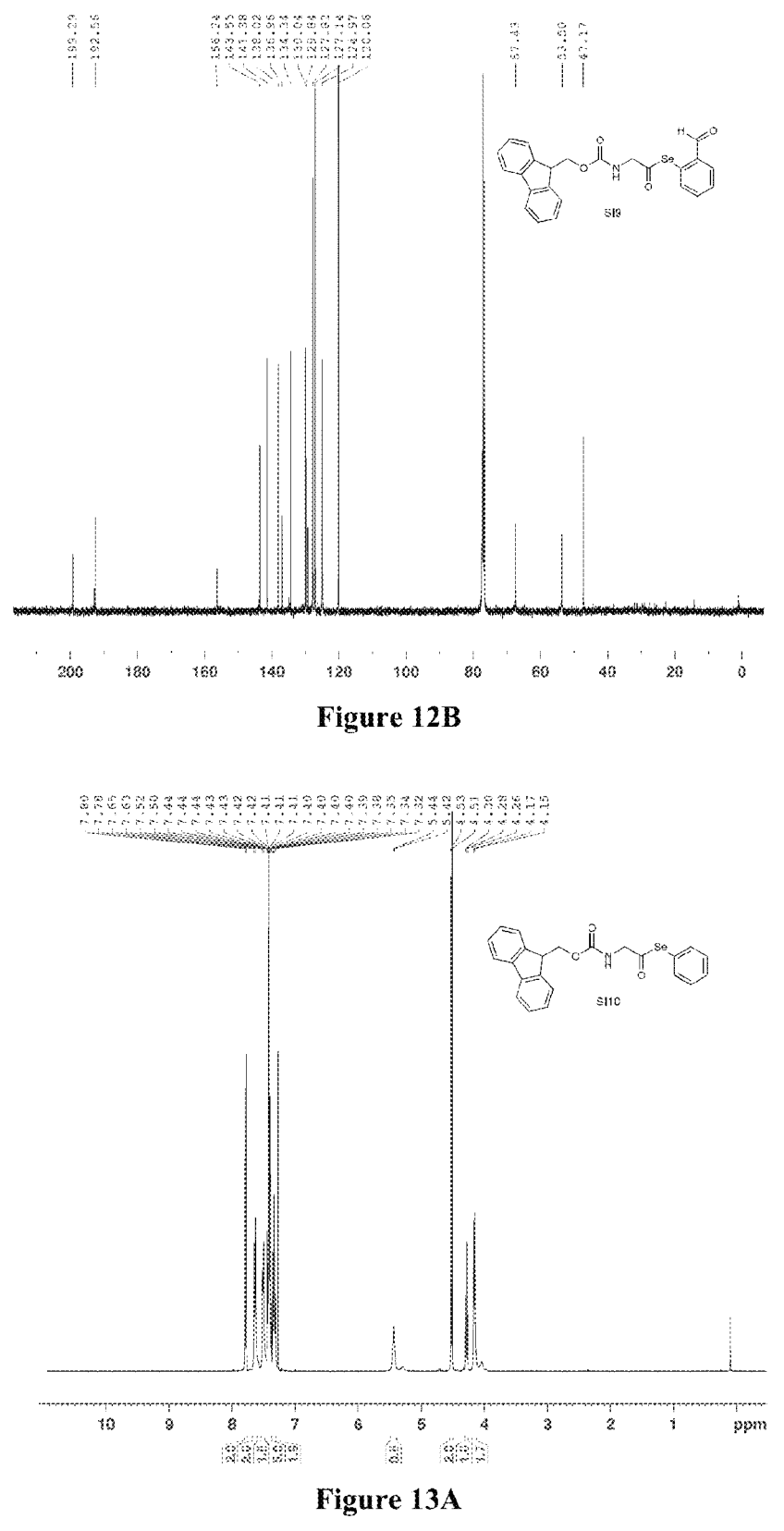

Seleno-benzaldehyde ester SI9 was synthesized as described in Example 13. Isolated yield: 69%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time $(R_t)$=21.5 min. $^1$H NMR (FIG. 12A): (400 MHz, CDCl$_3$) δ 10.14 (s, 1H), 8.05 (m, 1H), 7.78 (d, J=7.6 Hz, 2H), 7.66-7.64 (m, 3H), 7.60-7.58 (m, 2H), 7.41 (m, 2H), 7.34 (t, J=7.2 Hz, 2H), 5.46 (bs, 1H), 4.56 (d, J=6.8 Hz, 2H), 4.29 (m, 1H), 4.17 (m, 2H). $^{13}$C NMR (FIG. 12B): (101 MHz, CDCl$_3$) δ 199.3, 192.6, 156.2, 143.6, 141.4, 138.0, 136.9, 134.3, 130.0, 129.8, 127.8, 127.1, 124.9, 120.0, 67.4, 53.5, 47.2. $^{77}$Se NMR (CDCl$_3$) δ 600.887. HRMS: exact mass calcd. for C$_{24}$H$_{19}$NO$_4$Se [M+Na]$^+$ 488.0372. found 488.0370. FT-IR: 1726.35 cm$^{-1}$, 1695.72 cm$^{-1}$.

Example 21

Synthesis of Seleno-Phenyl Ester SI10

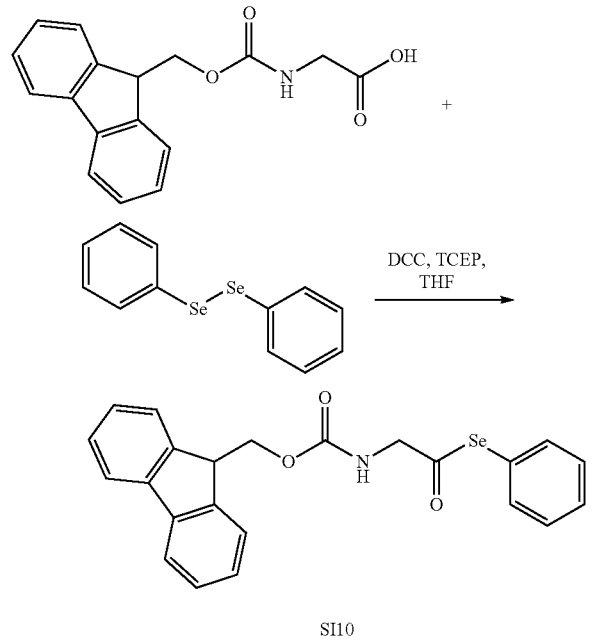

SI10

Figure 13B:
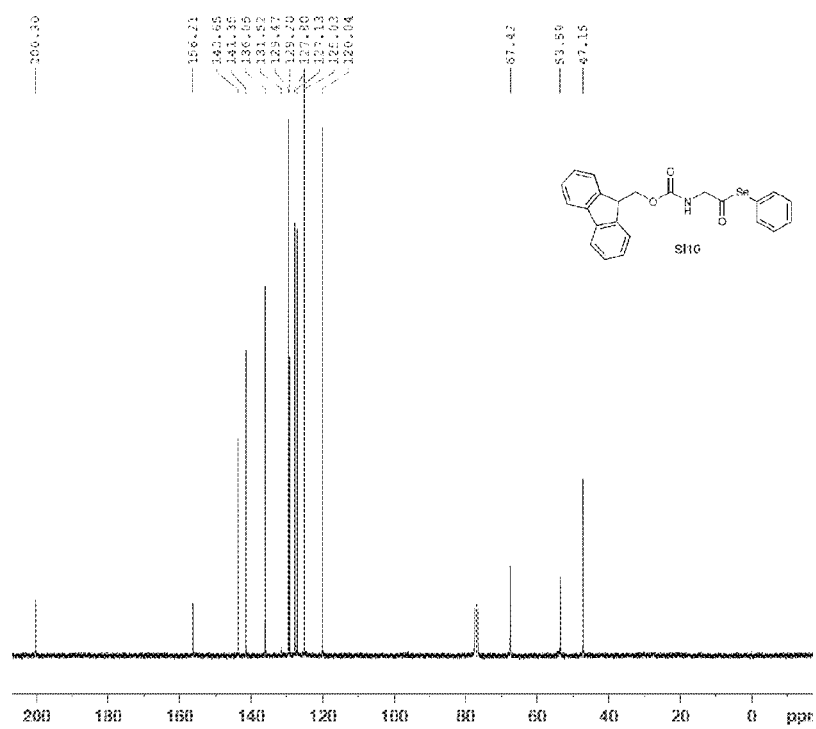

Seleno-phenyl ester SI10 was synthesized as described in Example 13. Isolated yield: 75%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=23.4 min. 1H NMR (FIG. 13A): (400 MHz, CDCl$_3$) δ 7.78 (d, J=7.6 Hz, 2H), 7.64 (d, J=7.2 Hz, 2H), 7.51 (m, 2H), 7.44-7.38 (m, 5H), 7.35-7.32 (m, 2H), 5.44 (bs, 1H), 4.51 (d, J=6.8 Hz, 2H), 4.28 (t, J=6.8 Hz, 1H), 4.16 (d, J=6.4 Hz, 2H). 13C NMR (FIG. 13B): (101 MHz, CDCl$_3$) δ 200.3, 156.2, 143.6, 141.4, 136.0, 131.5, 129.5, 129.2, 127.8, 127.1, 125.0, 120.0, 67.4, 53.6, 47.1. 77Se NMR: (CDCl$_3$) δ 657.852. HRMS: exact mass calcd. for C$_{23}$H$_{19}$NO$_3$Se [M+Na]$^+$ 460.0422. found 460.0440. FT-IR: 1719.67 cm$^{-1}$, 1701.70 cm$^{-1}$.

Example 22

Synthesis of Seleno-Benzaldehyde Ester SI11/3

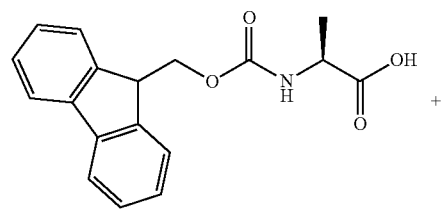

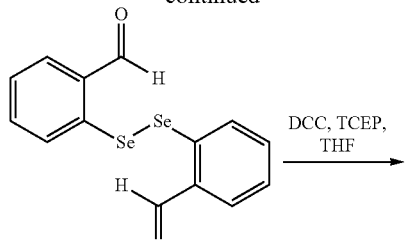

SI11

Figure 14A:
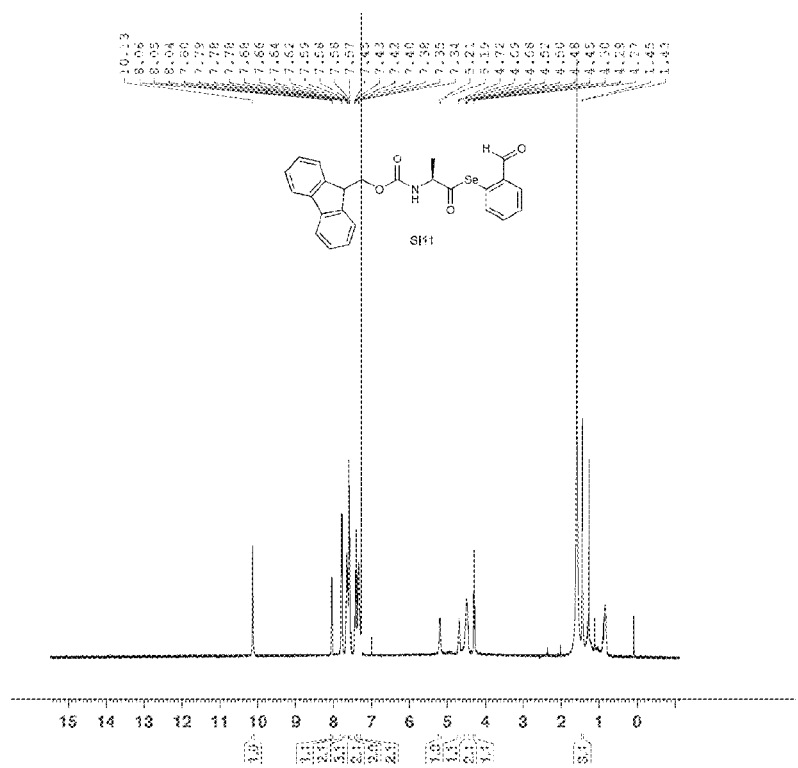
FIGS. 14A-B show $^1$H-NMR and $^{13}$C-NMR spectra of peptide SI11/3 in CDCl$_3$.
Figure 14B:
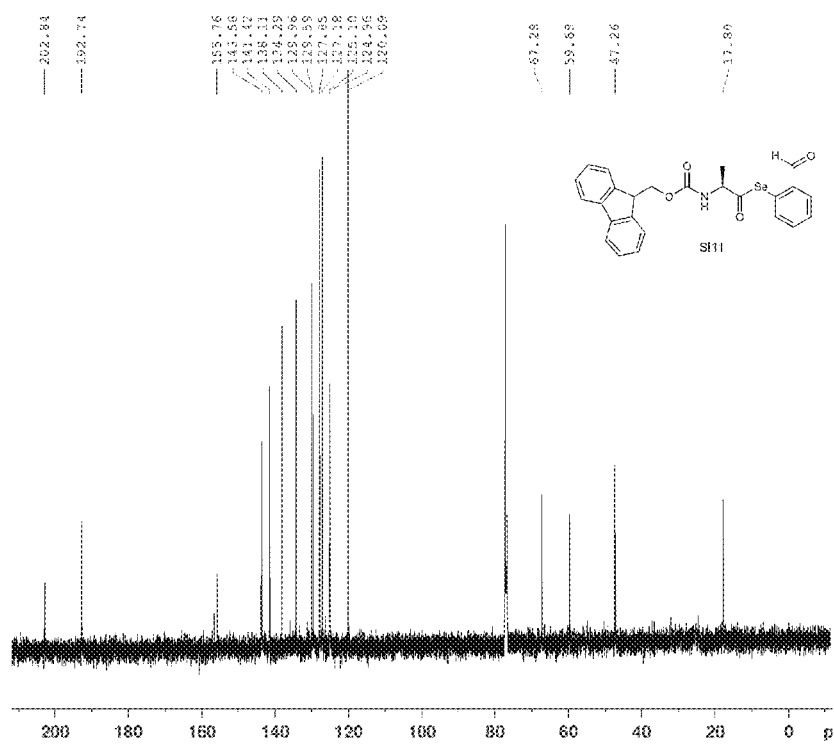

Seleno-benzaldehyde ester SI11 (also referred to as 3 herein) was synthesized as described in Example 13 (Li et al., *Org. Lett.* 12:1724-27 (2010), which is hereby incorporated by reference in its entirety). Isolated yield: 66%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=22.8 min. 1H NMR (FIG. 14A): (400 MHz, CDCl$_3$) δ 10.13 (s, 1H), 8.05 (m, 1H), 7.78 (m, 2H), 7.65 (m, 3H), 7.58 (m, 2H), 7.41 (m, 2H), 7.34 (d, J=4.0 Hz, 2H), 5.20 (d, J=8.0 Hz, 1H), 4.70 (m, 1H), 4.49 (m, 2H), 4.29 (m, 1H), 1.44 (d, J=8.0 Hz, 3H). 13C NMR (FIG. 14B): (101 MHz, CDCl$_3$) δ 202.8, 192.7, 155.7, 143.6, 141.4, 138.1, 134.3, 129.9, 129.6, 127.8, 127.2, 125.1, 124.9, 120.1, 67.3, 59.7, 47.3, 17.8. 77Se NMR: (CDCl$_3$) δ 586.750. HRMS: exact mass calcd. for C$_{25}$H$_{21}$NO$_4$Se [M+Na]$^+$ 502.0528. found 502.0518. FT-IR: 1717.99 cm$^{-1}$, 1697.02 cm$^{-1}$.

Example 23

Synthesis of Seleno-Phenyl Ester SI12

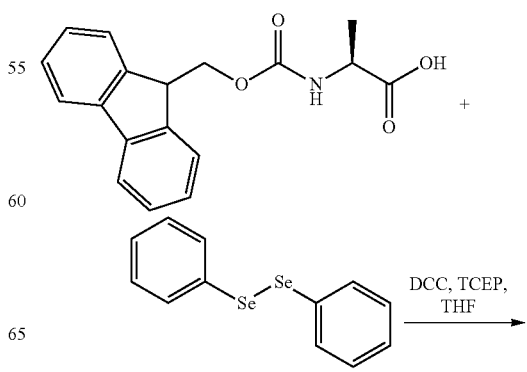

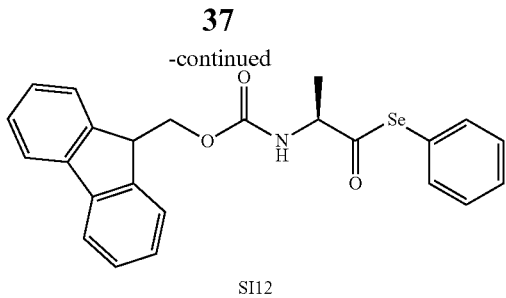

SI12

Figure 15A:
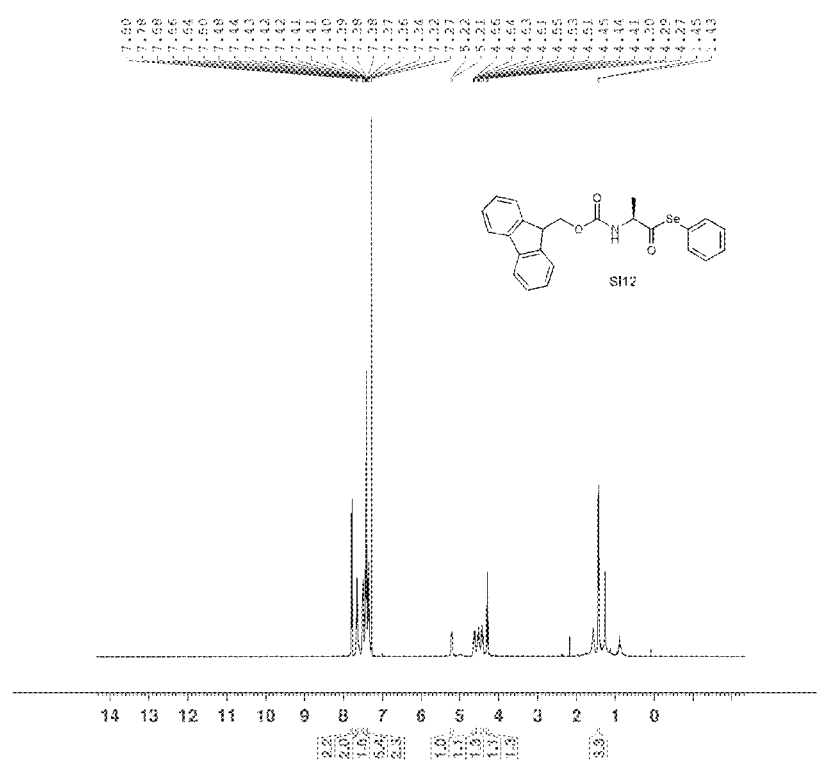
FIGS. 15A-B show $^1$H-NMR and $^{13}$C-NMR spectra of peptide SI12/4 in CDCl$_3$.
Figure 15B:
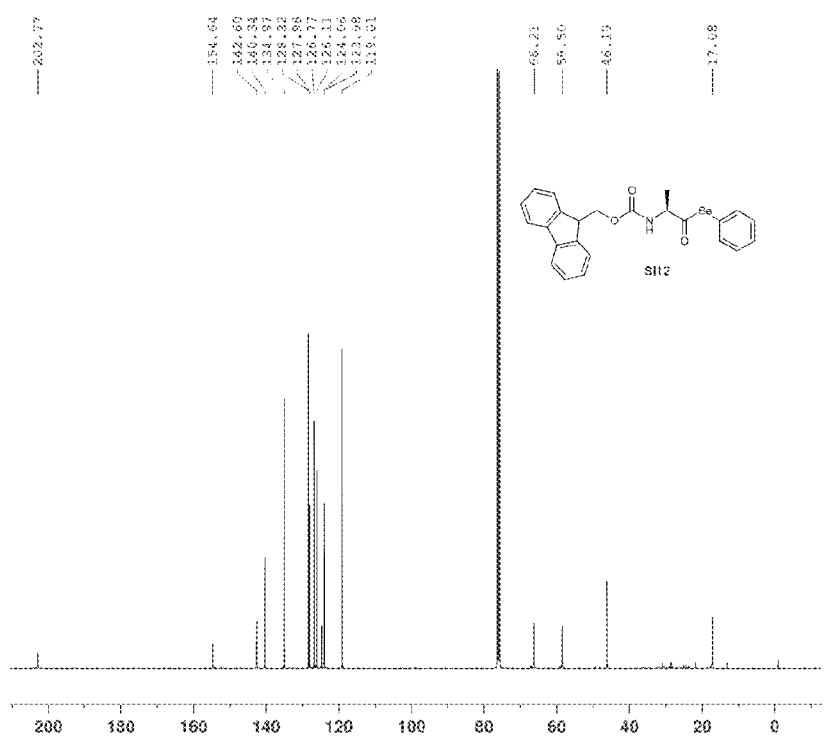

Seleno-phenyl ester SI12 (also referred to as 4 herein) was synthesized as described in Example 13 (FMOC SOLID PHASE PEPTIDE SYNTHESIS: A PRACTICAL APPROACH (Weng C. Chan & Peter D. White eds., 2000), which is hereby incorporated by reference in its entirety). Isolated yield: 72%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=25.5 min. 1H NMR (FIG. 15A): (400 MHz, CDCl$_3$) δ 7.79 (d, J=7.60 Hz, 2H), 7.66 (t, J=7.60 Hz, 2H), 7.49 (m, 2H), 7.44-7.38 (m, 5H), 7.34 (m, 2H), 5.21 (d, J=7.20 Hz, 1H), 4.64 (m, 1H), 4.53 (m, 1H), 4.44 (m, 1H), 4.29 (t, J=6.4 Hz, 1H), 1.44 (d, J=7.20 Hz, 3H). $^{13}$C NMR (FIG. 15B): (101 MHz, CDCl$_3$) δ 202.8, 154.6, 142.6, 140.3, 134.9, 128.3, 127.9, 126.8, 126.1, 124.1, 123.9, 119.0, 66.2, 58.5, 46.2, 17.1. $^{77}$Se NMR: (CDCl$_3$) δ 645.645. HRMS: exact mass calcd. for C$_{24}$H$_{21}$NO$_3$Se [M+Na]$^+$ 474.0579. found 474.0450. FT-IR: 1717.94 cm$^{-1}$.

Example 24

Synthesis of Seleno-Benzaldehyde Ester SI13

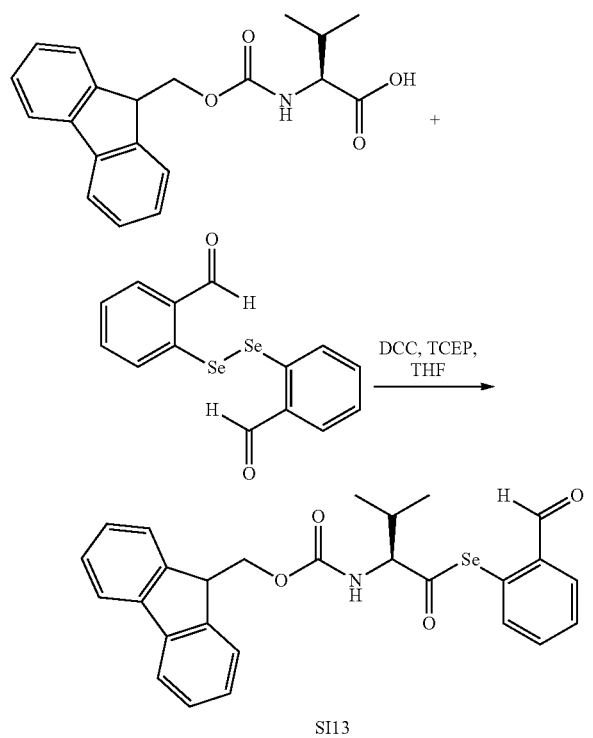

SI13

Figure 16A:
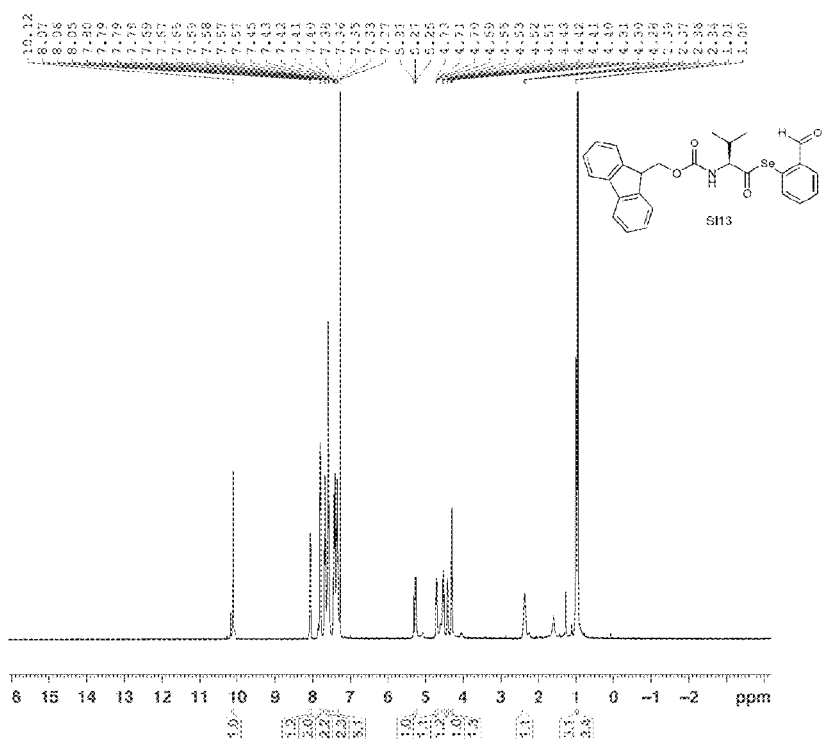
FIGS. 16A-B show $^1$H-NMR and $^{13}$C-NMR spectra of peptide SI13 in CDCl$_3$.
Figure 16B:
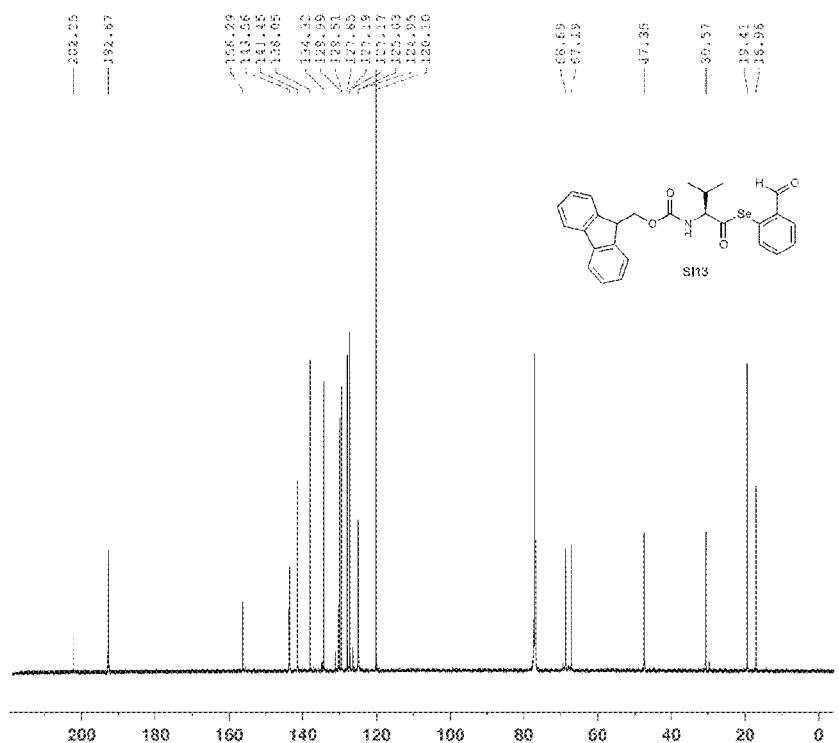

Seleno-benzaldehyde ester SI13 was synthesized as described in Example 13. Isolated yield: 58%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time (R)=26.4 min. $^1$H NMR (FIG. 16A): (400 MHz, CDCl$_3$) δ 10.12 (s, 1H), 8.06 (m, 1H), 7.80-7.77 (m, 2H), 7.67 (t, J=7.20 Hz, 2H), 7.58 (m, 2H), 7.45-7.33 (m, 5H), 5.26 (d, J=9.20 Hz, 1H), 4.71 (dd, J=10.4, 6.4 Hz, 1H), 4.53 (m, 1H), 4.41 (dd, J=9.20, 4.40 Hz, 1H), 4.30 (t, J=6.4 Hz, 1H), 2.36 (m, 1H), 1.00 (d, J=6.4 Hz, 3H), 0.95 (d, J=6.8 Hz, 3H). $^{13}$C NMR (FIG. 16B): (101 MHz, CDCl$_3$) δ 202.3, 192.7, 156.3, 143.6, 141.5, 138.1, 134.3, 129.9, 129.5, 127.8, 127.2, 125.0, 124.9, 120.1, 68.7, 67.2, 47.4, 30.6, 19.4, 16.9. $^{77}$Se NMR: (CDCl$_3$) δ 615.409. HRMS: exact mass calcd. for C$_{27}$H$_{25}$NO$_4$Se [M+Na]$^+$ 530.0841. found 530.0847. FT-IR: 1722.02 cm$^1$, 1715.02 cm$^{-1}$, 1695.12 cm$^{-1}$.

Example 25

Synthesis of Seleno-Phenyl Ester SI14

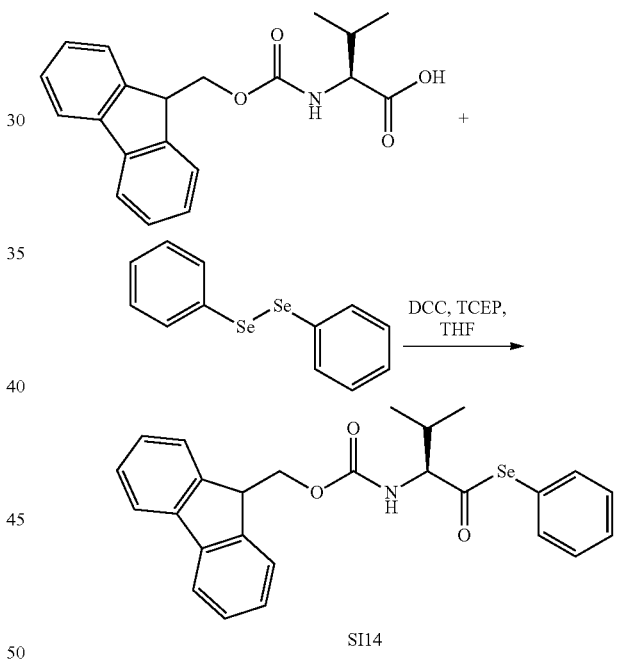

SI14

Figure 17A:
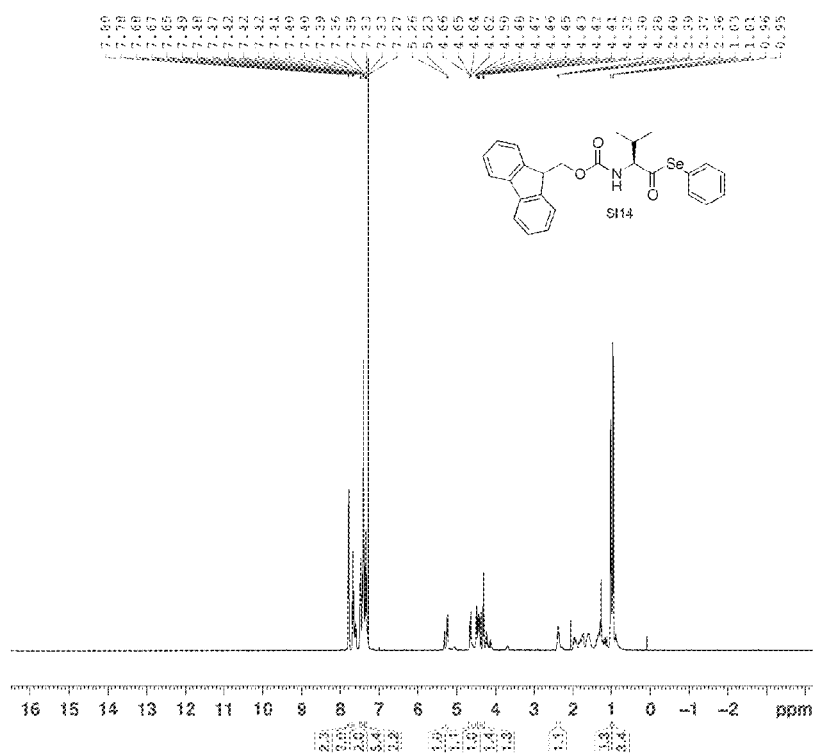
FIGS. 17A-B show $^1$H-NMR and $^{13}$C-NMR spectra of peptide SI14 in CDCl$_3$.
Figure 17B:
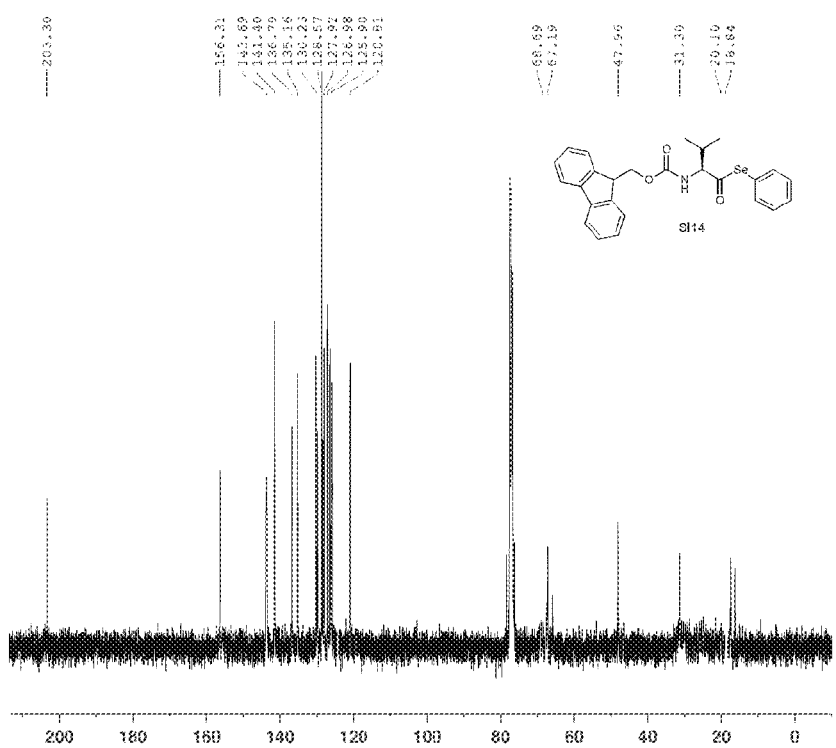

Seleno-phenyl ester SI14 was synthesized as described in Example 13. Isolated yield: 68%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=27.1 min. 1H NMR (FIG. 17A): (400 MHz, CDCl$_3$) δ 7.79 (m, 2H), 7.67 (m, 2H), 7.48 (m, 2H), 7.42-7.39 (m, 5H), 7.35 (m, 2H), 5.24 (d, J=9.60 Hz, 1H), 4.64 (dd, J=10.80, 6.80 Hz, 1H), 4.48 (m, 1H), 4.43 (m, 1H), 4.30 (m, 1H), 2.38 (m, 1H), 1.01 (d, J=6.8 Hz, 3H), 0.95 (d, J=6.8 Hz, 3H). $^{13}$C NMR (FIG. 17B): (101 MHz, CDCl$_3$) δ 203.3, 156.3, 143.7, 141.4, 136.8, 135.2, 130.2, 128.6, 127.9, 126.9, 125.9, 120.8, 68.7, 67.2, 47.9, 31.3, 20.1, 18.8. $^{77}$Se NMR: (CDCl$_3$) δ 674.131. HRMS: exact mass calcd. for C$_{26}$H$_{25}$NO$_3$Se [M+Na]$^+$ 502.1000. found 502.1452. FT-IR 1712.91 cm$^{-1}$.

Example 26

Synthesis of Seleno-Benzaldehyde Ester SI15

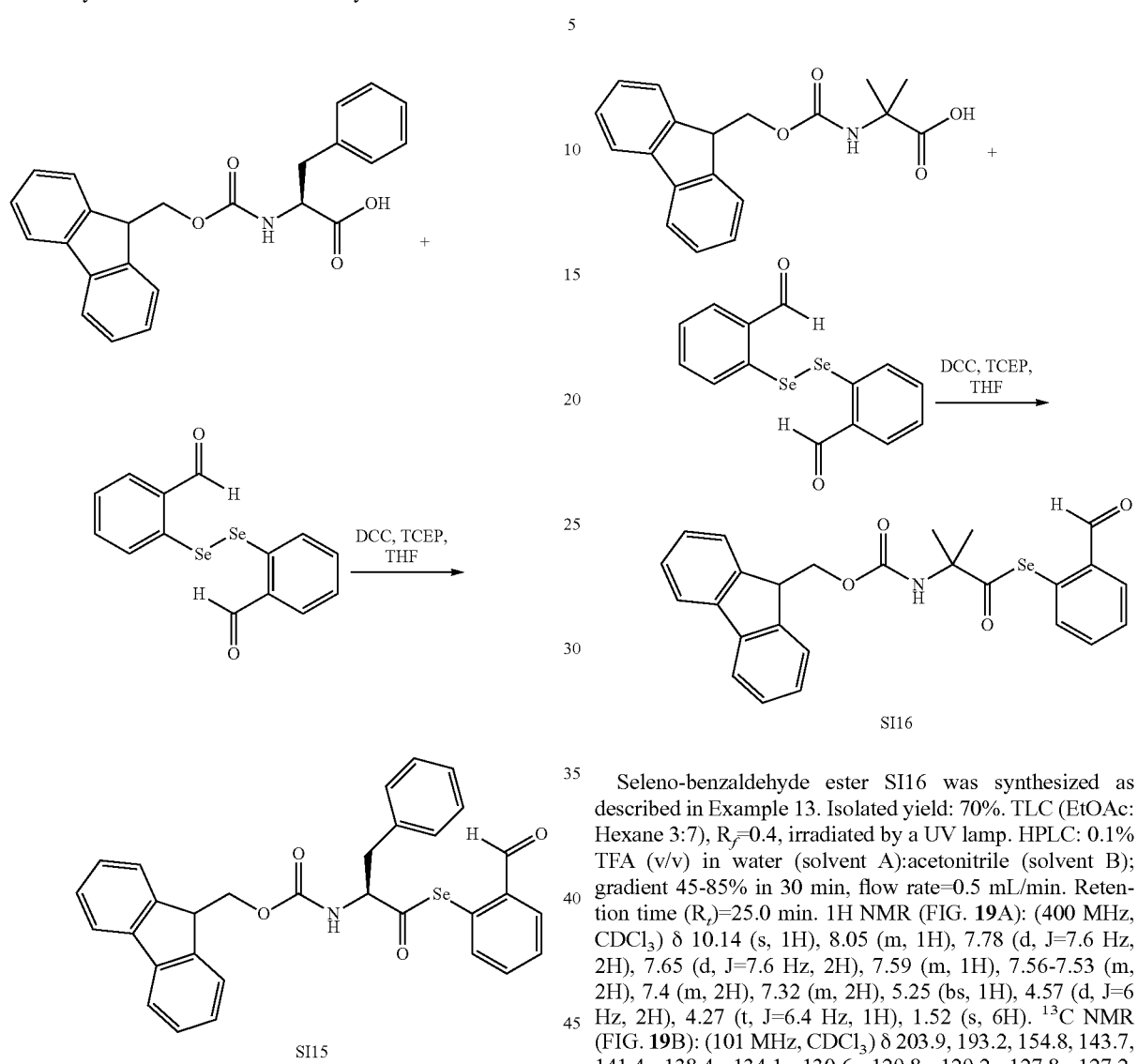

Figure 18A:
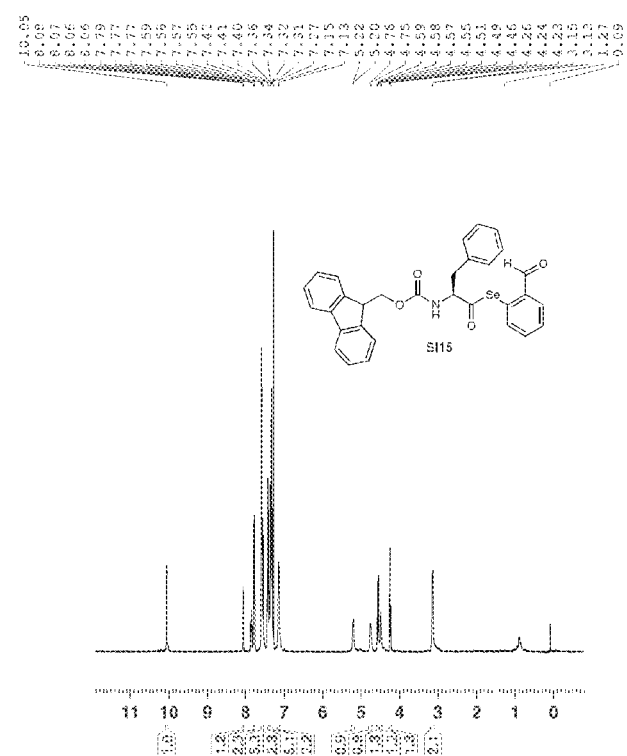
FIGS. 18A-B show $^1$H-NMR and $^{13}$C-NMR spectra of peptide SI15 in CDCl$_3$.
Figure 18B:
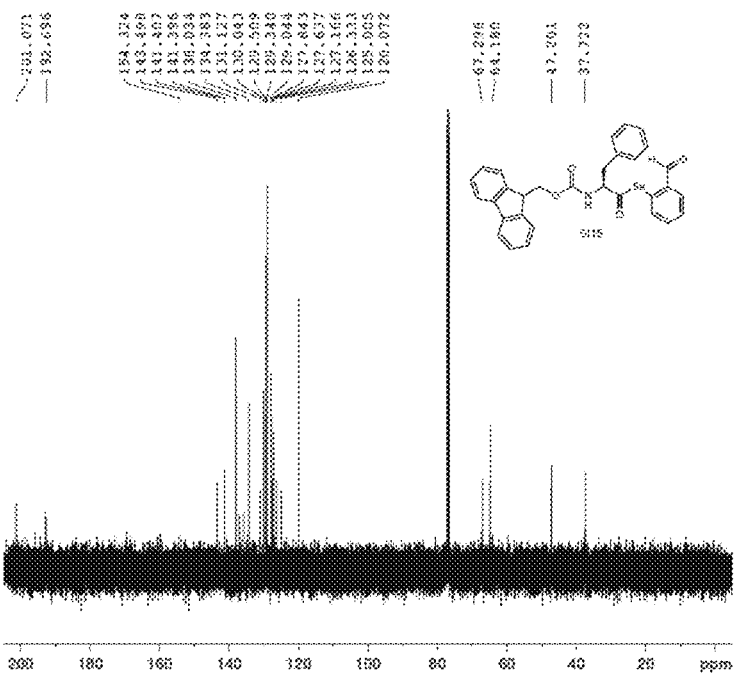

Seleno-benzaldehyde ester SI15 was synthesized as described in Example 13. Isolated yield: 63%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=27.2 min. 1H NMR (FIG. 18A): (400 MHz, CDCl$_3$) δ 10.05 (s, 1H), 8.06 (dd, J=6.4, 3.2 Hz, 1H), 7.78 (m, 2H), 7.59-7.55 (m, 5H), 7.42-7.40 (m, 2H), 7.35-7.30 (m, 5H), 7.14 (d, J=6.4 Hz, 2H), 5.21 (d, J=7.6 Hz, 1H), 4.75 (m, 1H), 4.59-4.51 (m, 1H), 4.48 (m, 1H), 4.24 (m, 1H), 3.14 (d, J=5.2 Hz, 2H). $^{13}$C NMR (FIG. 18B): (101 MHz, CDCl$_3$) δ 201.1, 192.7, 154.3, 143.5, 141.4, 138.0, 134.4, 131.1, 130.0, 129.5, 129.3, 129.0, 127.8, 127.6, 127.2, 126.3, 125.0, 120.1, 67.3, 64.2, 47.2, 37.7. $^{77}$Se NMR: (CDCl$_3$) δ 611.009. HRMS: exact mass calcd. for C$_{31}$H$_{25}$NO$_4$Se [M+Na]$^+$ 578.0841. found 578.0855. FT-IR: 1724.45 cm$^{-1}$, 1695.82 cm$^{-1}$.

Example 27

Synthesis of Seleno-Benzaldehyde Ester SI16

Figure 19A:
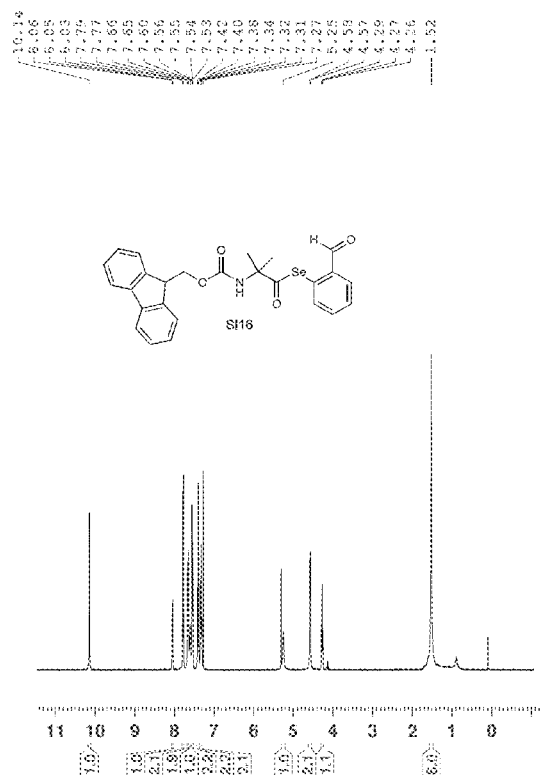
FIGS. 19A-B show $^1$H-NMR and $^{13}$C-NMR spectra of peptide SI16 in CDCl$_3$.
Figure 19B:
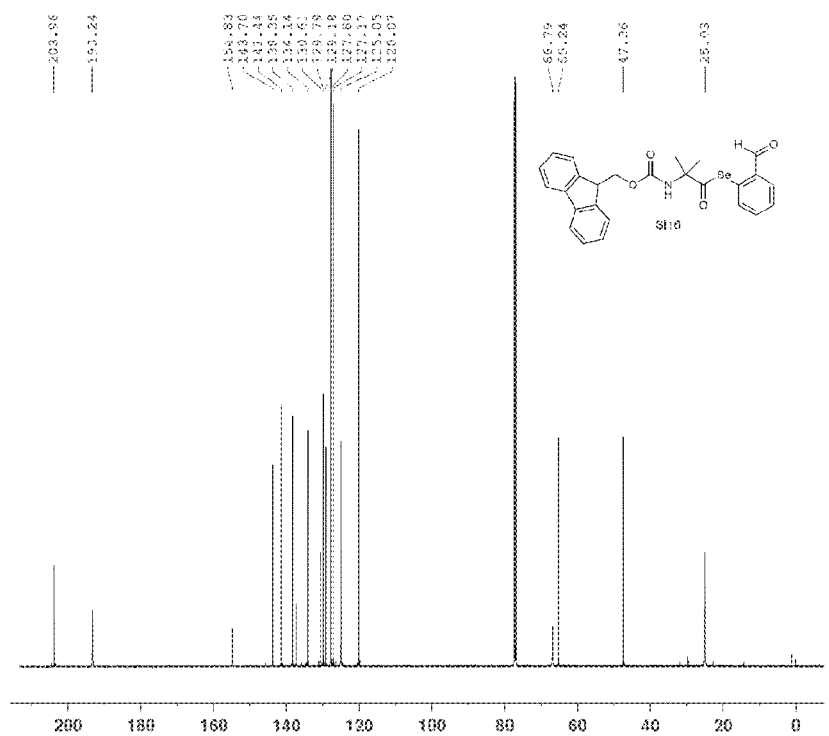

Seleno-benzaldehyde ester SI16 was synthesized as described in Example 13. Isolated yield: 70%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=25.0 min. 1H NMR (FIG. 19A): (400 MHz, CDCl$_3$) δ 10.14 (s, 1H), 8.05 (m, 1H), 7.78 (d, J=7.6 Hz, 2H), 7.65 (d, J=7.6 Hz, 2H), 7.59 (m, 1H), 7.56-7.53 (m, 2H), 7.4 (m, 2H), 7.32 (m, 2H), 5.25 (bs, 1H), 4.57 (d, J=6 Hz, 2H), 4.27 (t, J=6.4 Hz, 1H), 1.52 (s, 6H). $^{13}$C NMR (FIG. 19B): (101 MHz, CDCl$_3$) δ 203.9, 193.2, 154.8, 143.7, 141.4, 138.4, 134.1, 130.6, 129.8, 129.2, 127.8, 127.2, 125.1, 120.1, 66.8, 65.2, 47.4, 25.0. $^{77}$Se NMR: (CDCl$_3$) δ 570.771. HRMS: exact mass calcd. for C$_{26}$H$_{23}$NO$_4$Se [M+Na]$^+$ 516.0685. found 516.0699. FT-IR: 1728.45 cm$^{-1}$, 1694.40 cm$^{-1}$.

Example 28

Synthesis of Seleno-Benzaldehyde Ester SI17

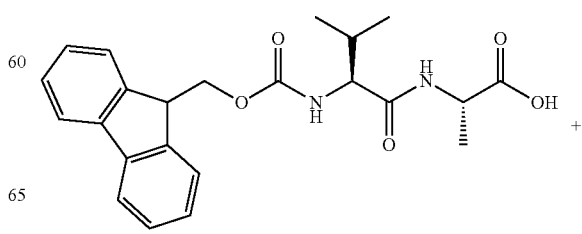

41
-continued

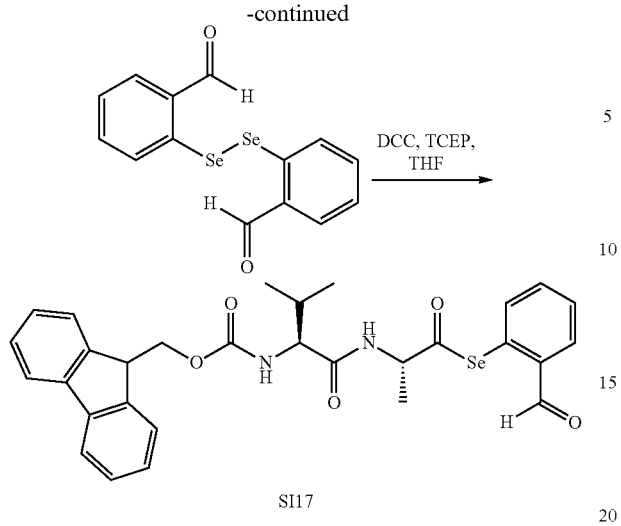

SI17

Figure 20A:
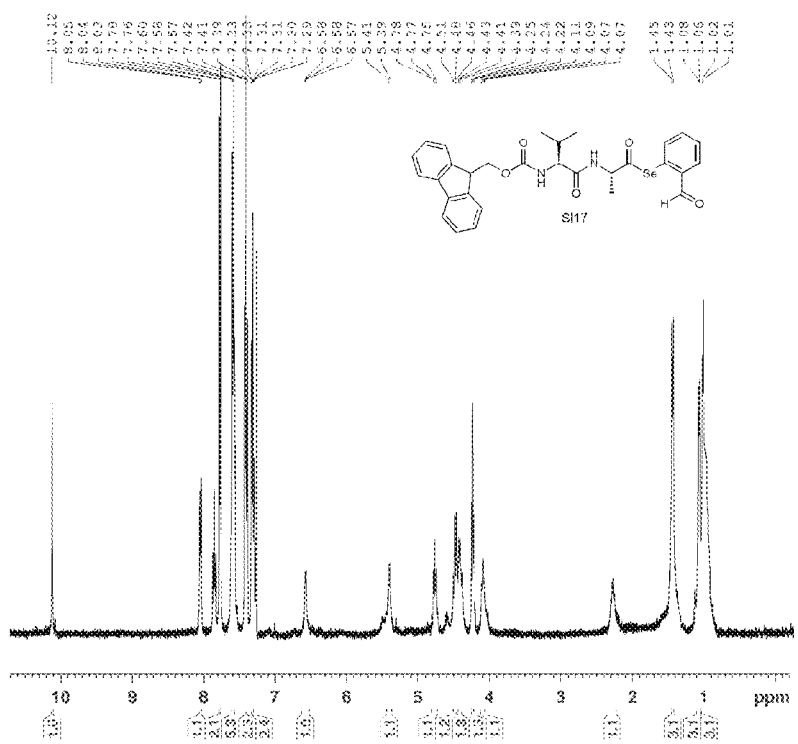
FIGS. 20A-B show $^1$H-NMR and $^{13}$C-NMR spectra of peptide SI17 in CDCl$_3$.
Figure 20B:
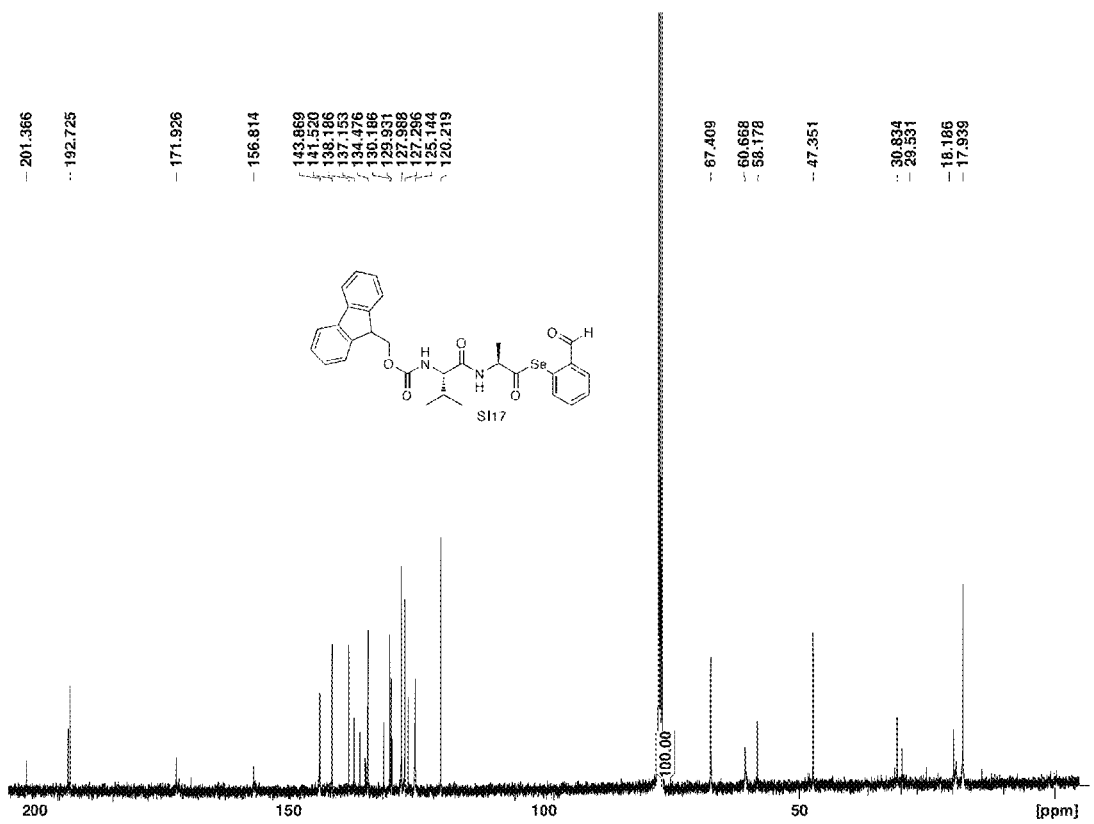

Seleno-benzaldehyde ester SI17 was synthesized as described in Example 13. Isolated yield: 55%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=23.2 min. 1H NMR (FIG. 20A): (400 MHz, CDCl$_3$) δ 10.12 (s, 1H), 8.04 (m, 1H), 7.77 (d, J=7.2 Hz, 2H), 7.60-7.55 (m, 5H), 7.41 (m, 2H), 7.31 (m, 2H), 6.58 (m, 1H), 5.40 (m, 1H), 4.77 (m, 1H), 4.48 (m, 1H), 4.41 (m, 1H), 4.24 (m, 1H), 4.09 (m, 1H), 2.25 (m, 1H), 1.43 (d, J=7.2 Hz, 3H), 1.06 (d, J=6.4 Hz, 3H), 1.01 (d, J=6.4 Hz, 3H). $^{13}$C NMR (FIG. 20B): (101 MHz, CDCl$_3$) δ 201.4, 192.7, 171.9, 156.8, 143.8, 141.5, 138.2, 137.2, 134.5, 130.2, 129.9, 127.9, 127.3, 125.1, 120.2, 67.4, 60.7, 58.2, 47.3, 30.8, 17.9. $^{77}$Se NMR: (CDCl$_3$) δ 583.803. HRMS: exact mass calcd. for C$_{30}$H$_{30}$N$_2$O$_5$Se [M+Na]$^+$ 601.0952. found 601.1240. FT-IR: 1729.82 cm$^{-1}$, 1722.02 cm$^{-1}$, 1702.39 cm$^{-1}$, 1684.29 cm$^{-1}$.

Example 29

Synthesis of Seleno-Benzaldehyde Ester SI18

42
-continued

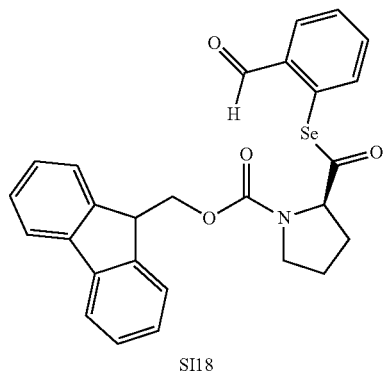

SI18

Figure 21A:
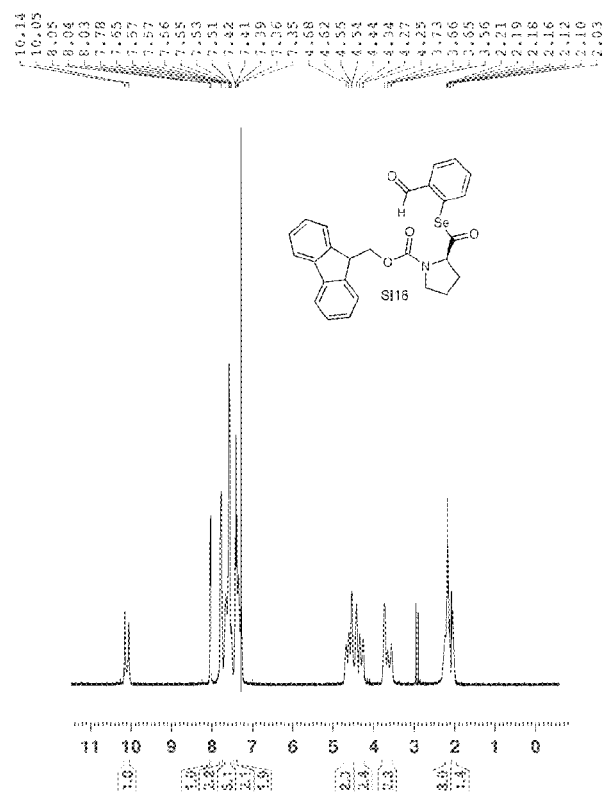
FIGS. 21A-B show $^1$H-NMR and $^{13}$C-NMR spectra of peptide SI18 in CDCl$_3$.
Figure 21B:
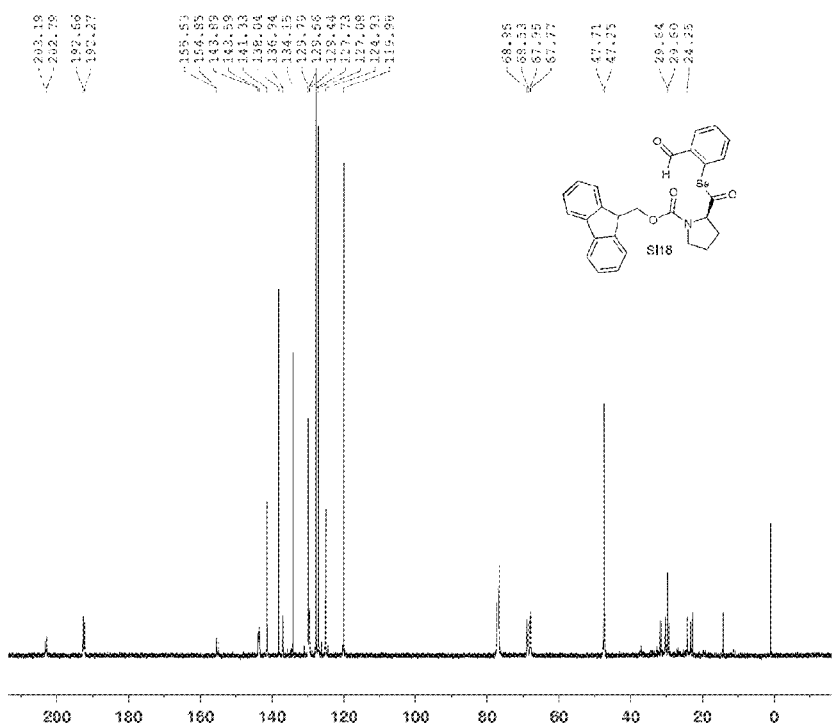

Seleno-benzaldehyde ester SI18 was synthesized as described in Example 13. Isolated yield: 67%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=26.1 min. 1H NMR (FIG. 21A): (400 MHz, CDCl$_3$) δ 10.10 (s, 1H), 8.04 (m, 1H), 7.78 (m, 2H), 7.65-7.51 (m, 5H), 7.41 (m, 2H), 7.35 (m, 2H), 4.68-4.54 (m, 2H), 4.44-4.25 (m, 2H), 3.74-3.56 (m, 2H), 2.21-2.10 (m, 3H), 2.03 (m, 1H). $^{13}$C NMR (FIG. 21B): (101 MHz, CDCl$_3$) δ 203.2, 202.8, 192.7, 192.3, 155.5, 154.8, 143.8, 141.3, 138.0, 136.9, 134.1, 129.8, 129.5, 127.7, 127.1, 124.9, 119.9, 68.9, 68.5, 67.9, 67.8, 47.7, 47.3, 29.6, 24.3. $^{77}$Se NMR: (CDCl$_3$) δ 603.608, 601.790. HRMS: exact mass calcd. for C$_{27}$H$_{23}$NO$_4$Se [M+Na]$^+$ 528.0685. found 528.0719. FT-IR: 1715.89 cm$^{-1}$, 1699.00 cm$^{-1}$, 1719.55 cm$^{-1}$.

Example 30

Synthesis of Fmoc-Proline Selenophenyl Ester SI18A

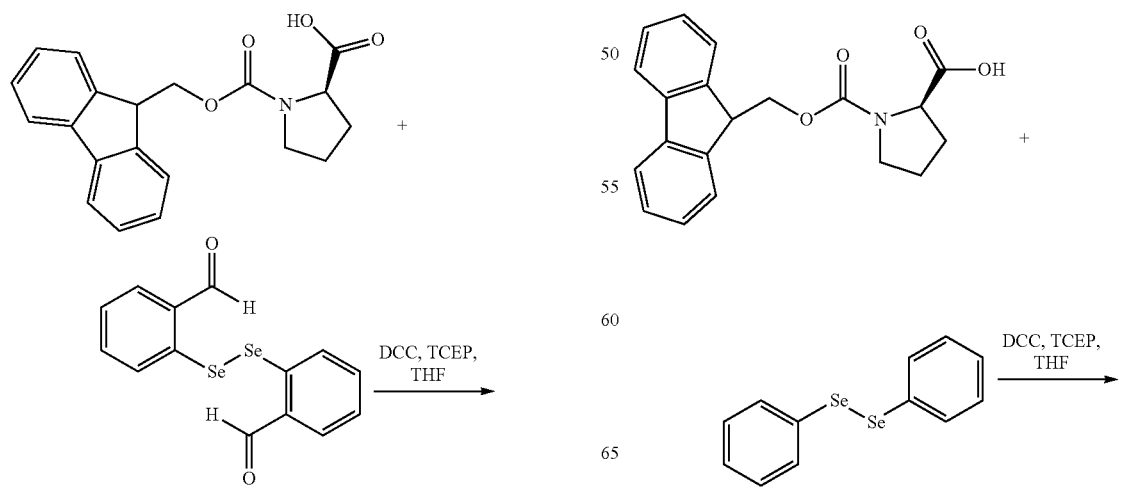

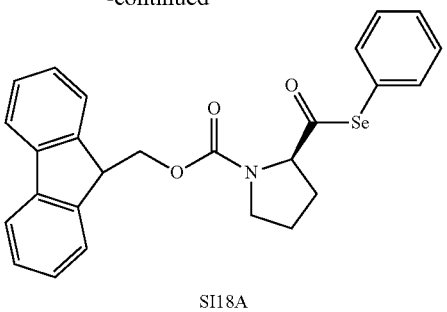

SI18A

Figure 22A:
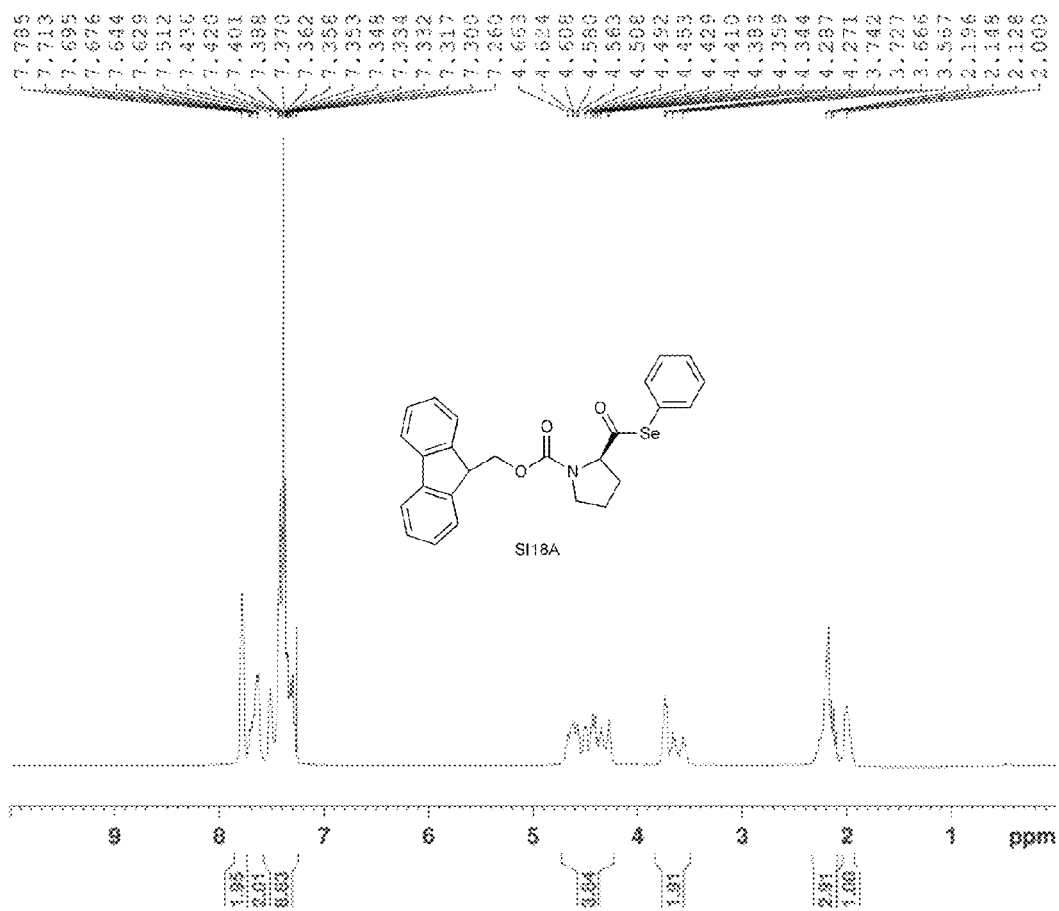
FIGS. 22A-B show $^1$H-NMR and $^{13}$C-NMR spectra of peptide SI18A in CDCl$_3$.
Figure 22B:
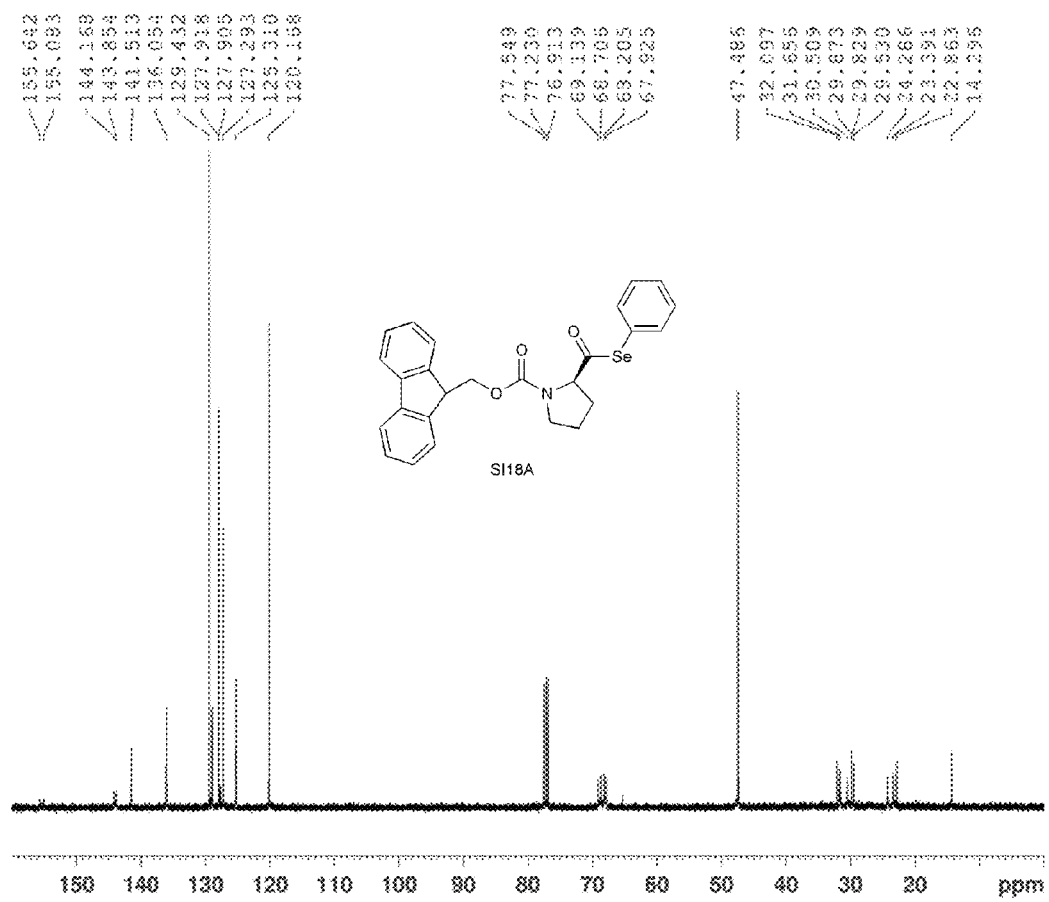

Fmoc-proline selenophenylester SI18A was synthesized as described in Example 13. Isolated yield: 66%. TLC (EtOAc:Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=23.4 min. $^1$H NMR (FIG. 22A): (400 MHz, CDCl$_3$) δ 7.78 (m, 2H), 7.68 (m, 2H), 7.51-7.26 (m, 9H), 4.66-4.27 (m, 4H), 3.74-3.57 (m, 2H), 2.19-2.13 (m, 3H), 2.00 (m, 1H). $^{13}$C NMR (FIG. 22B): (101 MHz, CDCl$_3$) 155.6, 155.1, 144.1, 143.8, 141.5, 136.0, 129.4, 127.9, 127.3, 125.3, 120.2, 69.1, 68.7, 68.2, 67.9, 47.5, 31.7, 29.8, 24.3, 23.4, 22.9. $^{77}$Se NMR: (CDCl$_3$) δ 622.1, 658.5. HRMS: exact mass calcd. for C$_{26}$H$_{23}$NO$_3$Se [M+Na]$^+$ 500.0843. found 500.0723. FT-IR: 1705.61 cm$^{-1}$.

Example 31

Synthesis of Seleno-Benzaldehyde Ester SI19

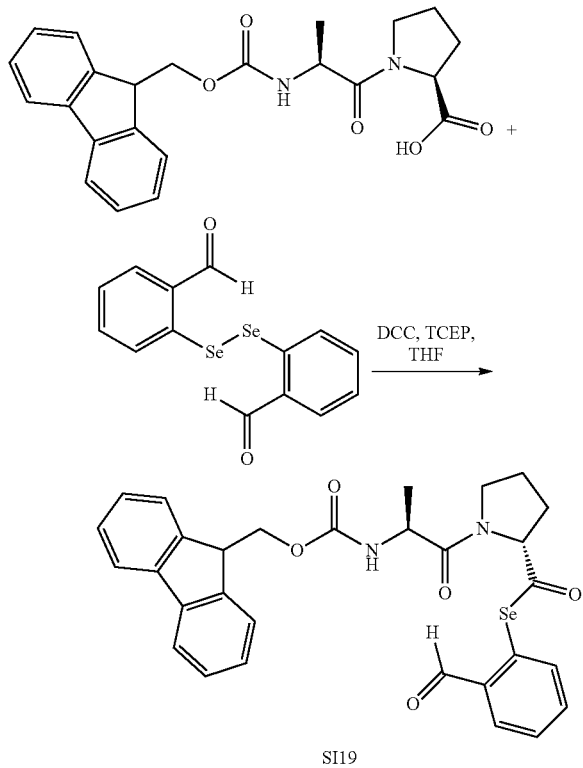

SI19

Figure 23A:
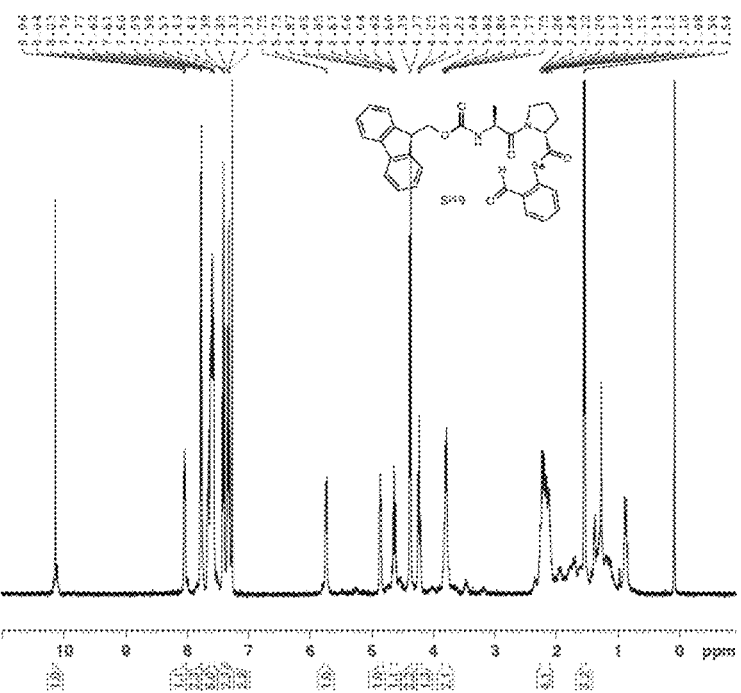
FIGS. 23A-B show $^1$H-NMR and $^{13}$C-NMR spectra of peptide SI19 in CDCl$_3$.
Figure 23B:
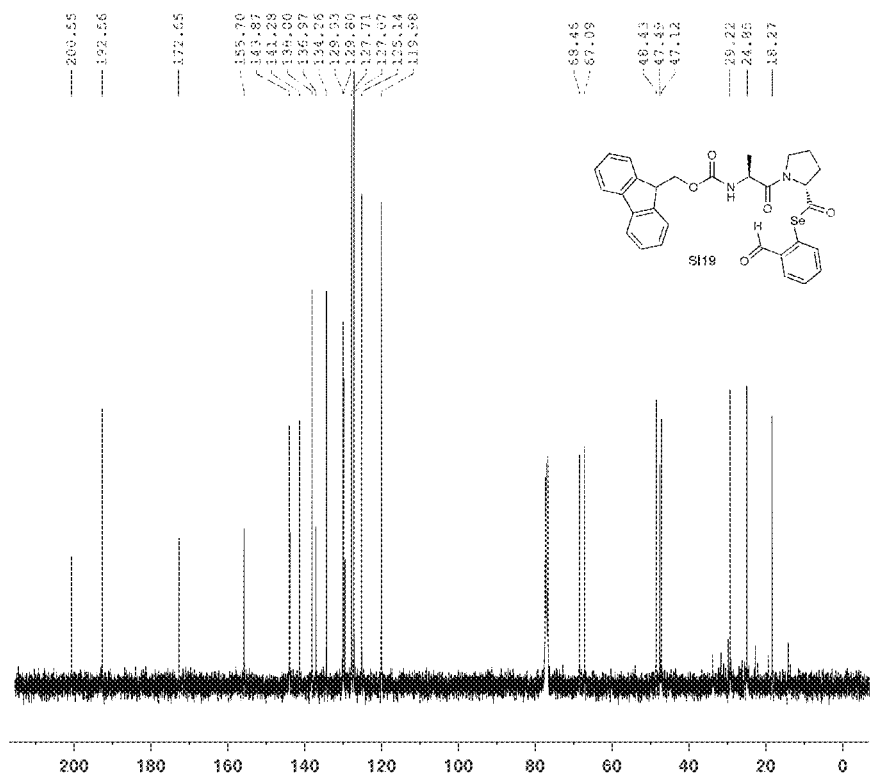

Seleno-benzaldehyde ester SI19 was synthesized as described in Example 13. Isolated yield: 56%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=21.9 min. 1H NMR (FIG. 23A): (400 MHz, CDCl$_3$) δ 10.14 (s, 1H), 8.04 (m, 1H), 7.77 (d, J=7.20 Hz, 2H), 7.60 (m, 5H), 7.41 (m, 2H), 7.33 (m, 2H), 5.73 (d, J=8 Hz, 1H), 4.85 (m, 1H), 4.64 (m, 1H), 4.37 (d, J=7.2 Hz, 2H), 4.23 (t, J=7.2 Hz, 1H), 3.79 (m, 2H), 2.19 (m, 4H), 1.54 (d, J=6.8 Hz, 3H). $^{13}$C NMR (FIG. 23B): (101 MHz, CDCl$_3$) δ 200.5, 192.6, 172.6, 155.7, 143.9, 141.3, 138.0, 136.9, 134.3, 129.9, 129.8, 127.7, 127.1, 125.1, 120.0, 68.5, 67.1, 48.4, 47.5, 47.1, 29.2, 24.8, 18.3. $^{77}$Se NMR (CDCl$_3$) δ 590.64. HRMS exact mass calcd. for C$_{30}$H$_{28}$N$_2$O$_5$Se [M+Na]$^+$ 599.1058. found 599.1063. FT-IR 1717.07 cm$^{-1}$, 1697.06 cm$^{-1}$, 1653.30 cm$^{-1}$.

Example 32

Synthesis of Seleno-Benzaldehyde Ester SI20

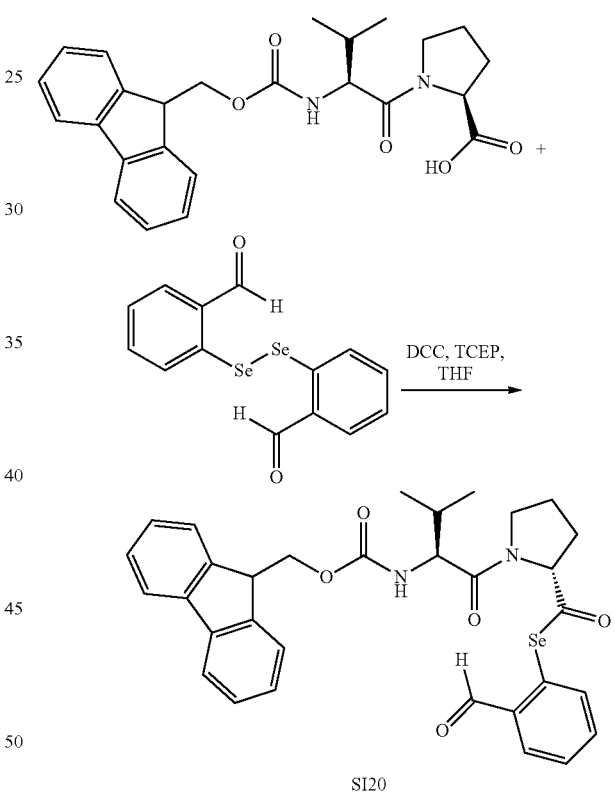

SI20

Figure 24A:
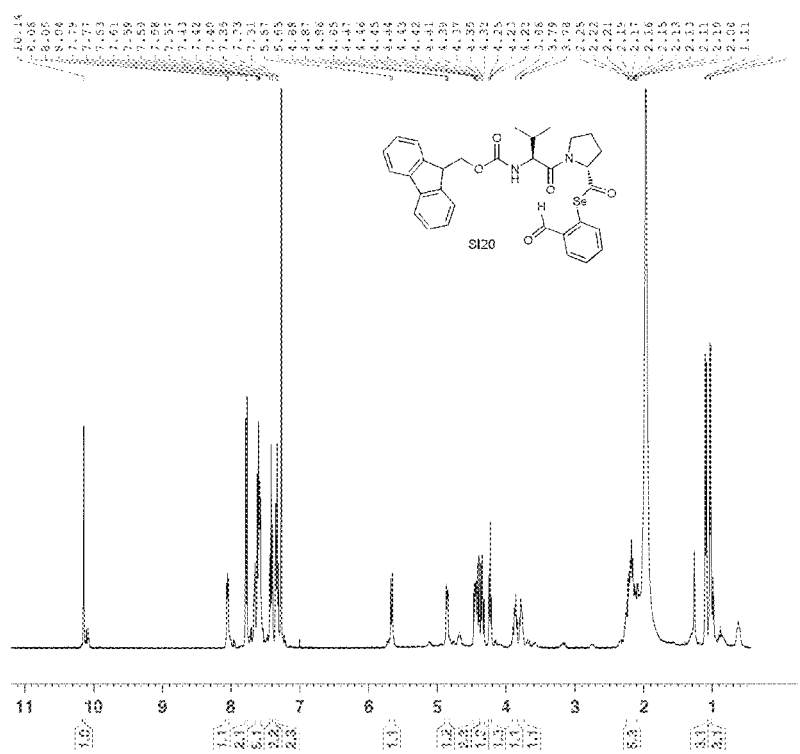
FIGS. 24A-B show $^1$H-NMR and $^{13}$C-NMR spectra of peptide SI20 in CDCl$_3$.
Figure 24B:
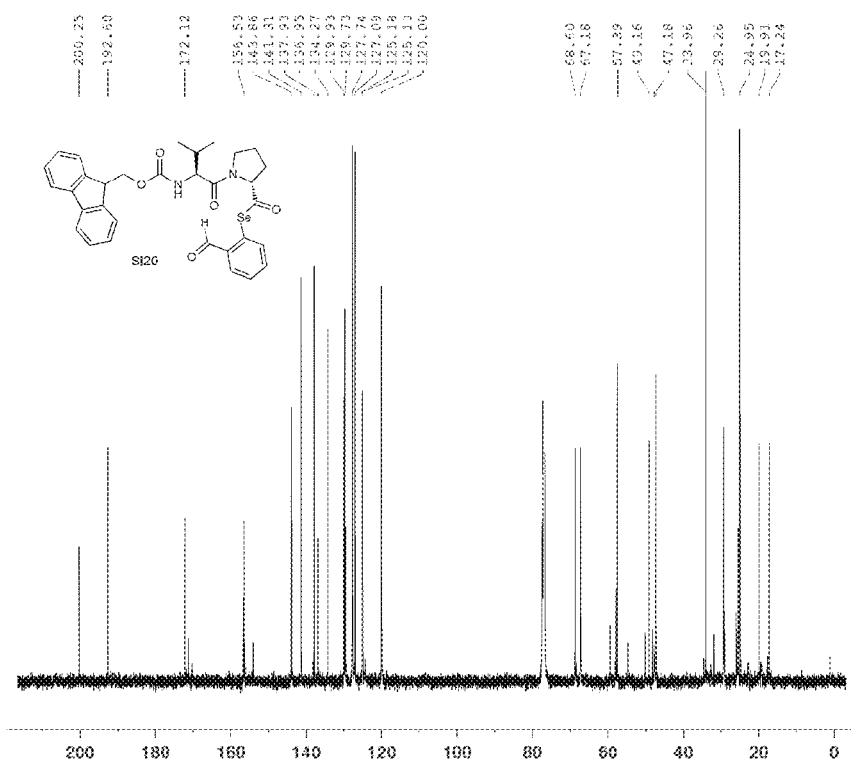

Seleno-benzaldehyde ester SI20 was synthesized as described in Example 13. Isolated yield: 59%. TLC (EtOAc: Hexane 3:7), $R_f$=0.4, irradiated by a UV lamp. HPLC: 0.1% TFA (v/v) in water (solvent A):acetonitrile (solvent B); gradient 45-85% in 30 min, flow rate=0.5 mL/min. Retention time ($R_t$)=26.1 min. 1H NMR (FIG. 24A): (400 MHz, CDCl$_3$) δ 10.14 (s, 1H), 8.05 (m, 1H), 7.77 (d, J=7.6 Hz, 2H), 7.63-7.57 (m, 5H), 7.41 (m, 2H), 7.33 (m, 2H), 5.66 (d, J=9.20 Hz, 1H), 4.86 (dd, J=8.0, 3.6 Hz, 1H), 4.44 (m, 2H), 4.34 (m, 1H), 4.23 (t, J=6.8 Hz, 1H), 3.88 (m, 1H), 3.78 (m, 1H), 2.25-2.09 (m, 5H) 1.10 (d, J=6.8 Hz, 3H), 1.03 (d, J=6.8 Hz, 3H). $^{13}$C NMR (FIG. 24B): (101 MHz, CDCl$_3$) δ 200.3, 192.6, 172.1, 156.5, 143.9, 141.3, 137.9, 136.9, 134.3, 129.9, 129.7, 127.7, 127.1, 125.1, 120.0, 68.6, 67.2, 57.4, 49.2, 47.2, 33.9, 29.3, 24.9, 19.9, 17.2. $^{77}$Se NMR (CDCl$_3$) δ 588.51. HRMS: exact mass calcd. for C$_{32}$H$_{32}$N$_2$O$_5$Se [M+Na]$^+$ 627.1371. found 627.1363. FT-IR 1716.02 cm$^{-1}$, 1696.41 cm$^{-1}$, 1653.37 cm$^{-1}$.

Example 33

Synthesis of Seleno-Benzaldehyde Ester SI20A

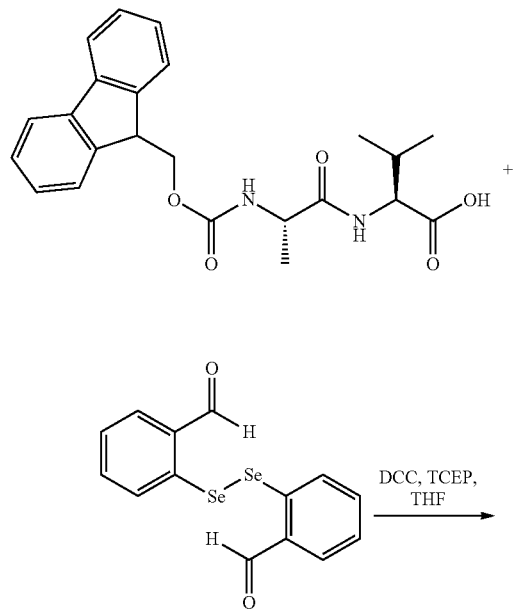

Figure 25A:
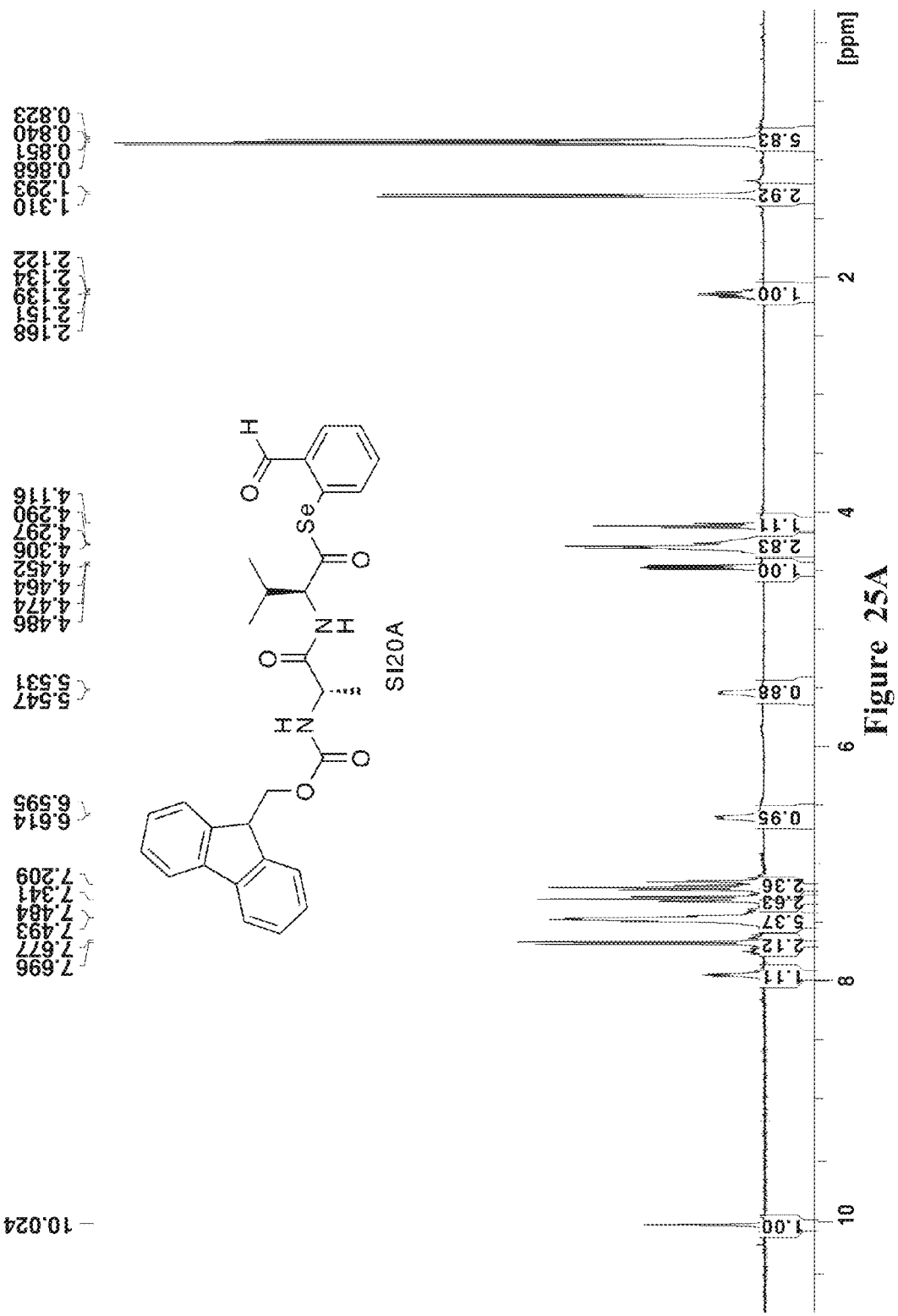
FIGS. 25A-B show $^1$H-NMR and $^{13}$C-NMR spectra of peptide SI20A in CDCl$_3$.
Figure 25B:
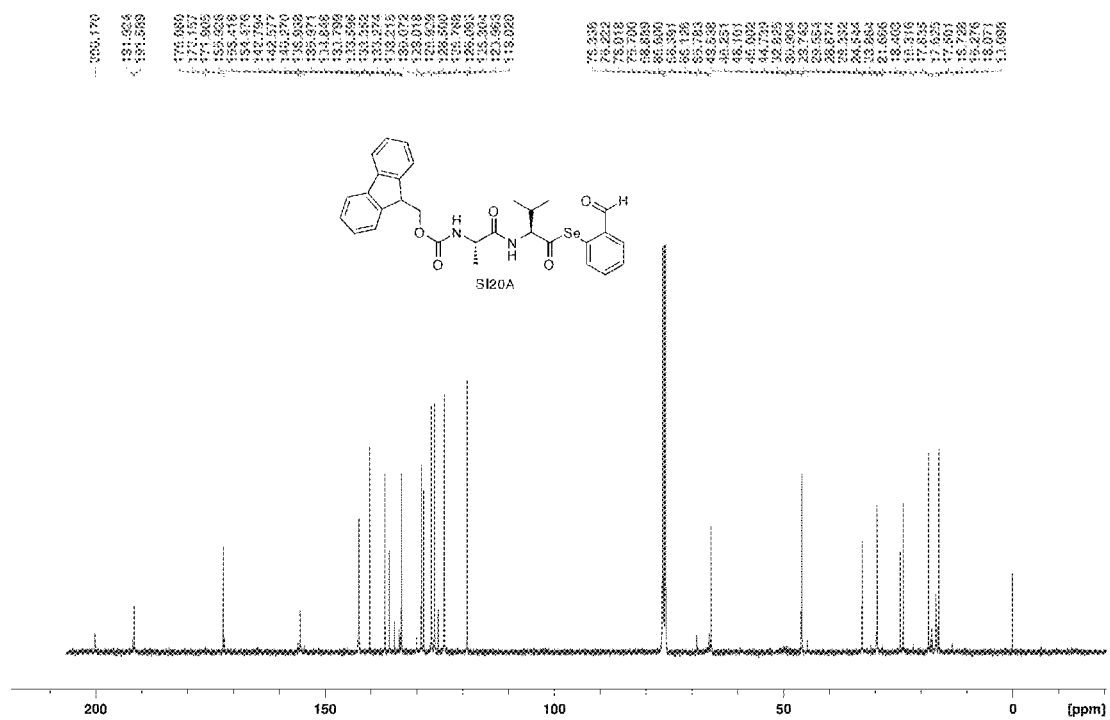

Seleno-benzaldehyde ester SI20A was synthesized as described in Example 13. Isolated yield: 58%. TLC (EtOAc:Hexane 3:7), R$_f$=0.4, irradiated by a UV lamp. H NMR (FIG. 25A): (400 MHz, CDCl$_3$) δ 10.02 (s, 1H), 7.98 (m, 1H), 7.68 UV lamp. $^1$H NMR (FIG. 25A): (400 MHz, CDCl$_3$) δ 10.02 (s, 1H), 7.98 (m, 1H), 7.68 (d, J=7.6 Hz, 2H), 7.49-7.48 (m, 5H), 7.38 (m, 2H), 7.31 (m, 2H), 6.60 (m, 1H), 5.54 (m, 1H), 4.47 (m, 1H), 4.31-4.29 (m, 3H), 4.12 (m, 1H), 2.39 (m, 1H), 1.30 (d, J=6.8 Hz, 3H), 0.85 (d, J=6.8 Hz, 3H), 0.83 (d, J=6.8 Hz, 3H). $^{13}$C NMR (FIG. 25B): (101 MHz, CDCl$_3$) δ 200.2, 191.9, 176.1, 155.4, 142.7, 140.3, 136.9, 134.8, 133.2, 129.0, 128.9, 126.8, 126.1, 123.9, 119.0, 66.3, 46.1, 29.5, 23.8, 21.6, 18.4, 17.5, 16.7. $^{77}$Se NMR: (CDCl$_3$) δ 612.602. HRMS: exact mass calcd. for C$_{30}$H$_{30}$N$_2$O$_5$Se [M+Na]$^+$ 600.9152. found 601.3240. FT-IR: 1728.74 cm$^{-1}$, 1720.10 cm$^{-1}$, 1700.26 cm$^{-1}$, 1687.17 cm$^{-1}$.

Example 34

Synthesis of Succinimide Ester SI20B

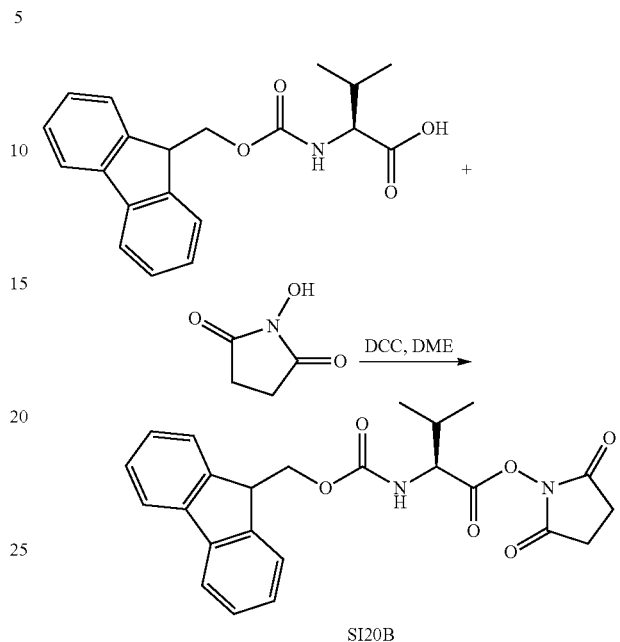

Figure 26A:
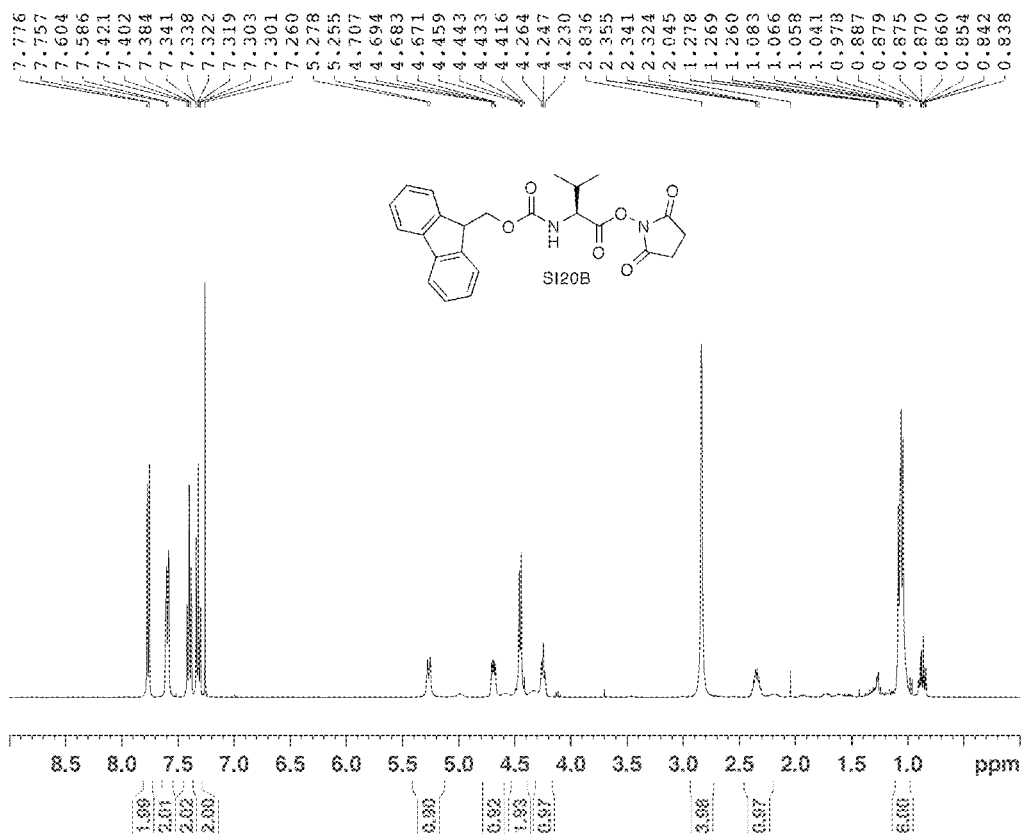
FIGS. 26A-B show $^1$H-NMR and $^{13}$C-NMR spectra of peptide SI20B in CDCl$_3$.
Figure 26B:
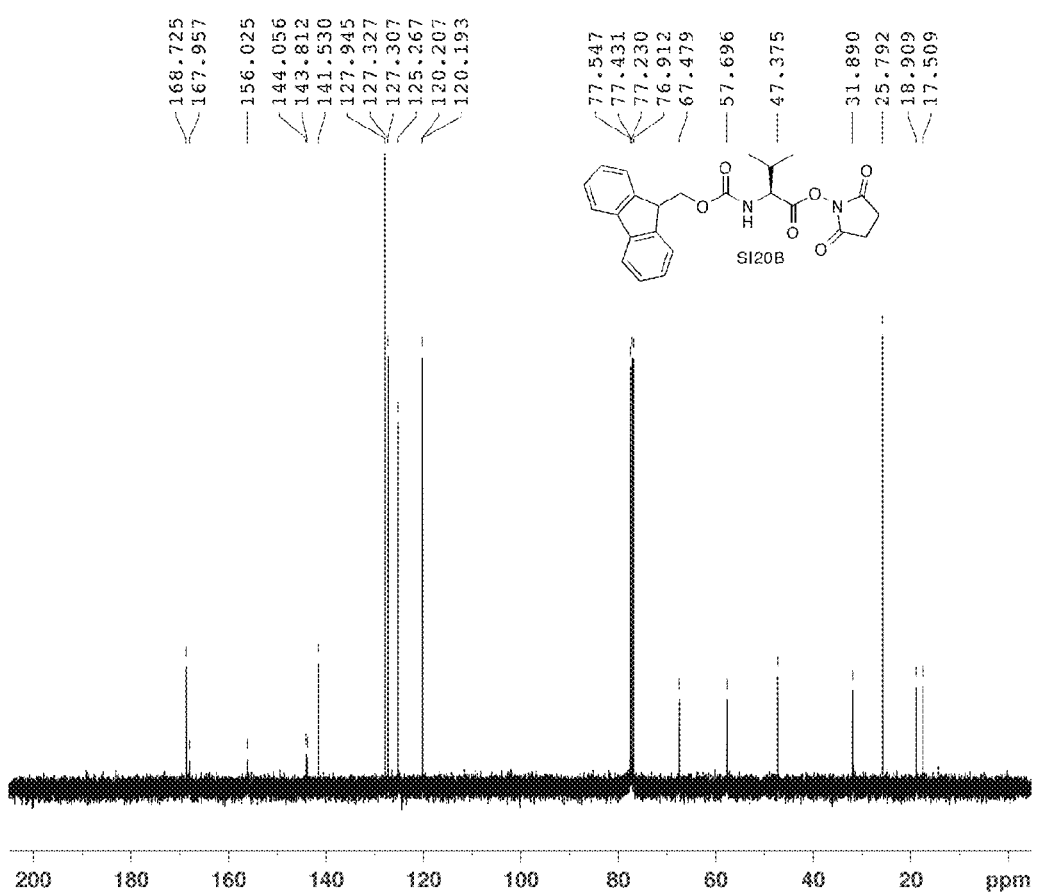

Fmoc-Valine (1.02 g, 3 mmol) and N-hydroxysuccinimide (0.345 g, 3 mmol) were dissolved in dimethoxy ethane (35 ml) and cooled in an ice bath, then DCC (0.681 g, 3.3 mmol) was added. The resulting mixture was stirred in the ice bath for 3 hours, then at room temperature for 20 hours. The precipitate formed was filtered off and the filtrate concentrated under vacuo. The crude product was further purified by flash chromatography (ethyl acetate/hexane, v:v, 4:6) to afford SI20B as a white solid. Isolated yield: 65%. TLC (EtOAc:Hexane 3:2). R$_f$=0.57, irradiated by a UV lamp. HPLC: 0.1% TFA (v/v) in water (solvent A):acetonitrile (solvent B); gradient 45-85% in 30 min, flow rate=0.5 mL/min. Retention time (R$_t$)=15.77 min. 1H NMR (FIG. 26A): (400 MHz, CDCl$_3$) δ 7.76-7.78 (d, J=7.20 Hz, 2H), 7.59-7.60 (d, J=7.20 Hz, 2H), 7.38-7.42 (t, J=7.20 Hz, 2H), 7.30-7.34 (m, 2H), 5.26-5.28 (d, J=9.20 Hz, 1H), 4.67-4.71 (dd, J=4.8, 5.2 Hz, 1H), 4.42-4.46 (dd, J=6.8, 6.4 Hz, 2H), 4.23-4.26 (t, J=6.8 Hz, 1H), 2.84 (s, 4H), 2.04-2.36 (m, 1H), 0.83-088 (m, 6H). $^{13}$C NMR (FIG. 26B): (101 MHz, CDCl$_3$) δ 168.7, 141.5, 127.9, 127.3, 127.3, 125.3, 120.2, 120.2, 67.5, 57.7, 47.4, 31.9, 25.8, 18.9, 17.5.

Example 35

Synthesis of Azodye Selenoester 10

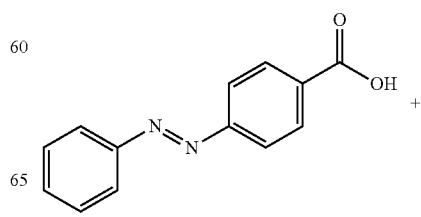

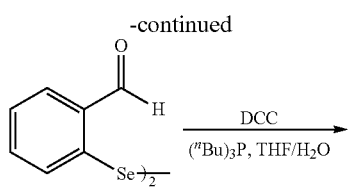

(125 MHz, CDCl$_3$) δ 193.0, 191.5, 156.0, 152.8, 139.1, 138.4, 137.4, 134.6, 132.3, 130.4, 130.0, 129.8, 129.5, 128.9, 123.6. HRMS: exact mass calcd. for C$_{20}$H$_{14}$N$_2$O$_2$Se [M+Na]$^+$ 417.0289. found 417.0114.

Example 36

Synthesis of Peptides SI21-SI43 Using Aldehyde Capture Ligation (ACL)

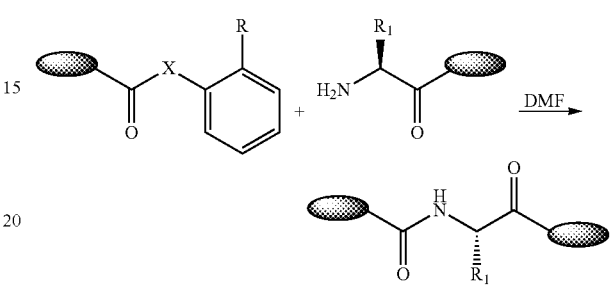

Figure 27A:
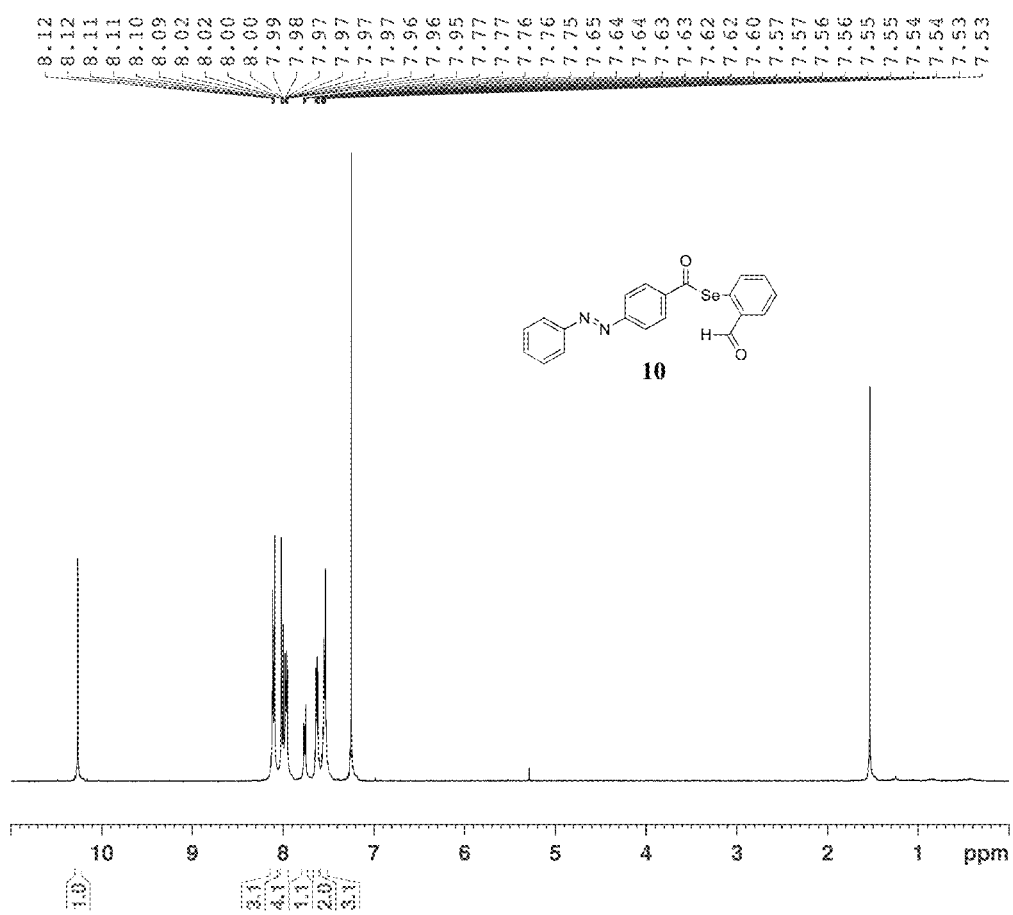
FIGS. 27A-B show $^1$H-NMR and $^{13}$C-NMR spectra of selenoester 10 in CDCl$_3$.
Figure 27B:
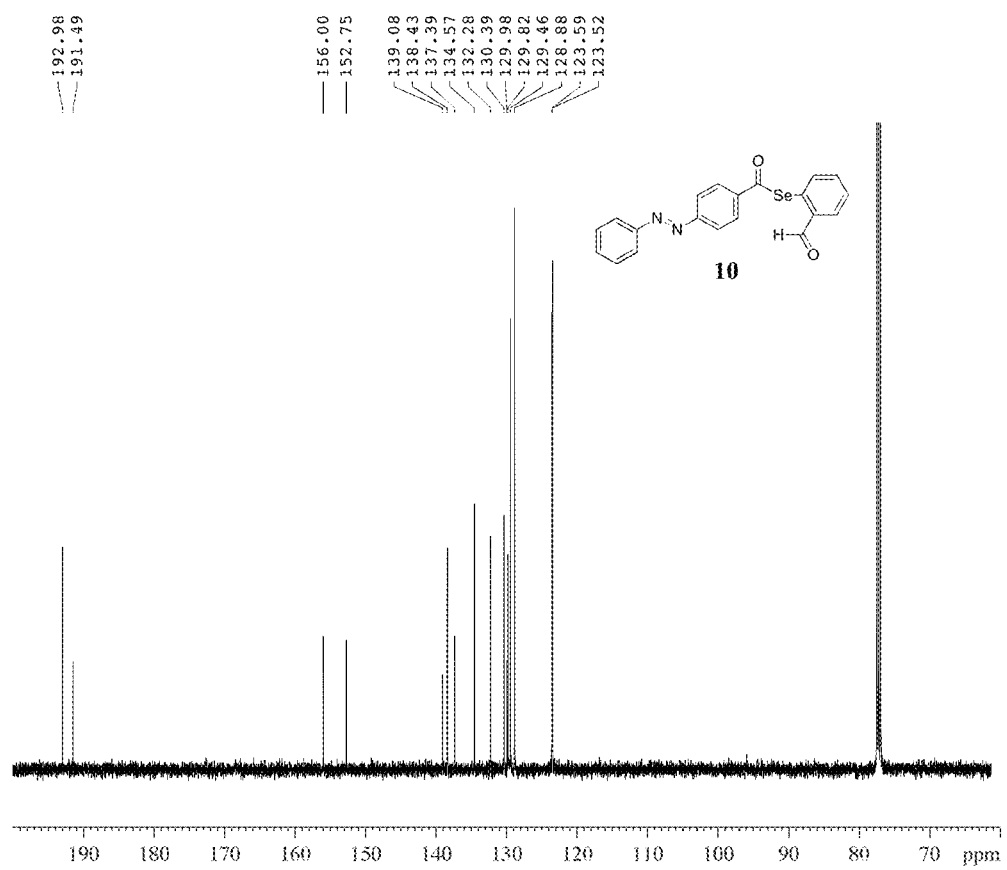

4-(Phenylazo)benzoic acid (67.8 mg, 0.3 mmol), DCC (61.8 mg, 0.3 mmol), and di-seleno benzaldehyde (55.1 mg, 0.15 mmol) in a 10 ml round bottom flask was flushed with nitrogen for 20 minutes. Dry THF (3 ml) was added and the mixture was stirred under nitrogen for 40 minutes. A solution of n-butyl phosphine (0.4 mmol) in 1.5 ml THF and 40 µl H$_2$O was added into the reaction mixture. The resulting mixture was stirred for another 1.5 hour, filtered, concentrated under vacuo, and purified by silica gel chromatography (15% ethyl acetate in hexane). The product obtained from chromatography still contained some impurities, which could be further purified by washing with hexane to afford pure 10 as a red solid (70.1 mg, 60%). Isolated yield: 60%. TLC (EtOAc:Hexane 1:5), R$_f$=0.57, irradiated by a UV lamp. $^1$H NMR (FIG. 27A): (400 MHz, CDCl$_3$) δ10.27 (s, 1H), 8.12-8.10 (m, 3H), 8.05-7.95 (m, 4H), 7.76 (m, 1H), 7.65-7.60 (m, 2H), 7.57-7.53 (m, 3H). $^{13}$C NMR (FIG. 27B):

To a solution of C-terminal amino acid or peptide-oxo, thio, or seleno ester (2-10 µmol) in 1 mL DMF, was added N-terminal amino acid or peptide (20 µmol) and Et$_3$N (20 µmol). The reaction was stirred at 22° C. and monitored by analytical HPLC at regular intervals. The reaction mixture was lyophilized, or concentrated under vacuum, and purified by HPLC. HPLC: 0.1% TFA (v/v) in water (solvent A):acetonitrile (solvent B); gradient 45-85% in 30 min, flow rate=0.5 mL/min, detection wavelength 280 nm. This procedure was used to synthesize the peptides shown in Table 1 below.

TABLE 1

Ligation Products (see indicated figure for HPLC traces)

Figure 28:
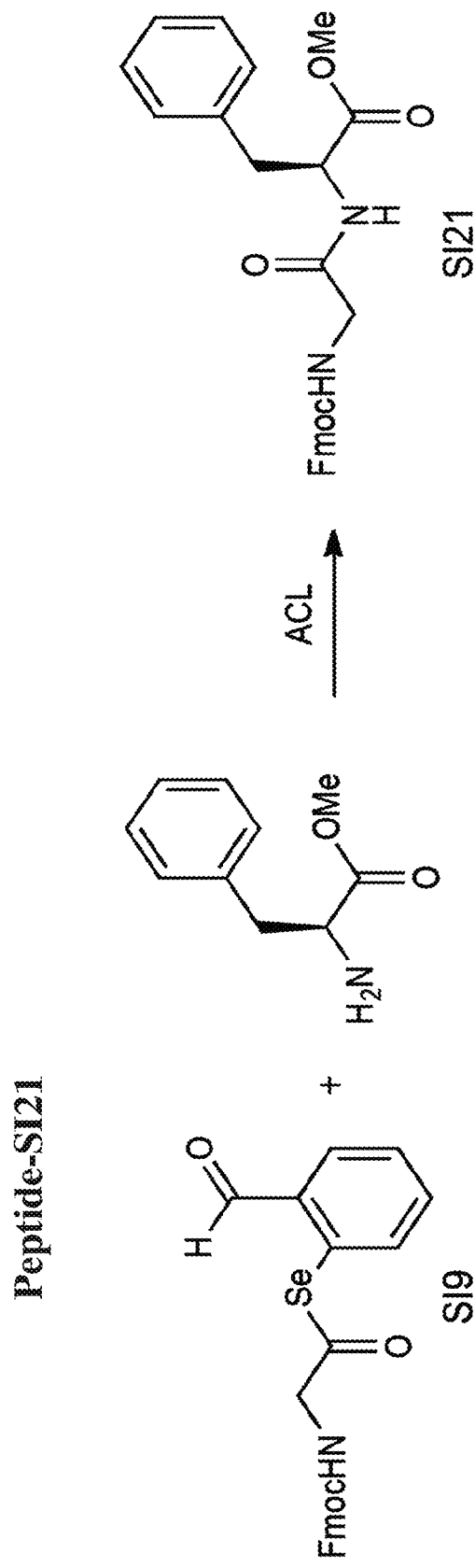
FIG. 28 shows HPLC spectra of the starting material and the crude reaction mixture of peptide SI21 after 2 min of incubation; the product peak is labeled.
Figure 28:
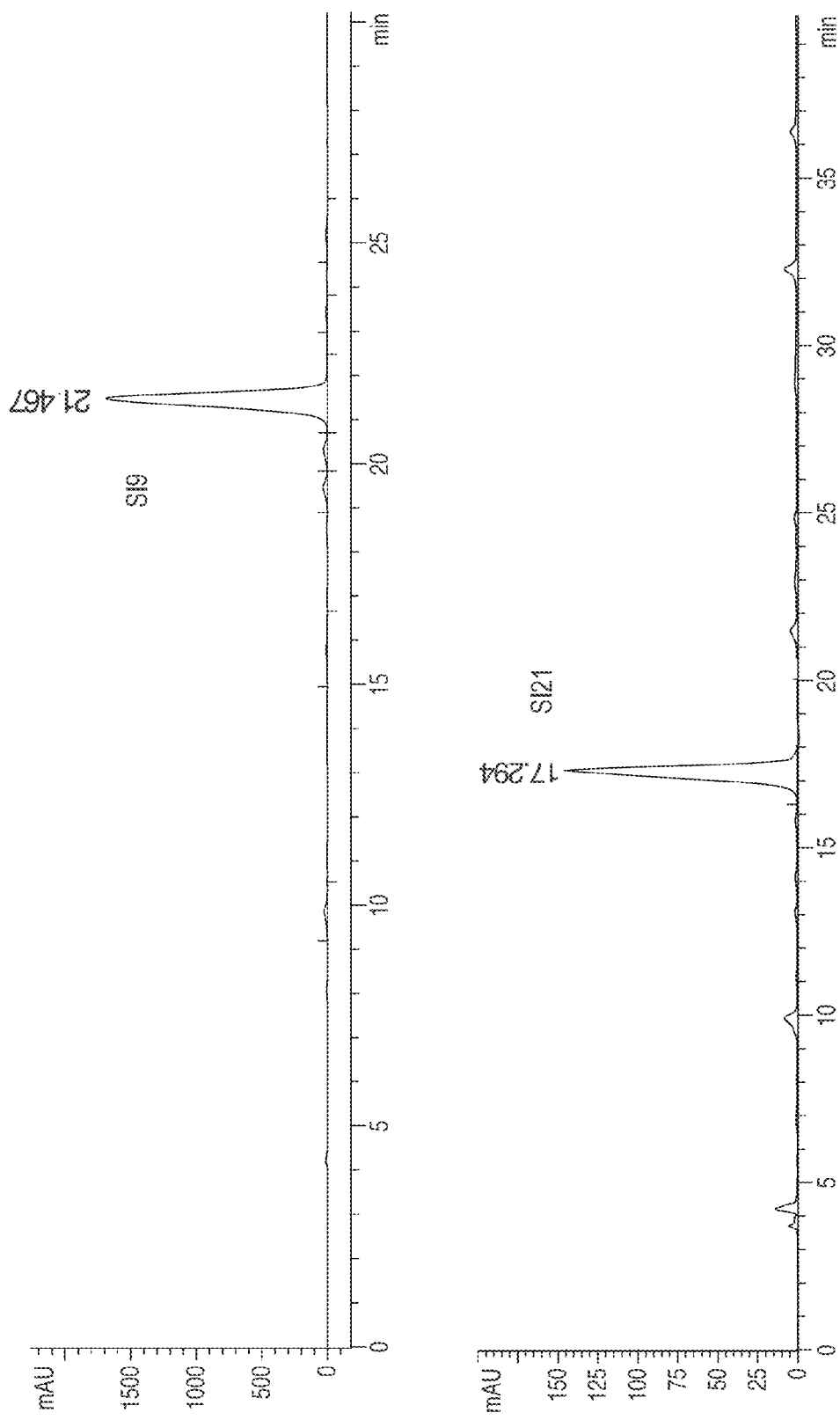
Figure 29:
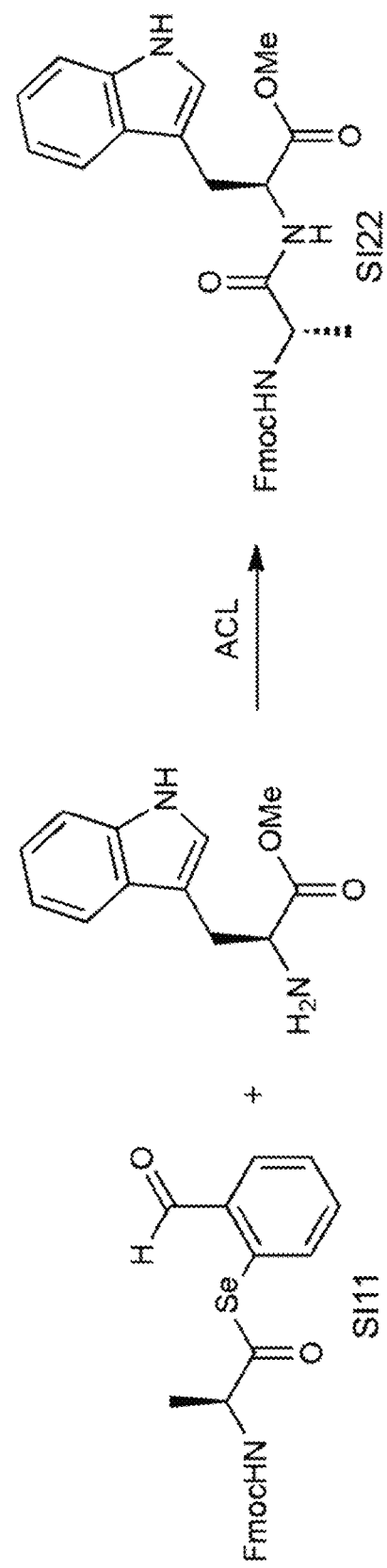
FIG. 29 shows HPLC spectra of the starting material and the crude reaction mixture of peptide SI22/5 after 2 min of incubation; the product peak is labeled.
Figure 29:
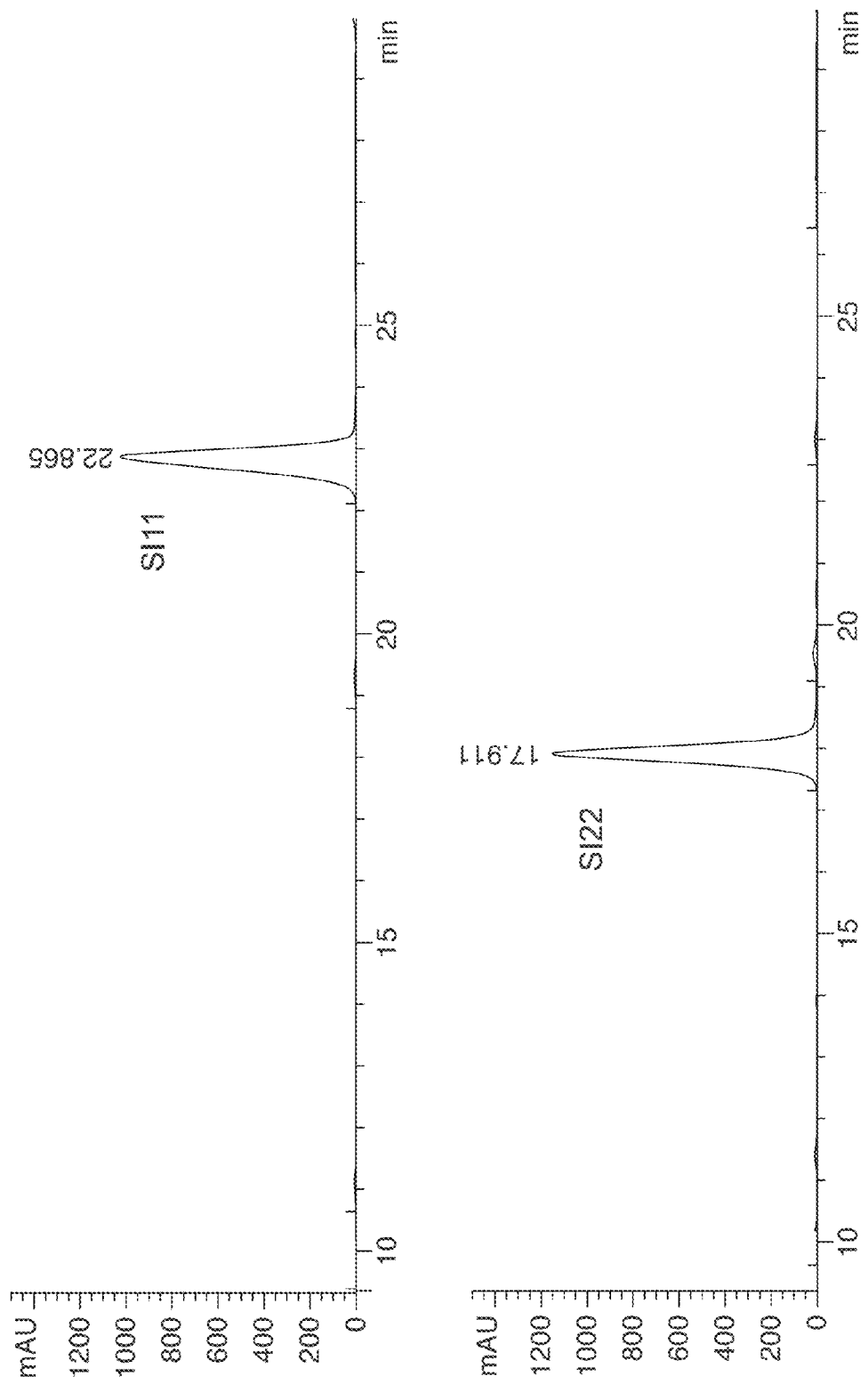

| Peptide | HPLC Trace(s) |
| --- | --- |
| 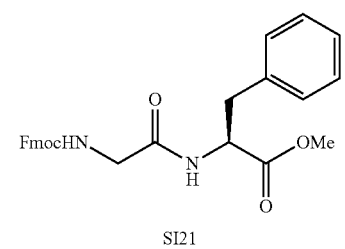<br>SI21 | FIG. 28 |
| 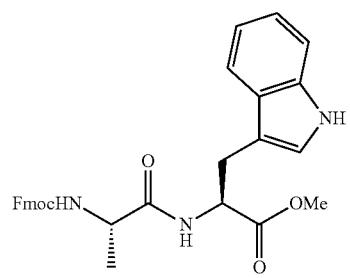<br>SI22<br>(also referred to as 5 herein) | FIG. 29 |

Figure 30:
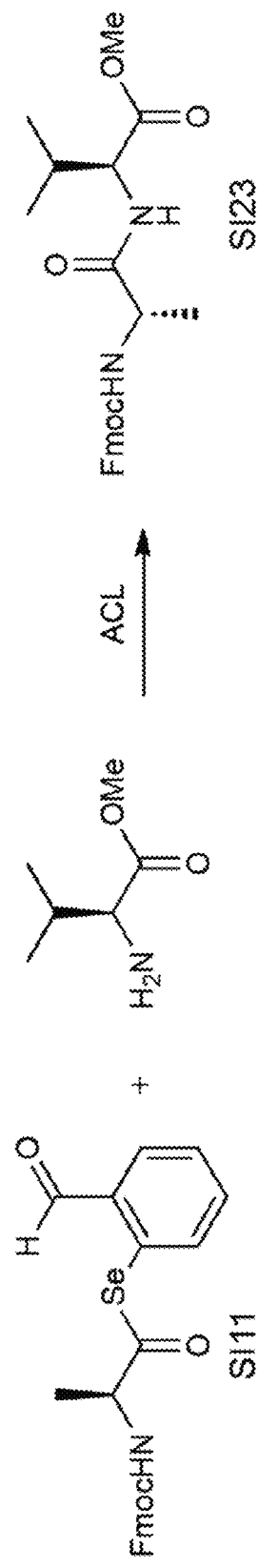
FIG. 30 shows HPLC spectra of the starting material and the crude reaction mixture of peptide SI23 after 2 min of incubation; the product peak is labeled.
Figure 31:
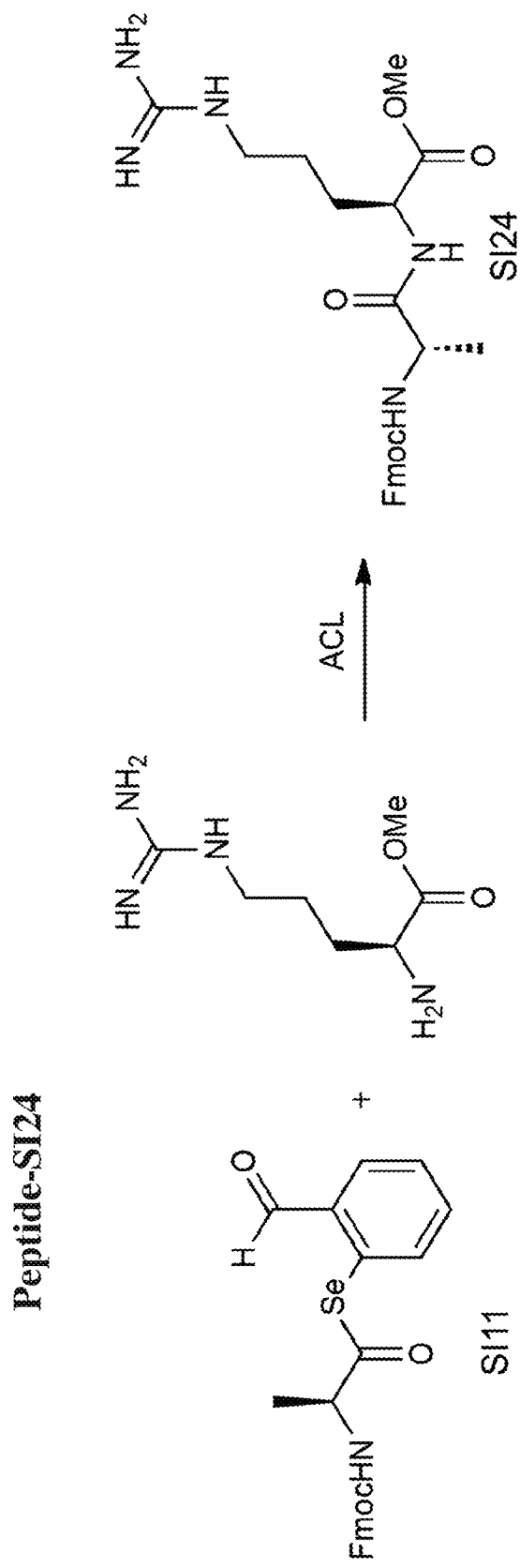
FIG. 31 shows HPLC spectra of the starting material and the crude reaction mixture of peptide SI24 after 2 min of incubation; the product peak is labeled.
Figure 31:
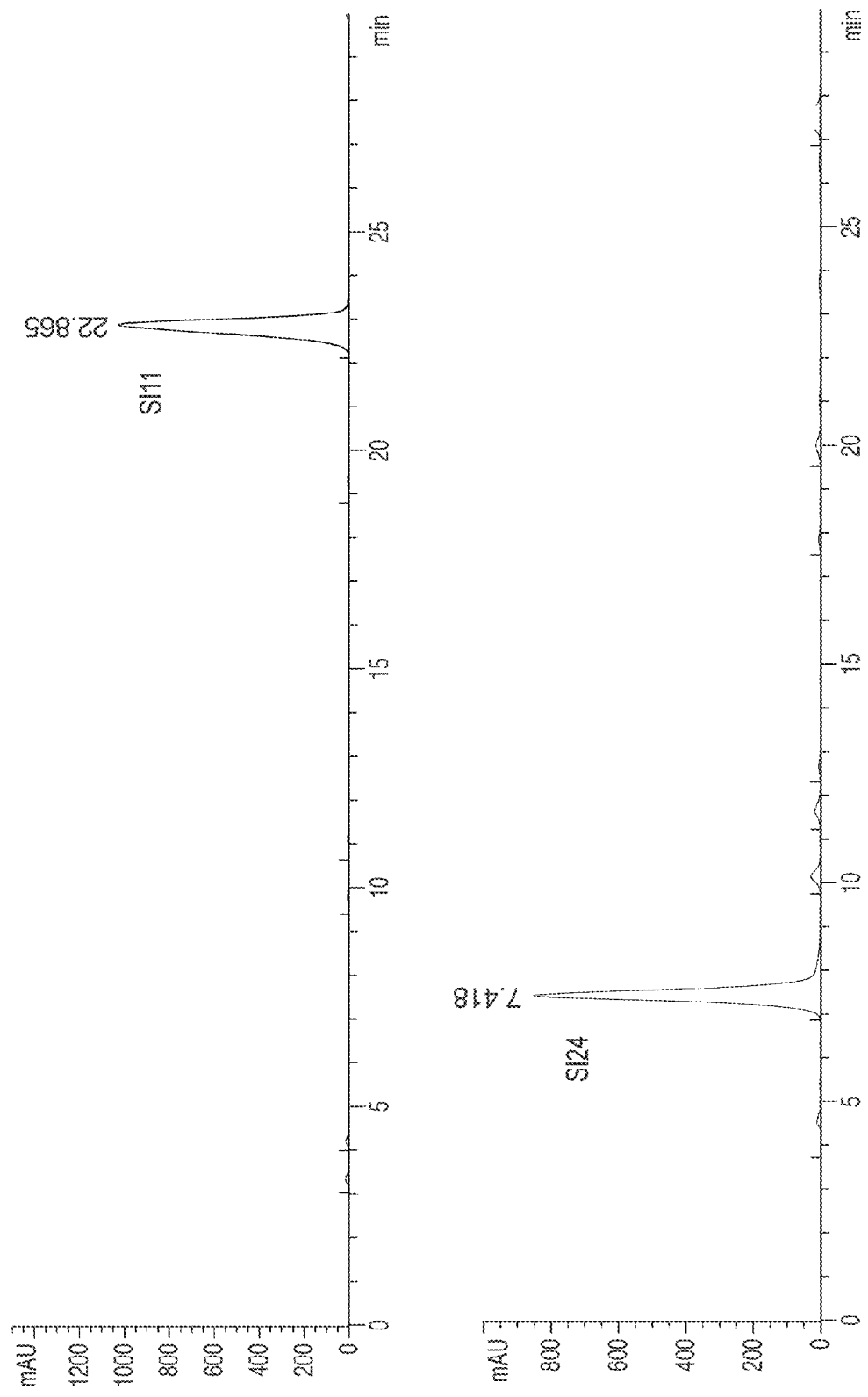
Figure 32:
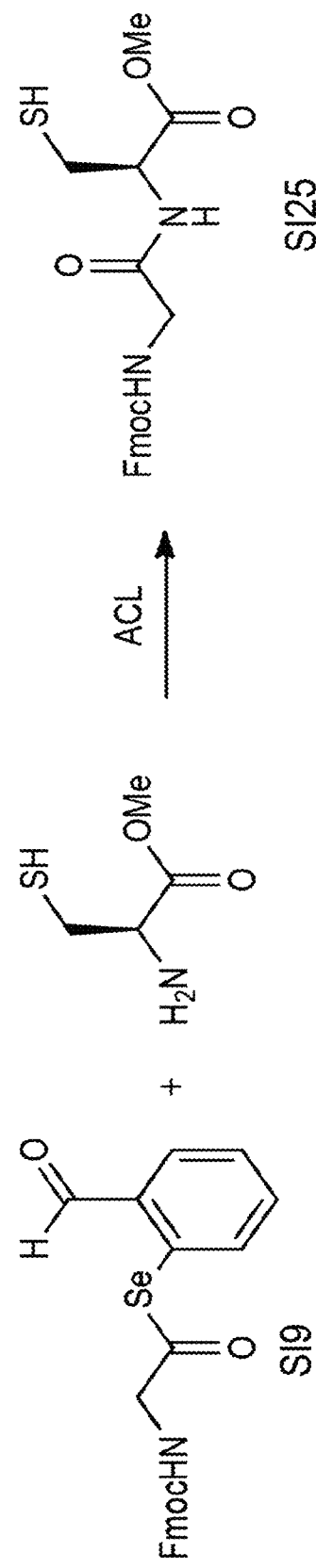
FIG. 32 shows HPLC spectra of the starting material and the crude reaction mixture of peptide SI125 after 5 min of incubation.
Figure 33:
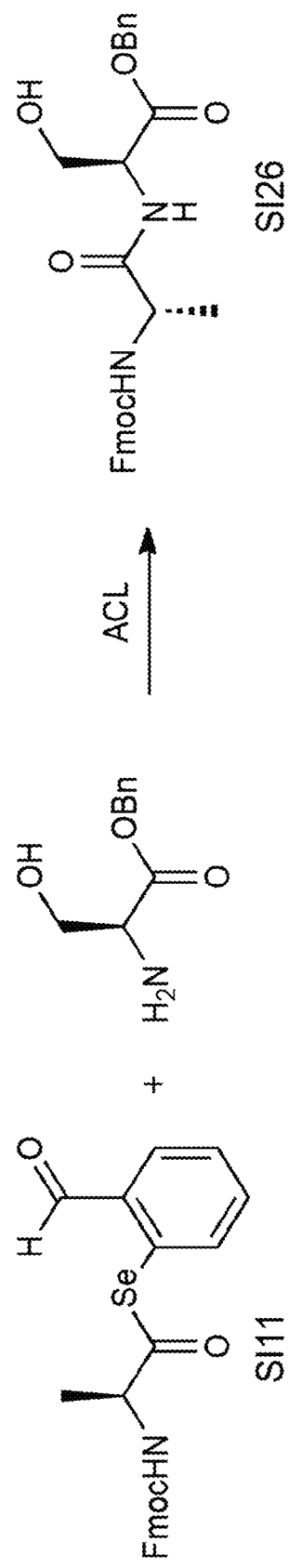
FIG. 33 shows HPLC spectra of the starting material and the crude reaction mixture of peptide SI126 after 5 min of incubation.
Figure 33:
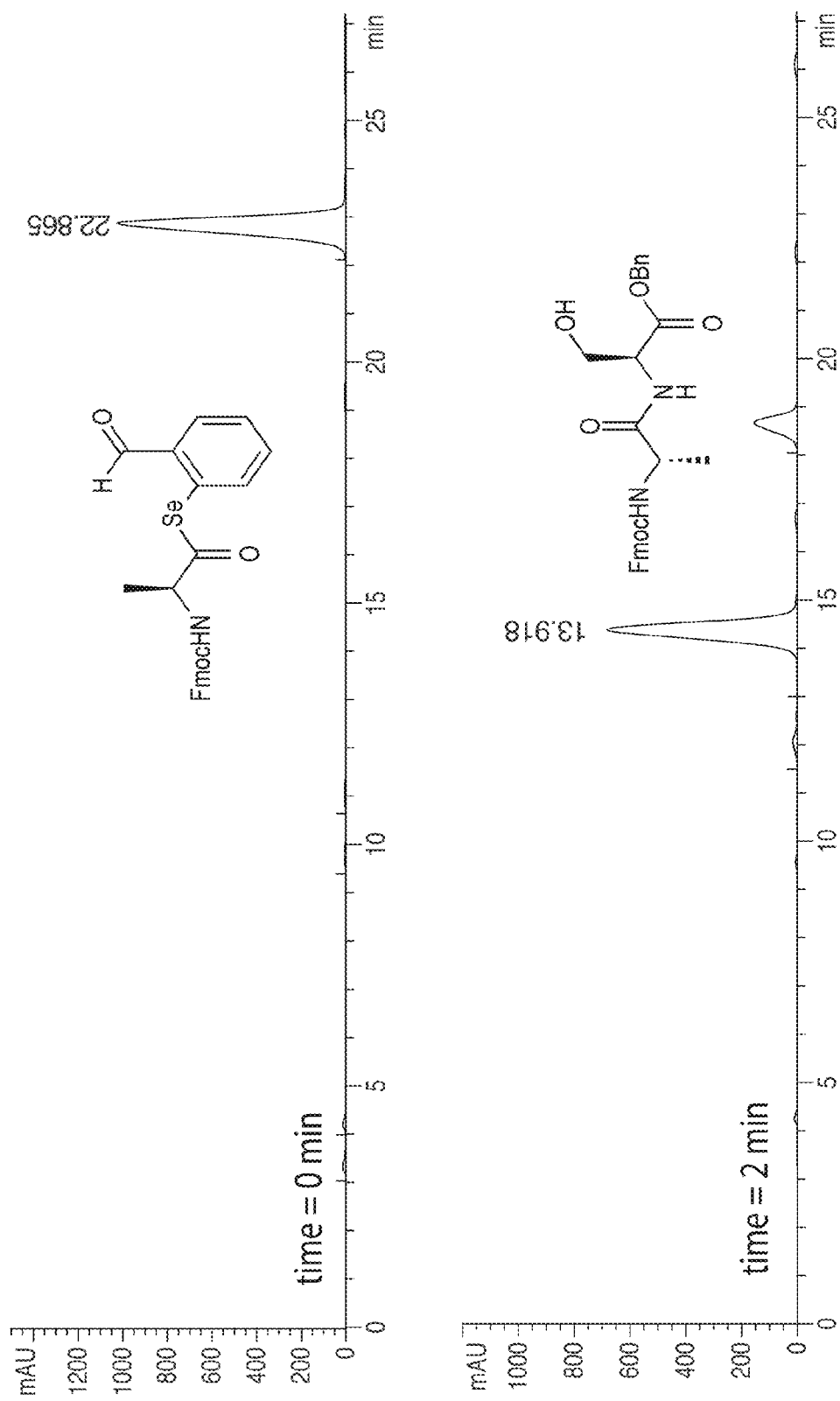
Figure 34:
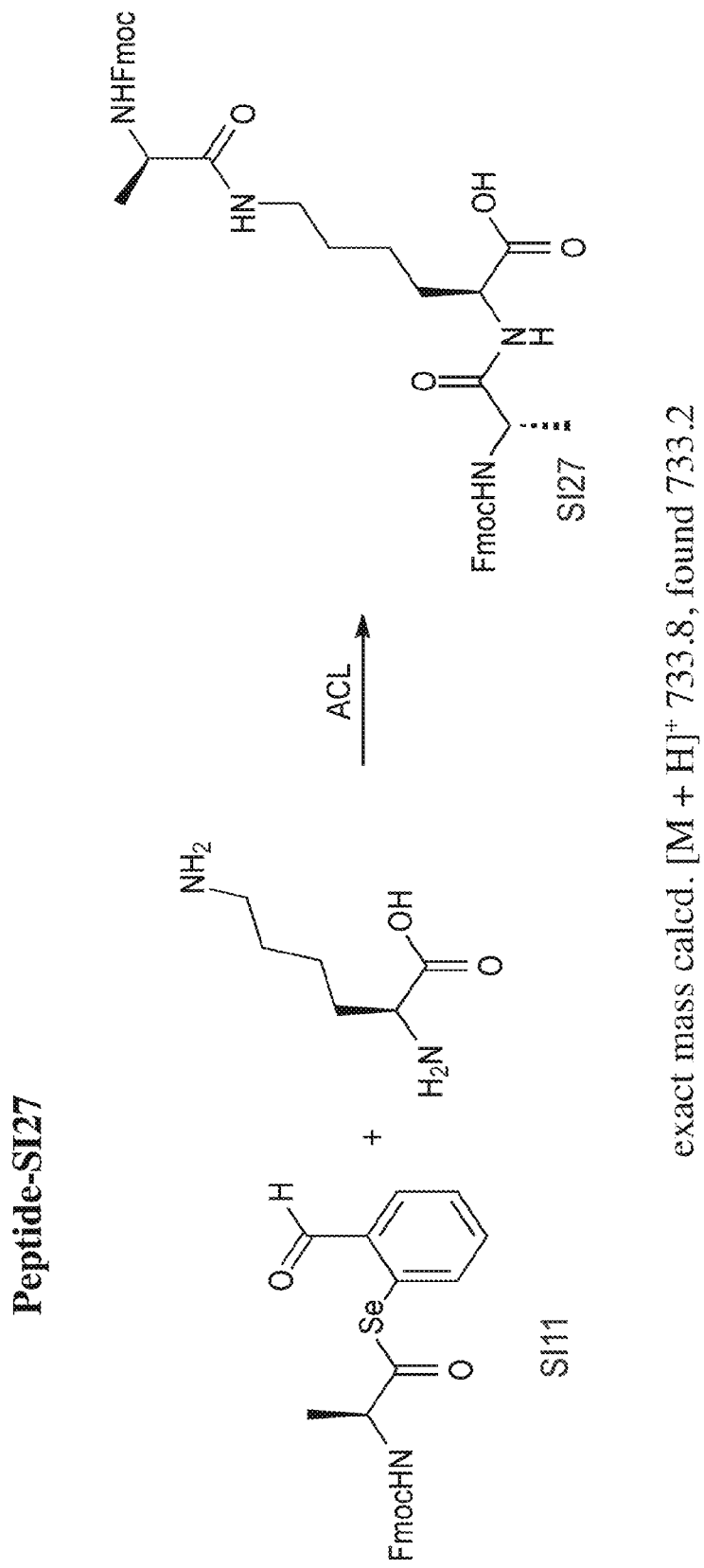
FIG. 34 shows HPLC spectra of the starting material and the crude reaction mixture of peptide SI127 after 5 min of incubation; the product peak is labeled.
Figure 34:
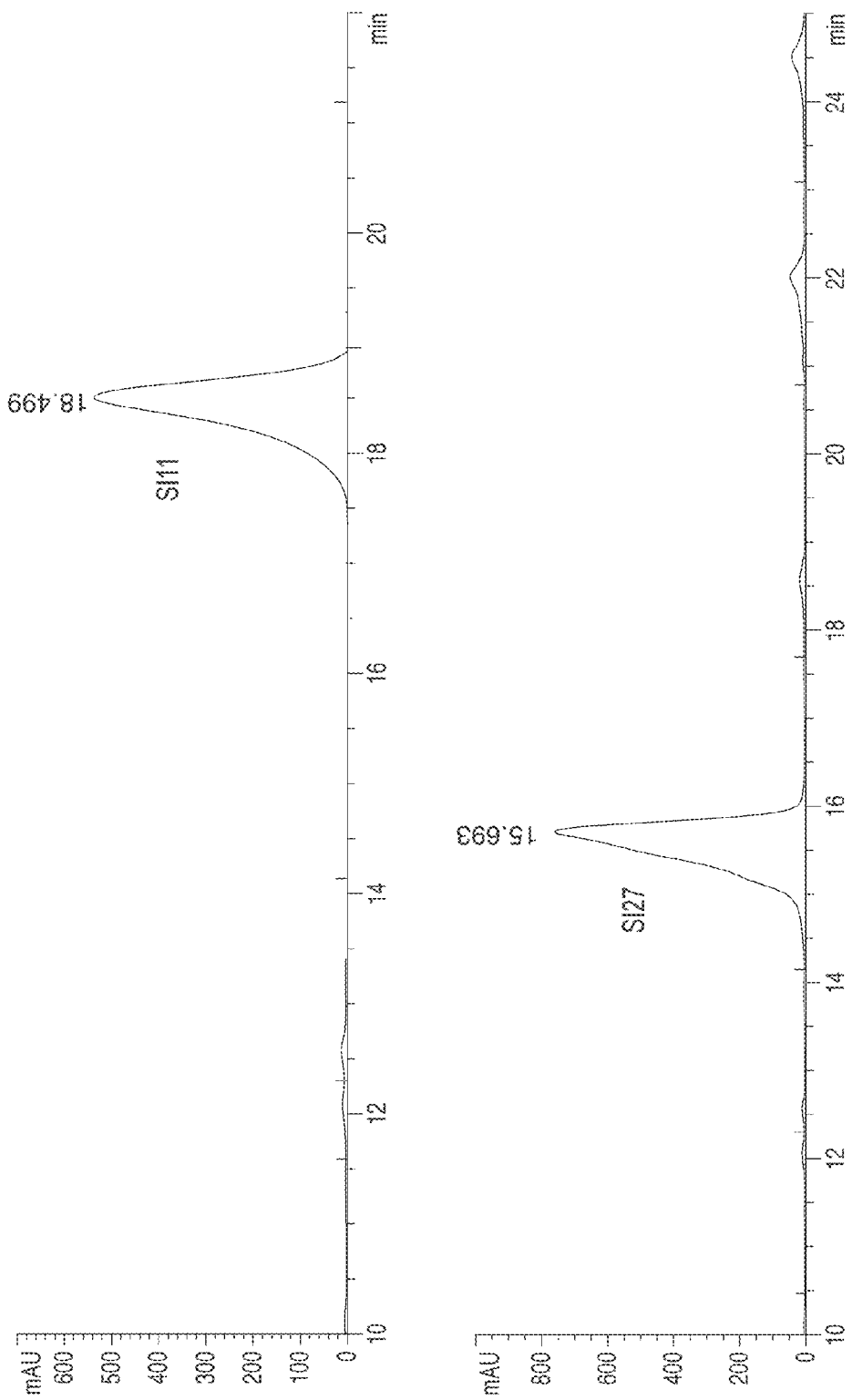

TABLE 1-continued
Ligation Products (see indicated figure for HPLC traces)
| Peptide | HPLC Trace(s) |
|---|---|
| 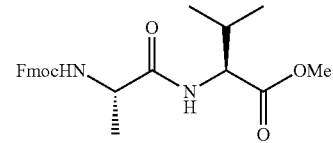 SI23 | FIG. 30 |
| 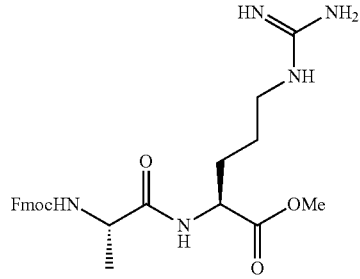 SI24 | FIG. 31 |
| 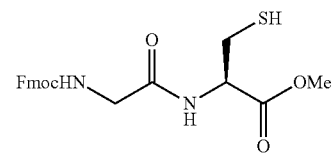 SI25 | FIG. 32 |
| 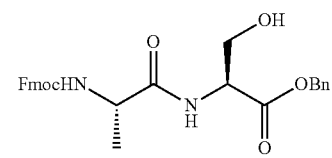 SI26 | FIG. 33 |
| 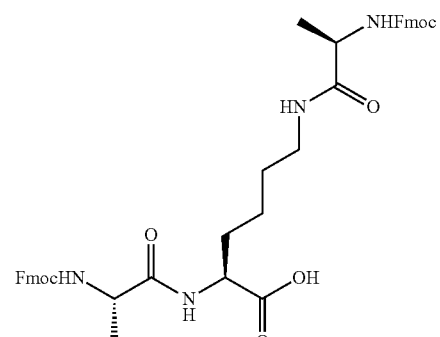 SI27 | FIG. 34 |

TABLE 1-continued

Ligation Products (see indicated figure for HPLC traces)

Figure 35:
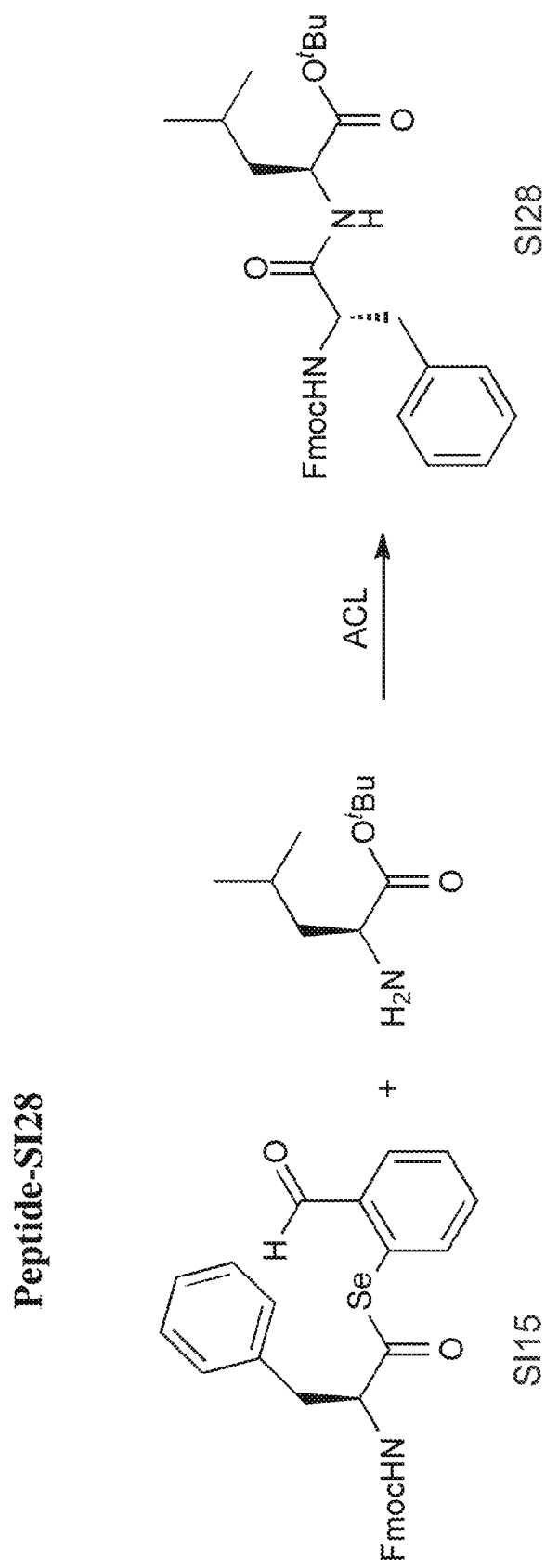
FIG. 35 shows HPLC spectra of the starting material and the crude reaction mixture of peptide SI128 after 3 min of incubation; the product peak is labeled.
Figure 35:
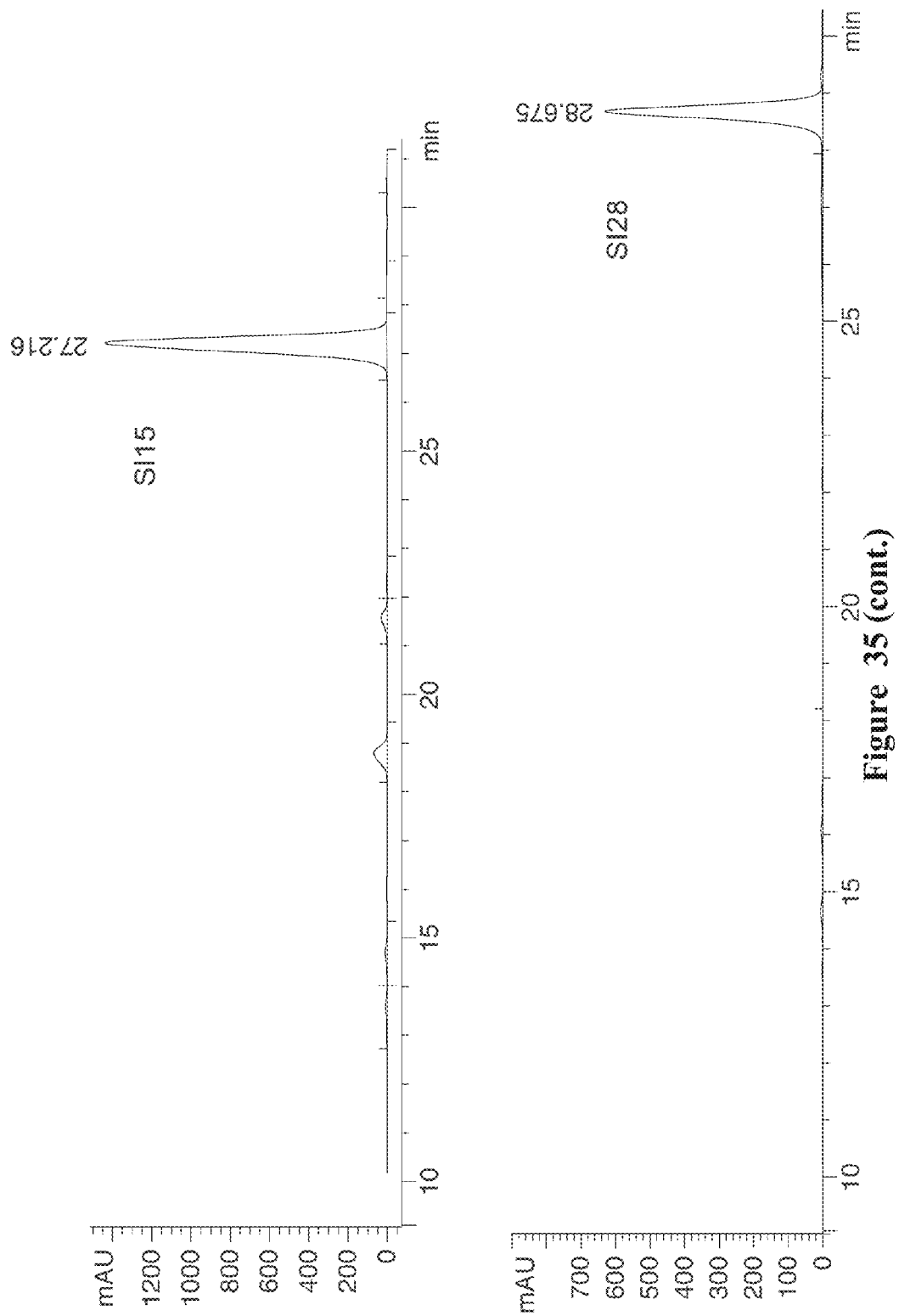
Figure 36:
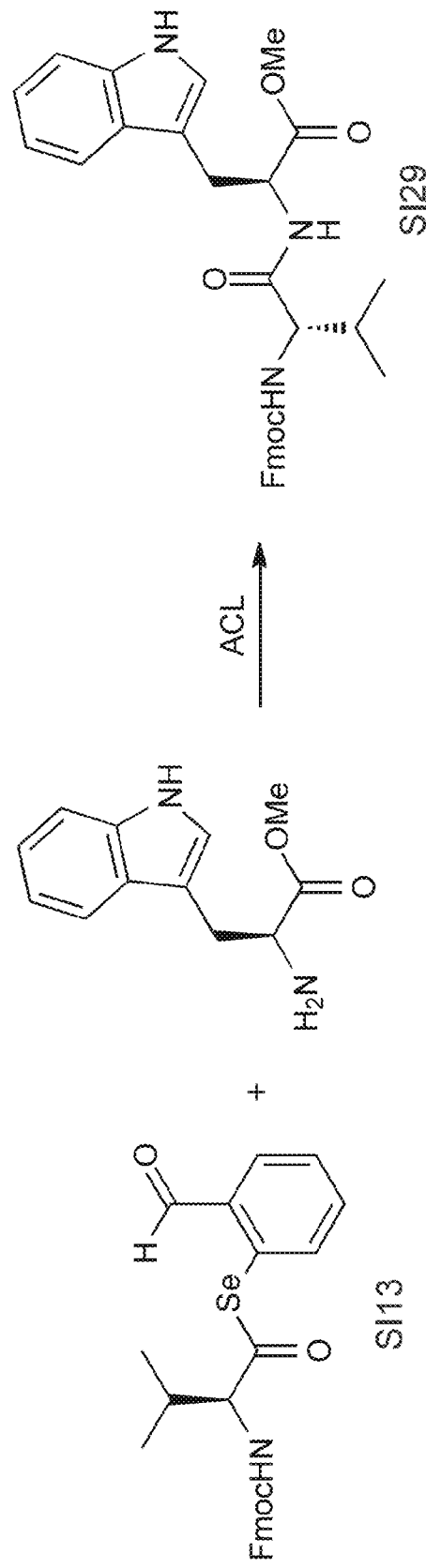
FIG. 36 shows HPLC traces related to the synthesis of peptide SI129.
Figure 36:
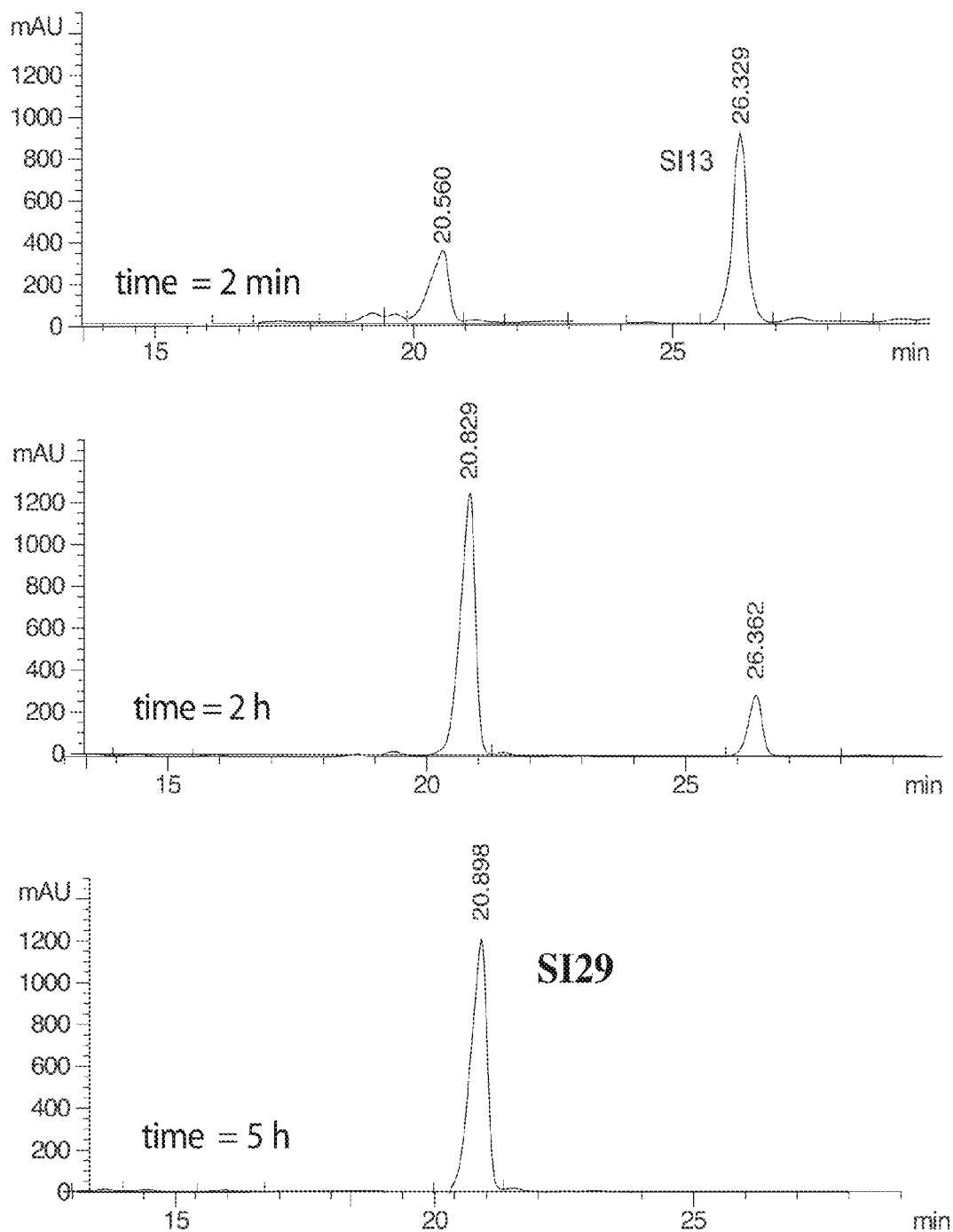
Figure 39:
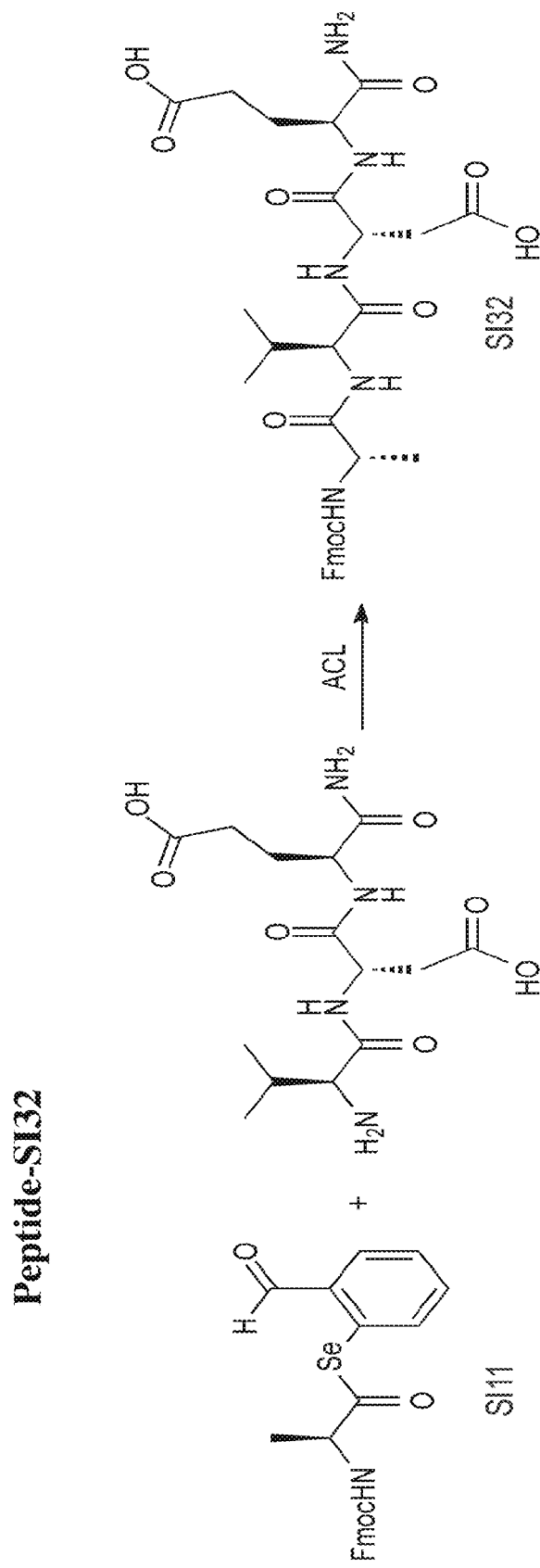
FIG. 39 shows HPLC spectra of the starting material and the crude reaction mixture of peptide SI132 after 5 min of incubation; the product peak is labeled.
Figure 39:
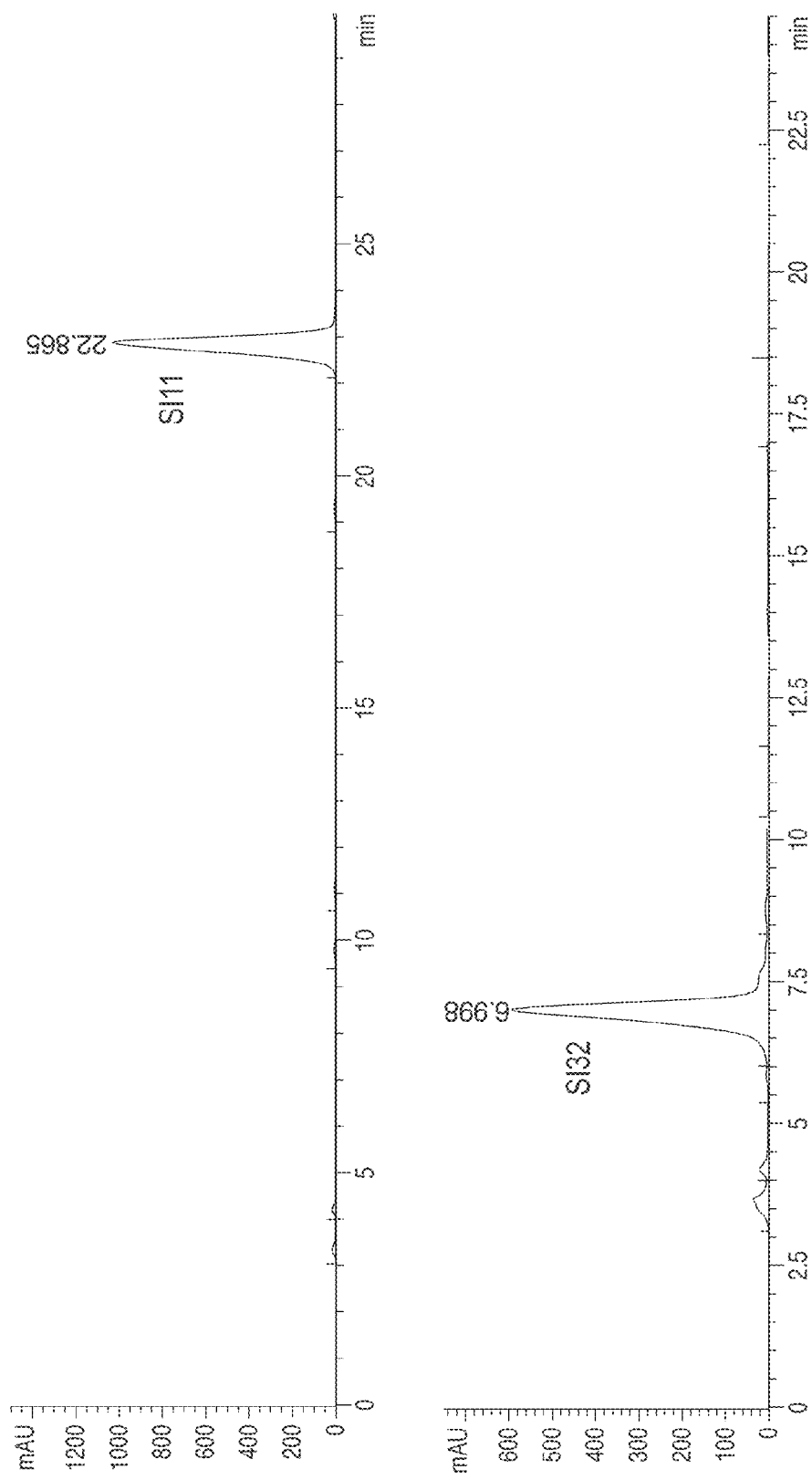

| Peptide | HPLC Trace(s) |
|---|---|
| SI28 | FIG. 35 |
| SI29 | FIG. 36 |
| SI30 | FIG. 37 |
| SI31 | FIG. 38 |
| SI32 | FIG. 39 |

TABLE 1-continued

Ligation Products (see indicated figure for HPLC traces)

Figure 40:
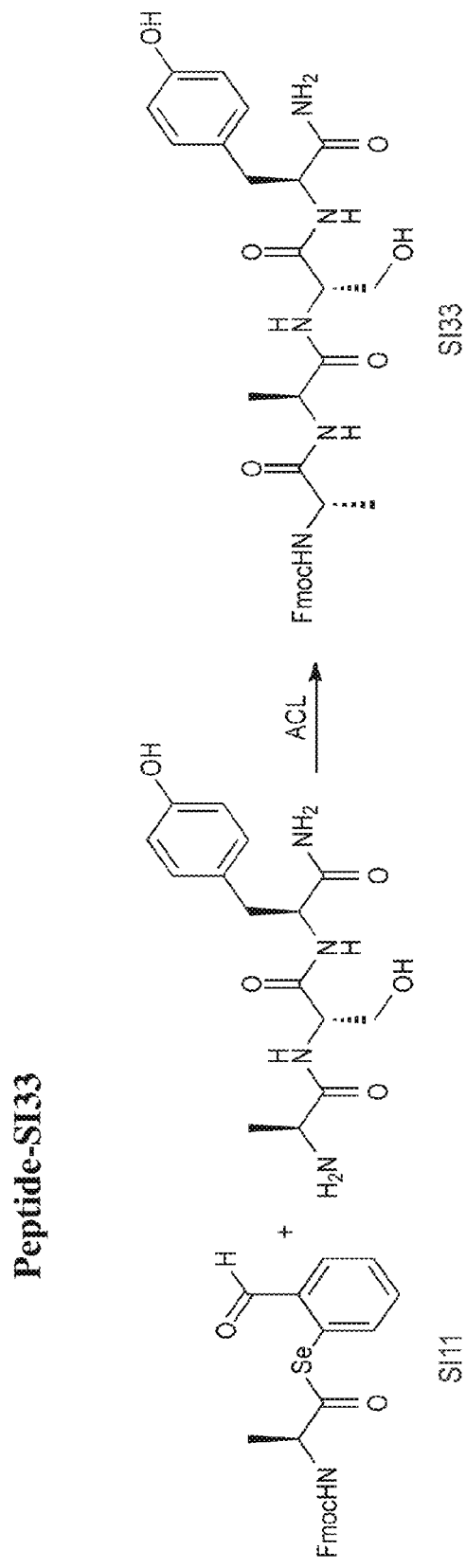
FIG. 40 shows HPLC spectra of the starting material and the crude reaction mixture of peptide SI133 after 2 min of incubation; the product peak is labeled.
Figure 40:
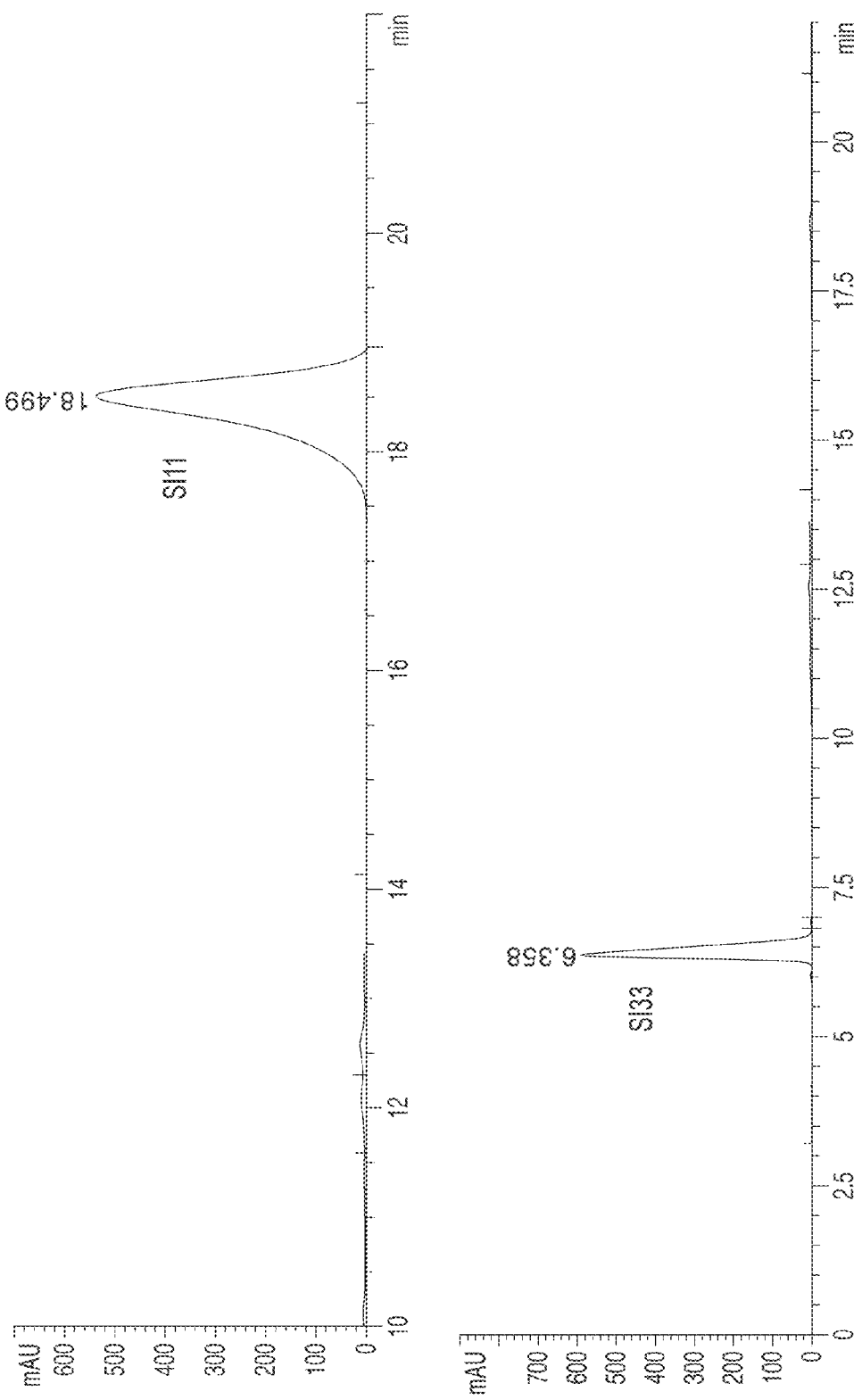
Figure 41:
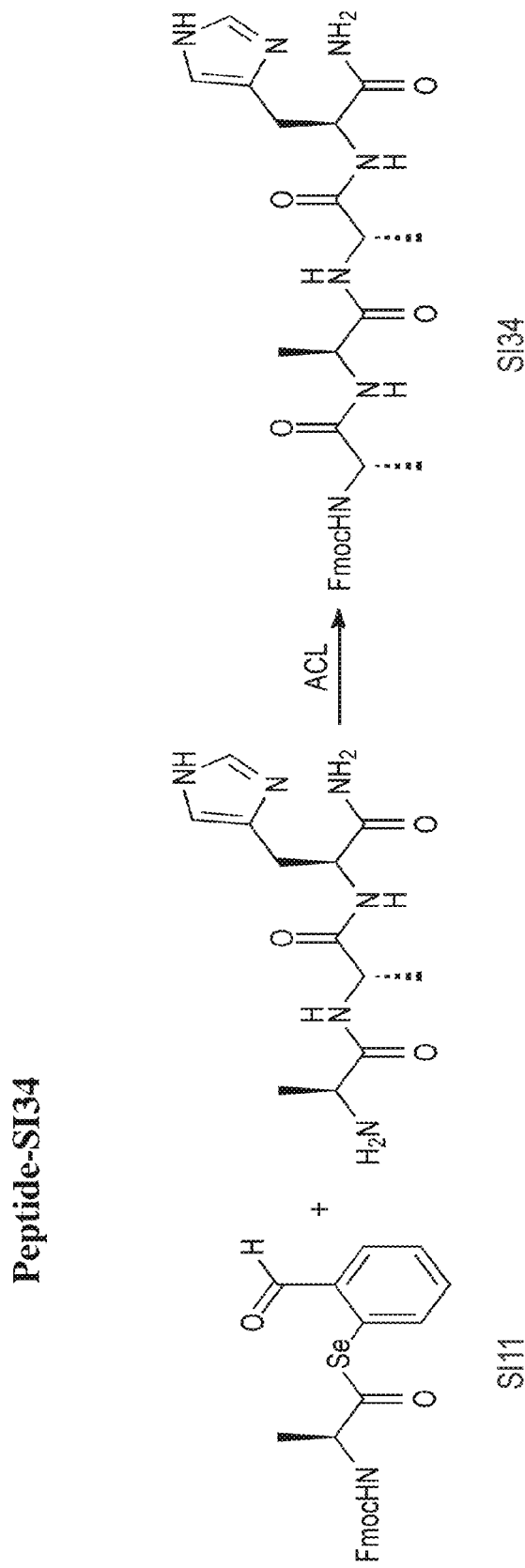
FIG. 41 shows HPLC spectra of the starting material and the crude reaction mixture of peptide SI134 after 2 min of incubation; the product peak is labeled.
Figure 41:
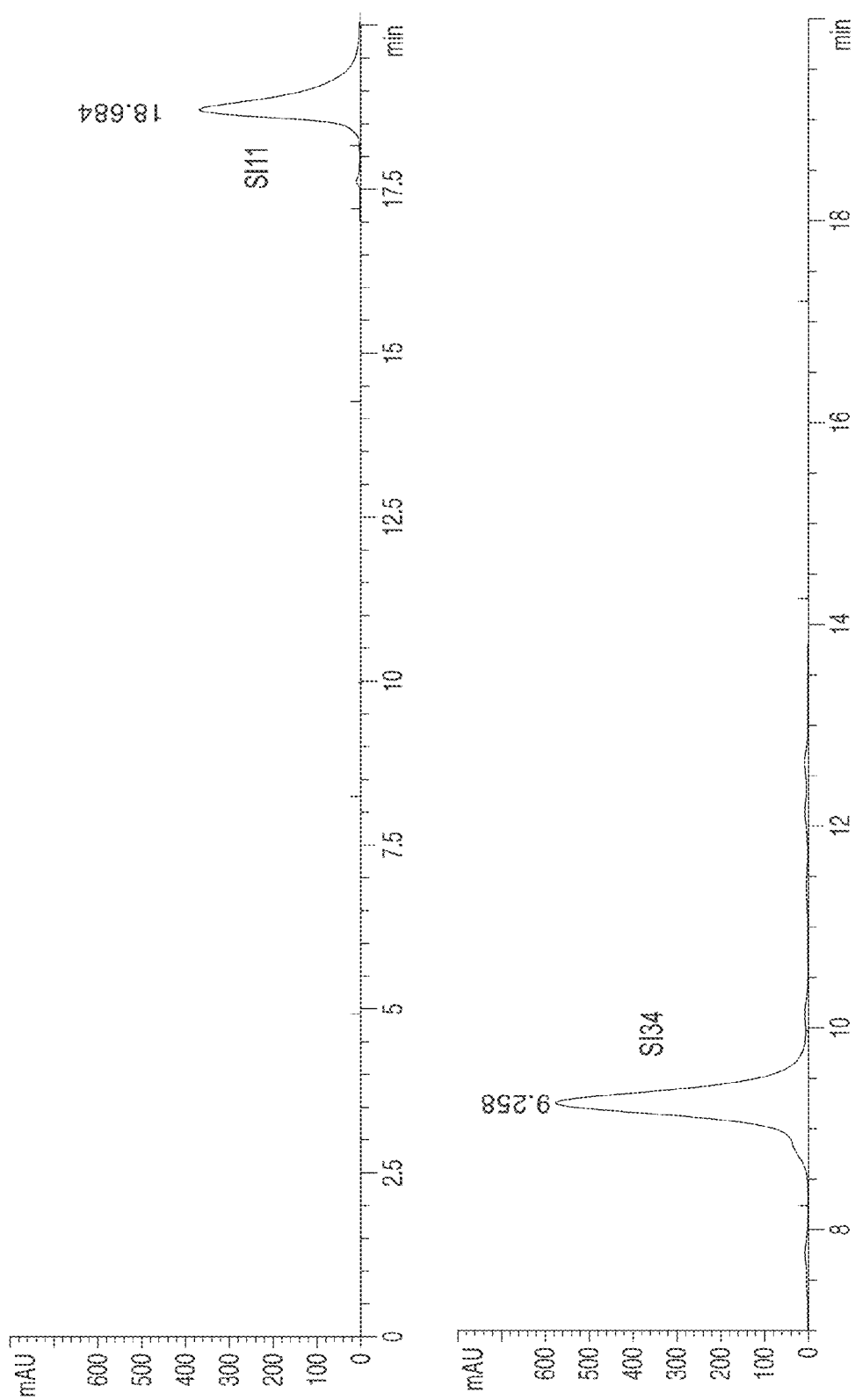
Figure 42:
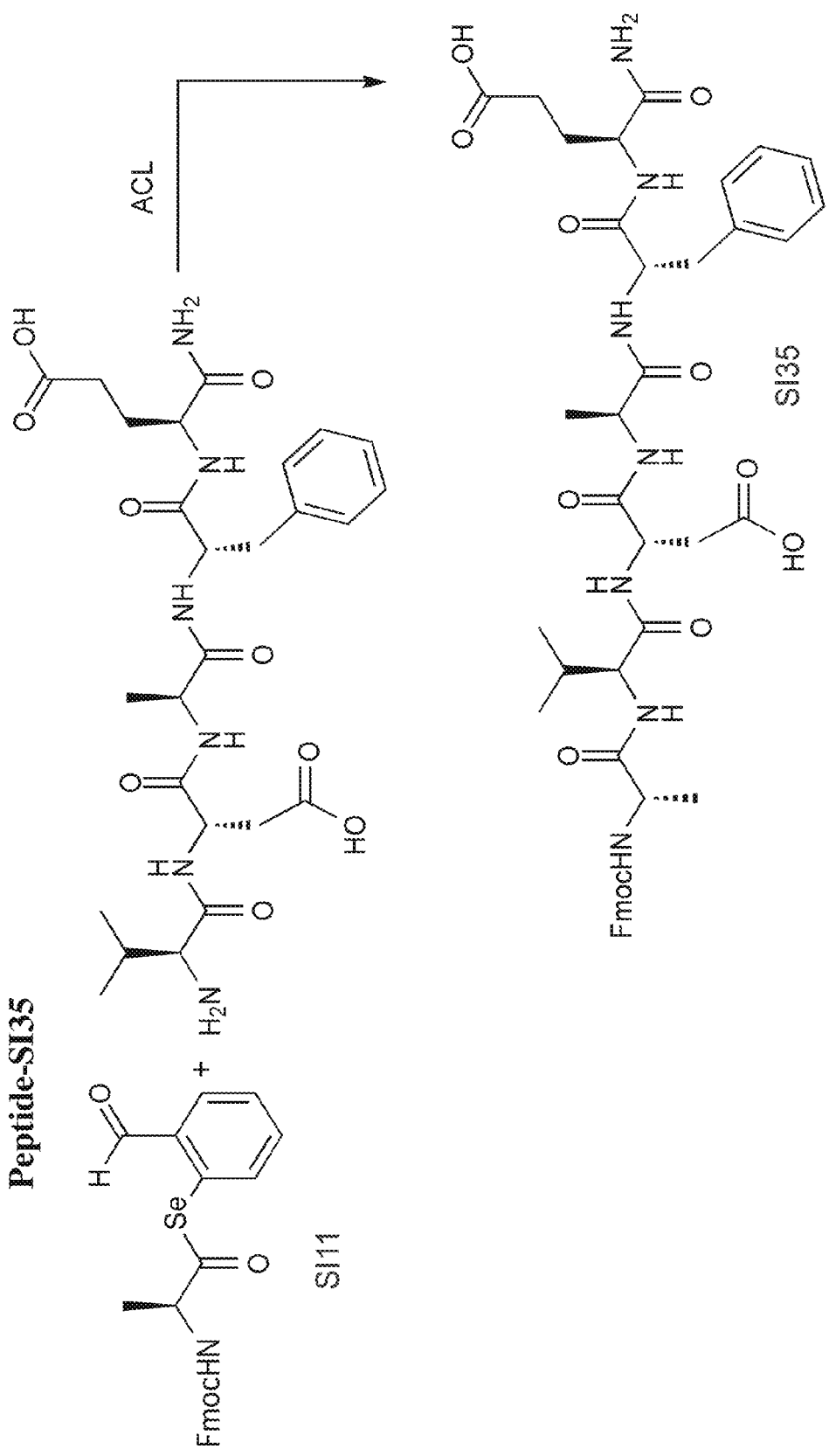
FIG. 42 shows HPLC spectra of the starting material and the crude reaction mixture of peptide SI135 after 5 min of incubation; the product peak is labeled.
Figure 42:
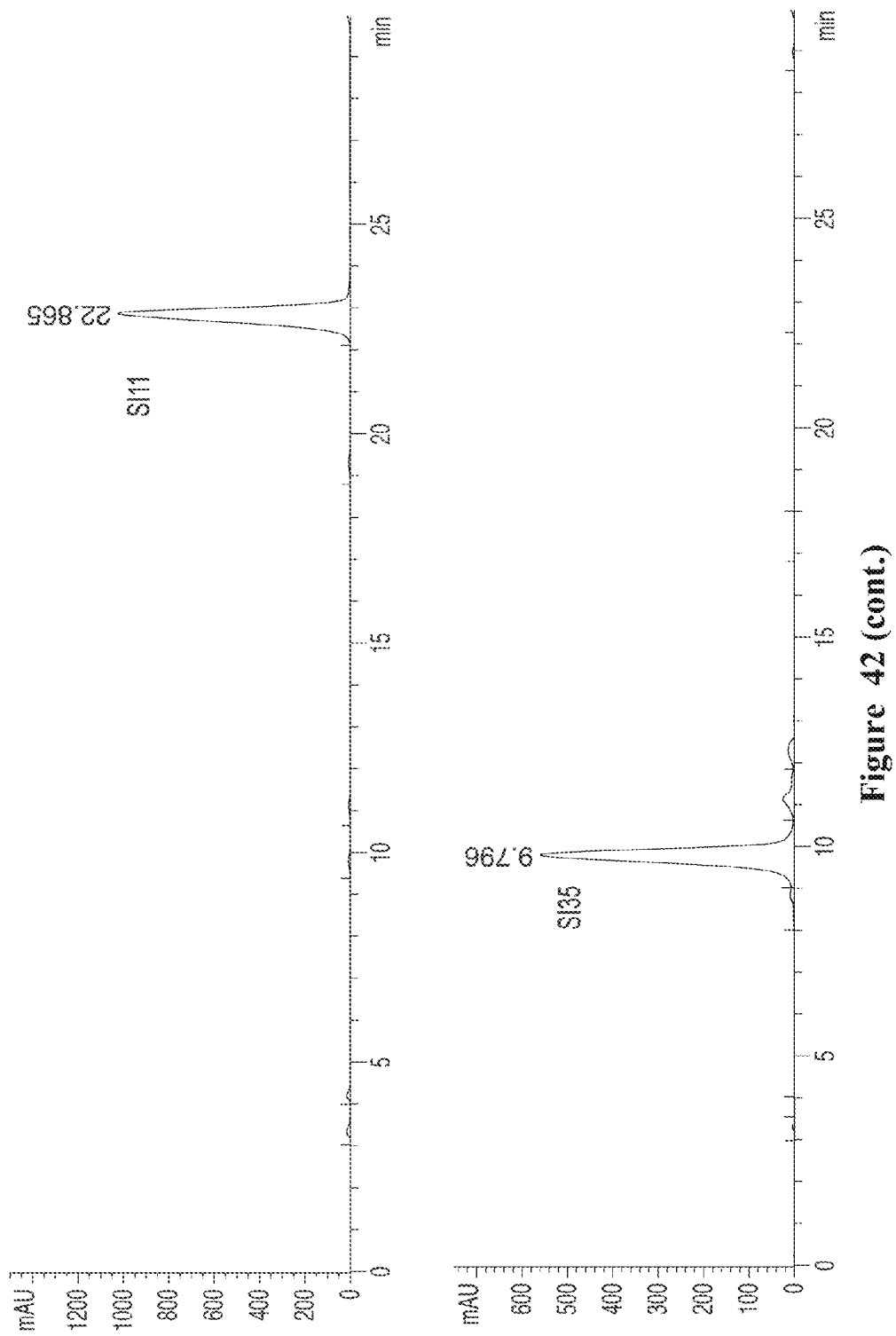
Figure 43:
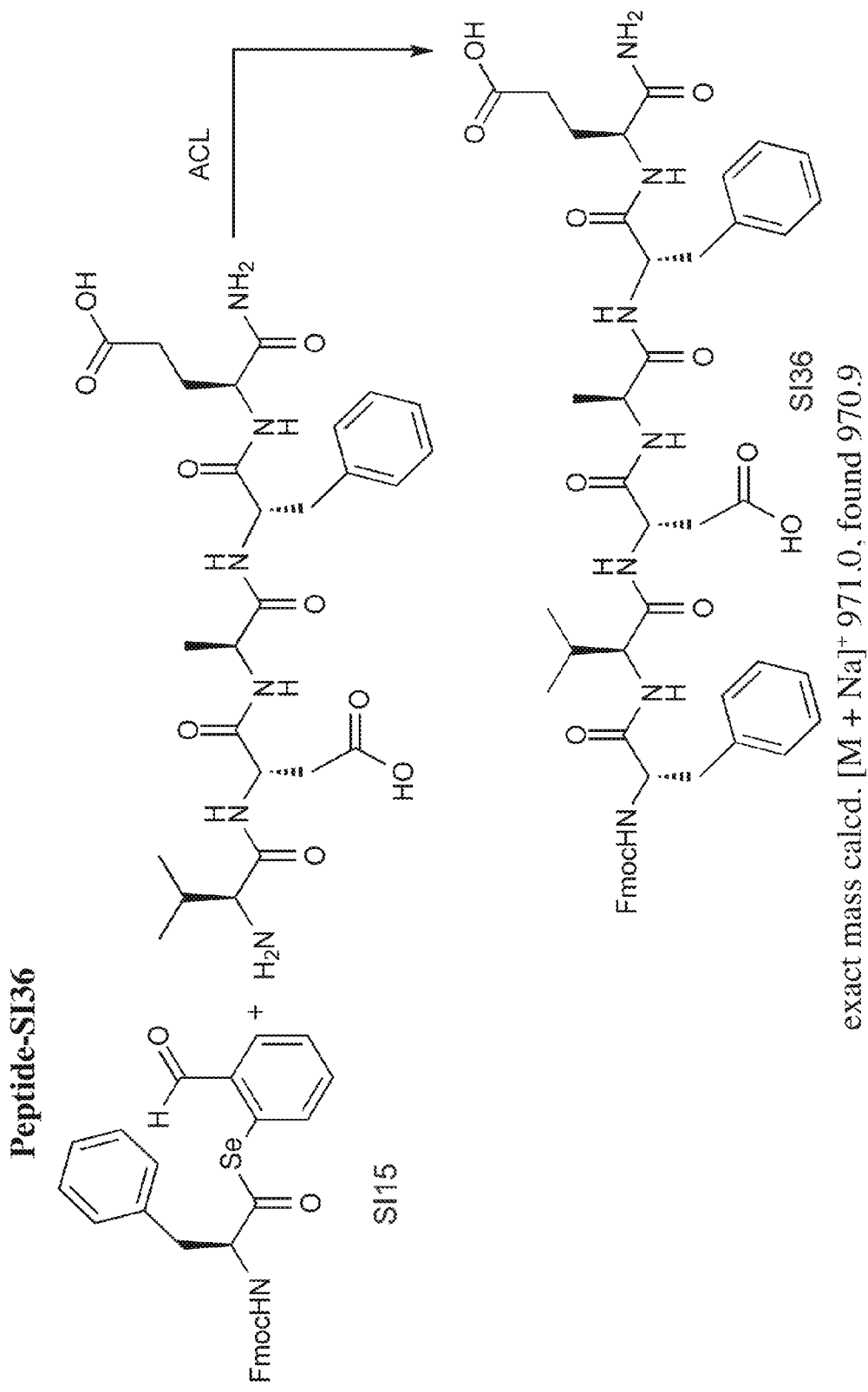
FIG. 43 shows HPLC spectra of the starting material and the crude reaction mixture of peptide SI136 after 5 min of incubation; the product peak is labeled.
Figure 43:
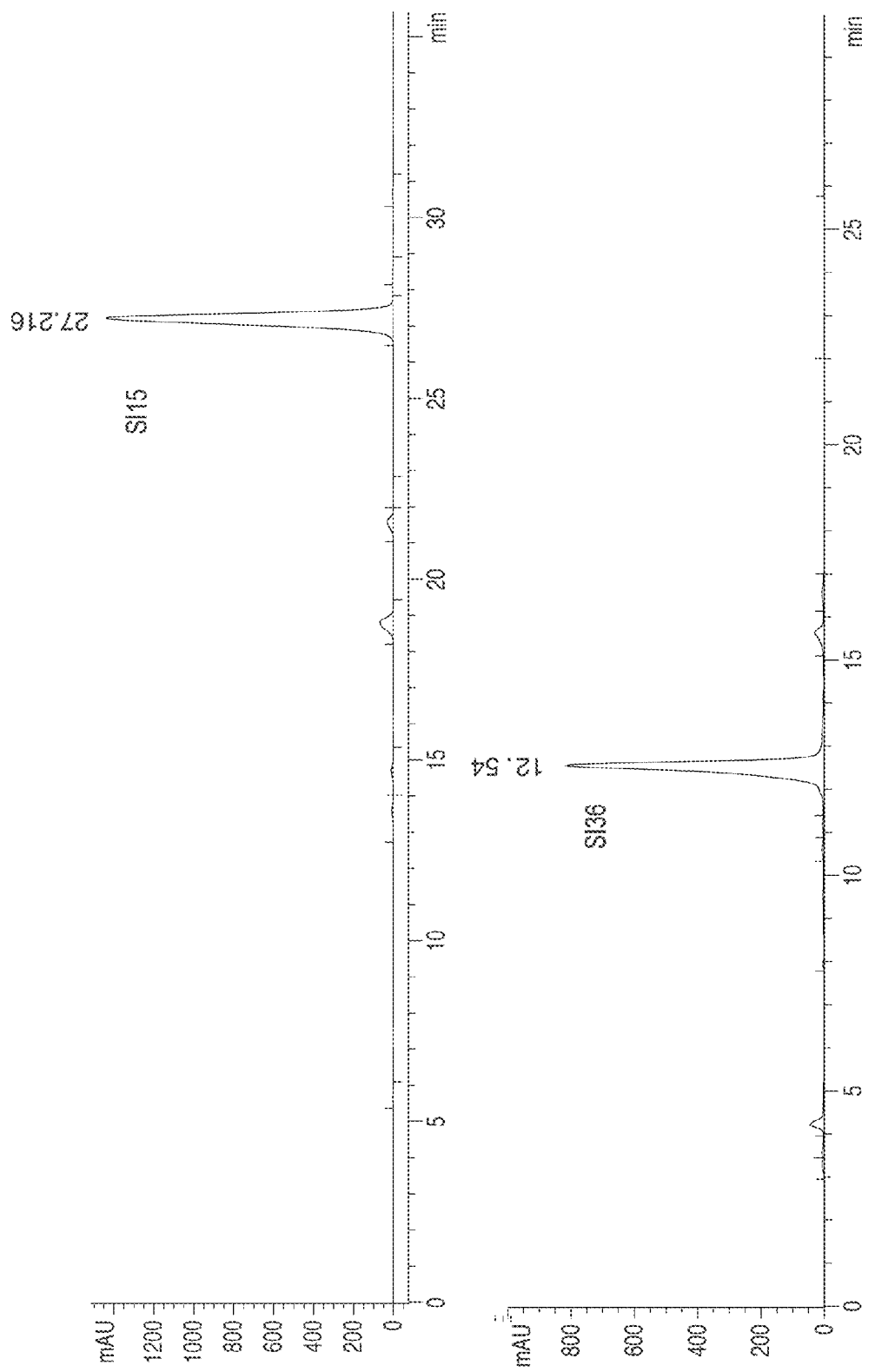
Figure 44:
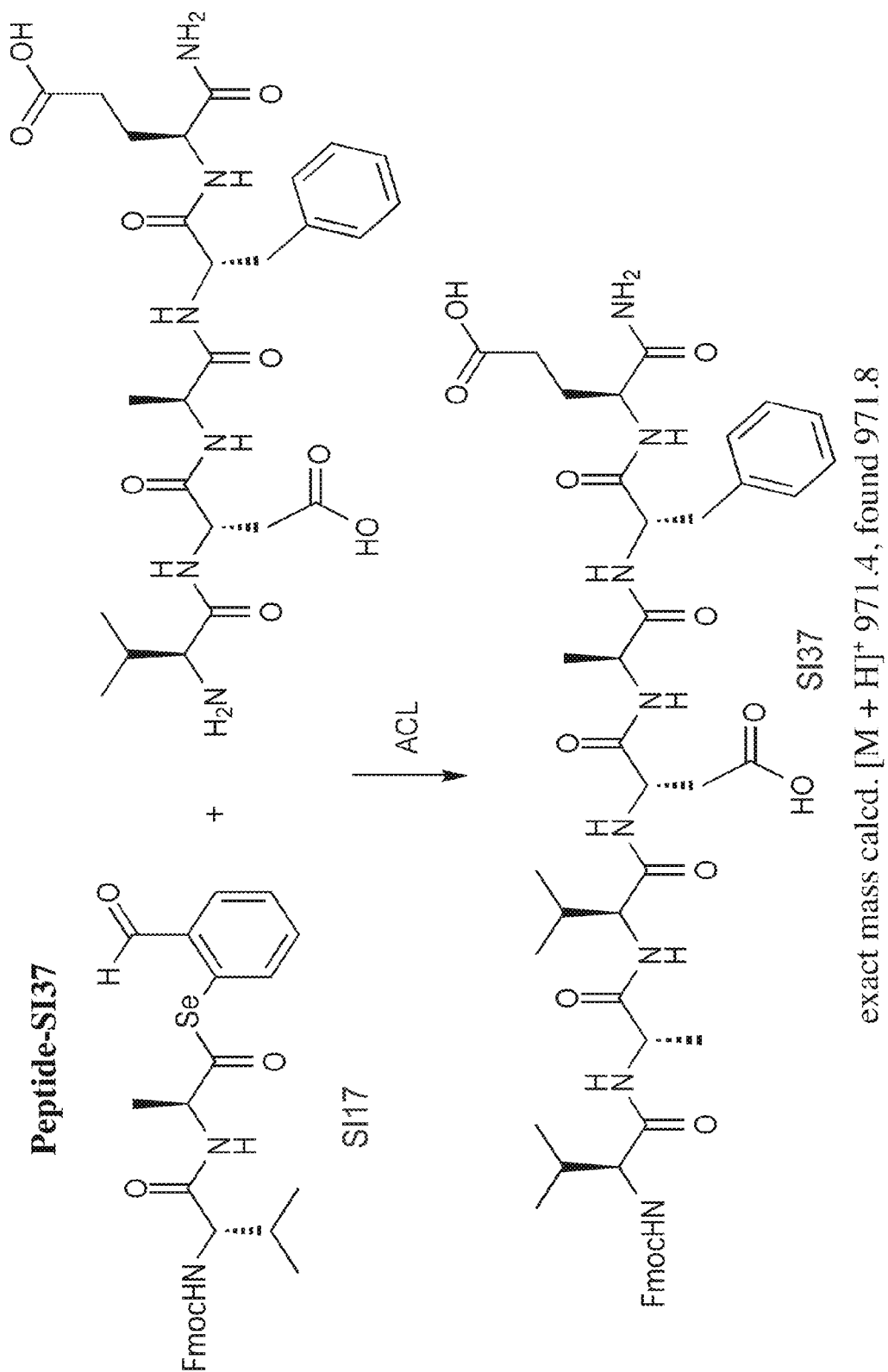
FIG. 44 shows HPLC spectra of the starting material and the crude reaction mixture of peptide SI137 after 5 min of incubation; the product peak is labeled.
Figure 44:
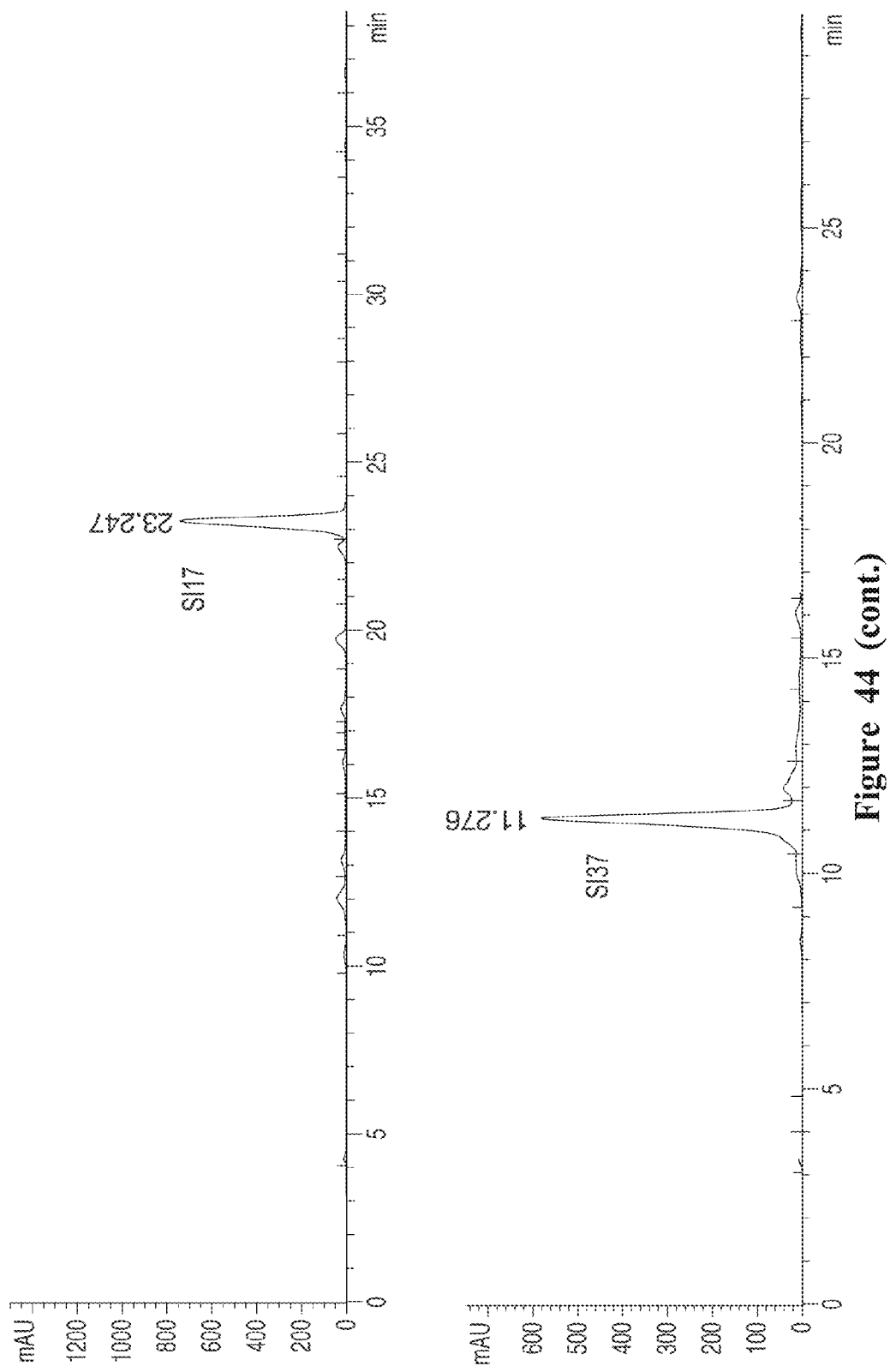

| Peptide | HPLC Trace(s) |
| --- | --- |
| SI33 | FIG. 40 |
| SI34 | FIG. 41 |
| SI35 | FIG. 42 |
| SI36 | FIG. 43 |
| SI37 | FIG. 44 |

Figure 45:
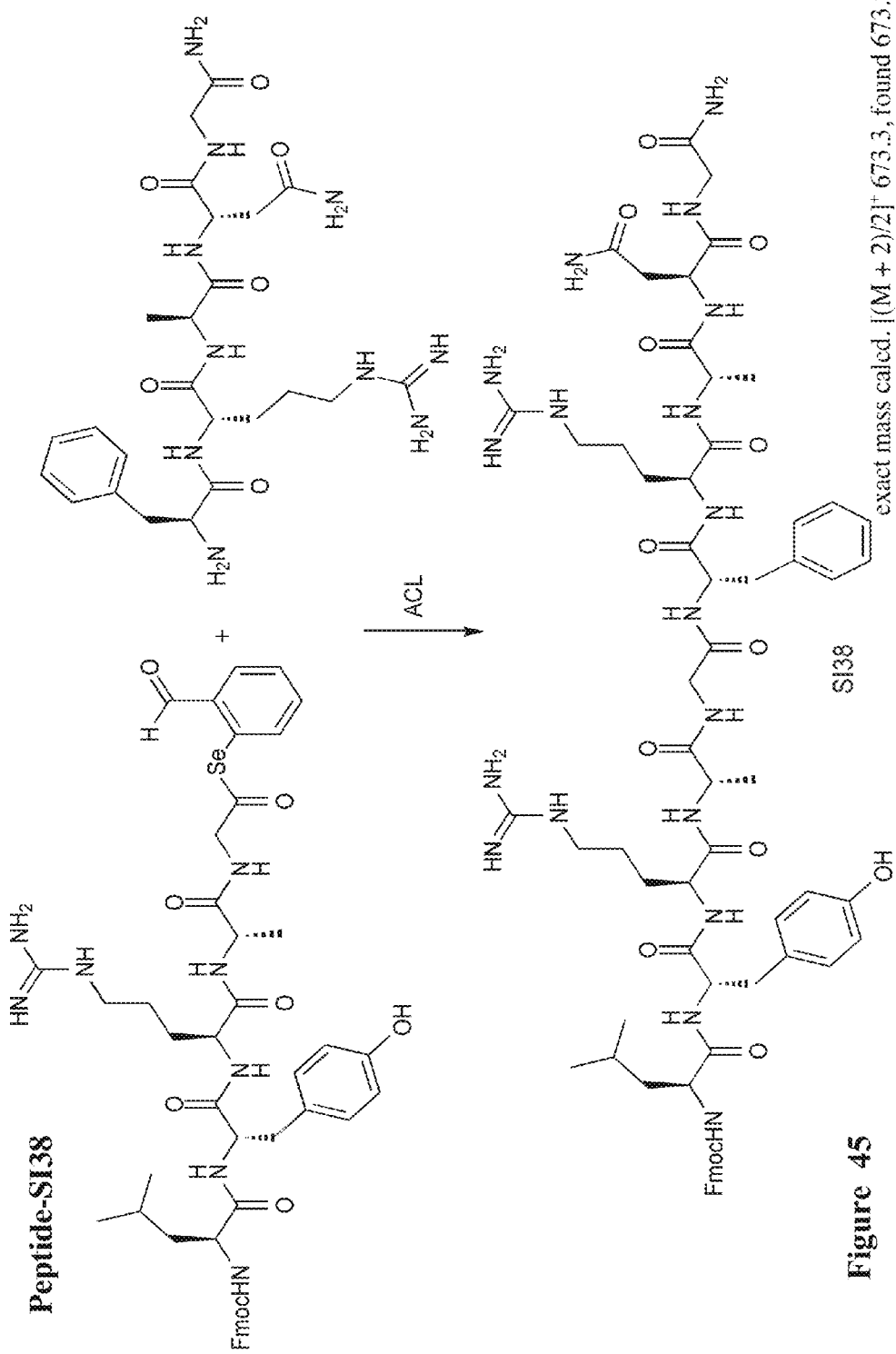
FIG. 45 shows HPLC spectra of the starting material and the crude reaction mixture of peptide SI138 after 30 min of incubation; the product peak is labeled.
Figure 45:
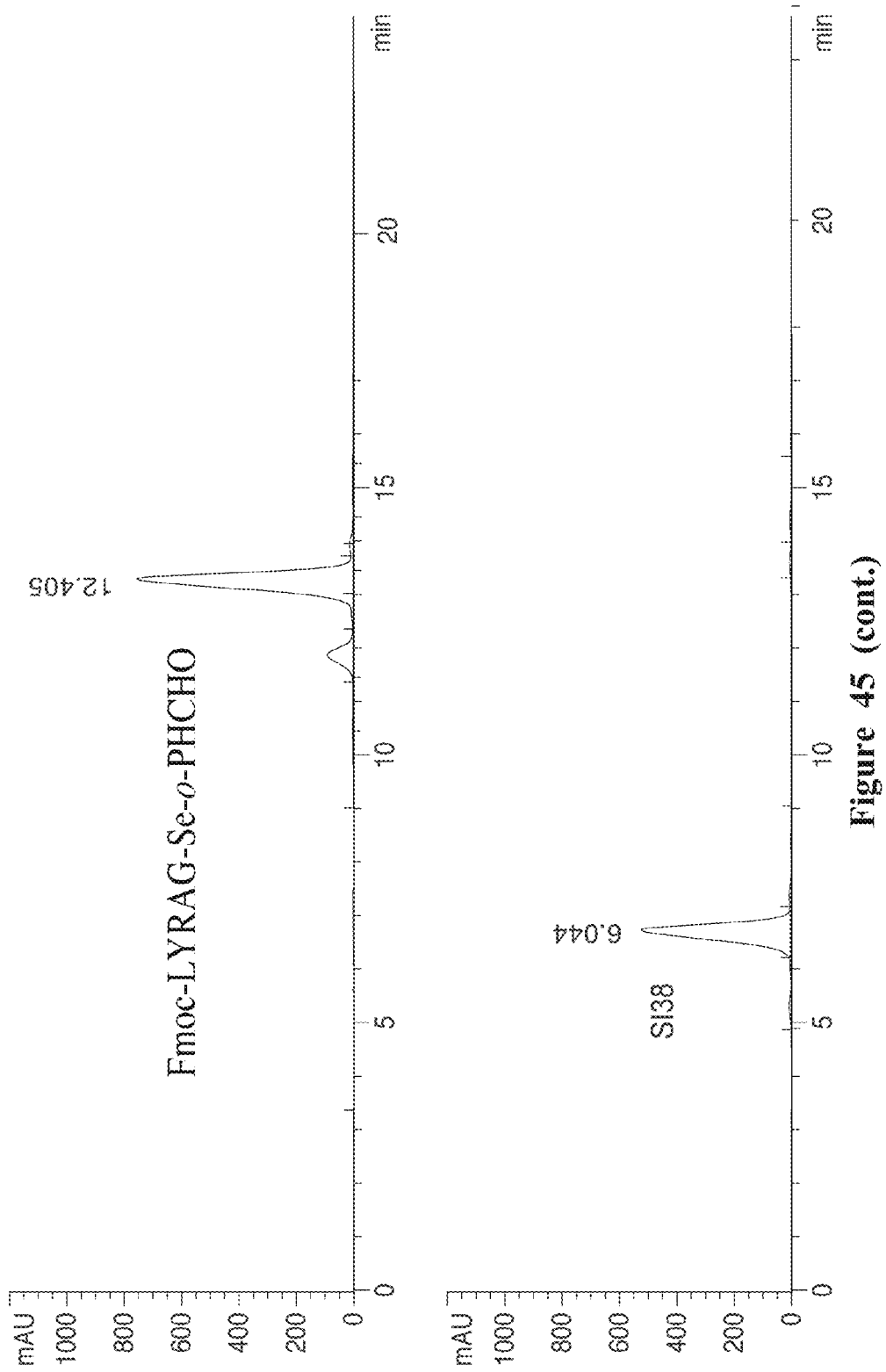
Figure 47:
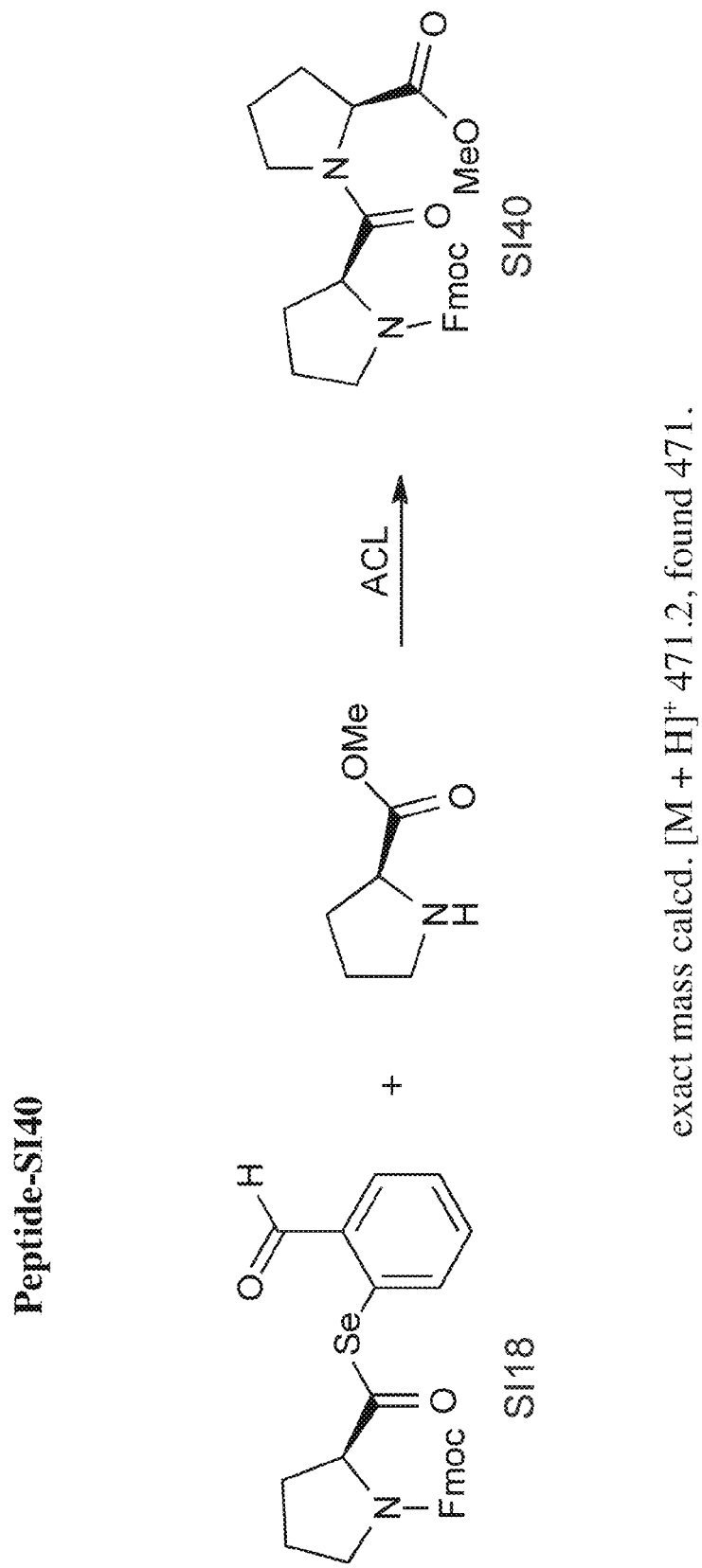
FIG. 47 shows HPLC spectra of the starting material and the crude reaction mixture of peptide SI140 after 30 min of incubation; the product peak is labeled.
Figure 47:
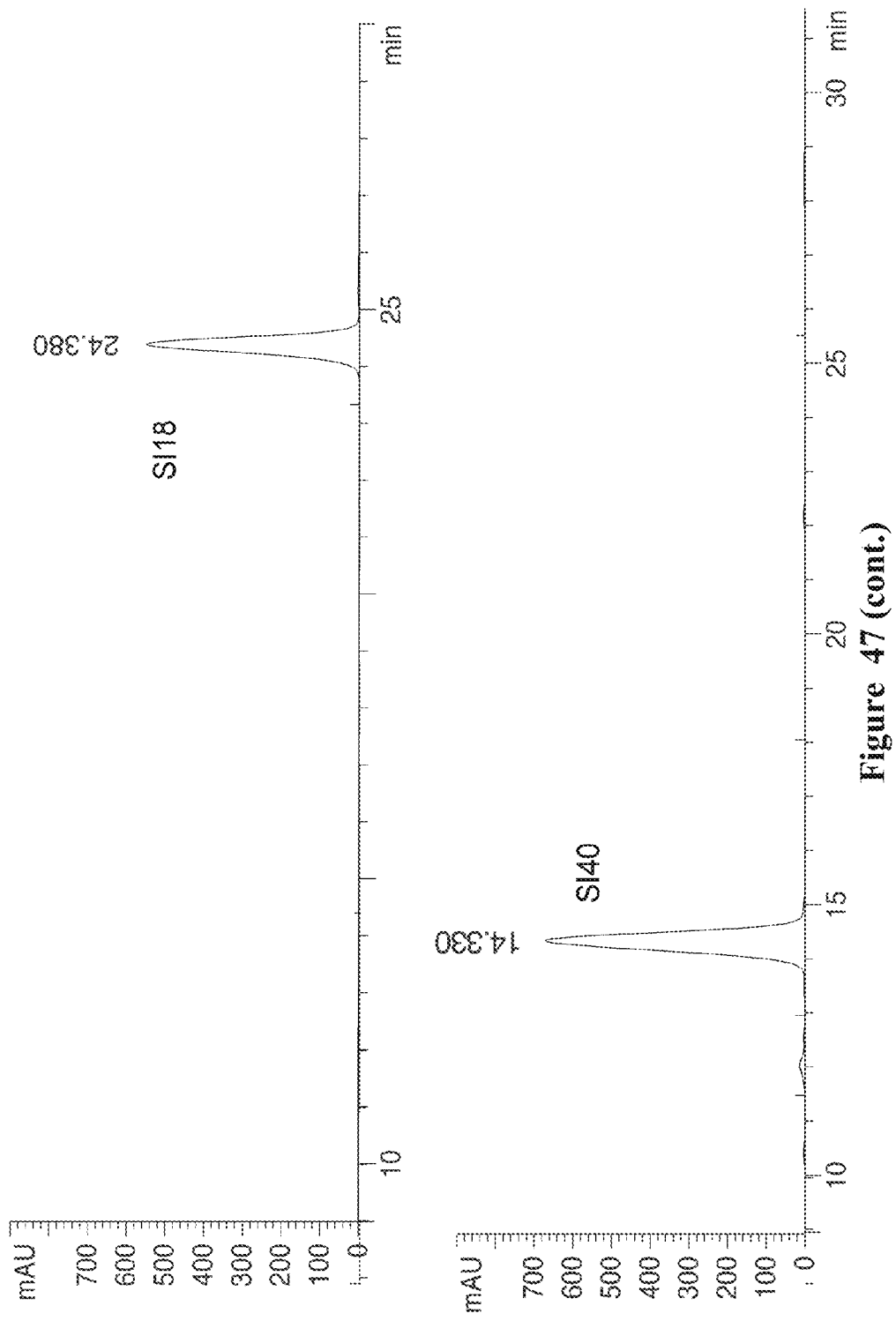
Figure 48:
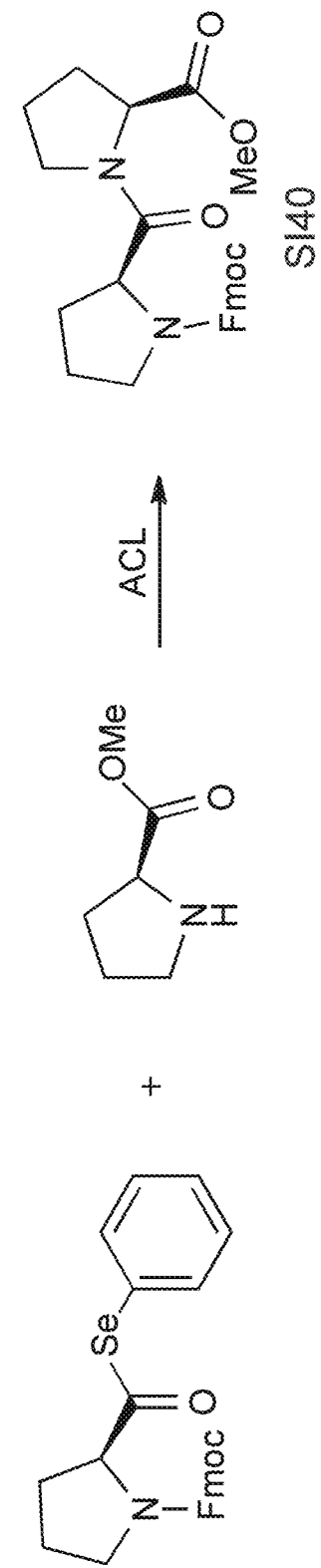
FIG. 48 shows HPLC traces related to the control reaction of the synthesis of peptide SI40.
Figure 48:
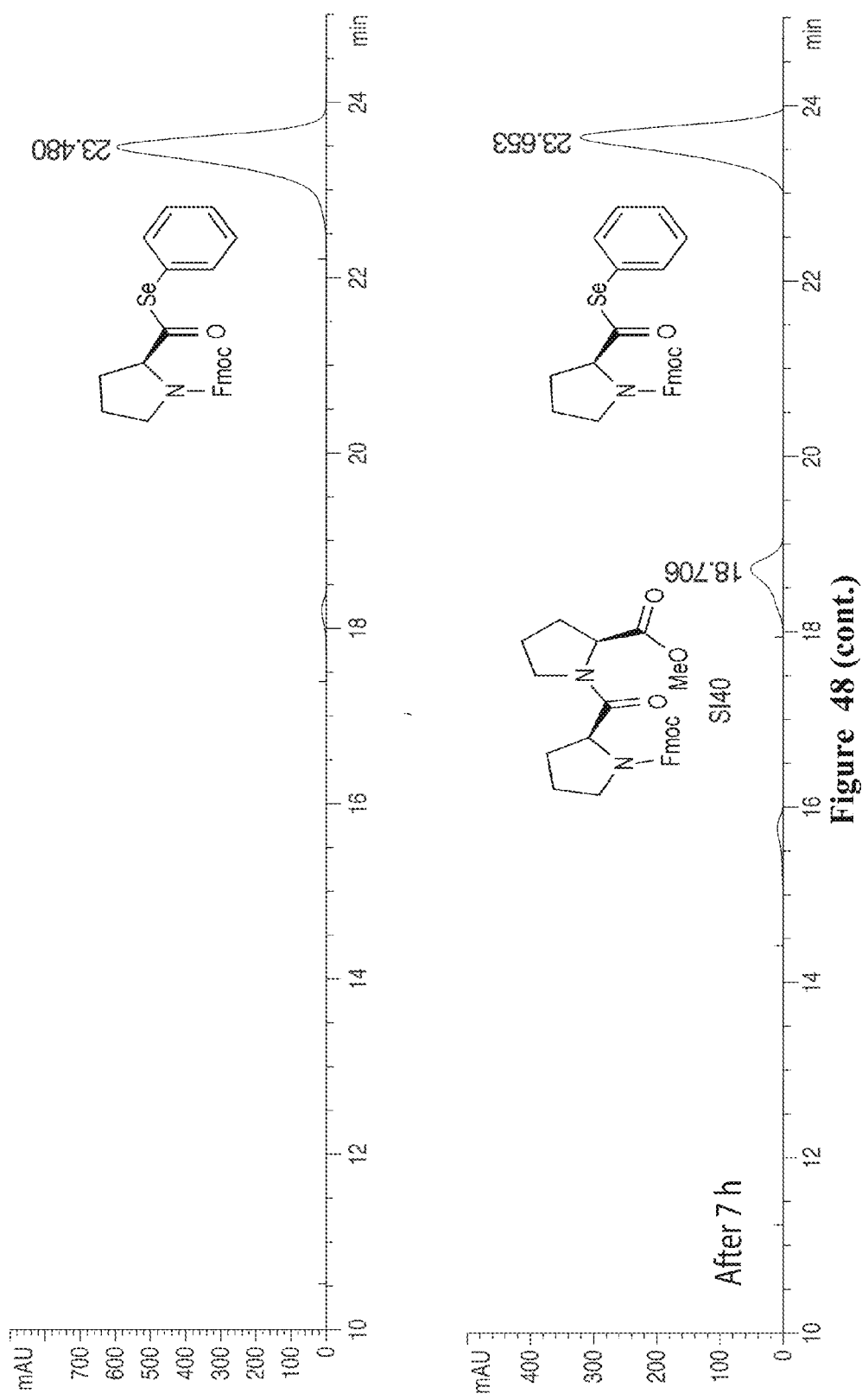
Figure 49:
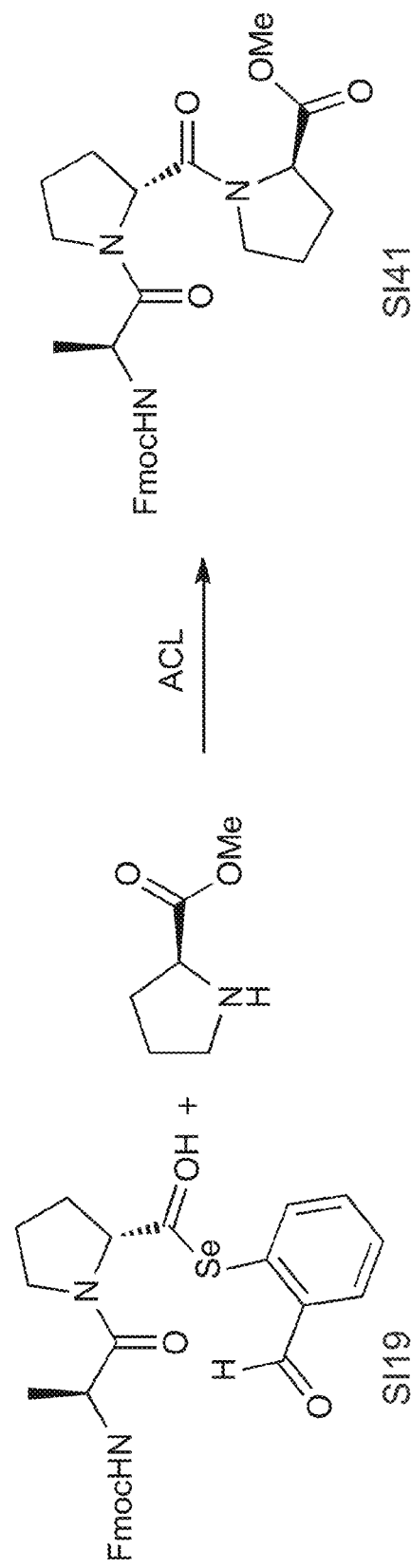
FIG. 49 shows HPLC spectra of the starting material and the crude reaction mixture of peptide SI41 after 30 min of incubation; the product peak is labeled.
Figure 49:
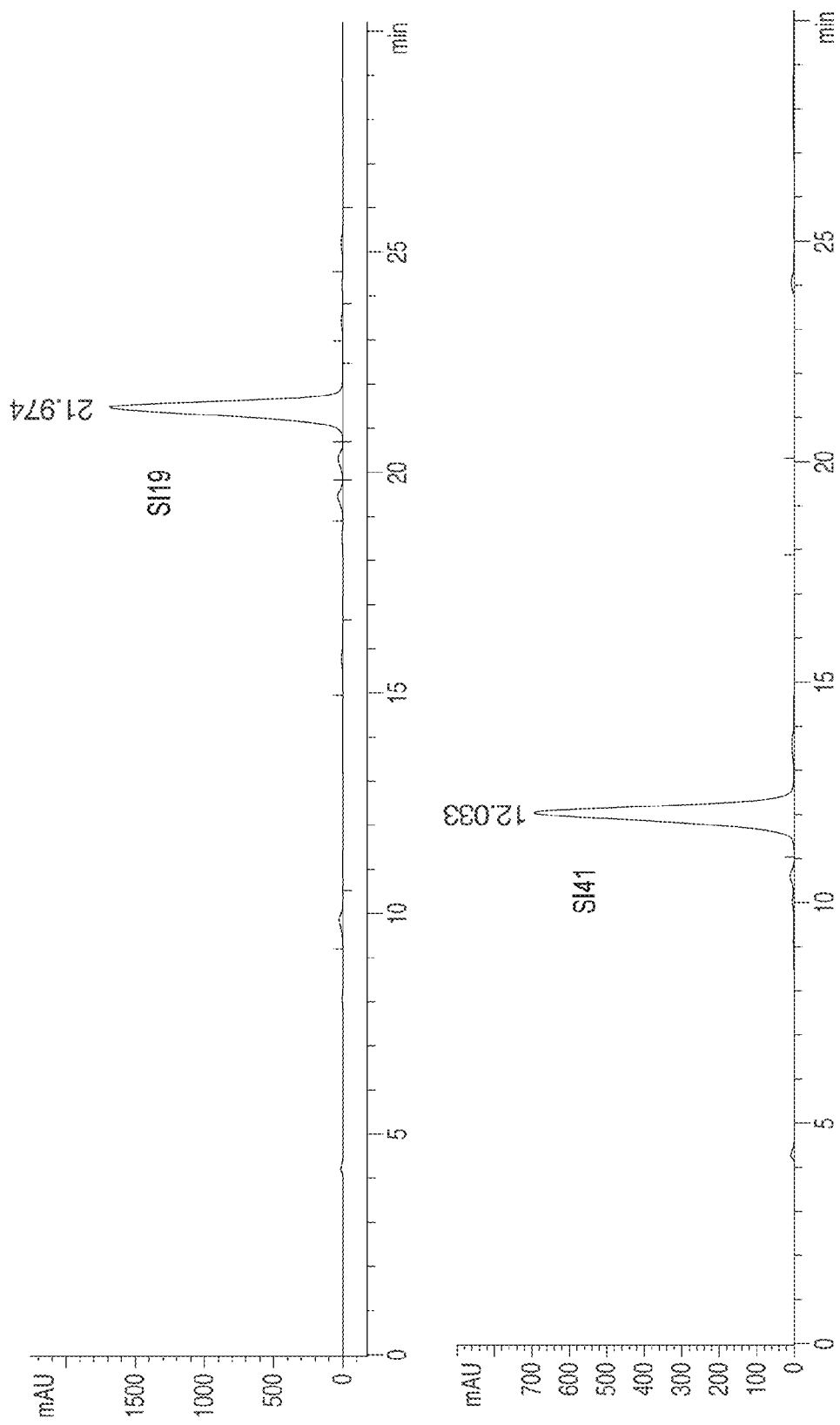
Figure 50:
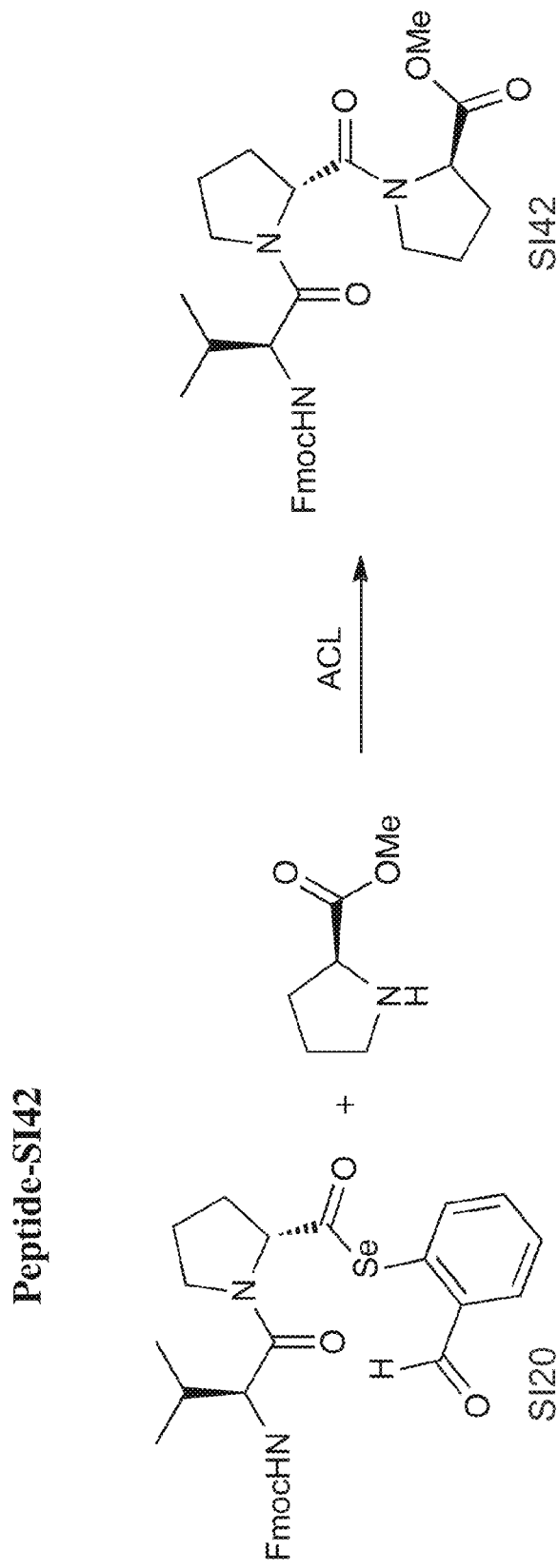
FIG. 50 shows HPLC spectra of the starting material and the crude reaction mixture of peptide SI42 after 30 min of incubation; the product peak is labeled.
Figure 50:
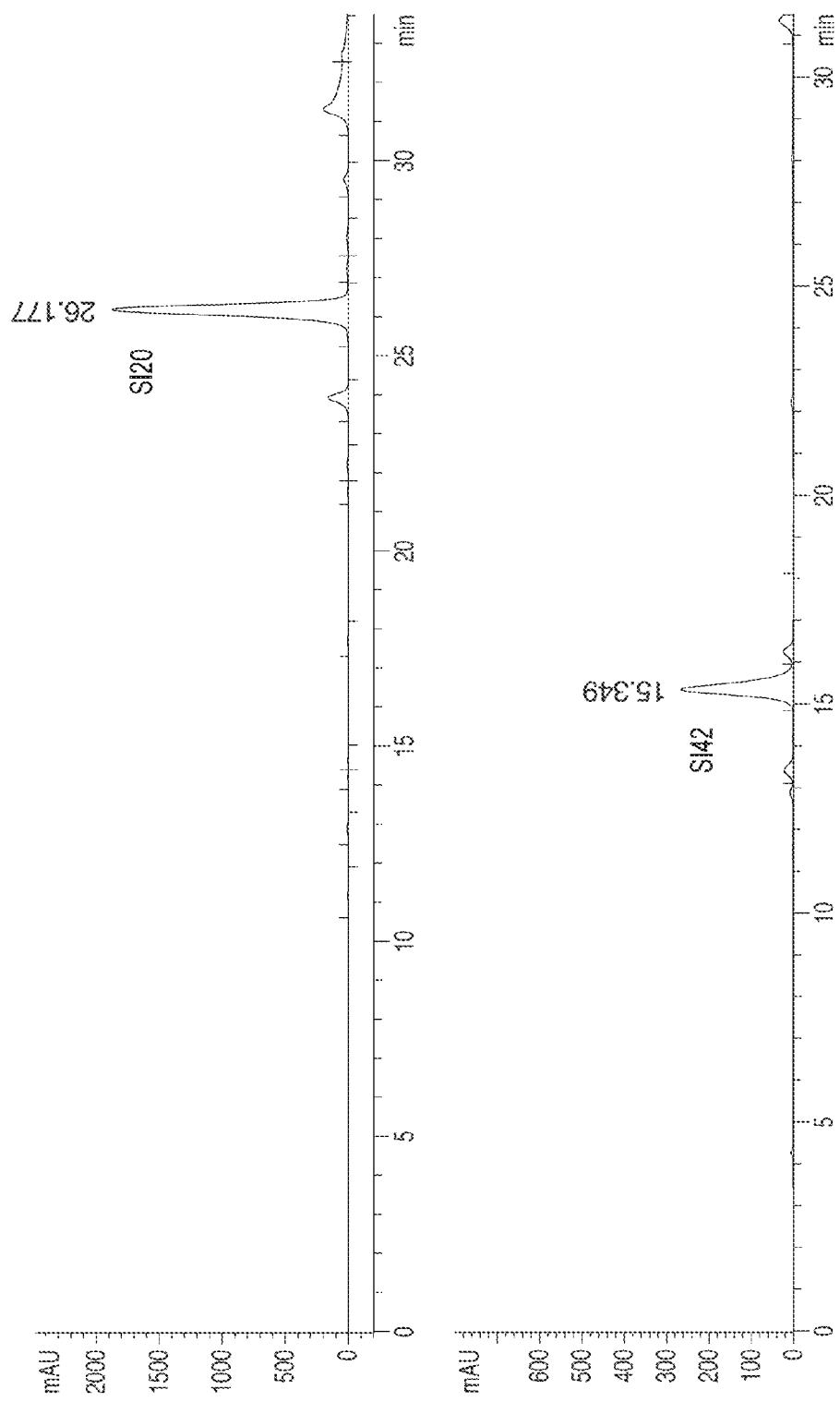

TABLE 1-continued
Ligation Products (see indicated figure for HPLC traces)
| Peptide | HPLC Trace(s) |
|---|---|
| 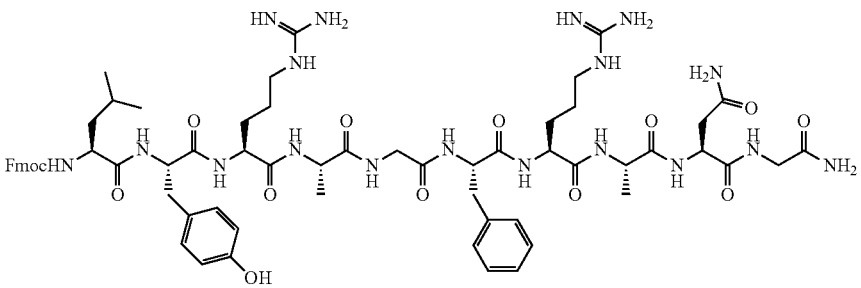 SI38 | FIG. 45 |
| 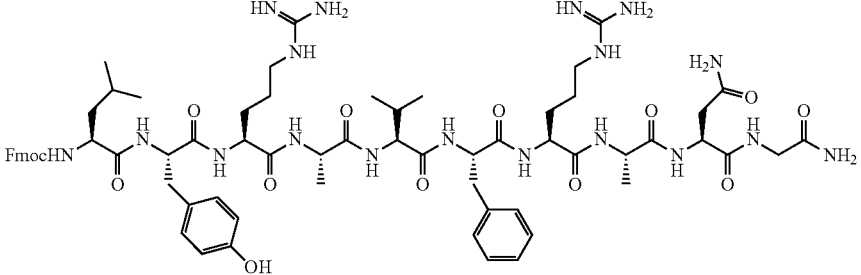 SI39 | FIG. 46 |
| 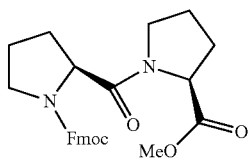 SI40 | FIG. 47 and FIG. 48 |
| 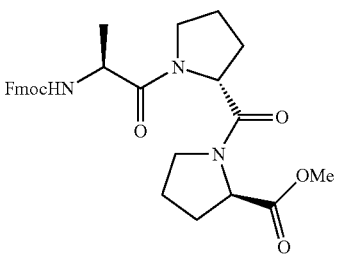 SI41 | FIG. 49 |
| 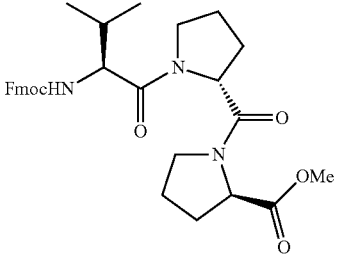 SI42 | FIG. 50 |

TABLE 1-continued

Ligation Products (see indicated figure for HPLC traces)

Figure 51:
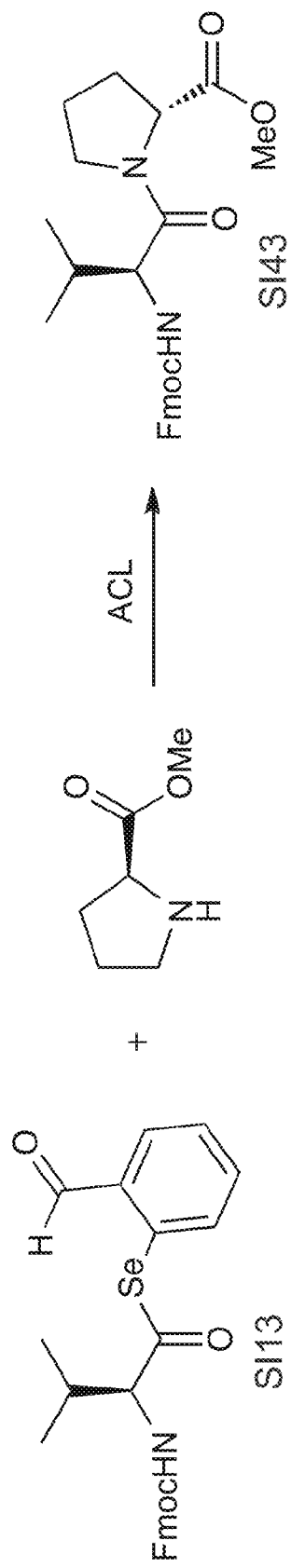
FIG. 51 shows HPLC spectra of the starting material and the crude reaction mixture of peptide SI43 after 2 hours of incubation; the product peak is labeled.
Figure 51:
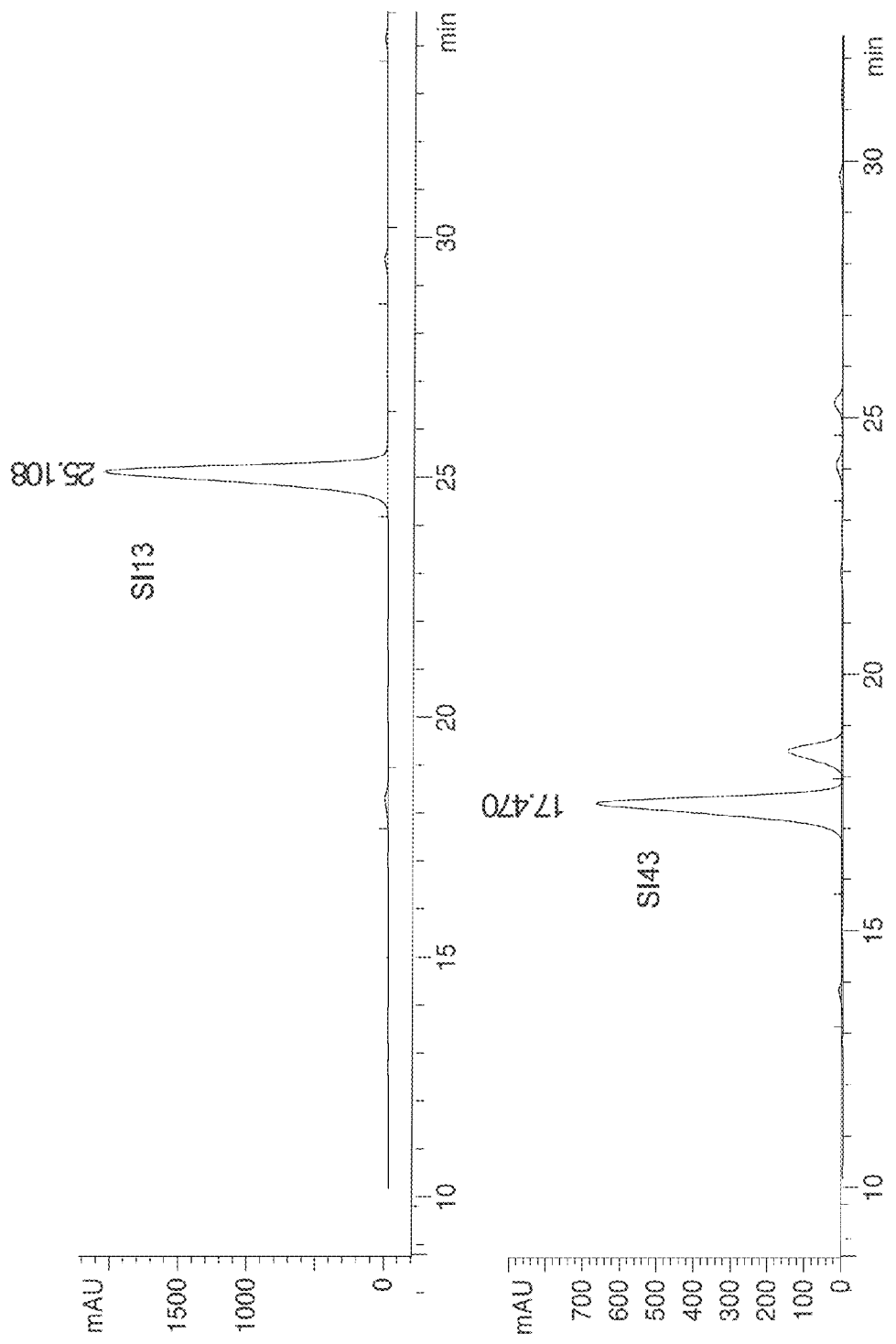

| Peptide | HPLC Trace(s) |
|---|---|
| 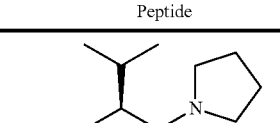<br>SI43 | FIG. 51 |

Example 32

Epimerization Studies

Two sets of tetrapeptides were prepared and tested to evaluate the extent of epimerization of the selenobenzaldehyde ester: (i) FmocVal-Ala-L-Ala-Gln-NH$_2$ and its expected epimerization product, FmocVal-Ala-D-Ala-Gln-NH$_2$, and (ii) FmocAla-Val-L-Ala-Gln-NH$_2$ and its expected epimerization product, FmocAla-Val-D-Ala-Gln-NH$_2$. The reactive selenobenzaldehyde esters in (i) and (ii) consist of alanine and valine residues, respectively. Rates of condensation of alanine selenobenzaldehyde ester is faster than the valine derivative. Comparison of the two sets of amino acid selenobenzaldehyde esters allows for the critical evaluation of the extent of racemization.

Example 33

Ubiquitin Labeling

A solution of Azodye-selenoester (500 μmol) in 10 μl DMF was mixed with ubiquitin ($^{15}$N labeled) (100 μmol) predissolved in 90 μl 1× phosphate buffered saline (PBS), pH 7.0. The reaction mixture was shaken and the progress monitored by MALDI-TOF Mass Spectrometry. See FIGS. 52A-F.

Example 35

Results and Discussion of Examples 1-33

Model Studies

As shown in Table 2 below, ACL auxiliary development studies were begun by condensing salicylaldehyde-derived benzylester 1a with benzylamine in DMF (Kemp D. S., Biopolymers 20:1793-804 (1981); Kemp et al., J. Org. Chem. 40:3003-04 (1975), each of which is hereby incorporated by reference in its entirety). Complete conversion of the ester to the amide 2 was observed in less than 5 hours as monitored by LCMS. Presence of the ortho-aldehyde group is critical for the ACL mechanism as phenyl and para-hydroxybenzaldehyde esters, 1b and 1c, respectively react at much slower rates. Compound 1c also served as a control for evaluating potential reactivity increases due to the presence of an electron-withdrawing group at the ortho or para positions of the aromatic ring. Aminolysis reactions are not considered to be sensitive to minor pKa differences in the leaving group, as the formation of the tetrahedral transition state is the rate limiting step; although, analysis is complicated by proton transfers (Holmquist et al., J. Am. Chem. Soc. 91:2985-93 (1969); Jencks et al., J. Am. Chem. Soc. 90:2622-37 (1968); Trmcic et al., Beilstein J. Org. Chem. 6:732-41 (2010); Yang et al., Org. Lett. 2:4133-36 (2000), each of which is hereby incorporated by reference in its entirety). The pKa's of the ortho-formylphenol is slightly lower than the para substituted analog while both pKa's are much lower than that of the basic amine nucleophile. The para-benzaldehyde ester analog, 1c, undergoes amide bond formation much slower than the ortho analog 1a reflecting the faster rate of reaction with the aldehyde group than direct acylation of the substituted phenylesters. While the transient hemiaminal/imine in the ortho analog is rapidly captured for acylation, a similar step is not possible for the para analog. Although direct acylation of amines cannot be ruled out as a minor contributor to the product formation, these studies support the aldehyde capture mechanism.

TABLE 2

Model Studies for the Development of ACL[a]

| Ester | X | R$^1$ | R$^2$ | Time[b] |
|---|---|---|---|---|
| 1a | O | CHO | H | 5 h |
| 1b | O | H | H | 40 h |
| 1c | O | H | CHO | 48 h |
| 1d | S | CHO | H | 10 min |
| 1e | S | H | H | 60 min |
| 1f | S | H | CHO | 10 h |
| 1g | Se | CHO | H | 1 min |
| 1h | Se | H | CHO | —[c] |

[a]Reaction conditions: esters (50 μmol) and benzyl amine (125 μmol) in 1 mL DMF.
[b]Time for >95% conversion of starting ester to the amide product at room temperature as determined by LCMS.
[c]The p-selenobenzaldehyde ester could not be isolated from the reaction of activated benzoic acid and bis-p-benzaldehyde diselenide (Figures 56A-G).

Figure 53A:
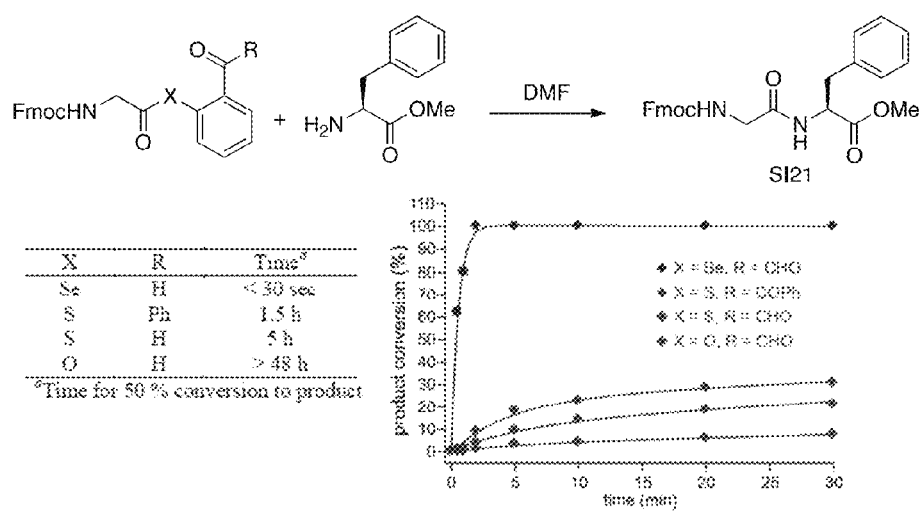
Figure 53B:
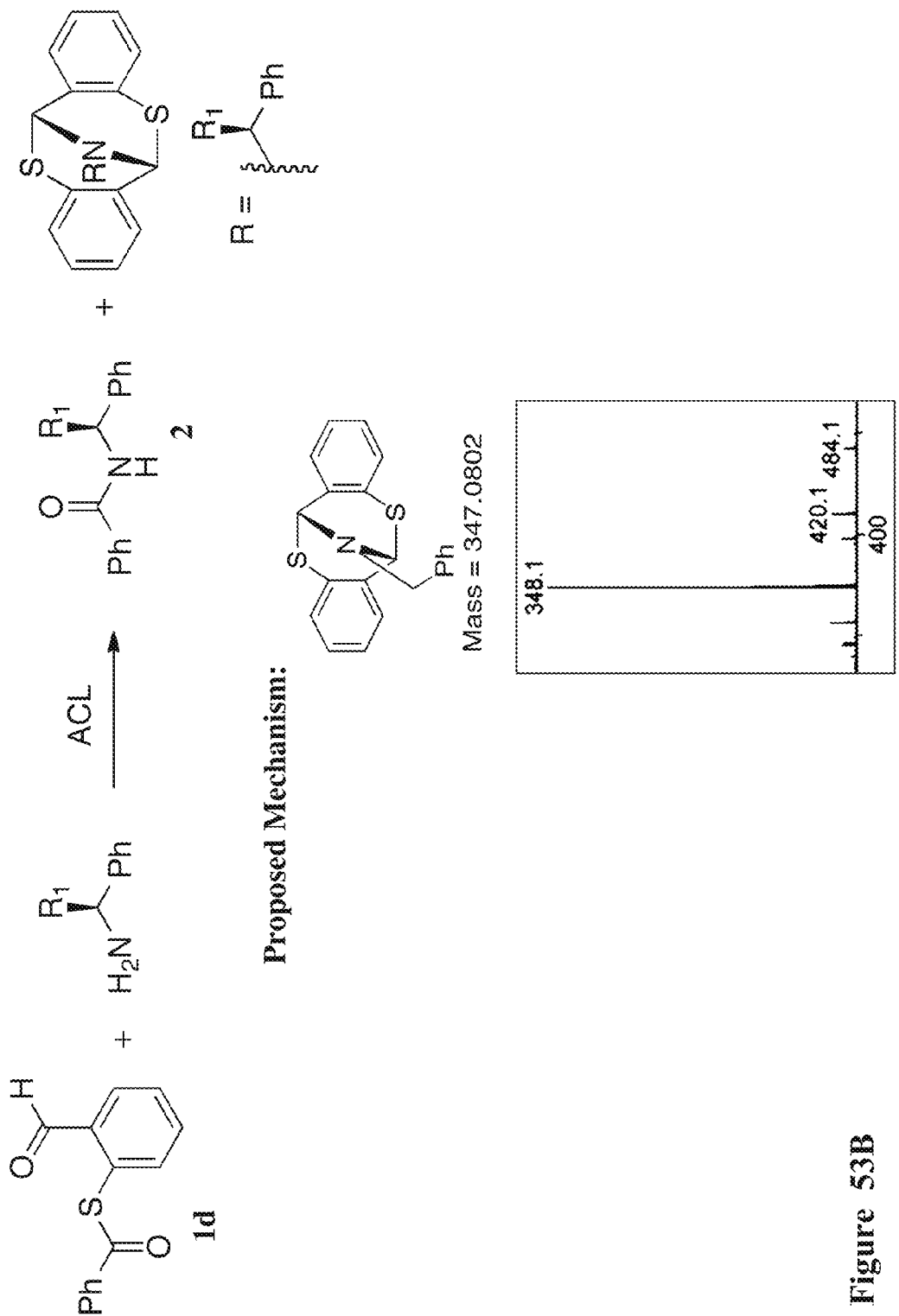
Figure 53B:
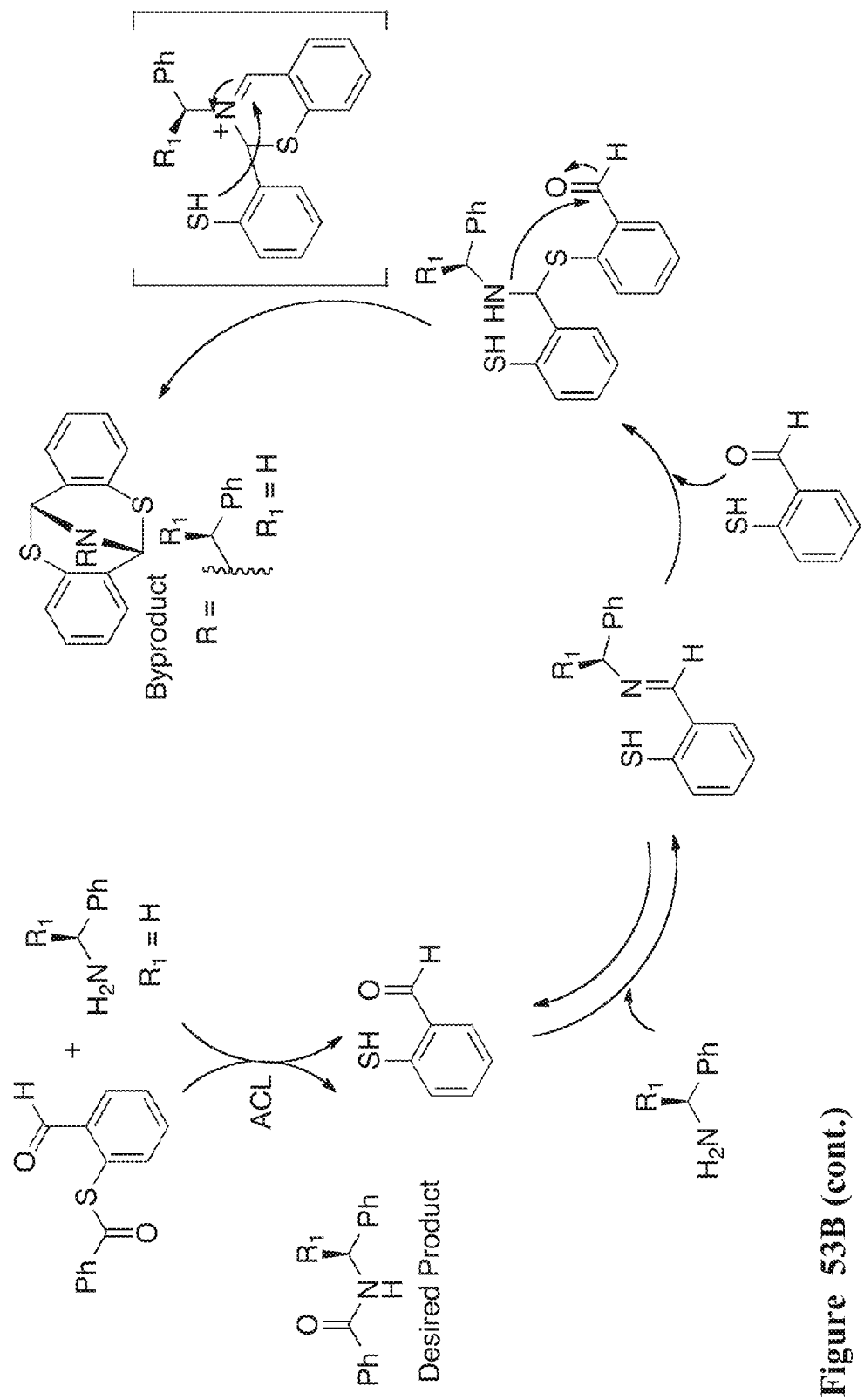
Figure 55A:
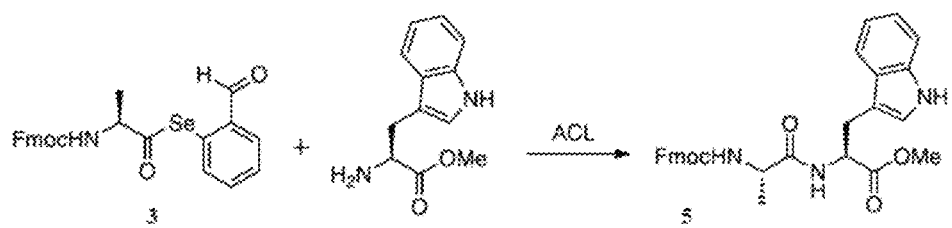
FIGS. 55A-G relate to the compatibility of ACL in aqueous buffers at different pH. Reaction progress was analyzed by analytical HPLC.
Figure 55B:
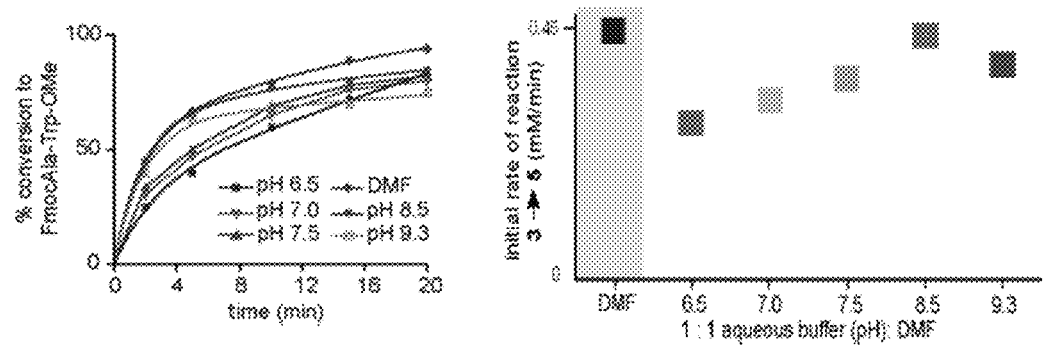
Figure 55C:
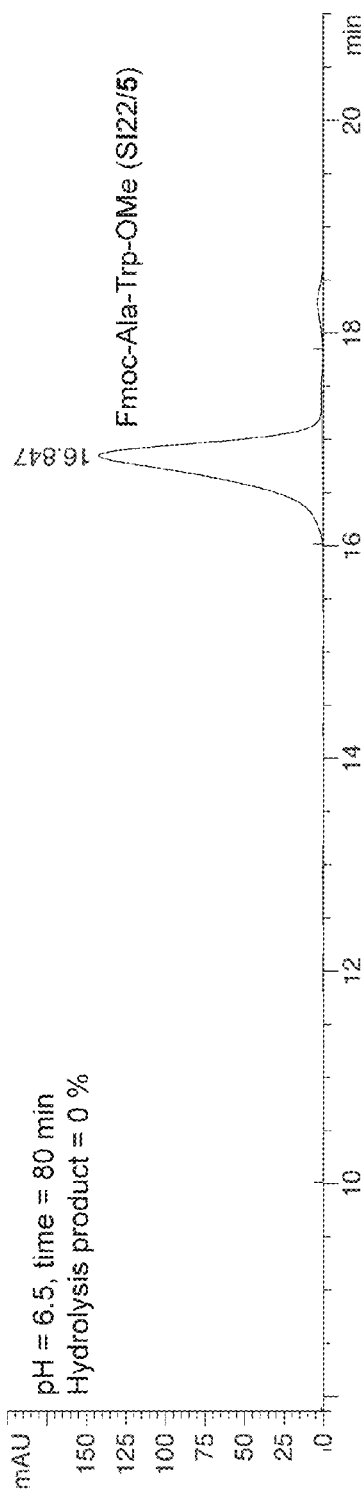
Figure 55D:
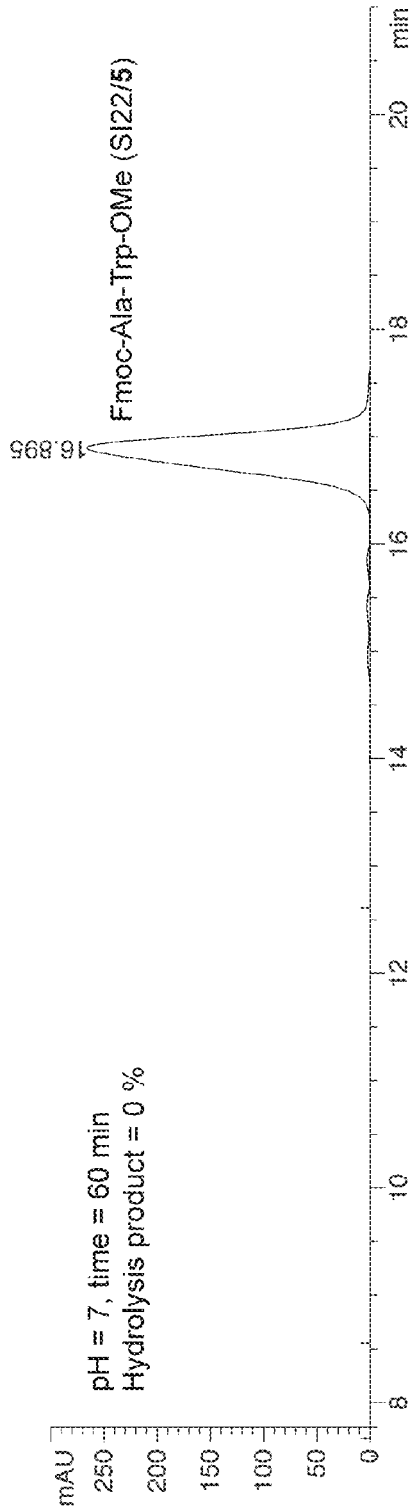
Figure 55E:
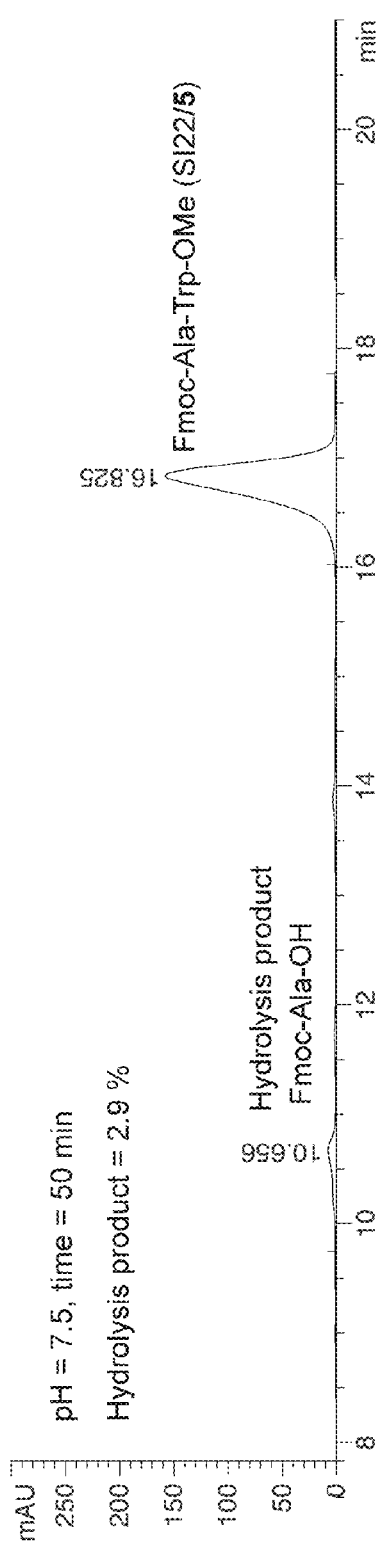
Figure 55F:
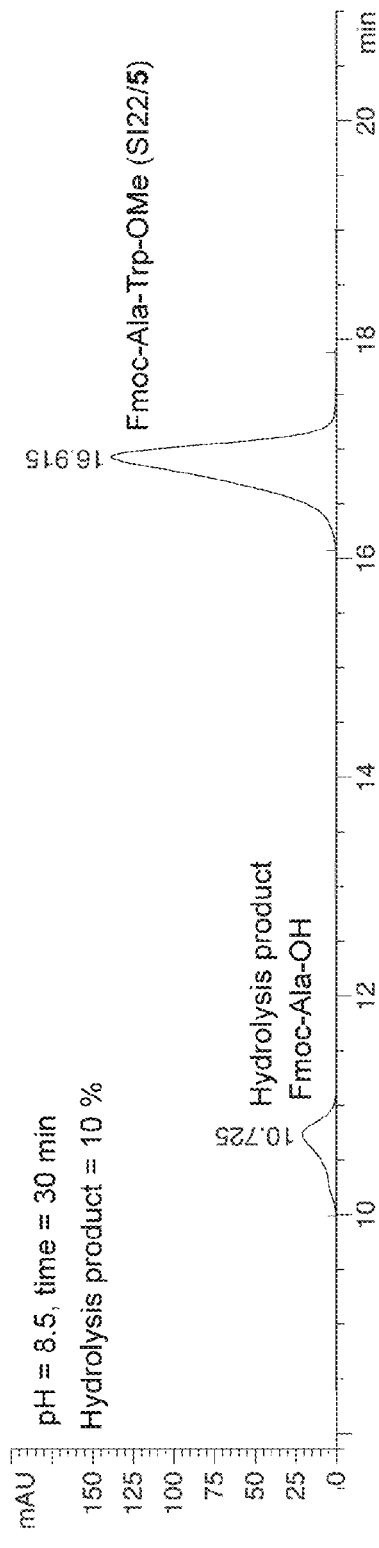
Figure 55G:
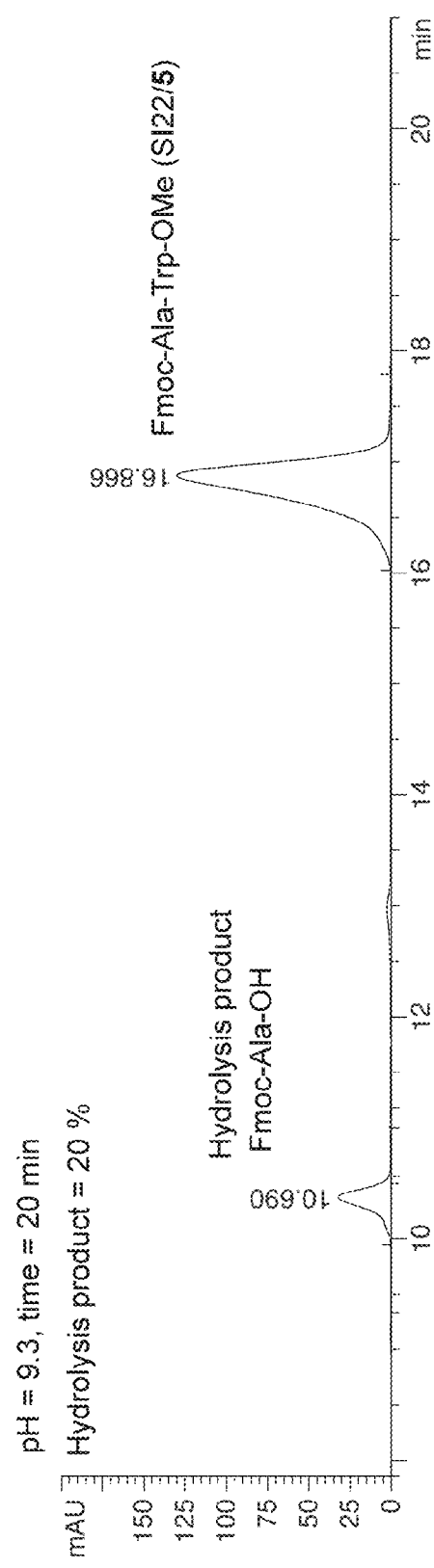

To further enhance the efficiency of the ACL reaction, the leaving group was converted from a phenol moiety to a thiophenol group. The importance of an ortho-aldehyde group for ACL is also evident in the thioester series 1d-1f, as 1d, with an ortho-aldehyde group, reacts more efficiently than the unsubstituted thiophenyl and para-thiobenzaldehyde esters, 1e and 1f, respectively (Table 2). Extensive analysis of aminolysis of thioesters suggests that N acylations also proceed through tetrahedral intermediates as oxoesters (Yang et al., *Org. Lett.* 2:4133-36 (2000); Castro, *Chem. Rev.* 99:3505-24 (1999), each of which is hereby incorporated by reference in its entirety). (The thiobenzaldehyde ester derivatives undergo a side reaction; this reaction can be suppressed by converting the benzaldehyde to the corresponding benzophenone (see FIGS. 53A-B).

To further accelerate the ACL reaction, the leaving group was converted from a thiophenol moiety to selenophenol derivative 1g (Table 2) (Durek et al., *Angew. Chem. Int. Ed.* 50:12042-45 (2011); Mautner et al., *J. Am. Chem. Soc.,* 85:3458-62 (1963); Chu et al., *J. Org. Chem.* 31:308-12 (1966), each of which is hereby incorporated by reference in its entirety). As predicted, substitution with selenol provided a significant boost to the reaction rate with complete conversion in less than one minute under the reaction conditions. Amino acid derived selenobenzaldehyde esters also provide the desired dipeptides more efficiently than the oxo- and thiobenzaldehyde ester analogs (see FIG. 53A).

Kinetic Studies

The above results support the aldehyde capture and acyl transfer mechanism outlined for aldehyde capture ligation, although the exact identity of the intermediate remains to be probed. The ACL reaction between alanine-derived selenobenzaldehyde ester, 3, and tryptophan methyl ester follows a second order rate constant (FmocAla-COSe-o-Ph-CHO, k=1.65±0.06 $M^{-1}S^{-1}$) (Table 3 below and FIGS. 54A-C). This reaction undergoes complete conversion to the dipeptide roughly 100-times faster as compared to the selenoester analog without the o-aldehyde group (FmocAla-COSePh, k=0.015±0.001 $M^{-1}S^{-1}$).

TABLE 3

Kinetics of the Aldehyde Capture Ligation[a]

FmocHN–CH(R')–C(O)–Se–C₆H₄(R) + Trp-OMe →(DMF) Fmoc-Ala-Trp-OMe 5

| Selenoester | R | k[$M^{-1}S^{-1}$] | Relative Rates |
|---|---|---|---|
| 3 | CHO | 1.653 ± 0.0587 | 110 |
| 4 | H | 0.015 ± 0.0011 | 1 |

[a]Conditions: FmocAla-seleno-ester, 3 or 4 (2 µmol), HCl—NH₂-Trp-OMe (2 µmol) and Et₃N (2 µmol) in 1 mL DMF.

pH Studies

The compatibility of ACL for synthesis of peptides was determined in aqueous buffers (with DMF as a co-solvent) for potential applications aimed at synthesis of large peptides and proteins or other bioconjugates by fragment coupling. The formation and reactions of hemiaminals and imines are known to be sensitive to buffer pHs (WILLIAM P. JENCKS, CATALYSIS IN CHEMISTRY AND ENZYMOLOGY (1st ed. 1969), which is hereby incorporated by reference in its entirety). However, hydrolysis of selenoesters is also pH dependent. The present work shows that initial rates of dipeptide formation were higher at basic pHs, with pH 8.5 proving to be optimal (FIGS. 55A-G). The initial rates were slightly lower at pH 9.3; however, hydrolysis of the selenoester becomes a competing side product.

Seleno- and Thio-o-Benzaldehyde Esters

Figure 56:
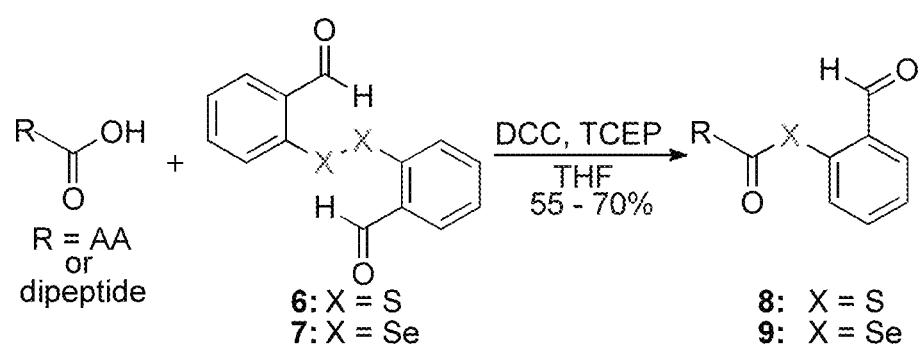
FIG. 56 illustrates the synthesis of seleno- and thio-o-benzaldehyde esters from Fmoc amino acids (AA) or peptides.

In the exploratory studies designed to determine the scope of ACL, the amino acid and peptide thio- and seleno-benzaldehyde esters were initially prepared by coupling activated carboxylic acids and o-benzaldehyde disulfide (6) or diselenide (7) in the presence of a reducing agent, such as TCEP (FIG. 56). The diselenide itself is available in one step from 2-bromobenzaldehyde (Example 11) (Syper et al., *Tetrahedron* 44:6119-30 (1988), which is hereby incorporated by reference in its entirety). Solid phase synthesis of peptide selenoesters was also explored (see infra).

Epimerization Studies

Epimerization of activated amino acids is a critical concern in peptide synthesis. The selenobenzaldehyde bearing peptide may be expected to undergo epimerization during the course of aldehyde capture ligation, possibly through the formation of an azalactone. To investigate this possibility and quantify the amount of epimerized product, a tetrapeptide FmocVal-Ala-L-Ala-Gln-NH₂ and its "fully epimerized" analog, FmocVal-Ala-D-Ala-Gln-NH₂, were prepared. These products would result from ligation of FmocVal-Ala-L-COSe-ortho-PhCHO with NH₂-Ala-Gln-CONH₂. An HPLC assay that allows detection of as low as 2% epimerization was developed. Careful analysis of HPLC traces show that detectable levels of epimerization do not occur, under the reported reaction conditions (FIGS. 57A-D).

Condensation of FmocVal-Ala selenobenzaldehyde with NH₂-Ala-Gln-CONH₂ is a relatively fast reaction. To rule out the possibility that the racemization is occurring but at a slower rate, condensation of FmocAla-Val-L-COSe-o-Ph-CHO with NH₂-Ala-Gln-CONH₂ was tested under the same reaction conditions. Amide bond formation involving valine selenobenzaldehyde esters is relatively slow (see Table 4 below, entries 8 and 9). Roughly 2% epimerization was observed for this slower ACL coupling (FIGS. 58A-B).

TABLE 4

Aldehyde Capture Ligation: Substrate Scope[a]

| Entry | Ligation product[b] | Time[c] |
|---|---|---|
| 1 | Fmoc-<u>AW</u>-COOMe | 2 min |
| 2 | Fmoc-<u>AV</u>-COOMe | 2 min |
| 3 | Fmoc-<u>AR</u>-COOMe | 2 min |
| 4 | Fmoc-<u>GC</u>-COOMe | 2 min |
| 5 | Fmoc-<u>AS</u>-COOBn | 5 min |
| 6[d] | (Fmoc-A)₂K—COOH | 5 min |
| 7 | Fmoc-<u>FL</u>-COOtBu | 3 min |
| 8 | Fmoc-<u>VW</u>-COOMe | 2 h |
| 9 | Fmoc-<u>VV</u>-COOMe | 4 h |
| 10 | Fmoc-AibW-COOMe | 2 h |
| 11 | Fmoc-<u>AV</u>DE-CONH₂ | 5 min |
| 12 | Fmoc-<u>AA</u>SY-CONH₂ | 2 min |
| 13[e] | Fmoc-<u>AA</u>SY-CONH₂ | 2 min |
| 14 | Fmoc-<u>AA</u>AH-CONH₂ | 2 min |
| 15 | Fmoc-AVDAFE-CONH₂ | 5 min |
| 16 | Fmoc-<u>F</u>VDAFE-CONH₂ | 5 min |
| 17 | Fmoc-V<u>AV</u>DAFE-CONH₂ | 5 min |

[a]Reaction conditions: Fmoc amino acid-selenobenzaldehyde ester (10 µmol), N-terminal amino acid/peptide HCl or CF₃COOH salts (20 µmol) and Et₃N (20 µmol) in 1 mL DMF.
[b]Residues at the junction are underlined.
[c]Time for >95% conversion to product at room temperature. Analysis by HPLC traces of the crude reaction mixture.
[d]Double acylation of lysine occurs on the α- and ε-amine groups occurs.
[e]FmocAla-selenobenzaldehyde ester (20 µmol), N-terminal CF₃COOH•ASY-CONH₂ (10 µmol) and Et₃N (10 µmol ) in 1 mL DMF; after 6 h only the amidation product is obtained.

ACL Substrate Scope

Figure 59A:
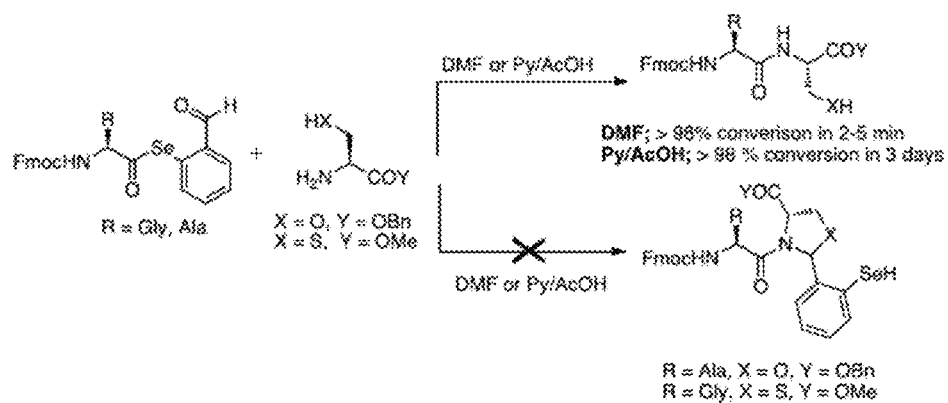
FIGS. 59A-C illustrate that pseudoproline formation was not observed in reactions with N-terminal serine and cysteine residues.
Figure 59B:
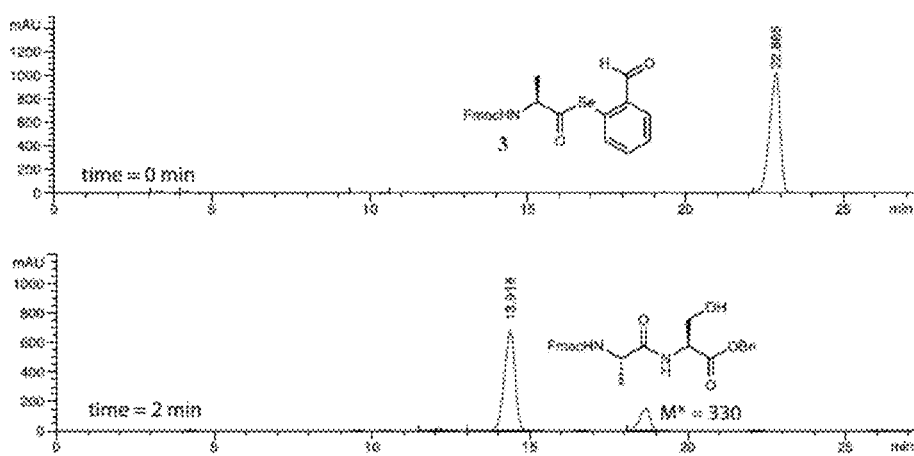
Figure 59C:
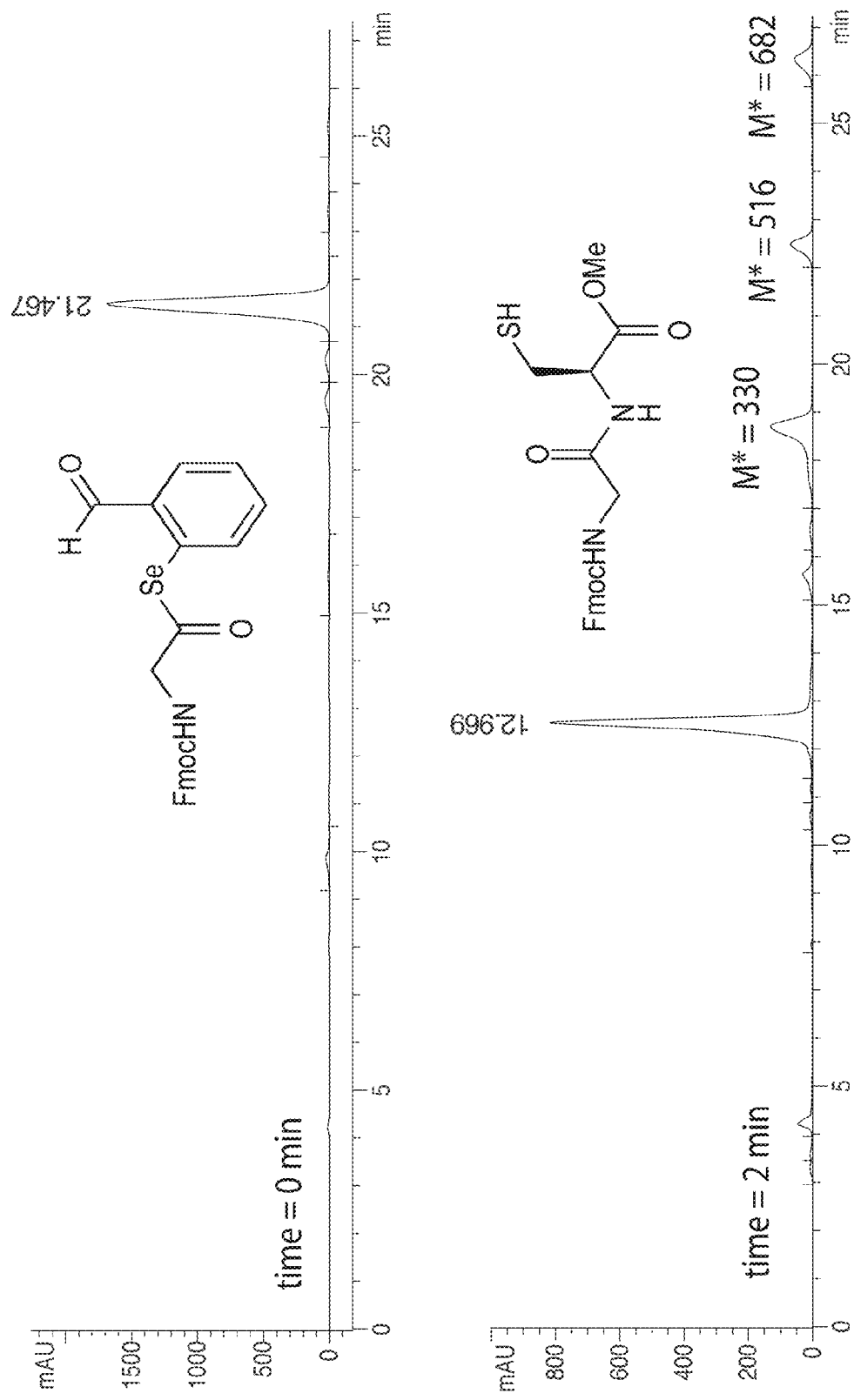

The utility and attractiveness of native chemical ligation results from the fact that it affords chemoselective ligation of peptides, and other biomolecules, without need of protecting groups on reactive side chain functionality. The tolerance of ACL was explored for unprotected side chain groups for a variety of amino acid partners, including Arg, Asp, Cys, Glu, His, Leu, Phe, Ser, Trp, Tyr, and Val (see Table 4), was explored. These amino acid residues underwent the desired ligation, suggesting that ACL is a chemoselective reaction. Reactions of selenobenzaldehyde esters with N-terminal serine and cysteine residues may provide the amide products through the formation of respective pseudoproline intermediates, as reported for oxobenzaldehyde esters (Liu, *J. Am. Chem. Soc.* 116:4149-4153 (1994); Liu et al., *Proc. Natl. Acad. Sci. USA* 91:6584-6588 (1994); Li et al., *Org. Lett.* 12:1724-1727 (2010); Zhang et al., *Proc. Nat'l Acad. Sci. USA* 110:6657-6662 (2013), each of which is hereby incorporated by reference in its entirety), rather than through an ACL mechanism. This possibility was investigated, but the formation of the pseudoproline derivatives with selenobenzaldehyde esters was not observed in DMF or pyridine/acetic acid mixtures (FIGS. 59A-C). N-terminal cysteine may undergo condensation under an NCL or ACL mechanism.

A potential limitation of ACL is that the aldehyde group on selenobenzaldehyde esters may react with any amine, i.e., c-amino of lysine would undergo an ACL as well as N-terminal amines (Table 4, entry 6). Possible solutions to control reactions of lysine side chain amines would include standard protecting group strategies or reactions with peptides and proteins under pH-controlled conditions. The N-terminal amino group of proteins has a significantly lower $pK_a$ value than the c-amine of lysines (Grimsley et al., *Protein Sci.* 18:247-51 (2009), which is hereby incorporated by reference in its entirety). Prior studies have shown that this $pK_a$ difference can be exploited to selectively modify the N-terminal amine in the presence of lysine residues (Chan et al., *J. Am. Chem. Soc.* 134:2589-98 (2012), which is hereby incorporated by reference in its entirety). The possibility of selectively modifying N-terminal amines of proteins using ACL has been explored (vide infra).

Also investigated was the possibility of side chain alcohol groups of serine or tyrosine residues becoming acylated, especially with an excess of selenobenzaldehyde esters. Tripeptide $NH_2$-ASY—$CONH_2$ was treated with 2 or 0.5 eq of Fmoc-alanine selenobenzaldehyde ester (Table 4, entries 12-13). Acylation of the side chain alcohol group was not observed even after prolonged reaction periods. C-terminal aspartic and glutamic acid thioesters can undergo reactions with side chain carboxylates (Villain et al., *Eur. J. Org. Chem.* 2003:3267-72 (2003), which is hereby incorporated by reference in its entirety). This side reaction will likely also preclude placement of Asp and Glu residues, along with other reactive side chains such as cysteine, at the C-terminus in peptido selenobenzaldehydes, as in NCL.

The efficiency of peptide fragment couplings by native chemical ligation, and by other coupling agents, is significantly reduced for bulky amino acid substrates (Hackeng et al., *Proc. Natl. Acad. Sci. USA* 96:10068-10073 (1999), which is hereby incorporated by reference in its entirety). A range of selenobenzaldehyde esters featuring bulky C-terminal residues including valine and aminoisobutyric acid (Aib) were examined to evaluate the potential of ACL for these challenging couplings. The sterically demanding Val and Aib selenobenzaldehyde esters require longer ligation times (2-4 hours) for >95% conversion (Table 4, entries 8-10) as compared to 2-5 minutes for Ala, Gly, and Phe analogs (Table 4, entries 1-7) (Hackeng et al., *Proc. Natl. Acad. Sci. USA* 96:10068-73 (1999), which is hereby incorporated by reference in its entirety). Ligation of selenobenzaldehyde esters with pentapeptide (VDAFE) underwent completion in just 5 minutes (Table 4, entries 15-17), suggesting that ACL with peptides is as efficient as with single amino acid residues).

To extend the ACL technology to large peptides, a solid phase method for the synthesis of seleno-benzaldehyde esters was explored using the approach outlined by Dawson et al. for the solid phase synthesis of thioesters (FIG. 60) (Blanco-Canosa et al., *Angew. Chem. Int. Ed.*, 47:6851-55 (2008), which is hereby incorporated by reference in its entirety). A model pentapeptide (FmocLYRAG)N-acyl-benzimidazolinone (Nbz) was synthesized using the Dawson Nbz protocol. The peptide was cleaved as the o-benzaldehydeselenoester by treatment of the resin with diselenide 7 (FIG. 60) and tributylphosphine. The crude yield of the cleaved peptide was calculated to be 59% based on resin loading using the Fmoc absorbance. The selenoester was characterized using LCMS (FIG. 61A). The HPLC analysis showed a peak for the hydrolyzed peptide along with the desired selenoester. It is posited that the selenoester likely hydrolyzes during the HPLC run under the acidic aqueous conditions utilized for the analysis and not during the selenoester synthesis. The hydrolysed peptide is not observed upon further reaction of the unpurified selenoester with an amine (FIG. 61B), supporting this hypothesis.

The solid phase synthesis methodology was utilized to evaluate the applicability of ACL to the synthesis of model peptides in aqueous solution. For direct comparison with NCL, sequences that have previously been explored by Dawson et al. (Hackeng et al., *Proc. Natl. Acad. Sci. USA* 96:10068-10073 (1999), which is hereby incorporated by reference in its entirety) were prepared. Dawson et al. noted that NCL rates of pentapeptides AcLYRAX-SPh, where X is any residue, with CRANK-$CONH_2$ are largely dependent on the identity of X, with bulky residues (i.e., valine) at this position leading to inefficient couplings. Analogs of these pentapeptide sequences, FmocLYRAG and FmocLYRAV selenobenzaldehyde esters, were used herein to probe the effectiveness of ACL for peptide ligations with peptide FRANG-$CONH_2$ (Table 5). As expected, ACL with glycinyl selenobenzaldehyde proceeds much faster than the analogous valinyl selenobenzaldehyde, which requires 8 hours. Yet, the ACL reaction rate with FmocLYRAV-Se-o-PhCHO is remarkable considering native chemical ligation between AcLYRAV-SPh and CRANK-$CONH_2$ needs more than 48 hours for 60% completion (Hackeng et al., *Proc. Natl. Acad. Sci. USA* 96:10068-73 (1999), which is hereby incorporated by reference in its entirety). The ACL-mediated condensation of peptides in aqueous solutions is slower than in DMF, requiring roughly three times longer for completion. The HPLC analysis of crude reaction mixture shows efficient conversion of the selenoester to the desired peptide (FIGS. 61A-B).

TABLE 5

Aldehyde capture ligation of peptide segments

| Ligation product[a] | Solvent | Time[b] |
|---|---|---|
| Fmoc-LYRA<u>GF</u>RANG-$CONH_2$[c] | DMF | 30 min |
| Fmoc-LYRA<u>GF</u>RANG-$CONH_2$[d] | 10% DMF in $H_2O$ | 90 min[d] |
| Fmoc-LYRA<u>VF</u>RANG-$CONH_2$[c] | DMF | 8 h |

[a]Reaction progress analyzed by HPLC; residues at the junction are underlined.
[b]Time required for 95% conversion to product at room temperature.
[c]FmocLYRAX-Se-o-PhCHO (2 μmol), FRANG-$CONH_2$ (4 μmol) and $Et_3N$ (4 μmol) in 1 mL DMF.
[d]FmocLYRAG-Se-o-PhCHO (1 μmol), FRANG-$CONH_2$ (2 μmol) and $Et_3N$ (2 μmol) in 0.5 mL of 100 mM $NaH_2PO_4$ buffer (pH 6.5):DMF (90:10).

Acylated proline thioesters react slowly (<15% yield in >48 h) under NCL conditions (Hackeng et al., *Proc. Natl. Acad. Sci. USA* 96:10068-73 (1999), which is hereby incorporated by reference in its entirety). The rates of these NCL reactions have been reported to be independent of the number of residues attached to the N-terminus of proline (Pollock et al., *Chem. Commun.* 47:2342-44 (2011); Townsend et al., *J. Am. Chem. Soc.* 134:3912-16 (2012), each of which is hereby incorporated by reference in its entirety). This observation is consistent with the postulated contribution of the n-π* interaction on proline reactivity as only the carbonyl attached directly to the proline residue perturbs the rate of the reaction (Choudhary et al., *Protein Sci.* 20:1077-81 (2011), which is hereby incorporated by reference in its entirety). Various acylated proline derivatives were synthesized to gauge the potential of proline ligations using the ACL approach (Table 6, entries 1 and 2), and ACL was found to excel at the difficult ligation of proline residues indiscriminant of whether it is a C-terminal or N-terminal residue. Couplings of FmocVal, FmocPro, FmocAla-Pro, and FmocVal-Pro selenobenzaldehyde esters with proline methyl ester proceed rapidly, indicating that both N-terminal and C-terminal proline residues are efficient substrates for ACL (Table 6, entries 1 and 3). Analogous reactions of FmocVal and FmocPro selenophenyl esters (without the ortho-aldehyde group) require significantly longer periods (Table 6, entries 2 and 4). These studies demonstrate that preformed phenylselenoesters, which are typically considered to be highly reactive (Durek et al., *Angew. Chem. Int. Ed.* 50:12042-45 (2011), which is hereby incorporated by reference in its entirety), are much less efficient than the ACL auxiliary for difficult couplings.

TABLE 6

Coupling of proline residues with ACL[a]

| Entry | C-terminus | N-terminus | Ligation site | Conversion (%)[b] | Time[c] |
|---|---|---|---|---|---|
| 1 | X = Fmoc, P[1d], P[2] | | | >95 | 30 min |
| 2[e] | | | | ~20 | 7 h |
| 3 | | | | >95 | 2 h |
| 4 | | | | >95 | >96 h |

[a]Reaction conditions: C-terminal seleno-benzaldehyde ester (10 μmol), N-terminal AA/peptide (20 μmol) and Et₃N (20 μmol) in 1 mL DMF.
[b]Analysis by HPLC traces of the crude reaction mixture.
[c]Room temperature.
[d]Reaction in buffer (pH 8.5) >95% conversion in 90 min
[e]After 10 h, unidentified side products are observed. P[1]: Fmoc-A—, P[2]: Fmoc-V—

ACL adds to a growing list of methods that allow chemoselective formation of the amide bond in aqueous buffers. The attractiveness of ACL is that it potentially allows coupling of any set of amino acid residues, without requiring specific N-terminal amino acids such as cysteine. A potentially significant limitation is that the aldehyde may capture any amine, i.e., it may be difficult to selectively modify lysine side chains or the N-terminal amines. Two solutions may be envisioned to address this potential limitation: (a) in short peptides or other synthetic oligomers and small molecules, the appropriate amine may be protected using standard approaches; (b) the pKa difference between the N-terminal amino group and the ε-amine of lysine may be exploited to achieve selective modification of the N-terminus (Grimsley et al., *Protein Sci.* 18:247-51 (2009); Chan et al., *J. Am. Chem. Soc.* 134:2589-98 (2012); Bernal-Perez et al., *Anal. Biochem.* 428:13-15 (2012), each of which is hereby incorporated by reference in its entirety).

Figure 52A:
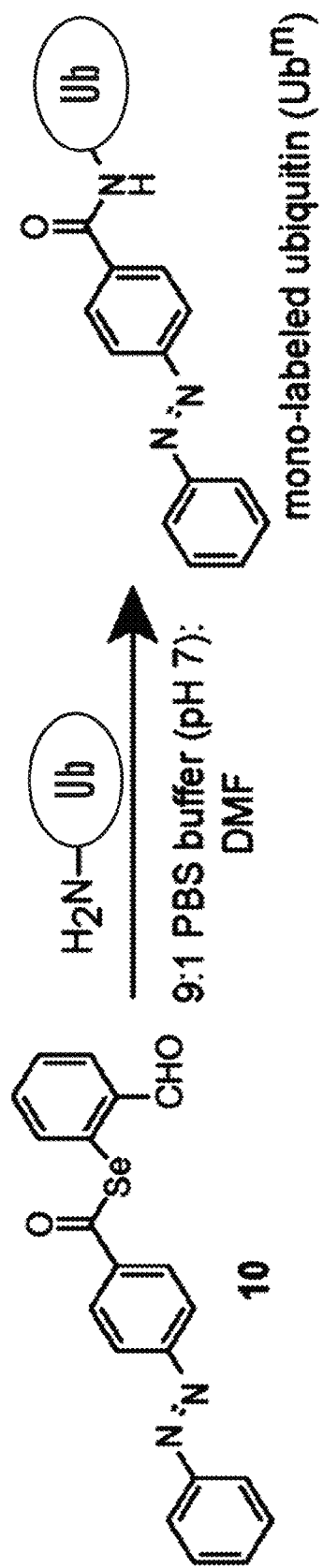
FIGS. 52A-F relate to the reaction between ubiquitin and selenoester 10.
Figure 52B:
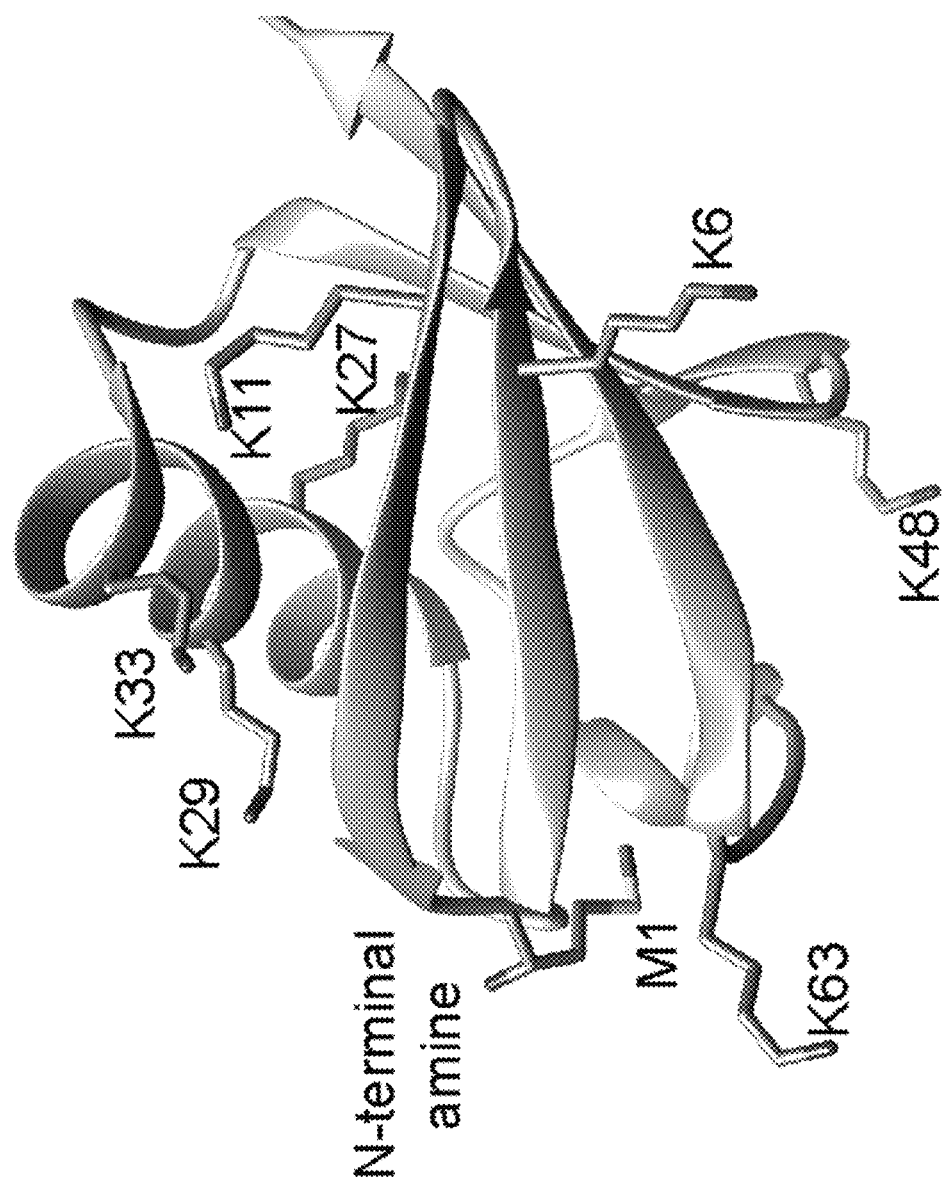
Figure 52C:
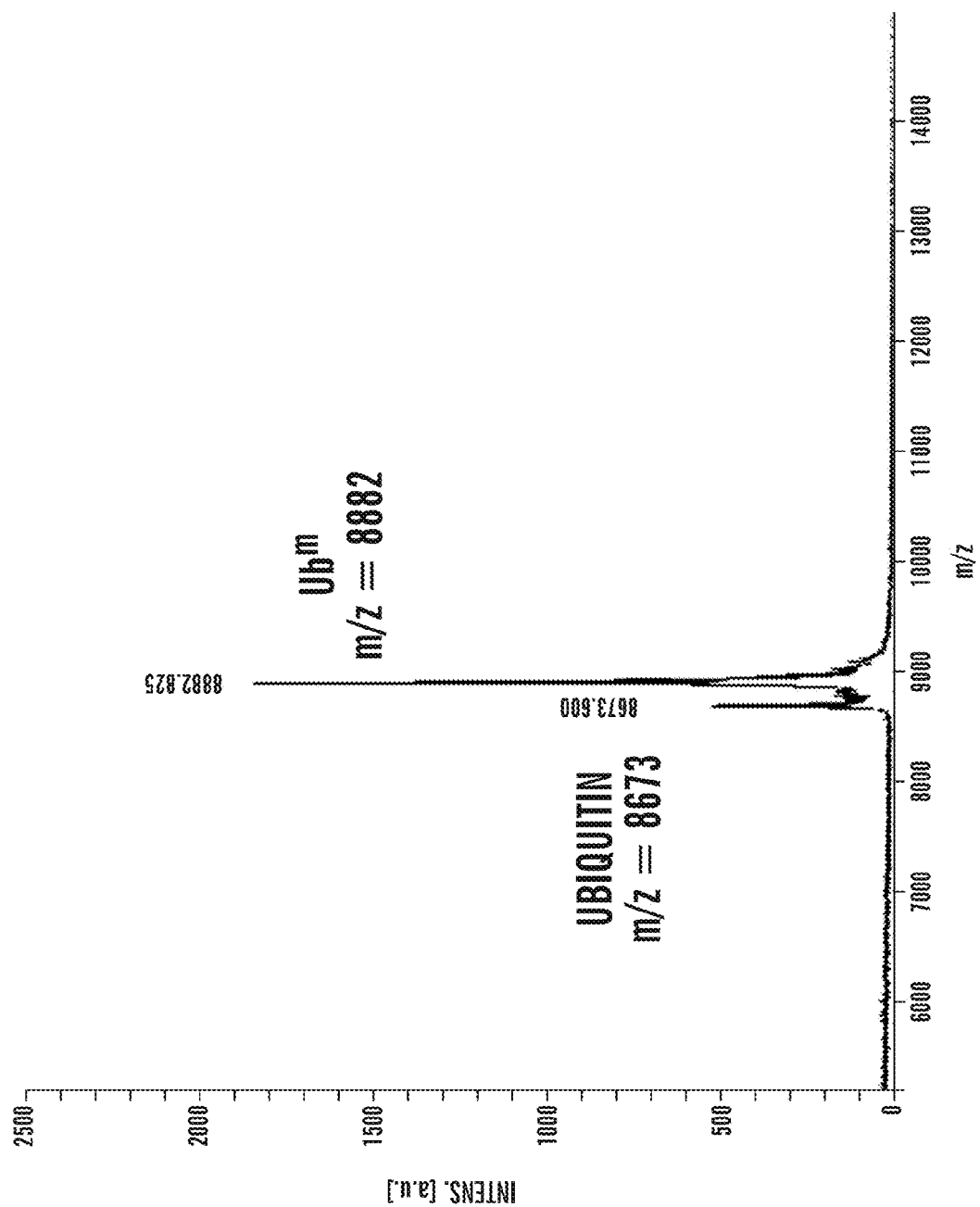
Figure 52D:
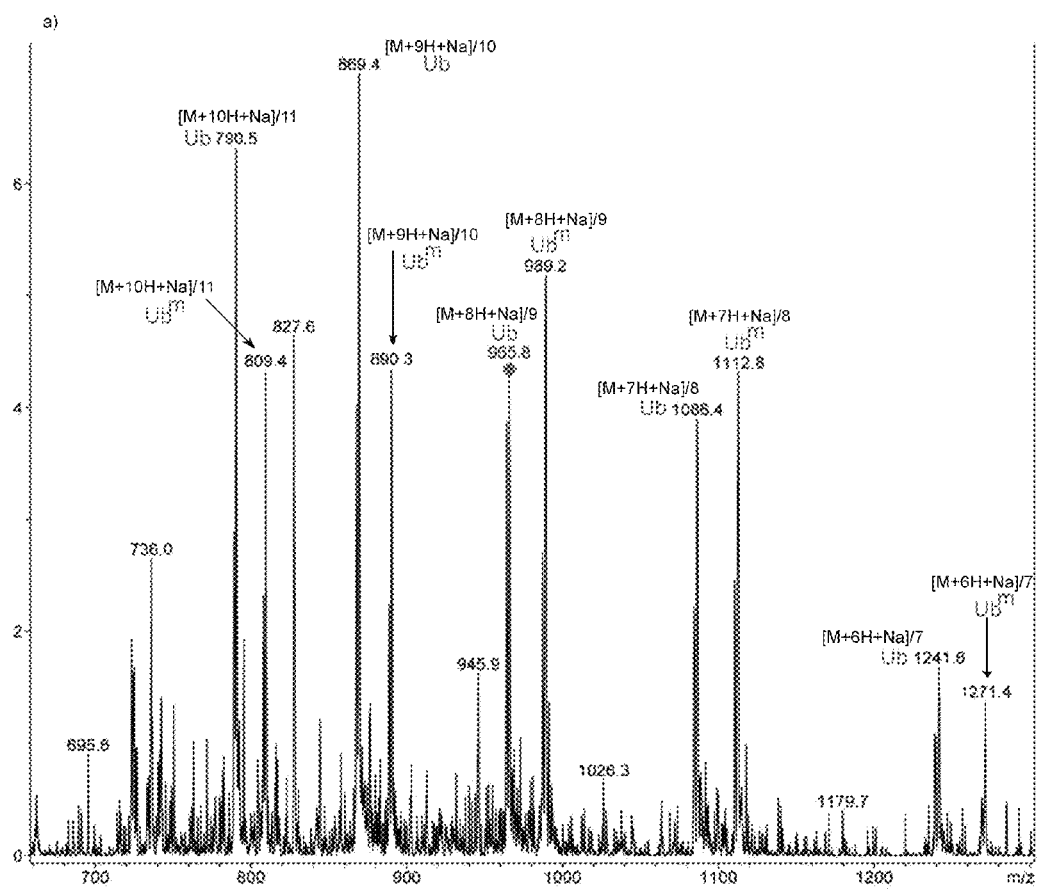
Figure 52E:
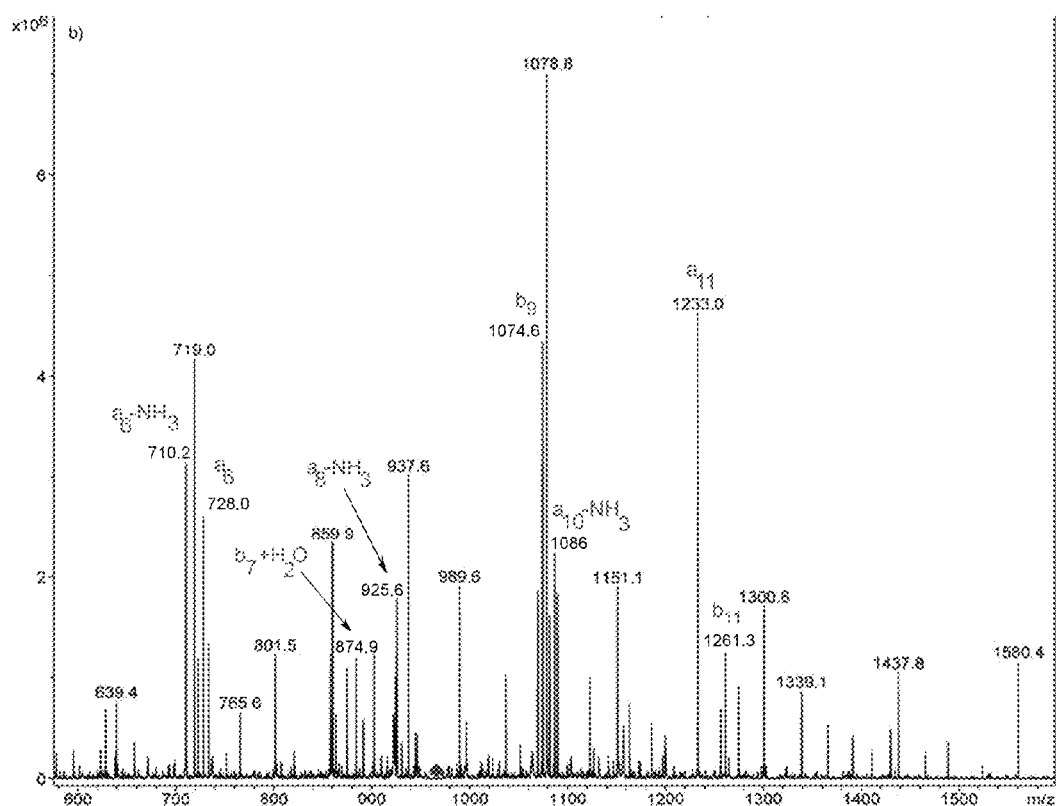
Figure 52F:
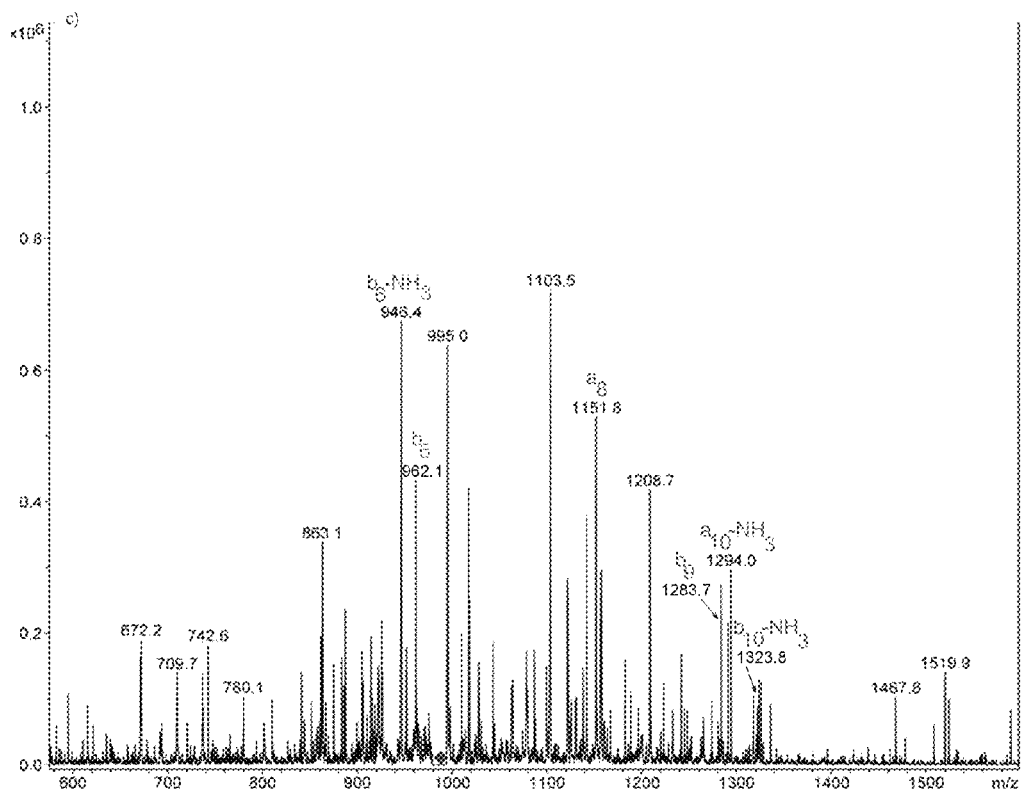

The potential of ACL to specifically acylate the N-terminus of ubiquitin was evaluated (FIGS. 52A-F). It was conjectured that ubiquitin would provide a stringent test to determine the specificity of reaction at the N-terminus, because it contains seven lysine residues (see FIG. 52B). Diazobenzene dye 10 (see FIG. 52A) was used as a model substrate for reaction with ubiquitin. Five-fold excess of the dye selenoester was incubated with the protein (100 μM) in 10% DMF in 1×PBS buffer, pH 7.0. The reaction was monitored using mass spectroscopy (MALDI and LCMS). After 96 hours, roughly 70% of ubiquitin was modified by the dye and only the peak corresponding to mono-labeled ubiquitin (Ub$^m$) was observed by Maldi and LCMS (FIG. 52C). Further analysis by MS/MS showed that the modification is localized to the N-terminal hexapeptide fragment of ubiquitin (FIGS. 52D-F). This result further highlights the attractiveness of the ligation strategy proposed herein, and suggests potential uses of ACL as a strategy for N-terminal modification of proteins (Gilmore et al., *Angew. Chem. Int. Ed.* 45:5307-11 (2006); Theile et al., *Nat. Protocols,* 8:1800-07 (2013); Williamson et al., *Angew. Chem. Int. Ed.* 51:9377-80 (2012), each of which is hereby incorporated by reference in its entirety).

Chemoselective reactions for amide bond formation have transformed the ability to access synthetic proteins and other bioconjugates through ligation of fragments. In these ligations, amide bond formation is accelerated by transient enforcement of an intramolecular reaction between the carboxyl and the amine termini of two fragments. A new method for peptide ligation has been introduced herein—aldehyde capture ligation, which parlays the high chemoselective reactivity of aldehydes and amines to enforce amide bond formation between amino acid residues and peptides that are difficult to ligate by existing technologies. One key feature of aldehyde capture ligation is that it employs the rapid association between an aldehyde group and an amine to enforce an intramolecular reaction leading to the desired native amide bond formation. Because primary and secondary amines react with the selenobenzaldehyde esters readily, it was postulated that the hemiaminal II (see FIG. 2) is the active intermediate in the reaction, but contributions from the imine as a reactive intermediate with primary amines or direct acylation of selenoesters cannot be ruled out. The potential of this approach for ligating a variety of unprotected amino acids and peptides, including difficult sequences, has been demonstrated. Preliminary results indicating mono-labeling of ubiquitin, a model protein, highlight the potential of ACL as a strategy for protein modification. Importantly, a strategy for the facile synthesis of peptide selenoesters on solid phase, which will further enable evaluation of the ACL methodology for the synthesis of more complex peptides, has also been outlined.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A method of forming an amide ligation product, said method comprising:
reacting a compound containing an amino group with a ligation agent, said ligation agent comprising a seleno ester group, under conditions effective to produce an amide ligation product;
wherein:
(i) the compound containing an amino group does not have an N-terminal cysteine, an N-terminal serine, or an N-terminal threonine; or
(ii) the method does not proceed through the formation of a pseudoproline intermediate.

2. The method of claim 1, wherein the amide ligation product has the formula A-C(O)—N(R$^9$)—B,
wherein
A and B are each independently selected from the group consisting of H, (R$^1$)$_2$N(C(R$^2$)$_2$)$_n$—, —NR$^5$R$^6$, C$_1$-C$_6$ alkyl, C$_2$-C$_6$ alkenyl, C$_2$-C$_6$ alkynyl, —OH, C$_1$-C$_6$ alkoxy, aryl, amino acids, peptides, proteins, carbohydrates, nucleic acids, cytotoxic small molecule drugs, dyes, and polymers;
each n is 1-3;
each R$^1$ is independently selected from the group consisting of H, C$_1$-C$_6$ alkyl, C$_2$-C$_6$ alkenyl, C$_2$-C$_6$ alkynyl, aryl, amino acids, peptides, and protecting groups for the protection of an amine;
each R$^2$ is independently selected from the group consisting of H, —C(O)R$^7$, —C(O)OR$^8$, —C(O)NR$^5$R$^6$, NO$_2$, —NR$^5$R$^6$, halogen, OH, C$_1$-C$_6$ alkyl, C$_2$-C$_6$ alkenyl, C$_2$-C$_6$ alkynyl, aryl, C$_1$-C$_6$ alkoxy, and amino acid side chains;
R$^5$, R$^6$, R$^7$, and R$^8$ are each independently selected from the group consisting of H, C$_1$-C$_6$ alkyl, C$_2$-C$_6$ alkenyl, C$_2$-C$_6$ alkynyl, and aryl; and
R$^9$ is selected from the group consisting of H, OH, C$_1$-C$_6$ alkyl, C$_2$-C$_6$ alkenyl, C$_2$-C$_6$ alkynyl, aryl, C$_1$-C$_6$ alkoxy, amino acids, peptides, proteins, carbohydrates, and nucleic acids.

3. The method of claim 1, wherein the compound containing an amino group has the formula B—N(R$^9$)H,
wherein
B is selected from the group consisting of H, (R$^1$)$_2$N(C (R$^2$)$_2$)$_n$—, —NR$^5$R$^6$, C$_1$-C$_6$ alkyl, C$_2$-C$_6$ alkenyl, C$_2$-C$_6$ alkynyl, —OH, C$_1$-C$_6$ alkoxy, aryl, amino acids, peptides, proteins, carbohydrates, nucleic acids, cytotoxic small molecule drugs, dyes, and polymers;
R$^5$ and R$^6$ are each independently selected from the group consisting of H, C$_1$-C$_6$ alkyl, C$_2$-C$_6$ alkenyl, C$_2$-C$_6$ alkynyl, and aryl; and
R$^9$ is selected from the group consisting of H, OH, C$_1$-C$_6$ alkyl, C$_2$-C$_6$ alkenyl, C$_2$-C$_6$ alkynyl, aryl, C$_1$-C$_6$ alkoxy, amino acids, peptides, proteins, carbohydrates, and nucleic acids.

4. The method of claim 1, wherein the compound containing an amino group is selected from the group consisting of amino acids, peptides, proteins, carbohydrates, and nucleic acids.

5. The method of claim 1, wherein the ligation agent has the formula:

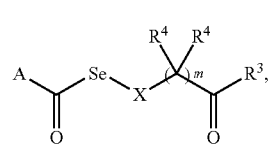

wherein

A is selected from the group consisting of H, $(R^1)_2N(C(R^2)_2)_n-$, $-NR^5R^6$, $C_1-C_6$ alkyl, $C_2-C_6$ alkenyl, $C_2-C_6$ alkynyl, $-OH$, $C_1-C_6$ alkoxy, aryl, amino acids, peptides, proteins, carbohydrates, nucleic acids, cytotoxic small molecule drugs, dyes, and polymers;

X is selected from the group consisting of

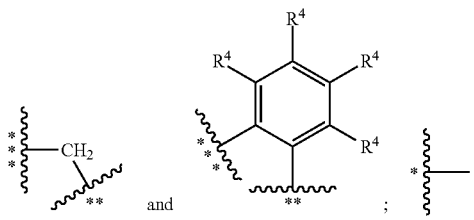

represents a point of attachment to $-C(O)-Se-X-(CR^4_2)_mC(O)R^3$;

represents a point of attachment to $(CR^4_2)_mC(O)R^3$;

represents a point of attachment to $-Se-C(O)-A$;

n is 1-3;
m is 0-3;
each $R^1$ is independently selected from the group consisting of H, $C_1-C_6$ alkyl, $C_2-C_6$ alkenyl, $C_2-C_6$ alkynyl, aryl, amino acids, peptides, and protecting groups for the protection of an amine;
each $R^2$ is independently selected from the group consisting of H, $-C(O)R^7$, $-C(O)OR^8$, $-C(O)NR^5R^6$, $NO_2$, $-NR^5R^6$, halogen, OH, $C_1-C_6$ alkyl, $C_2-C_6$ alkenyl, $C_2-C_6$ alkynyl, aryl, $C_1-C_6$ alkoxy, and amino acid side chains;
$R^3$ is selected from the group consisting of H, $C_1-C_6$ alkyl, and aryl;
each $R^4$ is independently selected from the group consisting of H, $-C(O)R^7$, $-C(O)OR^8$, $NO_2$, $-NR^5R^6$, halogen, OH, $C_1-C_6$ alkyl, aryl, and $C_1-C_6$ alkoxy; and
$R^5$, $R^6$, $R^7$, and $R^8$ are each independently selected from the group consisting of H, $C_1-C_6$ alkyl, $C_2-C_6$ alkenyl, $C_2-C_6$ alkynyl, and aryl;

with the proviso that m is 0-3 when A is $(R^1)_2N(C(R^2)_2)_n-$ and X is

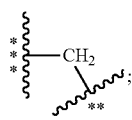

and with the proviso that m is 0-2 when A is $(R^1)_2N(C(R^2)_2)_n-$ and X is

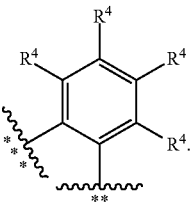

6. The method of claim 5, wherein A is $(R^1)_2N(C(R^2)_2)_n-$, a fluorescent dye, or a cytotoxic small molecule drug.

7. The method of claim 6, wherein X is

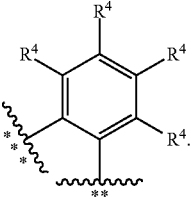

8. The method of claim 7, wherein the ligation agent is selected from the group consisting of:

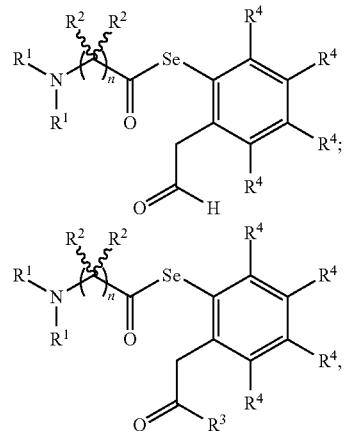

wherein $R^3$ is an aryl or an alkyl;

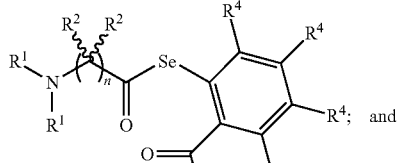

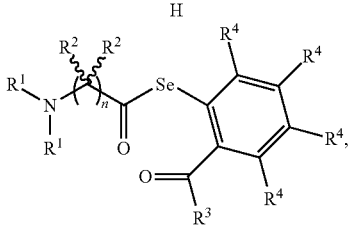

wherein $R^3$ is an aryl or an alkyl.

9. The method of claim 6, wherein X is

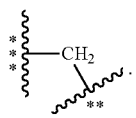

10. The method of claim 9, wherein the ligation agent is selected from the group consisting of:

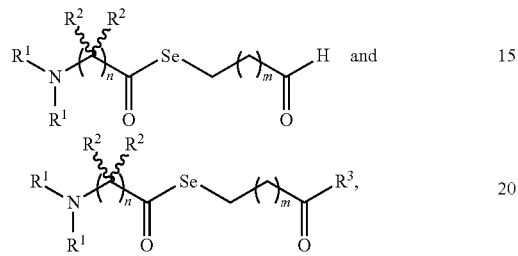

wherein R3 is an aryl or an alkyl.

11. The method of claim 1, wherein the compound containing an amino group does not have an N-terminal cysteine, an N-terminal serine, or an N-terminal threonine.

12. The method of claim 1, wherein the method does not proceed through the formation of a pseudoproline intermediate.

* * * * *